United States Patent
Angel et al.

(10) Patent No.: US 9,758,797 B2
(45) Date of Patent: *Sep. 12, 2017

(54) METHODS AND PRODUCTS FOR EXPRESSING PROTEINS IN CELLS

(71) Applicant: Factor Bioscience Inc., Cambridge, MA (US)

(72) Inventors: Matthew Angel, Cambridge, MA (US); Christopher Rohde, Cambridge, MA (US)

(73) Assignee: FACTOR BIOSCIENCE, INC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/487,088

(22) Filed: Apr. 13, 2017

(65) Prior Publication Data

US 2017/0218400 A1    Aug. 3, 2017

Related U.S. Application Data

(63) Continuation of application No. 15/270,469, filed on Sep. 20, 2016, now Pat. No. 9,657,282, which is a continuation of application No. 15/156,829, filed on May 17, 2016, now Pat. No. 9,487,768, which is a continuation of application No. 14/735,603, filed on Jun. 10, 2015, now Pat. No. 9,376,669, which is a continuation of application No. 14/701,199, filed on Apr. 30, 2015, now Pat. No. 9,447,395, which is a continuation of application No. PCT/US2013/068118, filed on Nov. 1, 2013.

(60) Provisional application No. 61/721,302, filed on Nov. 1, 2012, provisional application No. 61/785,404, filed on Mar. 14, 2013, provisional application No. 61/842,874, filed on Jul. 3, 2013.

(51) Int. Cl.

| | | |
|---|---|---|
| *C07H 21/04* | (2006.01) | |
| *C12N 9/14* | (2006.01) | |
| *C12N 15/90* | (2006.01) | |
| *C12N 9/22* | (2006.01) | |
| *C12N 15/10* | (2006.01) | |
| *C12N 15/86* | (2006.01) | |
| *G01N 33/50* | (2006.01) | |
| *A61K 48/00* | (2006.01) | |
| *A61K 38/46* | (2006.01) | |
| *A01K 67/00* | (2006.01) | |

(52) U.S. Cl.
CPC ......... *C12N 15/907* (2013.01); *A61K 38/465* (2013.01); *A61K 48/005* (2013.01); *C12N 9/22* (2013.01); *C12N 15/1024* (2013.01); *C12N 15/86* (2013.01); *C12Y 301/21004* (2013.01); *G01N 33/5014* (2013.01); *C12N 2800/80* (2013.01)

(58) Field of Classification Search
CPC .... C12N 15/907; C12N 9/22; C12N 15/1024; C12N 15/86; C12N 2800/80; C12Y 301/21004; A61K 48/005; A61K 38/465
See application file for complete search history.

(56) References Cited

U.S. PATENT DOCUMENTS

| | | |
|---|---|---|
| 3,539,465 A | 11/1970 | Jensen et al. |
| 5,843,780 A | 12/1998 | Thomson |
| 7,276,489 B2 | 10/2007 | Agrawal et al. |
| 7,442,548 B2 | 10/2008 | Thomson et al. |
| 7,449,334 B2 | 11/2008 | Thomson et al. |
| 7,621,606 B2 | 11/2009 | Page et al. |
| 7,682,828 B2 | 3/2010 | Jaenisch et al. |
| 7,687,266 B2 | 3/2010 | Chambers et al. |
| 7,812,000 B2 | 10/2010 | Agrawal et al. |
| 8,048,675 B1 | 11/2011 | Irion |
| 8,048,999 B2 | 11/2011 | Yamanaka et al. |
| 8,058,065 B2 | 11/2011 | Yamanaka et al. |
| 8,071,369 B2 | 12/2011 | Jaenisch et al. |
| 8,129,187 B2 | 3/2012 | Yamanaka et al. |
| 8,129,348 B2 | 3/2012 | Besman et al. |
| 8,202,850 B2 | 6/2012 | Agrawal et al. |
| 8,278,036 B2 | 10/2012 | Kariko et al. |
| 8,420,782 B2 | 4/2013 | Bonas et al. |

(Continued)

FOREIGN PATENT DOCUMENTS

| | | |
|---|---|---|
| EP | 2241572 | 10/2010 |
| WO | 9830679 | 7/1998 |

(Continued)

OTHER PUBLICATIONS

Anderson et al., "Incorporation of pseudouridine into mRNA enhances translation by diminishing PKR activation," Nucl. Acids Res. 38(17), pp. 1-9 (2010).

(Continued)

*Primary Examiner* — Quang Nguyen

(74) *Attorney, Agent, or Firm* — Morgan, Lewis & Bockius LLP

(57) ABSTRACT

The present invention relates in part to nucleic acids encoding proteins, therapeutics comprising nucleic acids encoding proteins, methods for inducing cells to express proteins using nucleic acids, methods, kits and devices for transfecting, gene editing, and reprogramming cells, and cells, organisms, and therapeutics produced using these methods, kits, and devices. Methods and products for altering the DNA sequence of a cell are described, as are methods and products for inducing cells to express proteins using synthetic RNA molecules. Therapeutics comprising nucleic acids encoding gene-editing proteins are also described.

9 Claims, 12 Drawing Sheets

(56) References Cited

U.S. PATENT DOCUMENTS

| | | |
|---|---|---|
| 8,440,431 B2 | 5/2013 | Voytas et al. |
| 8,440,432 B2 | 5/2013 | Voytas et al. |
| 8,450,471 B2 | 5/2013 | Voytas et al. |
| 8,470,973 B2 | 6/2013 | Bonas et al. |
| 8,586,526 B2 | 11/2013 | Gregory et al. |
| 8,691,966 B2 | 4/2014 | Kariko et al. |
| 8,710,200 B2 | 4/2014 | Schrum et al. |
| 8,716,465 B2 | 5/2014 | Rossi et al. |
| 8,748,089 B2 | 6/2014 | Kariko et al. |
| 8,802,438 B2 | 8/2014 | Rossi et al. |
| 8,822,663 B2 | 9/2014 | Schrum et al. |
| 8,835,108 B2 | 9/2014 | Kariko et al. |
| 8,883,506 B2 | 11/2014 | Rossi et al. |
| 9,376,669 B2 | 6/2016 | Angel et al. |
| 9,447,395 B2 | 9/2016 | Angel et al. |
| 9,464,285 B2 * | 10/2016 | Angel ............... A61K 31/7115 |
| 9,487,768 B2 * | 11/2016 | Angel ............... A61K 31/7115 |
| 2003/0083272 A1 | 5/2003 | Wiederholt et al. |
| 2005/0053588 A1 | 3/2005 | Yin |
| 2005/0130144 A1 | 6/2005 | Nakatsuji et al. |
| 2007/0134796 A1 | 6/2007 | Holmes et al. |
| 2008/0213377 A1 | 9/2008 | Bhatia et al. |
| 2008/0233610 A1 | 9/2008 | Thomson et al. |
| 2008/0260706 A1 | 10/2008 | Rabinovich et al. |
| 2009/0029465 A1 | 1/2009 | Thomson et al. |
| 2009/0093433 A1 | 4/2009 | Woolf et al. |
| 2009/0275128 A1 | 11/2009 | Thomson et al. |
| 2009/0286852 A1 | 11/2009 | Kariko et al. |
| 2010/0003757 A1 | 1/2010 | Mack et al. |
| 2010/0047261 A1 | 2/2010 | Hoerr et al. |
| 2010/0075421 A1 | 3/2010 | Yamanaka et al. |
| 2010/0120079 A1 | 5/2010 | Page et al. |
| 2010/0144031 A1 | 6/2010 | Jaenisch et al. |
| 2010/0167286 A1 | 7/2010 | Reijo Pera et al. |
| 2010/0168000 A1 | 7/2010 | Kiessling et al. |
| 2010/0184033 A1 | 7/2010 | West et al. |
| 2010/0184227 A1 | 7/2010 | Thomson et al. |
| 2010/0221829 A1 | 9/2010 | Amit et al. |
| 2010/0233804 A1 | 9/2010 | Zhou et al. |
| 2010/0267141 A1 | 10/2010 | Shi et al. |
| 2010/0272695 A1 | 10/2010 | Agulnick et al. |
| 2010/0273220 A1 | 10/2010 | Yanki et al. |
| 2010/0304481 A1 | 12/2010 | Thomson et al. |
| 2010/0311171 A1 | 12/2010 | Nakanishi et al. |
| 2010/0317103 A1 | 12/2010 | Elefanty et al. |
| 2011/0045001 A1 | 2/2011 | Klosel et al. |
| 2011/0065103 A1 | 3/2011 | Sahin et al. |
| 2011/0076678 A1 | 3/2011 | Jaenisch et al. |
| 2011/0104125 A1 | 5/2011 | Yu |
| 2011/0110899 A1 | 5/2011 | Shi et al. |
| 2011/0143397 A1 | 6/2011 | Kariko et al. |
| 2011/0143436 A1 | 6/2011 | Dahl et al. |
| 2011/0145940 A1 | 6/2011 | Voytas et al. |
| 2011/0151557 A1 | 6/2011 | Reh et al. |
| 2011/0165133 A1 | 7/2011 | Rabinovich et al. |
| 2011/0171185 A1 | 7/2011 | Klimanskaya et al. |
| 2011/0189137 A1 | 8/2011 | Rana et al. |
| 2011/0236978 A1 | 9/2011 | Stolzing et al. |
| 2011/0239315 A1 | 9/2011 | Bonas et al. |
| 2011/0244566 A1 | 10/2011 | Wu et al. |
| 2011/0263015 A1 | 10/2011 | D'Costa et al. |
| 2011/0301073 A1 | 12/2011 | Gregory et al. |
| 2012/0046346 A1 | 2/2012 | Rossi et al. |
| 2012/0064620 A1 | 3/2012 | Bonas et al. |
| 2012/0195936 A1 | 8/2012 | Rudolph et al. |
| 2012/0208278 A1 | 8/2012 | Yanik et al. |
| 2012/0237975 A1 | 9/2012 | Schrum et al. |
| 2012/0301455 A1 | 11/2012 | Hunt |
| 2013/0102034 A1 | 4/2013 | Schrum et al. |
| 2013/0115272 A1 | 5/2013 | de Fougerolles et al. |
| 2013/0122581 A1 | 5/2013 | Voytas et al. |
| 2013/0123481 A1 | 5/2013 | de Fougerolles et al. |
| 2013/0156849 A1 | 6/2013 | de Fougerolles et al. |
| 2013/0165504 A1 | 6/2013 | Bancel et al. |
| 2013/0189741 A1 | 7/2013 | Meis et al. |
| 2013/0203115 A1 | 8/2013 | Schrum et al. |
| 2013/0217119 A1 | 8/2013 | Bonas et al. |
| 2013/0244282 A1 | 9/2013 | Schrum et al. |
| 2013/0245103 A1 | 9/2013 | de Fougerolles et al. |
| 2013/0274129 A1 | 10/2013 | Katzen et al. |
| 2013/0302295 A1 | 11/2013 | Wang et al. |
| 2014/0073053 A1 | 3/2014 | Yanik et al. |
| 2014/0073687 A1 | 3/2014 | Chien et al. |
| 2014/0242154 A1 | 8/2014 | Ramunas et al. |
| 2014/0242155 A1 | 8/2014 | Ramunas et al. |
| 2014/0315988 A1 | 10/2014 | Dahl et al. |
| 2014/0349401 A1 | 11/2014 | Wang et al. |

FOREIGN PATENT DOCUMENTS

| | | |
|---|---|---|
| WO | 0226757 | 4/2002 |
| WO | 2007024708 | 3/2007 |
| WO | 2008065381 | 6/2008 |
| WO | 2009127230 | 10/2009 |
| WO | 2009147400 | 12/2009 |
| WO | 2010093655 | 8/2010 |
| WO | 2010123501 | 10/2010 |
| WO | 2011071931 | 6/2011 |
| WO | 2011071936 | 6/2011 |
| WO | 2011110886 | 9/2011 |
| WO | 2011114237 | 9/2011 |
| WO | 2011012316 | 10/2011 |
| WO | 2011130624 | 10/2011 |
| WO | 2011140397 | 11/2011 |
| WO | 2011141820 | 11/2011 |
| WO | 2011154393 | 12/2011 |
| WO | 2012019122 | 2/2012 |
| WO | 2012019168 | 2/2012 |
| WO | 2012036299 | 3/2012 |
| WO | 2012048213 | 4/2012 |
| WO | 2012060473 | 5/2012 |
| WO | 2012122318 | 9/2012 |
| WO | 2012138453 | 10/2012 |
| WO | 2013003475 | 1/2013 |
| WO | 2013102203 | 7/2013 |
| WO | 2013151671 | 10/2013 |
| WO | 2013163296 | 10/2013 |
| WO | 2013173248 | 11/2013 |
| WO | 2014190361 | 11/2014 |

OTHER PUBLICATIONS

Anderson et al., "Nucleofection induces transient eiF2a phosphorylation by GCN2 and PERK," Gene Ther., pp. 1-7 (Feb. 2, 2012).

Anderson et al., "Nucleoside modifications in RNA limit activation of 2'-5'-oligoadenylate synthetase and increase resistance to cleavage by RNase L," Nucl. Acids Res. 39(21), pp. 9329-9338 (2011).

Angel et al., "Innate Immune Suppression Enables Frequent Transfection with RNA Encoding Reprogramming Proteins," PLoS One, vol. 5(7), e11756, pp. 1-7 (Jul. 2010).

Angel, "Extended Transient Transfection by Repeated Delivery of an In Vitro-Transcribed RNA," Master of Science in Electrical Engineering and Computer Science, 56 pages (Massachusetts Institute of Technology, Cambridge, Massachusetts) (Sep. 2008).

Angel, "Reprogramming Human Somatic Cells to Pluripotency Using RNA", pp. 1-89 (Ph.D. diss., Massachusetts Institute of Technology) (Feb. 2012).

Angel, "Reprogramming human somatic cells to pluripotency using RNA," Doctor of Philosophy in Electrical Engineering and Computer Science, 55 pages (Massachusetts Institute of Technology, Cambridge, Massachusetts) (Oct. 11, 2011).

Arnold et al., "Reprogramming of Human Huntington Fibroblasts Using mRNA," ISRN Cell Biology 2012:Article ID 124878, pp. 1-12 (2012).

Barker et al., "A method for the deionization of bovine serum albumin," Tissue Culture Association, pp. 111-112 (1975).

Berg, "Proposed structure for the zinc-binding domains from transcription factor IIIA and related proteins," Proc. Natl. Acad. Sci. USA, vol. 85, pp. 99-102 (Jan. 1988).

(56) References Cited

OTHER PUBLICATIONS

Boch et al., "Breaking the Code of DNA Binding Specificity of TAL-Type III Effectors," Science, vol. 3126, pp. 1509-1512 (Dec. 11, 2009).
Bolli et al., "Cardiac stem cells in patients with ischaemic cardiomyopathy (SCIPIO): initial results of a randomised phase 1 trial," Lancet, pp. 1-11 (Nov. 14, 2011).
Braam et al., "Recombinant vitronectin is a functionally defined substrate that supports human embryonic stem cell self-renewal via αu β5 integrin," Stem Cells 26, pp. 2257-2265 (2008).
Carroll, "Progress and prospects: Zinc-finger nucleases as gene therapy agents," Gene Therapy, vol. 15, pp. 1463-1468 (2008).
Chen et al., "Chemically defined conditions for human iPSC derivation and culture," Nat. Methods 8, pp. 424-429 (May 2011).
Chen et al., "Rational optimization of reprogramming culture conditions for the generation of induced pluripotent stem cells with ultra-high efficiency and fast kinetics," Cell Research 21, pp. 884-894 (2011).
Christian et al., "Targeting DNA Double-Strand Breaks with TAL Effector Nucleases," Genetics, vol. 186, pp. 757-761 (Oct. 2010).
Cui et al., "Targeted integration in rat and mouse embryos with zinc-finger nucleases," Nat. Biotech., vol. 29, No. 1, pp. 54-67 (Jan. 2011).
Davis, "Stabilization of RNA stacking by pseudouriding," Nucleic Acids Research, vol. 23, No. 24, pp. 5020-5026 (1995).
Droge et al., "A comparative study of some physico-chemical properties of human serum albumin samples from different sources—I. Some physico-chemical properties of isoionic human serum albumin solutions," Biochem. Pharmacal. 31, pp. 3775-3779 (1982).
Efe et al., "Conversion of mouse fibroblasts into cardiomyocytes using a direct reprogramming strategy," Nat. Cell Biol. 13, pp. 215-222 (Mar. 2011).
Garcia-Gonzalo et al., "Albumin-associated lipids regulate human embryonic stem cell self-renewal," PLoS One 3: e1384, pp. 1-10 (Jan. 2008).
Geurts et al., "Knockout Rats via Embryo Microinjection of Zinc-Finger Nucleases," Science, vol. 325, p. 433 (Jul. 24, 2009).
Goldberg et al., "The incorporation of 5-ribosyluracil triphosphate into RNA in nuclear extracts of mammalian cells," Biochem. Biophys. Res. Commun. 6, pp. 394-398 (1961).
Goldberg et al., "The enzymic synthesis of pseudouridine triphosphate," Biochim. Biophys. Acta, vol. 54, pp. 202-204 (1961).
Goldberg, "Ribonucleic acid synthesis in nuclear extracts of mammalian cells grown in suspension culture; effect of ionic strength and surface-active agents," Biochim. Biophys. Acta, vol. 51, pp. 201-204 (1961).
Gurung et al., "β-Catenin Is a Mediator of the Response of Fibroblasts to Irradiation," The American Journal of Pathology, vol. 174, No. 1, pp. 248-255 (Jan. 2009).
Hamanaka et al., "Generation of Germline-Component Rat Induced Pluripotent Stem Cells," PlosOne, vol. 6, Issue 7, pp. 1-9 (Jul. 2011).
Hockemeyer et al., "Efficient targeting of expressed and silent genes in human ESCs and iPSCs using zinc-finger nucleases," Nature Biotechnology, vol. 27, No. 9, pp. 851-857 (Sep. 2009).
Hockemeyer et al., "Genetic engineering of human ES and iPS cells using TALE nucleases," Author Manuscript, available in PMC Feb. 1, 2012. Published in final edited form as: Nat Biotechnol.; 29(8): 731-734. doi:10.1038/nbt.1927.
Kahan et al., "The Role of Deoxyribonucleic Acid in Ribonucleic Acid Synthesis," The Journal of Biological Chemistry, vol. 237, No. 12, pp. 3778-3785 (Dec. 1962).
Kariko et al., "Generating the optimal mRNA for therapy: HPLC purification eliminates immune activation and improves translation of nucleoside-modified, protein-encoding mRNA," Nucl. Acids Res., pp. 1-10 (Sep. 2, 2011).
Kariko et al., "In vivo protein expression from mRNA delivered into adult rat brain," J. Neurosci. Methods 105, pp. 77-86 (2001).
Kariko et al., "Incorporation of pseudouridine into mRNA yields superior nonimmunogenic vector with increased translational capacity and biological stability," Mol. Ther. 16, pp. 1833-1840 (2008).
Kariko et al., "Increased Erythropoiesis in Mice Injected With Submicrogram Quantities of Pseudouridine-containing mRNA Encoding Erythropoietin," Mol. Ther. 20, pp. 948-953 (May 2012).
Kariko et al., "mRNA is an endogenous ligand for Toll-like receptor 3," J. Biol. Chem. 279, pp. 12542-12550 (2004).
Kariko et al., "Naturally occurring nucleoside modifications suppress the immunostimulatory activity of RNA: Implication for therapeutic RNA development," Drug Discovery & Development, vol. 10, No. 5, pp. 523-532 (2007).
Kariko et al., "Suppression of RNA recognition by Toll-like receptors: the impact of nucleoside modification and the evolutionary origin of RNA," Immunity 23, pp. 165-175 (2005).
Kawamata et al., "Generation of genetically modified rats from embryonic stem cells," PNAS, vol. 107, No. 32, pp. 14223-14228 (Aug. 10, 2010).
Kim et al., "Direct reprogramming of human neural stem cells by Oct4," Nature 461, pp. 649-653 (Oct. 2009).
Kim et al., "Generation of Human Induced Pluripotent Stem Cells by Direct Delivery of Reprogramming Proteins," Cell Stem Cell 4, pp. 472-476 (Jun. 5, 2009).
Kim et al., "Hybrid restriction enzymes: Zinc finger fusions to Fok I cleavage domain," Proc. Natl. Acad. Sci. USA, vol. 33, pp. 1156-1160 (Feb. 1996).
Kim et al., "Oct4-induced pluripotency in adult neural stem cells," Cell 136, pp. 411-419 (Feb. 6, 2009).
Kim et al., "Pluripotent stem cells induced from adult neural stem cells by reprogramming with two factors," Nature 154, pp. 1-6 (2008).
Lee et al., "Activation of Innate Immunity Is Required for Efficient Nuclear Reprogramming," Cell 151, pp. 547-558 (Oct. 26, 2012).
Lin et al., "A chemical platform for improved induction of human iPSCs," Nature Methods, vol. 6, No. 11, pp. 805-808 (Nov. 2009).
Liu et al., "A Small-Molecule Agonist of the Wnt Signaling Pathway," Angew. Chem. Int. Ed. 44, pp. 1987-1990 (2005).
Lu et al., "Defined culture conditions of human embryonic stem cells," PNAS 2006, vol. 103, pp. 5688-5693 (Apr. 11, 2006).
Ludwig et al., "Derivation of human embryonic stem cells in defined conditions," Nat. Biotechnol. 24, pp. 185-187 (Feb. 2006).
Ludwig et al., "Feeder-independent culture of human embryonic stem cells," Nat. Methods 3, pp. 637-646 (Aug. 2006).
Mahfouz et al., "De novo-engineered transcription activator-like effector (TALE) hybrid nuclease witgh novel DNA binding specificity creates double-strand breaks," PNAS vol. 108, No. 6, pp. 2623-2628 (Feb. 8, 2011).
Miller et al., "A TALE nuclease architecture for efficient genome editing," Nature Biotechnology, vol. 29, No. 2, pp. 143-148 (Feb. 2011).
Miller et al., "An improved zinc-finger nuclease architecture for highly specific genome editing," Nat. Biotechnol.; vol. 25, No. 7, pp. 778-785 (Jul. 2007).
MIT Thesis Record, "Reprogramming human somatic cells to pluripotency using RNA," (Matthew Angel, author) (May 15, 2012).
Moscou et al., "A Simple Cipher Governs DNA Recognition by TAL Effectors," Science, vol. 326, p. 1501 (Dec. 11, 2009).
Ng et al., "A protocol describing the use of a recombinant protein-based, animal product-free medium (APEL) for human embryonic stem cell differentiation as spin embryoid bodies," Nat. Protoc. 3, pp. 768-776 (Apr. 10, 2008).
Okita et al., "Generation of germline-competent induced pluripotent stem cells," Nature, vol. 448, pp. 313-317 (Jul. 19, 2007).
Plews et al., "Activation of pluripotency genes in human fibroblast cells by a novel mRNA based approach," PLoS One 5:e14397, pp. 1-10 (Dec. 2010).
Porteus et al., "Gene targeting using zinc finger nucleases," Nat. Biotechnol., vol. 23, No. 8,, pp. 967-973 (2005).
Rossi et al., "Anti-inflammatory cyclopentenone prostaglandins are direct inhibitors of Ikb kinase," Nature, vol. 403, pp. 103-108 (Jan. 6, 2000).

(56) References Cited

OTHER PUBLICATIONS

Sander et al., "Targeted gene disruption in somatic zebrafish cells using engineered TALENs," Author Manuscript, available in PMC on Feb. 5, 2012. Published in final edited form as: Nat Biotechnol.; 29(8): 697-698. doi:10.1038/nbt.1934.

Sanjana et al., "A transcription activator-like effector toolbox for genome engineering," Nature Protocols, vol. 7, No. 1, pp. 171-192 (2012).

Scheider et al., "An effective method for defatting albumin using resin columns," Biochim. Biophys. Acta, 221; 376-378 (1970).

Schwartz et al., "Embryonic stem cell trials for macular degeneration: a preliminary report," Lancet, pp. 1-8 (Jan. 23, 2012).

Shimizu et al., "Transformation by Wnt Family Proteins Correlates with Regulation of β-Catenin," Cell Growth & Differentiation, vol. 8, pp. 1349-1358 (Dec. 1997).

Soldner et al., "Generation of isogenic pluripotent stem cells differing exclusively at two early onset Parkinson point mutations," Author Manuscript, available in PMC on Jul. 22, 2012. Published in final edited form as: Cell. Jul. 22, 2011; 146(2): 318-331. doi:10.1016/j.cell.2011.06.019.

Takahashi et al., "Induction of pluripotent stem cells from adult human fibroblasts by defined factors," Cell 131, pp. 1-12 (Nov. 30, 2007).

Takahashi, et al., "Induction of pluripotent stem cells from mouse embryonic and adult fibroblast cultures by defined factors," Cell 126, pp. 1-14 (Aug. 25, 2006).

Tesson et al., "Knockout rats generated by embryo microinjection of TALENs," Nature Biotechnology, vol. 29, No. 8, pp. 695-696 (Aug. 2011).

Warren et al., "Highly efficient reprogramming to pluripotency and directed differentiation of human cells with synthetic modified mRNA," Cell. Stem Cell 7, pp. 1-13 (Nov. 5, 2010).

Watanabe et al., "A Rock inhibitor permits survival of dissociated human embryonic stem cells," Nature Biotechnology, vol. 25, No. 6, pp. 681-686 (Jun. 2007).

Wernig et al., "In vitro reprogramming of fibroblasts into a pluripotent ES-cell-like state," Nature, vol. 448, pp. 317-324 (Jul. 19, 2007).

Wood et al., "Targeted Genome Editing Across Species Using ZFNs and TALENs," Science, vol. 333, p. 307 (Jul. 15, 2011).

"Xeno-Free System for hESC & hiPSC. Facilitating the Shift from Stem Cell Research to Clincal Applications." 12 pages, Biological Industries Catalog (Stem Cell Products) (2011).

Xie et al., "Newly expressed proteins of mouse embryonic fibroblasts irradiated to be inactive," Biochem. Biophys. Res. Commun. 315, pp. 581-588 (2004).

Yakubov et al., "Reprogramming of human fibroblasts to pluripotent stem cells using mRNA of four transcription factors," Biochem. Biophys. Res. Commun. 394, pp. 189-193 (2010).

You et al., "Wnt signaling promotes oncogenic transformation by inhibiting c-Myc-induced apoptosis," The Journal of Cell Biology, vol. 157, No. 3, pp. 429-440 (Apr. 29, 2002).

Young et al., "Background Mutations in Parental Cells Account for Most of the Genetic Heterogeneity of Induced Pluripotent Stem Cells," Cell Stem Cell 10, pp. 570-582 (May 4, 2012).

Yu et al., "Induced pluripotent stem cell lines derived from human somatic cells," Science 318, pp. 1917-1920 (Dec. 21, 2007).

Zhou et al., "Generation of Induced Pluripotent Stem Cells Using Recombinant Proteins," Cell Stem Cell 4, pp. 1-4 (May 8, 2009).

\* cited by examiner

FIB. 3C

FIG. 4G

METHODS AND PRODUCTS FOR EXPRESSING PROTEINS IN CELLS

PRIORITY

The present application is a continuation of U.S. application Ser. No. 15/270,469, filed Sep. 20, 2016 (now U.S. Pat. No. 9,657,282), which is a continuation of U.S. application Ser. No. 15/156,829, filed May 17, 2016 (now U.S. Pat. No. 9,487,768), which is a continuation of U.S. application Ser. No. 14/735,603, filed Jun. 10, 2015 (now U.S. Pat. No. 9,376,669), which is a continuation of U.S. application Ser. No. 14/701,199, filed Apr. 30, 2015 (now U.S. Pat. No. 9,447,395), which is a continuation of International Application No. PCT/US2013/068118, filed Nov. 1, 2013, which claims priority to U.S. Provisional Application No. 61/721,302, filed on Nov. 1, 2012, U.S. Provisional Application No. 61/785,404, filed on Mar. 14, 2013, and U.S. Provisional Application No. 61/842,874, filed on Jul. 3, 2013, the contents of which are herein incorporated by reference in their entireties. The present application is related to U.S. application Ser. No. 13/465,490, filed on May 7, 2012, International Application No. PCT/US2012/067966, filed on Dec. 5, 2012, and U.S. application Ser. No. 13/931,251, filed on Jun. 28, 2013, the contents of which are herein incorporated by reference in their entireties.

FIELD OF THE INVENTION

The present invention relates in part to nucleic acids encoding proteins, therapeutics comprising nucleic acids encoding proteins, methods for inducing cells to express proteins using nucleic acids, methods, kits and devices for transfecting, gene editing, and reprogramming cells, and cells, organisms, and therapeutics produced using these methods, kits, and devices.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: FAB-005C3SL.txt; date recorded: May 16, 2016; file size: 410 KB).

BACKGROUND

Synthetic RNA and RNA Therapeutics

Ribonucleic acid (RNA) is ubiquitous in both prokaryotic and eukaryotic cells, where it encodes genetic information in the form of messenger RNA, binds and transports amino acids in the form of transfer RNA, assembles amino acids into proteins in the form of ribosomal RNA, and performs numerous other functions including gene expression regulation in the forms of microRNA and long non-coding RNA. RNA can be produced synthetically by methods including direct chemical synthesis and in vitro transcription, and can be administered to patients for therapeutic use.

Cell Reprogramming and Cell-Based Therapies

Cells can be reprogrammed by exposing them to specific extracellular cues and/or by ectopic expression of specific proteins, microRNAs, etc. While several reprogramming methods have been previously described, most that rely on ectopic expression require the introduction of exogenous DNA, which can carry mutation risks. DNA-free reprogramming methods based on direct delivery of reprogramming proteins have been reported. However, these methods are too inefficient and unreliable for commercial use. In addition, RNA-based reprogramming methods have been described (See, e.g., Angel. MIT Thesis. 2008. 1-56; Angel et al. PLoS ONE. 2010. 5, 107; Warren et al. Cell Stem Cell. 2010. 7, 618-630; Angel. MIT Thesis. 2011. 1-89; and Lee et al. Cell. 2012. 151, 547-558; the contents of all of which are hereby incorporated by reference). However, existing RNA-based reprogramming methods are slow, unreliable, and inefficient when performed on adult cells, require many transfections (resulting in significant expense and opportunity for error), can reprogram only a limited number of cell types, can reprogram cells to only a limited number of cell types, require the use of immunosuppressants, and require the use of multiple human-derived components, including blood-derived HSA and human fibroblast feeders. The many drawbacks of previously disclosed RNA-based reprogramming methods make them undesirable for both research and therapeutic use.

Gene Editing

Several naturally occurring proteins contain DNA-binding domains that can recognize specific DNA sequences, for example, zinc fingers (ZFs) and transcription activator-like effectors (TALEs). Fusion proteins containing one or more of these DNA-binding domains and the cleavage domain of FokI endonuclease can be used to create a double-strand break in a desired region of DNA in a cell (See, e.g., US Patent Appl. Pub. No. US 2012/0064620, US Patent Appl. Pub. No. US 2011/0239315, U.S. Pat. No. 8,470,973, US Patent Appl. Pub. No. US 2013/0217119, U.S. Pat. No. 8,420,782, US Patent Appl. Pub. No. US 2011/0301073, US Patent Appl. Pub. No. US 2011/0145940, U.S. Pat. No. 8,450,471, U.S. Pat. No. 8,440,431, U.S. Pat. No. 8,440,432, and US Patent Appl. Pub. No. 2013/0122581, the contents of all of which are hereby incorporated by reference). However, current methods for gene editing cells are inefficient and carry a risk of uncontrolled mutagenesis, making them undesirable for both research and therapeutic use. Methods for DNA-free gene editing of somatic cells have not been previously explored, nor have methods for simultaneous or sequential gene editing and reprogramming of somatic cells. In addition, methods for directly gene editing cells in patients (i.e., in vivo) have not been previously explored, and the development of such methods has been limited by a lack of acceptable targets, inefficient delivery, inefficient expression of the gene-editing protein/proteins, inefficient gene editing by the expressed gene-editing protein/proteins, due in part to poor binding of DNA-binding domains, excessive off-target effects, due in part to non-directed dimerization of the FokI cleavage domain and poor specificity of DNA-binding domains, and other factors. Finally, the use of gene editing in anti-bacterial, anti-viral, and anti-cancer treatments has not been previously explored.

Accordingly, there remains a need for improved compositions and methods for the expression of proteins in cells.

SUMMARY OF THE INVENTION

The present invention provides, in part, compositions, methods, articles, and devices for inducing cells to express proteins, methods, articles, and devices for producing these compositions, methods, articles, and devices, and compositions and articles, including cells, organisms, and therapeutics, produced using these compositions, methods, articles, and devices. Unlike previously reported methods, certain embodiments of the present invention do not involve exposing cells to exogenous DNA or to allogeneic or animal-derived materials, making products produced according to the methods of the present invention useful for therapeutic applications.

In some aspects, synthetic RNA molecules with low toxicity and high translation efficiency are provided. In one aspect, a cell-culture medium for high-efficiency transfection, reprogramming, and gene editing of cells is provided. Other aspects pertain to methods for producing synthetic RNA molecules encoding reprogramming proteins. Still further aspects pertain to methods for producing synthetic RNA molecules encoding gene-editing proteins.

In one aspect, the invention provides high-efficiency gene-editing proteins comprising engineered nuclease cleavage domains. In another aspect, the invention provides high-fidelity gene-editing proteins comprising engineered nuclease cleavage domains. Other aspects relate to high-efficiency gene-editing proteins comprising engineered DNA-binding domains. Still further aspects pertain to high-fidelity gene-editing proteins comprising engineered DNA-binding domains. Still further aspects relate to gene-editing proteins comprising engineered repeat sequences. Some aspects relate to methods for altering the DNA sequence of a cell by transfecting the cell with or inducing the cell to express a gene-editing protein. Other aspects relate to methods for altering the DNA sequence of a cell that is present in an in vitro culture. Still further aspects relate to methods for altering the DNA sequence of a cell that is present in vivo.

In some aspects, the invention provides methods for treating cancer comprising administering to a patient a therapeutically effective amount of a gene-editing protein or a nucleic-acid encoding a gene-editing protein. In one aspect, the gene-editing protein is capable of altering the DNA sequence of a cancer associated gene. In another aspect, the cancer-associated gene is the BIRC5 gene. Still other aspects relate to therapeutics comprising nucleic acids and/or cells and methods of using therapeutics comprising nucleic acids and/or cells for the treatment of, for example, type 1 diabetes, heart disease, including ischemic and dilated cardiomyopathy, macular degeneration, Parkinson's disease, cystic fibrosis, sickle-cell anemia, thalassemia, Fanconi anemia, severe combined immunodeficiency, hereditary sensory neuropathy, xeroderma pigmentosum, Huntington's disease, muscular dystrophy, amyotrophic lateral sclerosis, Alzheimer's disease, cancer, and infectious diseases including hepatitis and HIV/AIDS. In some aspects, the nucleic acids comprise synthetic RNA. In other aspects, the nucleic acids are delivered to cells using a virus. In some aspects, the virus is a replication-competent virus. In other aspects, the virus is a replication-incompetent virus.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

DETAILED DESCRIPTION OF THE FIGURES

Figure 2:
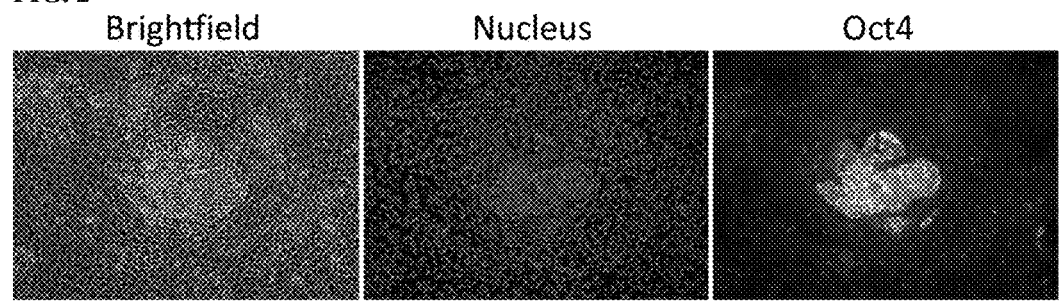

FIG. 2 depicts primary human neonatal fibroblasts reprogrammed by five transfections with RNA encoding reprogramming proteins. Cells were fixed and stained for Oct4 protein. Nuclei were counterstained with Hoechst 33342.

Figure 3A:
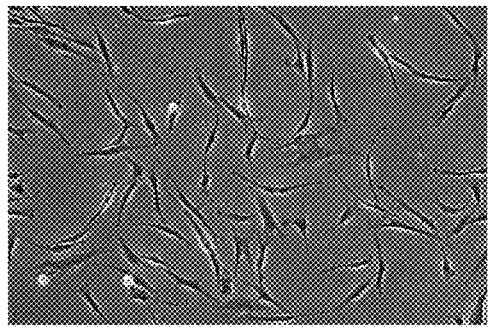

FIG. 3A depicts primary human adult fibroblasts.

Figure 3B:
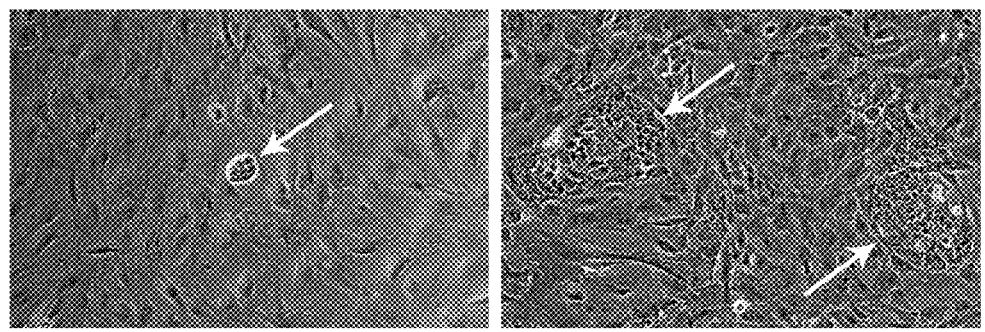
Figure 3B:
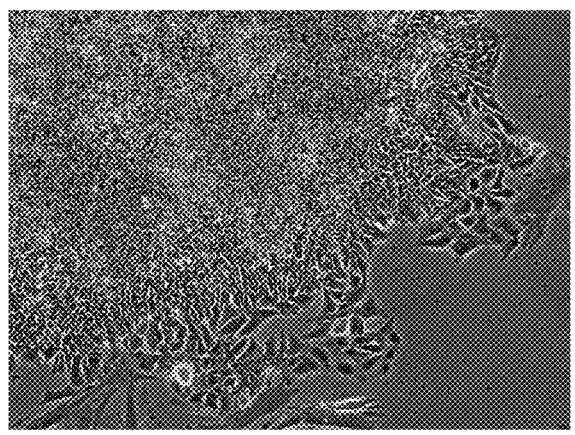

FIG. 3B depicts the primary human adult fibroblasts shown in FIG. 3A, reprogrammed by seven transfections with RNA encoding reprogramming proteins. Arrows indicate colonies of reprogrammed cells.

FIG. 3C depicts a large colony of reprogrammed primary human adult fibroblasts.

Figure 4A:
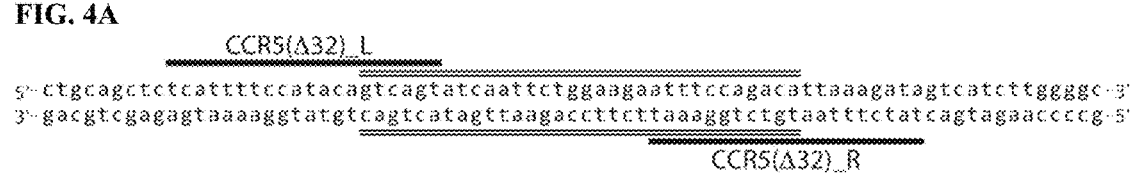

FIG. 4A depicts the location of a TALEN pair targeting the human CCR5 gene (SEQ ID NO: 649 and 650). Single-lines indicate the TALEN binding sites. Double-lines indicate the location of the Δ32 mutation.

Figure 4B:
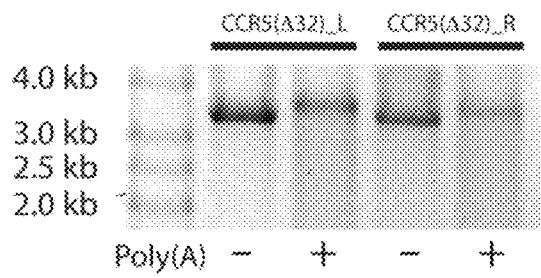

FIG. 4B depicts synthetic RNA encoding the TALEN pair of FIG. 4A, resolved on a denaturing formaldehyde-agarose gel.

Figure 4C:
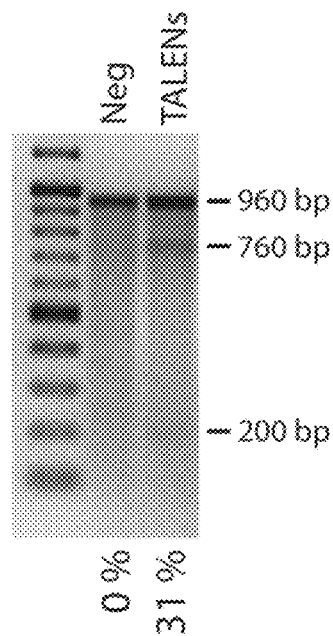

FIG. 4C depicts the results of a SURVEYOR assay testing the functionality of the RNA of FIG. 4B on human dermal fibroblasts (GM00609). The appearance of the 760 bp and 200 bp bands in the sample generated from cells transfected with RNA indicates successful gene editing. The percentage below each lane indicates the efficiency of gene editing (percentage of edited alleles).

Figure 4D:
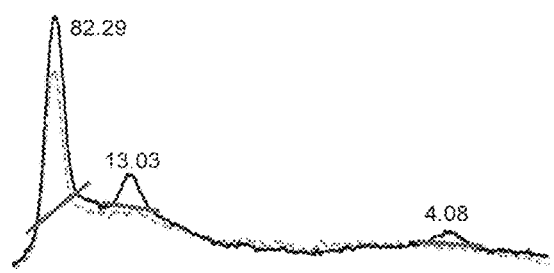

FIG. 4D depicts a line-profile graph of the "Neg" and "TALENs" lanes of FIG. 4C. Numbers indicate the integrated intensity of the three bands, relative to the total integrated intensity.

Figure 4E:
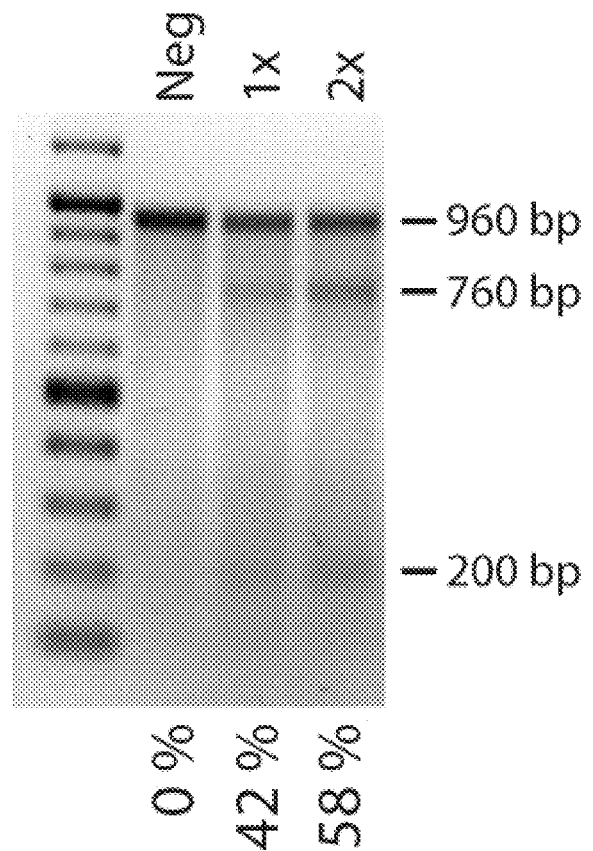

FIG. 4E depicts the results of a SURVEYOR assay performed as in FIG. 4C, and also including a sample generated from cells that were transfected twice with RNA (the lane labeled "2×").

Figure 4F:
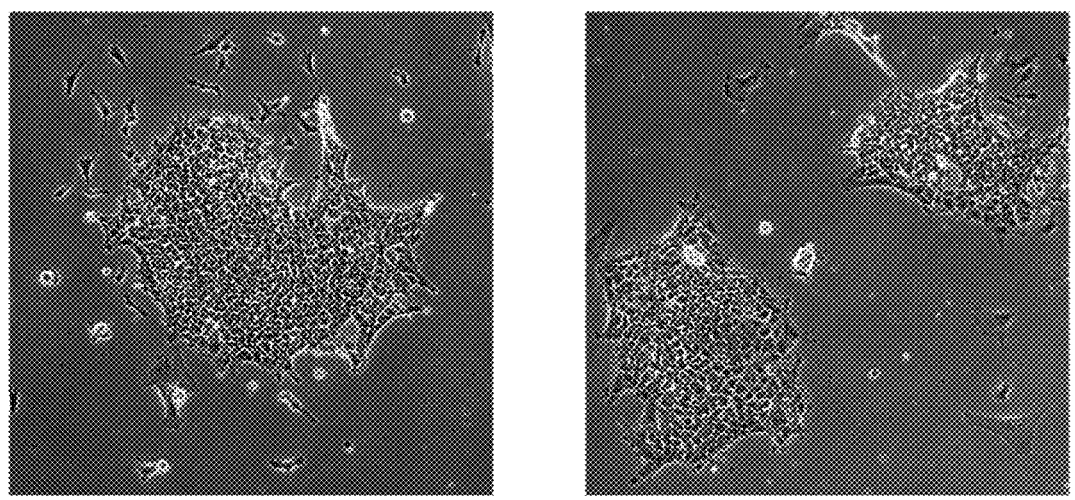

FIG. 4F depicts simultaneous gene editing and reprogramming of primary human cells (GM00609) using synthetic RNA. Images show representative colonies of reprogrammed cells.

Figure 4G:
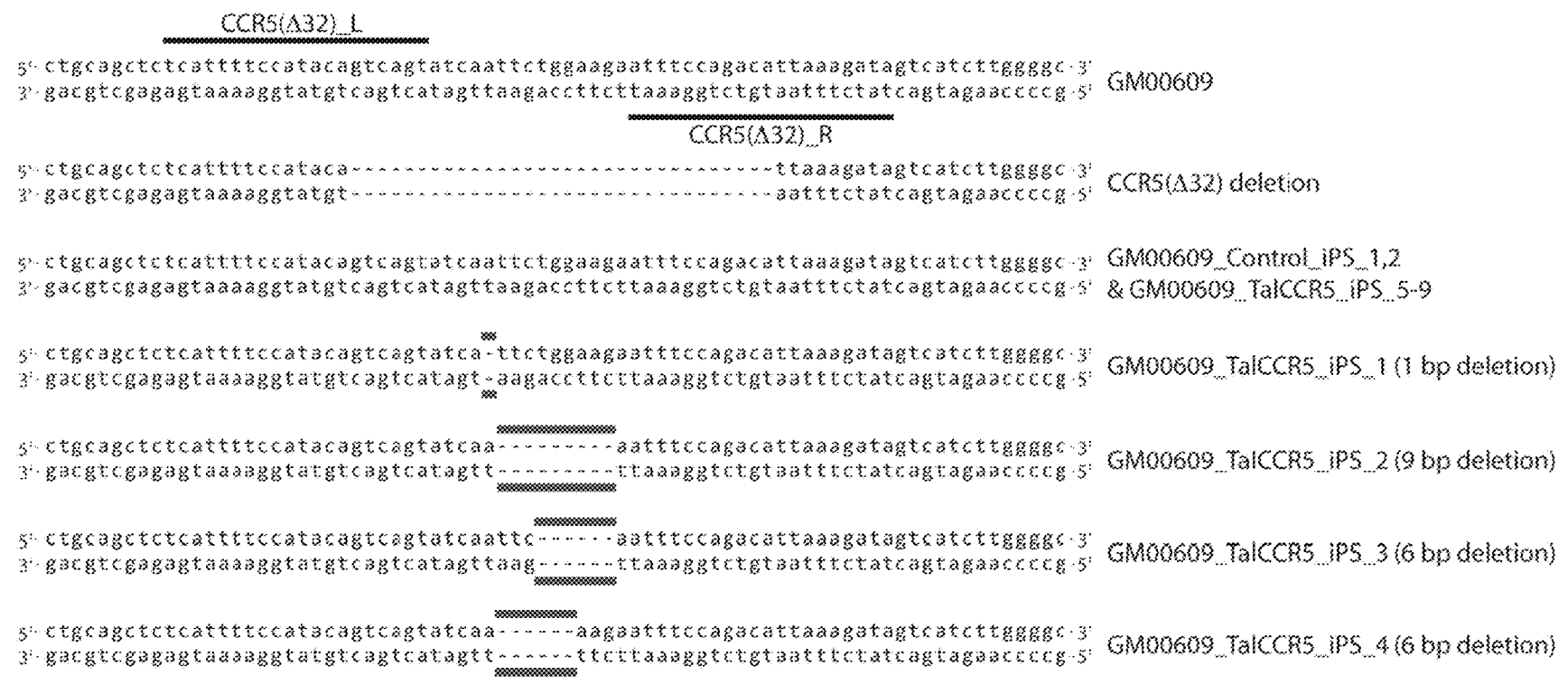

FIG. 4G depicts the results of direct sequencing of the CCR5 gene in gene-edited, reprogrammed cells generated as in FIG. 4F. Four of the nine lines tested contained a deletion between the TALEN binding sites, indicating efficient gene editing (SEQ ID NOS: 651-655, 676, and 656-663).

Figure 5:
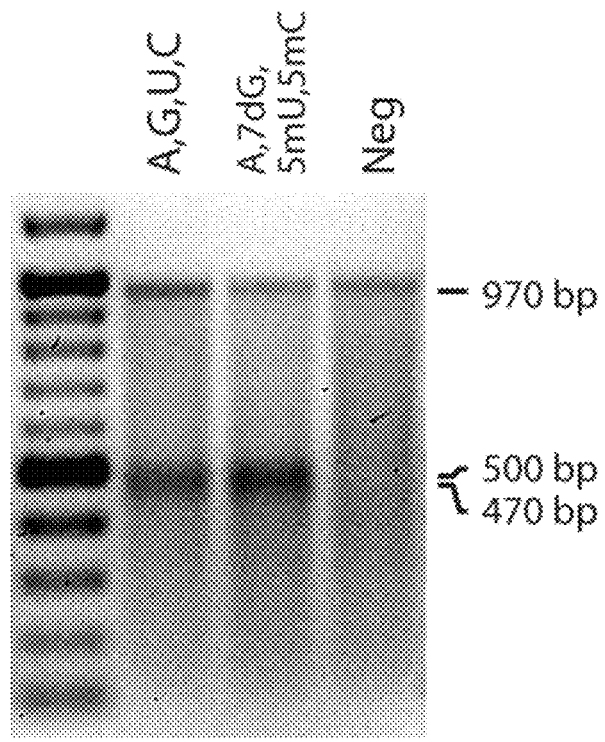

FIG. 5 depicts the results of a SURVEYOR assay performed as in FIG. 4C, except using RNA targeting the human MYC gene, and containing either canonical nucleotides ("A,G,U,C") or non-canonical nucleotides ("A,7dG, 5mU,5mC"). The dark bands at 470 bp and 500 bp indicate high-efficiency gene editing.

Figure 6:
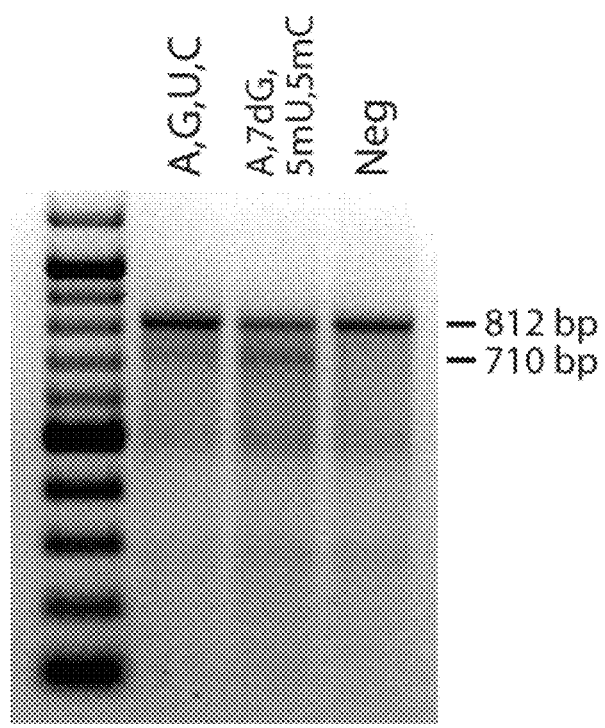

FIG. 6 depicts the results of a SURVEYOR assay performed as in FIG. 4C, except using RNA targeting the human BIRC5 gene, and containing either canonical nucleotides ("A,G,U,C") or non-canonical nucleotides ("A,7dG, 5mU,5mC"). The dark band at 710 bp indicates high-efficiency gene editing.

Figure 7A:
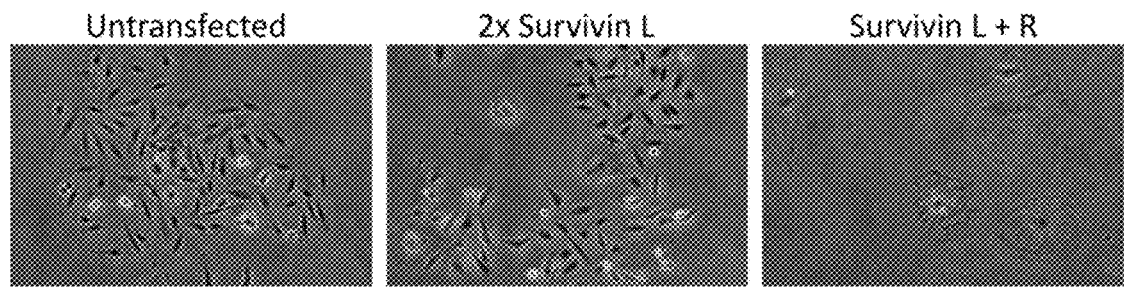

FIG. 7A depicts HeLa cells (cervical carcinoma) transfected with RNA targeting the human BIRC5 gene (RiboSlice). Cells were transfected with either a single RNA ("2× Survivin L") or equal amounts of each member of an RNA pair ("Survivin L+R"), with the same total amount of RNA delivered in each case. As shown in the right panel, cells transfected with the RNA pair became enlarged, and exhibited fragmented nuclei and markedly reduced proliferation, demonstrating the potent anti-cancer activity of RiboSlice.

Figure 7B:
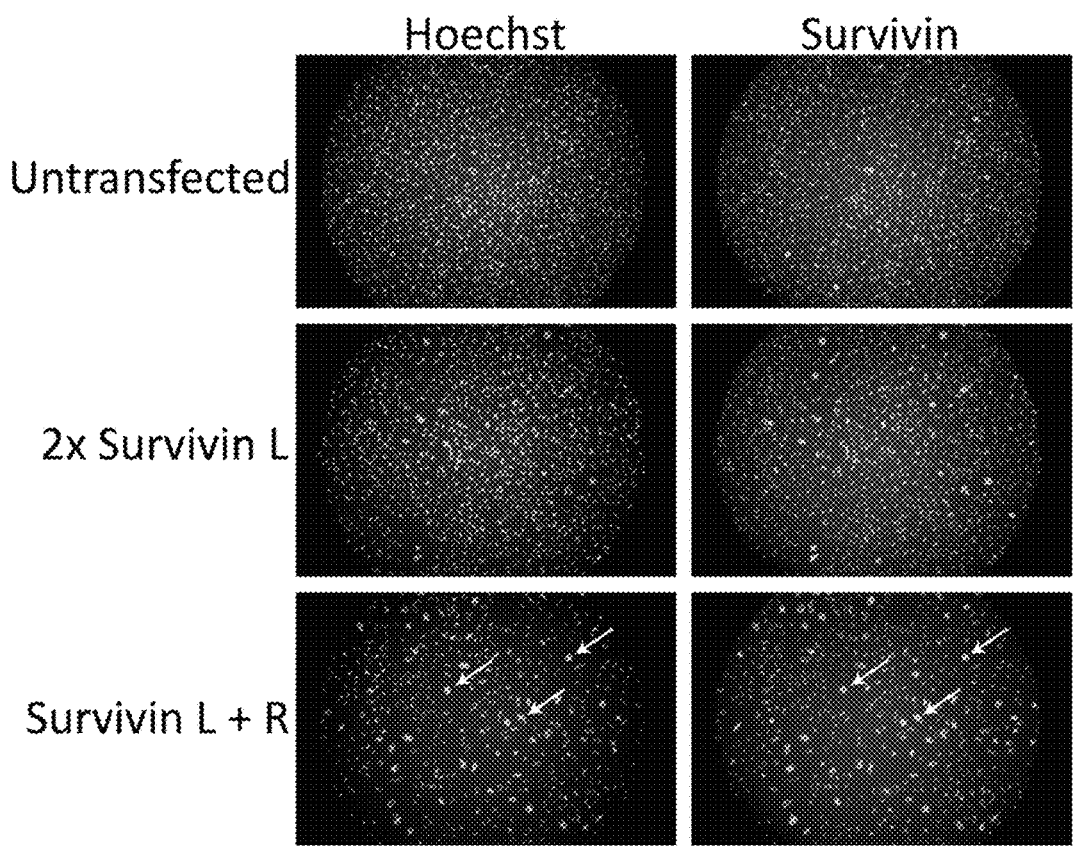

FIG. 7B depicts HeLa cells transfected with RNA targeting the human BIRC5 gene as in FIG. 7A. Cells were subsequently fixed and stained for survivin protein. Nuclei were counterstained with Hoechst 33342. The large, fragmented nuclei of cells transfected with RiboSlice are indicated with arrows.

Figure 8:
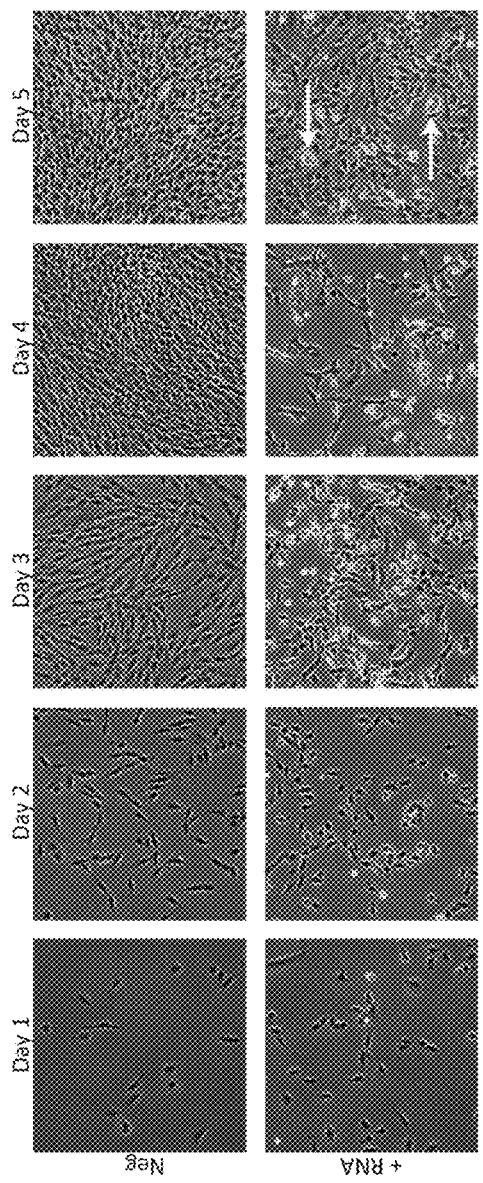

FIG. 8 depicts primary human adult fibroblasts reprogrammed using synthetic RNA. Arrows indicate compact colonies of cells that exhibit a morphology indicative of reprogramming.

Figure 9:
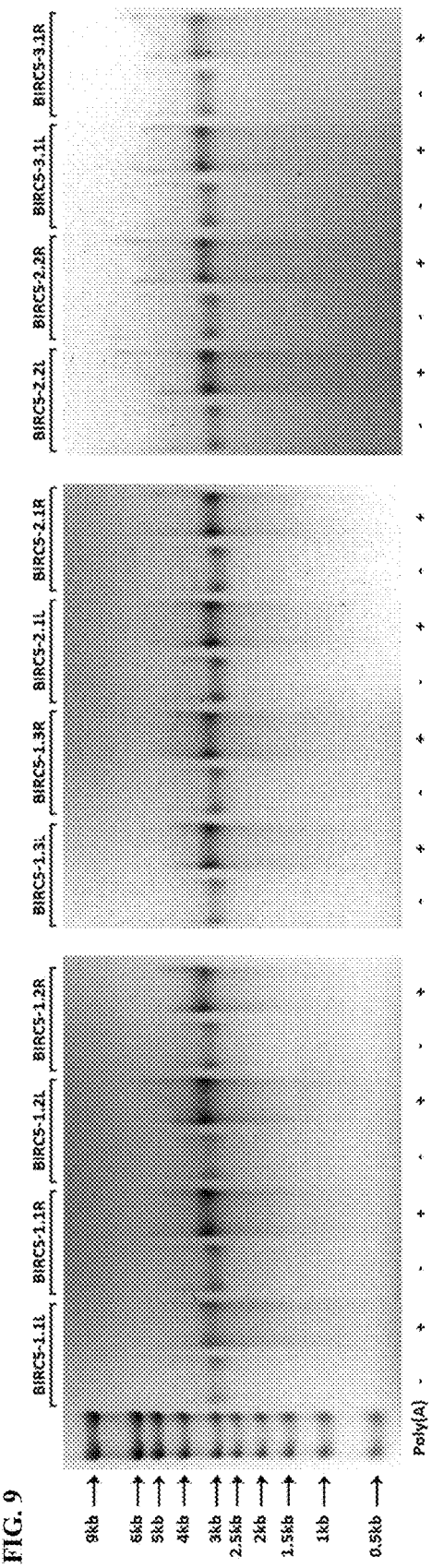

FIG. 9 depicts synthetic RNA encoding the indicated gene-editing proteins, resolved on a denaturing formaldehyde-agarose gel.

Figure 10A:
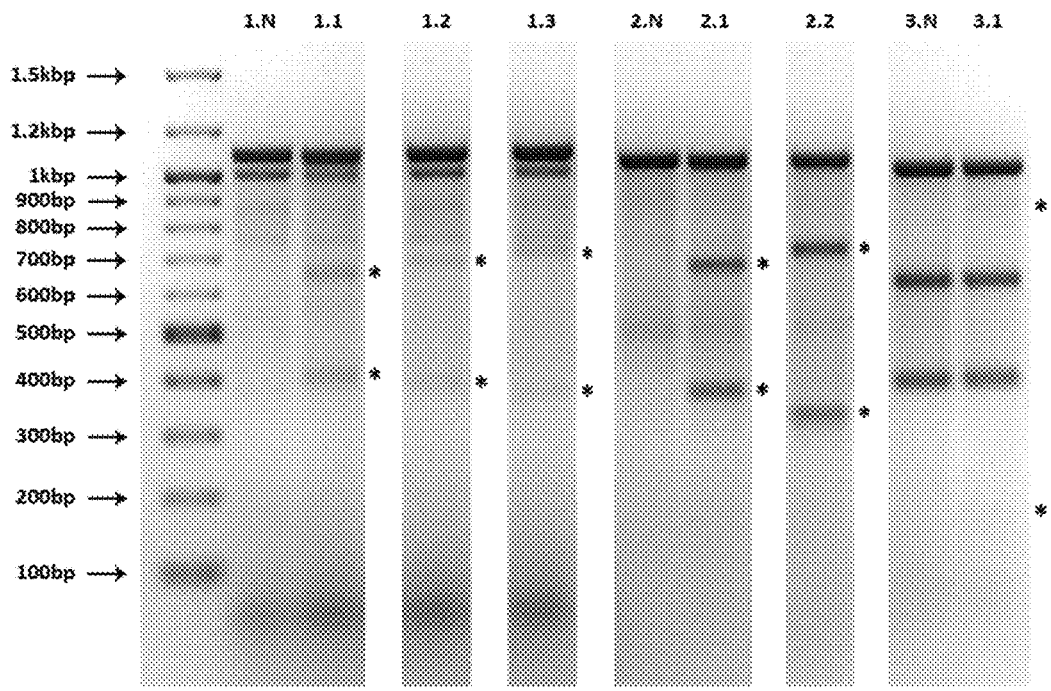

FIG. 10A depicts the results of a SURVEYOR assay testing the effectiveness of the RNA of FIG. 9 on human dermal fibroblasts. Cells were lysed approximately 48 h after transfection. Bands corresponding to digestion products resulting from successful gene editing are indicated with asterisks. Lane labels are of the form "X.Y", where X refers to the exon from which DNA was amplified, and Y refers to the gene-editing protein pair. For example, "1.1" refers to the gene-editing protein pair targeting the region of exon 1 closest to the start codon. "X.N" refers to untransfected cells.

Figure 10B:
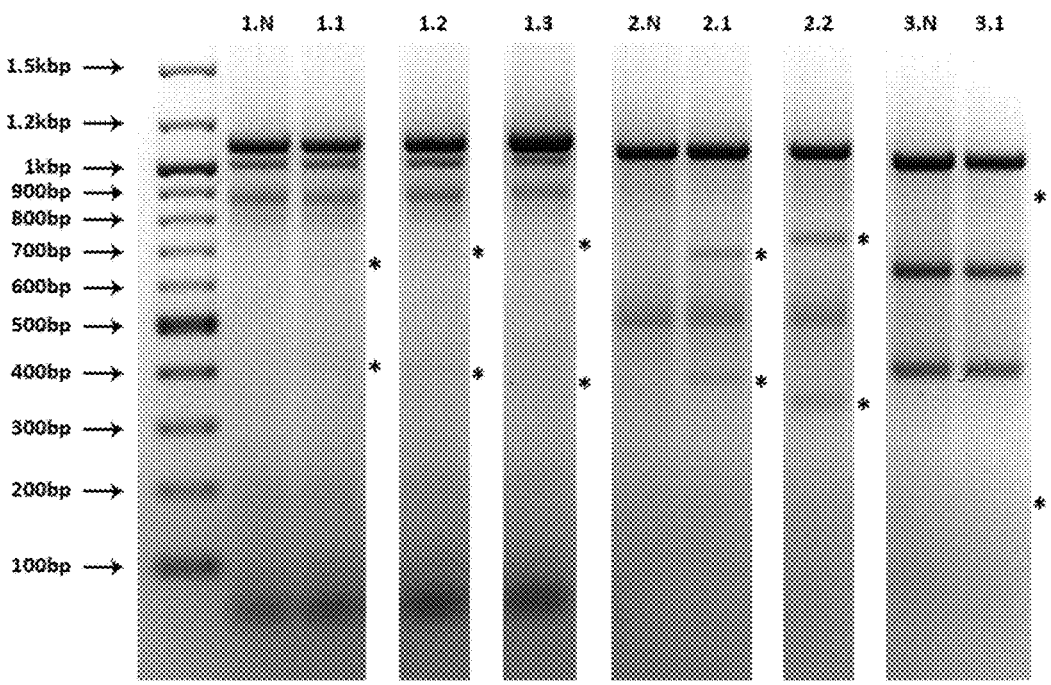

FIG. 10B depicts the results of a SURVEYOR assay testing the toxicity of the RNA of FIG. 9 on human dermal fibroblasts. Cells were lysed 11 days after transfection. Lanes and bands are labeled as in FIG. 10A. The appearance of the bands indicated with asterisks demonstrates that the transfected cells retained high viability.

Figure 11:
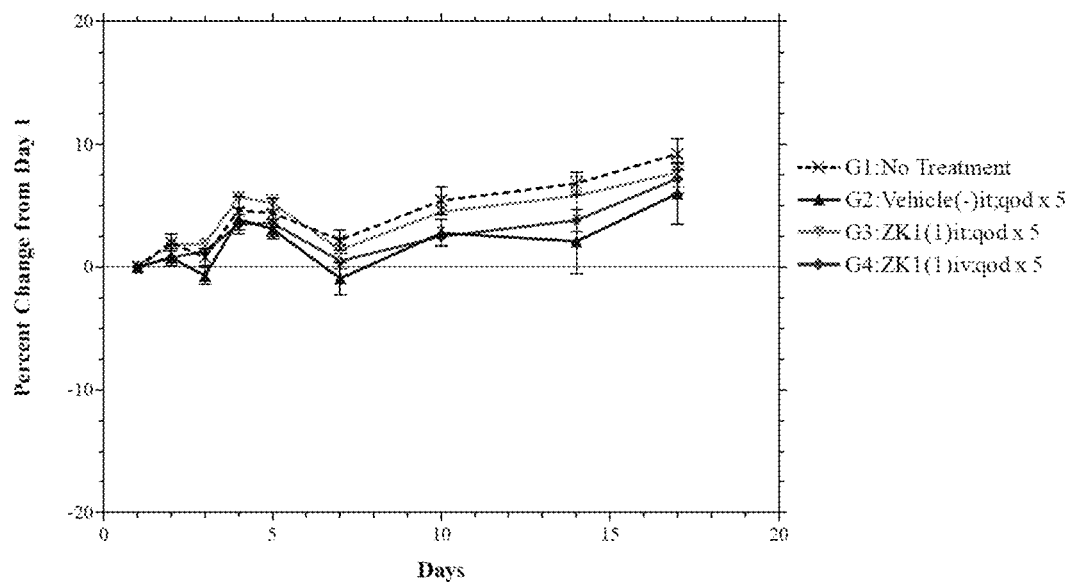

FIG. 11 depicts the results of a study designed to test the safety of RNA encoding gene-editing proteins in vivo. The graph shows the mean body weight of four groups of mice (10 animals in each group), including one untreated group, one vehicle-only group, one group treated with RiboSlice via intratumoral injection, and one group treated with RiboSlice via intravenous injection. For all treated groups, animals were given 5 doses, every other day, from day 1 to day 9. Animals were followed until day 17. The lack of a statistically significant difference between the mean body weights of the four groups demonstrates the in vivo safety of RiboSlice.

Figure 12A:
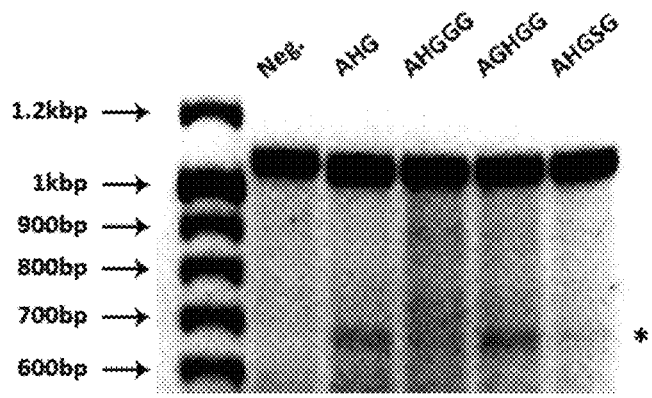

FIG. 12A depicts the results of a SURVEYOR assay testing the effectiveness of gene-editing proteins comprising various 36 amino-acid-long repeat sequences. Human dermal fibroblasts were lysed approximately 48 h after transfection with RNA encoding gene-editing proteins containing the indicated repeat sequence. The band corresponding to the digestion product resulting from successful gene editing is indicated with an asterisk. Lane labels refer to the amino acids at the C-terminus of the repeat sequence (SEQ ID Nos: 677-679, respectively, in order of appearance). "Neg." refers to untransfected cells.

Figure 12B:
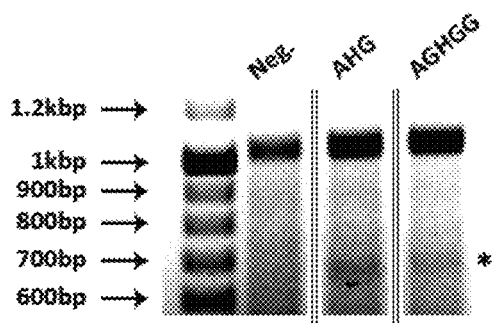

FIG. 12B depicts the results of a SURVEYOR assay testing the effectiveness of gene-editing proteins in which every other repeat sequence is 36 amino acids long. Human dermal fibroblasts were lysed approximately 48 h after transfection with RNA encoding gene-editing proteins containing the indicated repeat sequence. The band corresponding to the digestion product resulting from successful gene editing is indicated with an asterisk. Lane labels refer to the amino acids at the C-terminus of the repeat sequences ("AGHGG" disclosed as SEQ ID NO: 678). "Neg." refers to untransfected cells.

Figure 13A:
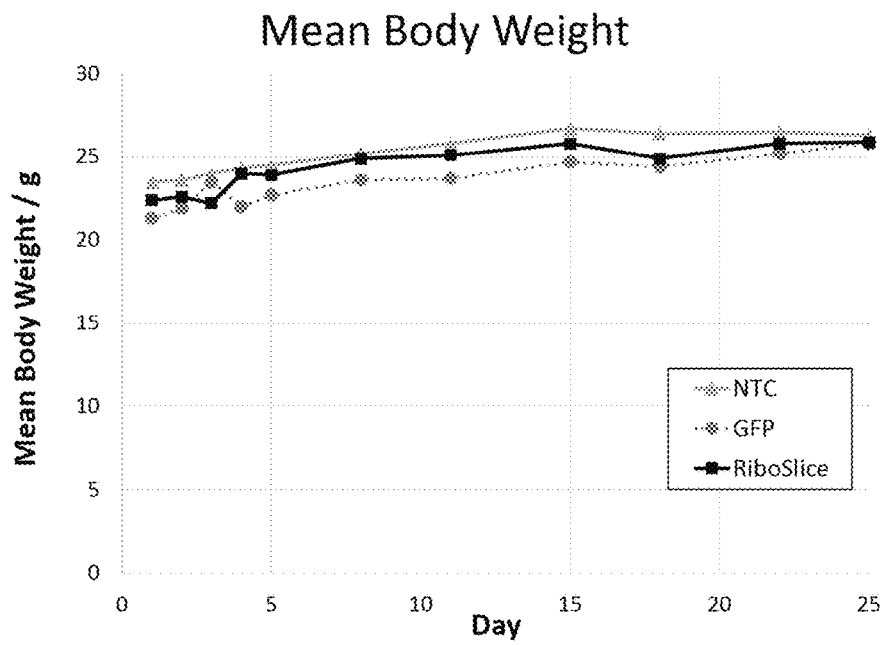

FIG. 13A depicts the results of a study designed to test the safety and efficacy of RiboSlice AAV replication-incompetent virus carrying nucleic acids encoding gene-editing proteins in vivo. The graph shows the mean body weight of three groups of mice carrying subcutaneous tumors comprising human glioma cells, including one untreated group (no treatment control, "NTC", n=6), one group treated with AAV encoding GFP ("GFP", n=2) via intratumoral injection, and one group treated with RiboSlice AAV encoding gene-editing proteins targeting the BIRC5 gene ("RiboSlice", n=2) via intratumoral injection. Animals were dosed on day 1 for the GFP group, and days 1 and 15 for the RiboSlice group. Animals were followed until day 25. The lack of a statistically significant difference between the mean body weights of the three groups demonstrates the in vivo safety of RiboSlice AAV.

Figure 13B:
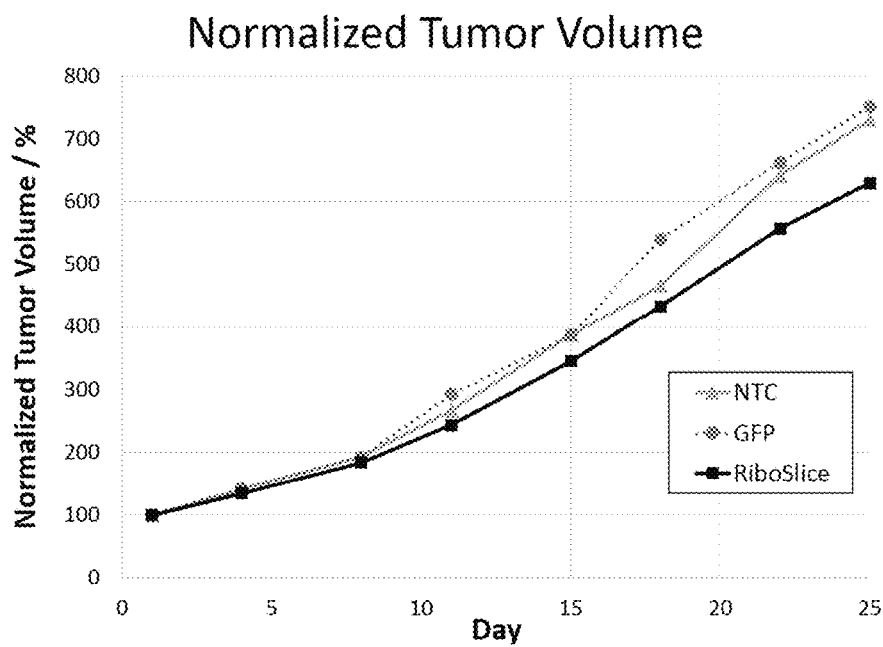

FIG. 13B depicts the normalized tumor volumes of the animals in the study shown in FIG. 13A. The slower increase in normalized tumor volume in the group treated with RiboSlice AAV compared to both the NTC and GFP groups demonstrates the in vivo efficacy of RiboSlice AAV.

Figure 14:
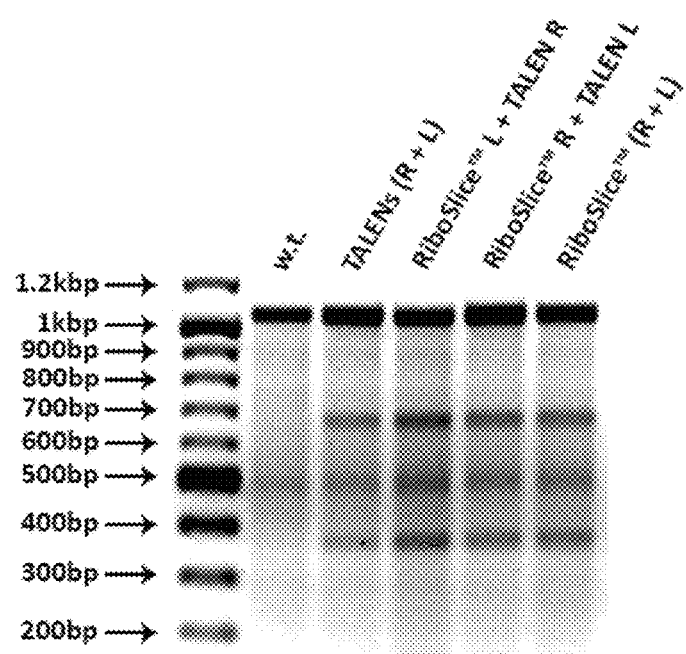

FIG. 14 depicts the results of a SURVEYOR assay testing the effectiveness of gene-editing proteins, as in FIG. 12B. "RiboSlice" refers to gene-editing proteins in which every other repeat sequence is 36 amino acids long. "w.t." refers to untransfected cells.

Figure 15:
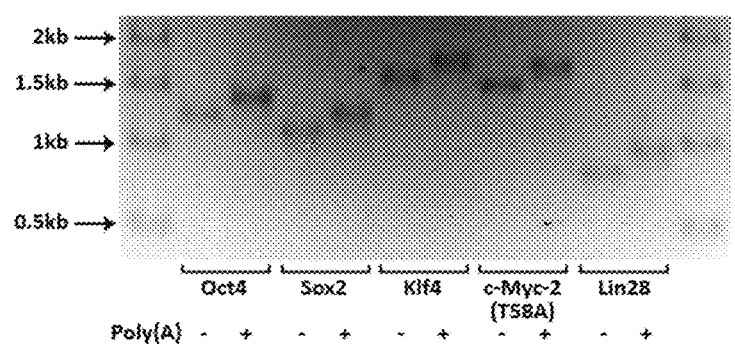

FIG. 15 depicts RNA encoding the indicated proteins and containing adenosine, 50% guanosine, 50% 7-deazaguanosine, 60% uridine, 40% 5-methyluridine, and 5-methylcytidine, resolved on a denaturing formaldehyde-agarose gel.

Figure 16:
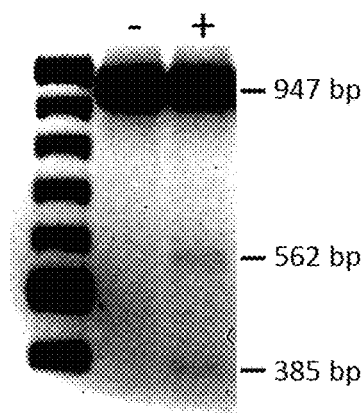

FIG. 16 depicts the results of an assay testing the integration of a repair template into the APP gene. The appearance of the 562 bp and 385 bp bands in the sample generated from cells transfected with RNA and a repair template indicates successful integration of a PstI restriction site. "−" refers to an undigested sample, "+" refers to a sample treated with PstI restriction nuclease.

DEFINITIONS

By "molecule" is meant a molecular entity (molecule, ion, complex, etc.).

By "RNA molecule" is meant a molecule that comprises RNA.

By "synthetic RNA molecule" is meant an RNA molecule that is produced outside of a cell or that is produced inside of a cell using bioengineering, by way of non-limiting example, an RNA molecule that is produced in an in vitro-transcription reaction, an RNA molecule that is produced by direct chemical synthesis or an RNA molecule that is produced in a genetically-engineered *E. coli* cell.

By "transfection" is meant contacting a cell with a molecule, wherein the molecule is internalized by the cell.

By "upon transfection" is meant during or after transfection.

By "transfection reagent" is meant a substance or mixture of substances that associates with a molecule and facilitates the delivery of the molecule to and/or internalization of the molecule by a cell, by way of non-limiting example, a cationic lipid, a charged polymer or a cell-penetrating peptide.

By "reagent-based transfection" is meant transfection using a transfection reagent.

By "cell-culture medium" is meant a medium that can be used for cell culture, by way of non-limiting example, Dulbecco's Modified Eagle's Medium (DMEM) or DMEM+10% fetal bovine serum (FBS).

By "complexation medium" is meant a medium to which a transfection reagent and a molecule to be transfected are added and in which the transfection reagent associates with the molecule to be transfected.

By "transfection medium" is meant a medium that can be used for transfection, by way of non-limiting example, Dulbecco's Modified Eagle's Medium (DMEM) or DMEM/F12.

By "recombinant protein" is meant a protein or peptide that is not produced in animals or humans. Non-limiting examples include human transferrin that is produced in bacteria, human fibronectin that is produced in an in vitro culture of mouse cells, and human serum albumin that is produced in a rice plant.

By "lipid carrier" is meant a substance that can increase the solubility of a lipid or lipid-soluble molecule in an aqueous solution, by way of non-limiting example, human serum albumin or methyl-beta-cyclodextrin.

By "Oct4 protein" is meant a protein that is encoded by the POU5F1 gene, or a natural or engineered variant, family-member, orthologue, fragment or fusion construct thereof, by way of non-limiting example, human Oct4 protein (SEQ ID NO: 8), mouse Oct4 protein, Oct1 protein, a protein encoded by POU5F1 pseudogene 2, a DNA-binding domain of Oct4 protein or an Oct4-GFP fusion protein. In some embodiments the Oct4 protein comprises an amino acid sequence that has at least 70% identity with SEQ ID NO: 8, or in other embodiments, at least 75%, 80%, 85%, 90%, or 95% identity with SEQ ID NO: 8. In some embodiments, the Oct4 protein comprises an amino acid sequence having from 1 to 20 amino acid insertions, deletions, or substitutions (collectively) with respect to SEQ ID NO: 8. Or in other embodiments, the Oct4 protein comprises an amino acid sequence having from 1 to 15 or from 1 to 10 amino acid insertions, deletions, or substitutions (collectively) with respect to SEQ ID NO: 8.

By "Sox2 protein" is meant a protein that is encoded by the SOX2 gene, or a natural or engineered variant, family-member, orthologue, fragment or fusion construct thereof, by way of non-limiting example, human Sox2 protein (SEQ ID NO: 9), mouse Sox2 protein, a DNA-binding domain of Sox2 protein or a Sox2-GFP fusion protein. In some embodiments the Sox2 protein comprises an amino acid sequence that has at least 70% identity with SEQ ID NO: 9, or in other embodiments, at least 75%, 80%, 85%, 90%, or 95% identity with SEQ ID NO: 9. In some embodiments, the Sox2 protein comprises an amino acid sequence having from 1 to 20 amino acid insertions, deletions, or substitutions (collectively) with respect to SEQ ID NO: 9. Or in other embodiments, the Sox2 protein comprises an amino acid sequence having from 1 to 15 or from 1 to 10 amino acid insertions, deletions, or substitutions (collectively) with respect to SEQ ID NO: 9.

By "Klf4 protein" is meant a protein that is encoded by the KLF4 gene, or a natural or engineered variant, family-member, orthologue, fragment or fusion construct thereof, by way of non-limiting example, human Klf4 protein (SEQ ID NO: 10), mouse Klf4 protein, a DNA-binding domain of Klf4 protein or a Klf4-GFP fusion protein. In some embodiments the Klf4 protein comprises an amino acid sequence that has at least 70% identity with SEQ ID NO: 10, or in other embodiments, at least 75%, 80%, 85%, 90%, or 95% identity with SEQ ID NO: 10. In some embodiments, the Klf4 protein comprises an amino acid sequence having from 1 to 20 amino acid insertions, deletions, or substitutions (collectively) with respect to SEQ ID NO: 10. Or in other embodiments, the Klf4 protein comprises an amino acid sequence having from 1 to 15 or from 1 to 10 amino acid insertions, deletions, or substitutions (collectively) with respect to SEQ ID NO: 10.

By "c-Myc protein" is meant a protein that is encoded by the MYC gene, or a natural or engineered variant, family-member, orthologue, fragment or fusion construct thereof, by way of non-limiting example, human c-Myc protein (SEQ ID NO: 11), mouse c-Myc protein, 1-Myc protein, c-Myc (T58A) protein, a DNA-binding domain of c-Myc protein or a c-Myc-GFP fusion protein. In some embodiments the c-Myc protein comprises an amino acid sequence that has at least 70% identity with SEQ ID NO: 11, or in other embodiments, at least 75%, 80%, 85%, 90%, or 95% identity with SEQ ID NO: 11. In some embodiments, the c-Myc protein comprises an amino acid having from 1 to 20 amino acid insertions, deletions, or substitutions (collectively) with respect to SEQ ID NO: 11. Or in other embodiments, the c-Myc protein comprises an amino acid sequence having from 1 to 15 or from 1 to 10 amino acid insertions, deletions, or substitutions (collectively) with respect to SEQ ID NO: 11.

By "reprogramming" is meant causing a change in the phenotype of a cell, by way of non-limiting example, causing a β-cell progenitor to differentiate into a mature β-cell, causing a fibroblast to dedifferentiate into a pluripotent stem cell, causing a keratinocyte to transdifferentiate into a cardiac stem cell or causing the axon of a neuron to grow.

By "reprogramming factor" is meant a molecule that, when a cell is contacted with the molecule and/or the cell expresses the molecule, can, either alone or in combination with other molecules, cause reprogramming, by way of non-limiting example, Oct4 protein.

By "feeder" is meant a cell that can be used to condition medium or to otherwise support the growth of other cells in culture.

By "conditioning" is meant contacting one or more feeders with a medium.

By "fatty acid" is meant a molecule that comprises an aliphatic chain of at least two carbon atoms, by way of non-limiting example, linoleic acid, α-linolenic acid, octanoic acid, a leukotriene, a prostaglandin, cholesterol, a glucocorticoid, a resolvin, a protectin, a thromboxane, a lipoxin, a maresin, a sphingolipid, tryptophan, N-acetyl tryptophan or a salt, methyl ester or derivative thereof.

By "short-chain fatty acid" is meant a fatty acid that comprises an aliphatic chain of between two and 30 carbon atoms.

By "albumin" is meant a protein that is highly soluble in water, by way of non-limiting example, human serum albumin.

By "associated molecule" is meant a molecule that is non-covalently bound to another molecule.

By "associated-molecule-component of albumin" is meant one or more molecules that are bound to an albumin polypeptide, by way of non-limiting example, lipids, hormones, cholesterol, calcium ions, etc. that are bound to an albumin polypeptide.

By "treated albumin" is meant albumin that is treated to reduce, remove, replace or otherwise inactivate the associated-molecule-component of the albumin, by way of non-limiting example, human serum albumin that is incubated at an elevated temperature, human serum albumin that is contacted with sodium octanoate or human serum albumin that is contacted with a porous material.

By "ion-exchange resin" is meant a material that, when contacted with a solution containing ions, can replace one or more of the ions with one or more different ions, by way of non-limiting example, a material that can replace one or more calcium ions with one or more sodium ions.

By "germ cell" is meant a sperm cell or an egg cell.

By "pluripotent stem cell" is meant a cell that can differentiate into cells of all three germ layers (endoderm, mesoderm, and ectoderm) in vivo.

By "somatic cell" is meant a cell that is not a pluripotent stem cell or a germ cell, by way of non-limiting example, a skin cell.

By "glucose-responsive insulin-producing cell" is meant a cell that, when exposed to a certain concentration of glucose, can produce and/or secrete an amount of insulin that is different from (either less than or more than) the amount of insulin that the cell produces and/or secretes when the cell is exposed to a different concentration of glucose, by way of non-limiting example, a β-cell.

By "hematopoietic cell" is meant a blood cell or a cell that can differentiate into a blood cell, by way of non-limiting example, a hematopoietic stem cell or a white blood cell.

By "cardiac cell" is meant a heart cell or a cell that can differentiate into a heart cell, by way of non-limiting example, a cardiac stem cell or a cardiomyocyte.

By "retinal cell" is meant a cell of the retina or a cell that can differentiate into a cell of the retina, by way of non-limiting example, a retinal pigmented epithelial cell.

By "skin cell" is meant a cell that is normally found in the skin, by way of non-limiting example, a fibroblast, a keratinocyte, a melanocyte, an adipocyte, a mesenchymal stem cell, an adipose stem cell or a blood cell.

By "Wnt signaling agonist" is meant a molecule that can perform one or more of the biological functions of one or more members of the Wnt family of proteins, by way of non-limiting example, Wnt1, Wnt2, Wnt3, Wnt3a or 2-amino-4-[3,4-(methylenedioxy)benzylamino]-6-(3-methoxyphenyl)pyrimidine.

By "IL-6 signaling agonist" is meant a molecule that can perform one or more of the biological functions of IL-6 protein, by way of non-limiting example, IL-6 protein or IL-6 receptor (also known as soluble IL-6 receptor, IL-6R, IL-6R alpha, etc.).

By "TGF-β signaling agonist" is meant a molecule that can perform one or more of the biological functions of one or more members of the TGF-β superfamily of proteins, by way of non-limiting example, TGF-β1, TGF-β3, Activin A, BMP-4 or Nodal.

By "immunosuppressant" is meant a substance that can suppress one or more aspects of an immune system, and that is not normally present in a mammal, by way of non-limiting example, B18R or dexamethasone.

By "single-strand break" is meant a region of single-stranded or double-stranded DNA in which one or more of the covalent bonds linking the nucleotides has been broken in one of the one or two strands.

By "double-strand break" is meant a region of double-stranded DNA in which one or more of the covalent bonds linking the nucleotides has been broken in each of the two strands.

By "nucleotide" is meant a nucleotide or a fragment or derivative thereof, by way of non-limiting example, a nucleobase, a nucleoside, a nucleotide-triphosphate, etc.

By "nucleoside" is meant a nucleotide or a fragment or derivative thereof, by way of non-limiting example, a nucleobase, a nucleoside, a nucleotide-triphosphate, etc.

By "gene editing" is meant altering the DNA sequence of a cell, by way of non-limiting example, by transfecting the cell with a protein that causes a mutation in the DNA of the cell.

By "gene-editing protein" is meant a protein that can, either alone or in combination with one or more other molecules, alter the DNA sequence of a cell, by way of non-limiting example, a nuclease, a transcription activator-like effector nuclease (TALEN), a zinc-finger nuclease, a meganuclease, a nickase, a clustered regularly interspaced short palindromic repeat (CRISPR)-associated protein or a natural or engineered variant, family-member, orthologue, fragment or fusion construct thereof.

By "repair template" is meant a nucleic acid containing a region of at least about 70% homology with a sequence that is within 10 kb of a target site of a gene-editing protein.

By "repeat sequence" is meant an amino-acid sequence that is present in more than one copy in a protein, to within at least about 10% homology, by way of non-limiting example, a monomer repeat of a transcription activator-like effector.

By "DNA-binding domain" is meant a region of a molecule that is capable of binding to a DNA molecule, by way of non-limiting example, a protein domain comprising one or more zinc fingers, a protein domain comprising one or more transcription activator-like (TAL) effector repeat sequences or a binding pocket of a small molecule that is capable of binding to a DNA molecule.

By "binding site" is meant a nucleic-acid sequence that is capable of being recognized by a gene-editing protein, DNA-binding protein, DNA-binding domain or a biologically active fragment or variant thereof or a nucleic-acid sequence for which a gene-editing protein, DNA-binding protein, DNA-binding domain or a biologically active fragment or variant thereof has high affinity, by way of non-limiting example, an about 20-base-pair sequence of DNA in exon 1 of the human BIRC5 gene.

By "target" is meant a nucleic acid that contains a binding site.

Other definitions are set forth in U.S. application Ser. No. 13/465,490, U.S. Provisional Application No. 61/664,494, U.S. Provisional Application No. 61/721,302, International Application No. PCT/US12/67966, U.S. Provisional Application No. 61/785,404, and U.S. Provisional Application No. 61/842,874, the contents of which are hereby incorporated by reference in their entireties.

It has now been discovered that the non-canonical nucleotide members of the 5-methylcytidine de-methylation pathway, when incorporated into synthetic RNA, can increase the efficiency with which the synthetic RNA can be translated into protein, and can decrease the toxicity of the synthetic RNA. These non-canonical nucleotides include, for example: 5-methylcytidine, 5-hydroxymethylcytidine, 5-formylcytidine, and 5-carboxycytidine (a.k.a. "cytidine-5-carboxylic acid"). Certain embodiments are therefore directed to a nucleic acid. In one embodiment, the nucleic acid is a synthetic RNA molecule. In another embodiment, the nucleic acid comprises one or more non-canonical nucleotides. In one embodiment, the nucleic acid comprises one or more non-canonical nucleotide members of the 5-methylcytidine de-methylation pathway. In another embodiment, the nucleic acid comprises at least one of: 5-methylcytidine, 5-hydroxymethylcytidine, 5-formylcytidine, and 5-carboxycytidine or a derivative thereof. In a further embodiment, the nucleic acid comprises at least one of: pseudouridine, 5-methylpseudouridine, 5-methyluridine, 5-methylcytidine, 5-hydroxymethylcytidine, N4-methylcytidine, N4-acetylcytidine, and 7-deazaguanosine or a derivative thereof.

5-Methylcytidine De-Methylation Pathway

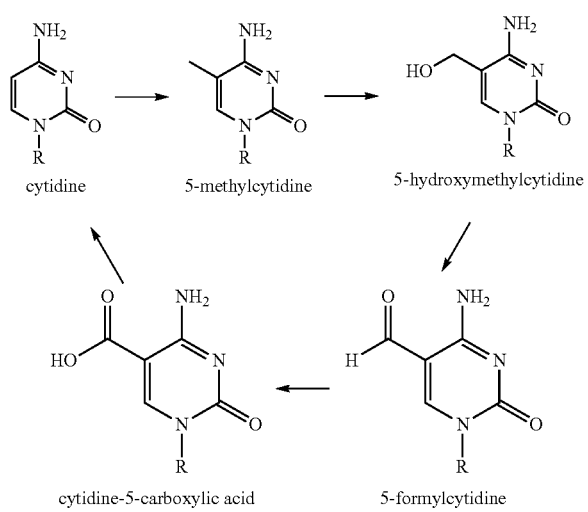

cytidine    5-methylcytidine    5-hydroxymethylcytidine cytidine-5-carboxylic acid    5-formylcytidine Certain embodiments are directed to a protein. Other embodiments are directed to a nucleic acid that encodes a protein. In one embodiment, the protein is a protein of interest. In another embodiment, the protein is selected from: a reprogramming protein and a gene-editing protein. In one embodiment, the nucleic acid is a plasmid. In another embodiment, the nucleic acid is present in a virus or viral vector. In a further embodiment, the virus or viral vector is replication incompetent. In a still further embodiment, the virus or viral vector is replication competent. In one embodiment, the virus or viral vector includes at least one of: an adenovirus, a retrovirus, a lentivirus, a herpes virus, an adeno-associated virus or a natural or engineered variant thereof, and an engineered virus.

It has also been discovered that certain combinations of non-canonical nucleotides can be particularly effective at increasing the efficiency with which synthetic RNA can be translated into protein, and decreasing the toxicity of synthetic RNA, for example, the combinations: 5-methyluridine and 5-methylcytidine, 5-methyluridine and 7-deazaguanosine, 5-methylcytidine and 7-deazaguanosine, 5-methyluridine, 5-methylcytidine, and 7-deazaguanosine, and 5-methyluridine, 5-hydroxymethylcytidine, and 7-deazaguanosine. Certain embodiments are therefore directed to a nucleic acid comprising at least two of: 5-methyluridine, 5-methylcytidine, 5-hydroxymethylcytidine, and 7-deazaguanosine or one or more derivatives thereof. Other embodiments are directed to a nucleic acid comprising at least three of: 5-methyluridine, 5-methylcytidine, 5-hydroxymethylcytidine, and 7-deazaguanosine or one or more derivatives thereof. Other embodiments are directed to a nucleic acid comprising all of: 5-methyluridine, 5-methylcytidine, 5-hydroxymethylcytidine, and 7-deazaguanosine or one or more derivatives thereof. In one embodiment, the nucleic acid comprises one or more 5-methyluridine residues, one or more 5-methylcytidine residues, and one or more 7-deazaguanosine residues or one or more 5-methyluridine residues, one or more 5-hydroxymethylcytidine residues, and one or more 7-deazaguanosine residues.

It has been further discovered that synthetic RNA molecules containing certain fractions of certain non-canonical nucleotides and combinations thereof can exhibit particularly high translation efficiency and low toxicity. Certain embodiments are therefore directed to a nucleic acid comprising at least one of: one or more uridine residues, one or more cytidine residues, and one or more guanosine residues, and comprising one or more non-canonical nucleotides. In one embodiment, between about 20% and about 80% of the uridine residues are 5-methyluridine residues. In another embodiment, between about 30% and about 50% of the uridine residues are 5-methyluridine residues. In a further embodiment, about 40% of the uridine residues are 5-methyluridine residues. In one embodiment, between about 60% and about 80% of the cytidine residues are 5-methylcytidine residues. In another embodiment, between about 80% and about 100% of the cytidine residues are 5-methylcytidine residues. In a further embodiment, about 100% of the cytidine residues are 5-methylcytidine residues. In a still further embodiment, between about 20% and about 100% of the cytidine residues are 5-hydroxymethylcytidine residues. In one embodiment, between about 20% and about 80% of the guanosine residues are 7-deazaguanosine residues. In another embodiment, between about 40% and about 60% of the guanosine residues are 7-deazaguanosine residues. In a further embodiment, about 50% of the guanosine residues are 7-deazaguanosine residues. In one embodiment, between about 20% and about 80% or between about 30% and about 60% or about 40% of the cytidine residues are N4-methylcytidine and/or N4-acetylcytidine residues. In another embodiment, each cytidine residue is a 5-methylcytidine residue. In a further embodiment, about 100% of the cytidine residues are 5-methylcytidine residues and/or 5-hydroxymethylcytidine residues and/or N4-methylcytidine residues and/or N4-acetylcytidine residues and/or one or more derivatives thereof. In a still further embodiment, about 40% of the uridine residues are 5-methyluridine residues, between about 20% and about 100% of the cytidine residues are N4-methylcytidine and/or N4-acetylcytidine residues, and about 50% of the guanosine residues are 7-deazaguanosine residues. In one embodiment, about 40% of the uridine residues are 5-methyluridine residues and about 100% of the cytidine residues are 5-methylcytidine residues. In another embodiment, about 40% of the uridine residues are 5-methyluridine residues and about 50% of the guanosine residues are 7-deazaguanosine residues. In a further embodiment, about 100% of the cytidine residues are 5-methylcytidine residues and about 50% of the guanosine residues are 7-deazaguanosine residues. In one embodiment, about 40% of the uridine residues are 5-methyluridine residues, about 100% of the cytidine residues are 5-methylcytidine residues, and about 50% of the guanosine residues are 7-deazaguanosine residues. In another embodiment, about 40% of the uridine residues are 5-methyluridine residues, between about 20% and about 100% of the cytidine residues are 5-hydroxymethylcytidine residues, and about 50% of the guanosine residues are 7-deazaguanosine residues. In some embodiments, less than 100% of the cytidine residues are 5-methylcytidine residues. In other embodiments, less than 100% of the cytidine residues are 5-hydroxymethylcytidine residues. In one embodiment, each uridine residue in the synthetic RNA molecule is a pseudouridine residue or a 5-methylpseudouridine residue. In another embodiment, about 100% of the uridine residues are pseudouridine residues and/or 5-methylpseudouridine residues. In a further embodiment, about 100% of the uridine residues are pseudouridine residues and/or 5-methylpseudouridine residues, about 100% of the cytidine residues are 5-methylcytidine residues, and about 50% of the guanosine residues are 7-deazaguanosine residues.

Other non-canonical nucleotides that can be used in place of or in combination with 5-methyluridine include, but are not limited to: pseudouridine and 5-methylpseudouridine (a.k.a. "1-methylpseudouridine", a.k.a. "N1-methylpseudouridine") or one or more derivatives thereof. Other non-canonical nucleotides that can be used in place of or in combination with 5-methylcytidine and/or 5-hydroxymethylcytidine include, but are not limited to: pseudoisocytidine, 5-methylpseudoisocytidine, 5-hydroxymethylcytidine, 5-formylcytidine, 5-carboxycytidine, N4-methylcytidine, N4-acetylcytidine or one or more derivatives thereof. In certain embodiments, for example, when performing only a single transfection or when the cells being transfected are not particularly sensitive to transfection-associated toxicity or innate-immune signaling, the fractions of non-canonical nucleotides can be reduced. Reducing the fraction of non-canonical nucleotides can be beneficial, in part, because reducing the fraction of non-canonical nucleotides can reduce the cost of the nucleic acid. In certain situations, for example, when minimal immunogenicity of the nucleic acid is desired, the fractions of non-canonical nucleotides can be increased.

Enzymes such as T7 RNA polymerase may preferentially incorporate canonical nucleotides in an in vitro-transcription reaction containing both canonical and non-canonical nucleotides. As a result, an in vitro-transcription reaction containing a certain fraction of a non-canonical nucleotide may yield RNA containing a different, often lower, fraction of the non-canonical nucleotide than the fraction at which the non-canonical nucleotide was present in the reaction. In certain embodiments, references to nucleotide incorporation fractions (for example, "50% 5-methyluridine") therefore can refer both to nucleic acids containing the stated fraction of the nucleotide, and to nucleic acids synthesized in a reaction containing the stated fraction of the nucleotide (or nucleotide derivative, for example, nucleotide-triphosphate), even though such a reaction may yield a nucleic acid containing a different fraction of the nucleotide than the fraction at which the non-canonical nucleotide was present in the reaction. In addition, different nucleotide sequences can encode the same protein by utilizing alternative codons. In certain embodiments, references to nucleotide incorporation fractions therefore can refer both to nucleic acids containing the stated fraction of the nucleotide, and to nucleic acids encoding the same protein as a different nucleic acid, wherein the different nucleic acid contains the stated fraction of the nucleotide.

The DNA sequence of a cell can be altered by contacting the cell with a gene-editing protein or by inducing the cell to express a gene-editing protein. However, previously disclosed gene-editing proteins suffer from low binding efficiency and excessive off-target activity, which can introduce undesired mutations in the DNA of the cell, severely limiting their use in therapeutic applications, in which the introduction of undesired mutations in a patient's cells could lead to the development of cancer. It has now been discovered that gene-editing proteins that comprise the StsI endonuclease cleavage domain (SEQ ID NO: 1) can exhibit substantially lower off-target activity than previously disclosed gene-editing proteins, while maintaining a high level of on-target activity. Other novel engineered proteins have also been discovered that can exhibit high on-target activity, low off-target activity, small size, solubility, and other desirable characteristics when they are used as the nuclease domain of a gene-editing protein: StsI-HA (SEQ ID NO: 2), StsI-HA2 (SEQ ID NO: 3), StsI-UHA (SEQ ID NO: 4), StsI-UHA2 (SEQ ID NO: 5), StsI-HF (SEQ ID NO: 6), and StsI-UHF (SEQ ID NO: 7). StsI-HA, StsI-HA2 (high activity), StsI-UHA, and StsI-UHA2 (ultra-high activity) can exhibit higher on-target activity than both wild-type StsI and wild-type FokI, due in part to specific amino-acid substitutions within the N-terminal region at the 34 and 61 positions, while StsI-HF (high fidelity) and StsI-UHF (ultra-high fidelity) can exhibit lower off-target activity than both wild-type StsI and wild-type FokI, due in part to specific amino-acid substitutions within the C-terminal region at the 141 and 152 positions. Certain embodiments are therefore directed to a protein that comprises a nuclease domain. In one embodiment, the nuclease domain comprises one or more of: the cleavage domain of FokI endonuclease (SEQ ID NO: 53), the cleavage domain of StsI endonuclease (SEQ ID NO: 1), StsI-HA (SEQ ID NO: 2), StsI-HA2 (SEQ ID NO: 3), StsI-UHA (SEQ ID NO: 4), StsI-UHA2 (SEQ ID NO: 5), StsI-HF (SEQ ID NO: 6), and StsI-UHF (SEQ ID NO: 7) or a biologically active fragment or variant thereof.

It has also been discovered that engineered gene-editing proteins that comprise DNA-binding domains comprising certain novel repeat sequences can exhibit lower off-target activity than previously disclosed gene-editing proteins, while maintaining a high level of on-target activity. Certain of these engineered gene-editing proteins can provide several advantages over previously disclosed gene-editing proteins, including, for example, increased flexibility of the linker region connecting repeat sequences, which can result in increased binding efficiency. Certain embodiments are therefore directed to a protein comprising a plurality of repeat sequences. In one embodiment, at least one of the repeat sequences contains the amino-acid sequence: GabG (SEQ ID NO: 674), where "a" and "b" each represent any amino acid. In one embodiment, the protein is a gene-editing protein. In another embodiment, one or more of the repeat sequences are present in a DNA-binding domain. In a further embodiment, "a" and "b" are each independently selected from the group: H and G. In a still further embodiment, "a" and "b" are H and G, respectively. In one embodiment, the amino-acid sequence is present within about 5 amino acids of the C-terminus of the repeat sequence. In another embodiment, the amino-acid sequence is present at the C-terminus of the repeat sequence. In some embodiments, one or more G in the amino-acid sequence GabG is replaced with one or more amino acids other than G, for example A, H or GG. In one embodiment, the repeat sequence has a length of between about 32 and about 40 amino acids or between about 33 and about 39 amino acids or between about 34 and 38 amino acids or between about 35 and about 37 amino acids or about 36 amino acids or greater than about 32 amino acids or greater than about 33 amino acids or greater than about 34 amino acids or greater than about 35 amino acids. Other embodiments are directed to a protein comprising one or more transcription activator-like effector domains. In one embodiment, at least one of the transcription activator-like effector domains comprises a repeat sequence. Other embodiments are directed to a protein comprising a plurality of repeat sequences generated by inserting one or more amino acids between at least two of the repeat sequences of a transcription activator-like effector domain. In one embodiment, one or more amino acids is inserted about 1 or about 2 or about 3 or about 4 or about 5 amino acids from the C-terminus of at least one repeat sequence. Still other embodiments are directed to a protein comprising a plurality of repeat sequences, wherein about every other repeat sequence has a different length than the repeat sequence immediately preceding or following the repeat sequence. In one embodiment, every other repeat sequence is about 36 amino acids long. In another embodiment, every other repeat sequence is 36 amino acids long. Still other embodiments are directed to a protein comprising a plurality of repeat sequences, wherein the plurality of repeat sequences comprises at least two repeat sequences that are each at least 36 amino acids long, and wherein at least two of the repeat sequences that are at least 36 amino acids long are separated by at least one repeat sequence that is less than 36 amino acids long. Some embodiments are directed to a protein that comprises one or more sequences selected from, for example, SEQ ID NO: 54, SEQ ID NO: 55, SEQ ID NO: 56, SEQ ID NO: 57, SEQ ID NO: 58, SEQ ID NO: 59, and SEQ ID NO: 60.

Other embodiments are directed to a protein that comprises a DNA-binding domain. In some embodiments, the DNA-binding domain comprises a plurality of repeat sequences. In one embodiment, the plurality of repeat sequences enables high-specificity recognition of a binding site in a target DNA molecule. In another embodiment, at least two of the repeat sequences have at least about 50%, or about 60%, or about 70%, or about 80%, or about 90%, or about 95%, or about 98%, or about 99% homology to each other. In a further embodiment, at least one of the repeat sequences comprises one or more regions capable of binding to a binding site in a target DNA molecule. In a still further embodiment, the binding site comprises a defined sequence of between about 1 to about 5 bases in length. In one embodiment, the DNA-binding domain comprises a zinc finger. In another embodiment, the DNA-binding domain comprises a transcription activator-like effector (TALE). In a further embodiment, the plurality of repeat sequences includes at least one repeat sequence having at least about 50% or about 60% or about 70% or about 80% or about 90% or about 95% or about 98%, or about 99% homology to a TALE. In a still further embodiment, the gene-editing protein comprises a clustered regularly interspaced short palindromic repeat (CRISPR)-associated protein. In one embodiment, the gene-editing protein comprises a nuclear-localization sequence. In another embodiment, the nuclear-localization sequence comprises the amino-acid sequence: PKKKRKV (SEQ ID NO: 61). In one embodiment, the gene-editing protein comprises a mitochondrial-localization sequence. In another embodiment, the mitochondrial-localization sequence comprises the amino-acid sequence: LGRVIPRKIASRASLM (SEQ ID NO: 62). In one embodiment, the gene-editing protein comprises a linker. In another embodiment, the linker connects a DNA-binding domain to a nuclease domain. In a further embodiment, the linker is between about 1 and about 10 amino acids long. In some embodiments, the linker is about 1, about 2, or about 3, or about 4, or about 5, or about 6, or about 7, or about 8, or about 9, or about 10 amino acids long. In one embodiment, the gene-editing protein is capable of generating a nick or a double-strand break in a target DNA molecule.

Certain embodiments are directed to a method for modifying the genome of a cell, the method comprising introducing into the cell a nucleic acid molecule encoding a non-naturally occurring fusion protein comprising an artificial transcription activator-like (TAL) effector repeat domain comprising one or more repeat units 36 amino acids in length and an endonuclease domain, wherein the repeat domain is engineered for recognition of a predetermined nucleotide sequence, and wherein the fusion protein recognizes the predetermined nucleotide sequence. In one embodiment, the cell is a eukaryotic cell. In another embodiment, the cell is an animal cell. In a further embodiment, the cell is a mammalian cell. In a still further embodiment, the cell is a human cell. In one embodiment, the cell is a plant cell. In another embodiment, the cell is a prokaryotic cell. In some embodiments, the fusion protein introduces an endonucleolytic cleavage in a nucleic acid of the cell, whereby the genome of the cell is modified.

Other embodiments are directed to a nucleic acid molecule encoding a non-naturally occurring fusion protein comprising an artificial transcription activator-like (TAL) effector repeat domain comprising one or more repeat units 36 amino acids in length and restriction endonuclease activity, wherein the repeat domain is engineered for recognition of a predetermined nucleotide sequence and wherein the fusion protein recognizes the predetermined nucleotide sequence. In one embodiment, the repeat units differ by no more than about seven amino acids. In another embodiment, each of the repeat units contains the amino acid sequence: LTPXQVVAIAS (SEQ ID NO: 63) where X can be either E or Q, and the amino acid sequence: LTPXQVVAIAS (SEQ ID NO: 64) is followed on the carboxyl terminus by either one or two amino acids that determine recognition for one of adenine, cytosine, guanine or thymine. In one embodiment, the nucleic acid encodes about 1.5 to about 28.5 repeat units. In another embodiment, the nucleic acid encodes about 11.5, about 14.5, about 17.5 or about 18.5 repeat units. In a further embodiment, the predetermined nucleotide sequence is a promoter region.

Some embodiments are directed to a vector comprising a nucleic acid molecule or sequence. In one embodiment, the vector is a viral vector. In another embodiment, the viral vector comprises one or more of: an adenovirus, a retrovirus, a lentivirus, a herpes virus, an adeno-associated virus or a natural or engineered variant thereof, and an engineered virus.

Certain embodiments are directed to a nucleic acid molecule encoding a non-naturally occurring fusion protein comprising a first region that recognizes a predetermined nucleotide sequence and a second region with endonuclease activity, wherein the first region contains an artificial TAL effector repeat domain comprising one or more repeat units about 36 amino acids in length which differ from each other by no more than seven amino acids, and wherein the repeat domain is engineered for recognition of the predetermined nucleotide sequence. In one embodiment, the first region contains the amino acid sequence: LTPXQVVAIAS (SEQ ID NO: 63) where X can be either E or Q. In another embodiment, the amino acid sequence LTPXQVVAIAS (SEQ ID NO: 64) of the encoded non-naturally occurring fusion protein is immediately followed by an amino acid sequence selected from: HD, NG, NS, NI, NN, and N. In a further embodiment, the fusion protein comprises restriction endonuclease activity. Some embodiments are directed to a nucleic acid molecule encoding a protein that comprises one or more sequences selected from: SEQ ID NO: 2, SEQ ID NO: 3, SEQ ID NO: 4, SEQ ID NO: 5, SEQ ID NO: 6, SEQ ID NO: 7, SEQ ID NO: 54, SEQ ID NO: 55, SEQ ID NO: 56, SEQ ID NO: 57, SEQ ID NO: 58, SEQ ID NO: 59, SEQ ID NO: 60.

In one embodiment, the repeat sequence comprises: LTPvQVVAIAwxyzHG (SEQ ID NO: 65), wherein "v" is D or E, "w" is S or N, "x" is N, H or I, "y" is any amino acid or no amino acid, and "z" is GGRPALE (SEQ ID NO: 664), GGKQALE (SEQ ID NO: 665), GGKQALETVQRLLPV- LCQDHG (SEQ ID NO: 666), GGKQALETVQRLLPVLCQAHG (SEQ ID NO: 667), GKQALETVQRLLPVLCQDHG (SEQ ID NO: 668), or GKQALETVQRLLPVLCQAHG (SEQ ID NO: 669). In another embodiment, the repeat sequence comprises: LTPvQVVAIAwxyzHG (SEQ ID NO: 66), wherein "v" is D or E, "w" is S or N, "x" is N, H or I, "y" is selected from: D, A, I, N, H, K, S, and G, and "z" is GGRPALE (SEQ ID NO: 664), GGKQALE (SEQ ID NO: 665), GGKQALETVQRLLPVLCQDHG (SEQ ID NO: 666), GGKQALETVQRLLPVLCQAHG (SEQ ID NO: 667), GKQALETVQRLLPVLCQDHG (SEQ ID NO: 668), or GKQALETVQRLLPVLCQAHG (SEQ ID NO: 669). In yet another embodiment, the repeat sequence comprises: LTPvQVVAIAwxyzHG (SEQ ID NO: 67), wherein "v" is D or E, "w" is S or N, "x" is any amino acid other than N, H and I, "y" is any amino acid or no amino acid, and "z" is GGRPALE (SEQ ID NO: 664), GGKQALE (SEQ ID NO: 665), GGKQALETVQRLLPVLCQDHG (SEQ ID NO: 666), GGKQALETVQRLLPVLCQAHG (SEQ ID NO: 667), GKQALETVQRLLPVLCQDHG (SEQ ID NO: 668), or GKQALETVQRLLPVLCQAHG (SEQ ID NO: 669). In yet another embodiment, the repeat sequence comprises: LTPvQVVAIAwIyzHG (SEQ ID NO: 68), wherein "v" is D or E, "w" is S or N, "y" is any amino acid other than G, and "z" is GGRPALE (SEQ ID NO: 664), GGKQALE (SEQ ID NO: 665), GGKQALETVQRLLPVLCQDHG (SEQ ID NO: 666), GGKQALETVQRLLPVLCQAHG (SEQ ID NO: 667), GKQALETVQRLLPVLCQDHG (SEQ ID NO: 668), or GKQALETVQRLLPVLCQAHG (SEQ ID NO: 669). In yet another embodiment, the repeat sequence comprises: LTPvQVVAIAwIAzHG (SEQ ID NO: 69), wherein "v" is D or E, "w" is S or N, and "z" is GGRPALE (SEQ ID NO: 664), GGKQALE (SEQ ID NO: 665), GGKQALETVQRLLPVLCQDHG (SEQ ID NO: 666), GGKQALETVQRLLPVLCQAHG (SEQ ID NO: 667), GKQALETVQRLLPVLCQDHG (SEQ ID NO: 668), or GKQALETVQRLLPVLCQAHG (SEQ ID NO: 669). In yet another embodiment, the repeat sequence comprises: LTPvQVVAIAwxyzHG (SEQ ID NO: 70), wherein "v" is D or E, "w" is S or N, "x" is S, T or Q, "y" is any amino acid or no amino acid, and "z" is GGRPALE (SEQ ID NO: 664), GGKQALE (SEQ ID NO: 665), GGKQALETVQRLLPVLCQDHG (SEQ ID NO: 666), GGKQALETVQRLLPVLCQAHG (SEQ ID NO: 667), GKQALETVQRLLPVLCQDHG (SEQ ID NO: 668), or GKQALETVQRLLPVLCQAHG (SEQ ID NO: 669). In yet another embodiment, the repeat sequence comprises: LTPvQVVAIAwxyzHG (SEQ ID NO: 71), wherein "v" is D or E, "w" is S or N, "x" is S, T or Q, "y" is selected from: D, A, I, N, H, K, S, and G, and "z" is GGRPALE (SEQ ID NO: 664), GGKQALE (SEQ ID NO: 665), GGKQALETVQRLLPVLCQDHG (SEQ ID NO: 666), GGKQALETVQRLLPVLCQAHG (SEQ ID NO: 667), GKQALETVQRLLPVLCQDHG (SEQ ID NO: 668), or GKQALETVQRLLPVLCQAHG (SEQ ID NO: 669). In yet another embodiment, the repeat sequence comprises: LTPvQVVAIAwx (SEQ ID NO: 72), wherein "v" is D or E, "w" is S or N, and "x" is S, T or Q. In yet another embodiment, the repeat sequence comprises: LTPvQVVAIAwxy (SEQ ID NO: 73), wherein "v" is D or E, "w" is S or N, "x" is S, T or Q, and "y" is selected from: D, A, I, N, H, K, S, and G. In yet another embodiment, the repeat sequence comprises: LTPvQVVAIAwxyzGHGG (SEQ ID NO: 74), wherein "v" is Q, D or E, "w" is S or N, "x" is N, H or I, "y" is any amino acid or no amino acid, and "z" is GGRPALE (SEQ ID NO: 664), GGKQALE (SEQ ID NO: 665), GGKQALETVQRLLPVLCQD (SEQ ID NO: 670), GGKQALETVQRLLPVLCQA (SEQ ID NO: 671), GKQALETVQRLLPVLCQD (SEQ ID NO: 672) or GKQALETVQRLLPVLCQA (SEQ ID NO: 673). In yet another embodiment, the repeat sequence comprises: LTPvQVVAIAwxyzGHGG (SEQ ID NO: 75), wherein "v" is Q, D or E, "w" is S or N, "x" is N, H or I, "y" is selected from: D, A, I, N, H, K, S, and G, and "z" is GGRPALE (SEQ ID NO: 664), GGKQALE (SEQ ID NO: 665), GGKQALETVQRLLPVLCQD (SEQ ID NO: 670), GGKQALETVQRLLPVLCQA (SEQ ID NO: 671), GKQALETVQRLLPVLCQD (SEQ ID NO: 672) or GKQALETVQRLLPVLCQA (SEQ ID NO: 673). In yet another embodiment, the repeat sequence comprises: LTPvQVVAIAwxyzGHGG (SEQ ID NO: 76), wherein "v" is Q, D or E, "w" is S or N, "x" is any amino acid other than N, H and I, "y" is any amino acid or no amino acid, and "z" is GGRPALE (SEQ ID NO: 664), GGKQALE (SEQ ID NO: 665), GGKQALETVQRLLPVLCQD (SEQ ID NO: 670), GGKQALETVQRLLPVLCQA (SEQ ID NO: 671), GKQALETVQRLLPVLCQD (SEQ ID NO: 672) or GKQALETVQRLLPVLCQA (SEQ ID NO: 673). In yet another embodiment, the repeat sequence comprises: LTPvQVVAIAwIyzGHGG (SEQ ID NO: 77), wherein "v" is Q, D or E, "w" is S or N, "y" is any amino acid other than G, and "z" is GGRPALE (SEQ ID NO: 664), GGKQALE (SEQ ID NO: 665), GGKQALETVQRLLPVLCQD (SEQ ID NO: 670), GGKQALETVQRLLPVLCQA (SEQ ID NO: 671), GKQALETVQRLLPVLCQD (SEQ ID NO: 672) or GKQALETVQRLLPVLCQA (SEQ ID NO: 673). In yet another embodiment, the repeat sequence comprises: LTPvQVVAIAwIAzGHGG (SEQ ID NO: 78), wherein "v" is Q, D or E, "w" is S or N, and "z" is GGRPALE (SEQ ID NO: 664), GGKQALE (SEQ ID NO: 665), GGKQALETVQRLLPVLCQD (SEQ ID NO: 670), GGKQALETVQRLLPVLCQA (SEQ ID NO: 671), GKQALETVQRLLPVLCQD (SEQ ID NO: 672) or GKQALETVQRLLPVLCQA (SEQ ID NO: 673). In yet another embodiment, the repeat sequence comprises: LTPvQVVAIAwxyzGHGG (SEQ ID NO: 79), wherein "v" is Q, D or E, "w" is S or N, "x" is S, T or Q, "y" is any amino acid or no amino acid, and "z" is GGRPALE (SEQ ID NO: 664), GGKQALE (SEQ ID NO: 665), GGKQALETVQRLLPVLCQD (SEQ ID NO: 670), GGKQALETVQRLLPVLCQA (SEQ ID NO: 671), GKQALETVQRLLPVLCQD (SEQ ID NO: 672) or GKQALETVQRLLPVLCQA (SEQ ID NO: 673). In yet another embodiment, the repeat sequence comprises: LTPvQVVAIAwxyzGHGG (SEQ ID NO: 80), wherein "v" is Q, D or E, "w" is S or N, "x" is S, T or Q, "y" is selected from: D, A, I, N, H, K, S, and G, and "z" is GGRPALE (SEQ ID NO: 664), GGKQALE (SEQ ID NO: 665), GGKQALETVQRLLPVLCQD (SEQ ID NO: 670), GGKQALETVQRLLPVLCQA (SEQ ID NO: 671), GKQALETVQRLLPVLCQD (SEQ ID NO: 672) or GKQALETVQRLLPVLCQA (SEQ ID NO: 673). In yet another embodiment, the repeat sequence comprises: LTPvQVVAIAwx (SEQ ID NO: 81), wherein "v" is Q, D or E, "w" is S or N, and "x" is S, T or Q. In yet another embodiment, the repeat sequence comprises: LTPvQVVAIAwxy (SEQ ID NO: 82), wherein "v" is Q, D or E, "w" is S or N, "x" is S, T or Q, and "y" is selected from: D, A, I, N, H, K, S, and G.

Certain fragments of an endonuclease cleavage domain, including fragments that are truncated at the N-terminus, fragments that are truncated at the C-terminus, fragments that have internal deletions, and fragments that combine N-terminus, C-terminus, and/or internal deletions, can maintain part or all of the catalytic activity of the full endonuclease cleavage domain. Determining whether a fragment can maintain part or all of the catalytic activity of the full domain can be accomplished by, for example, synthesizing a gene-editing protein that contains the fragment according to the methods of the present invention, inducing cells to express the gene-editing protein according to the methods of the present invention, and measuring the efficiency of gene editing. In this way, a measurement of gene-editing efficiency can be used to ascertain whether any specific fragment can maintain part or all of the catalytic activity of the full endonuclease cleavage domain. Certain embodiments are therefore directed to a biologically active fragment of an endonuclease cleavage domain. In one embodiment, the endonuclease cleavage domain is selected from: FokI, StsI, StsI-HA, StsI-HA2, StsI-UHA, StsI-UHA2, StsI-HF, and StsI-UHF or a natural or engineered variant or biologically active fragment thereof.

Certain fragments of a DNA-binding domain or repeat sequence, including fragments that are truncated at the N-terminus, fragments that are truncated at the C-terminus, fragments that have internal deletions, and fragments that combine N-terminus, C-terminus, and/or internal deletions, can maintain part or all of the binding activity of the full DNA-binding domain or repeat sequence. Examples of fragments of DNA-binding domains or repeat sequences that can maintain part or all of the binding activity of the full repeat sequence include *Ralstonia solanacearum* TALE-like proteins (RTLs). Determining whether a fragment can maintain part or all of the binding activity of the full DNA-binding domain or repeat sequence can be accomplished by, for example, synthesizing a gene-editing protein that contains the fragment according to the methods of the present invention, inducing cells to express the gene-editing protein according to the methods of the present invention, and measuring the efficiency of gene editing. In this way, a measurement of gene-editing efficiency can be used to ascertain whether any specific fragment can maintain part or all of the binding activity of the full DNA-binding domain or repeat sequence. Certain embodiments are therefore directed to a biologically active fragment of a DNA-binding domain or repeat sequence. In one embodiment, the fragment enables high-specificity recognition of a binding site in a target DNA molecule. In another embodiment, the fragment comprises a sequence that encodes a *Ralstonia solanacearum* TALE-like protein or a biologically active fragment thereof.

Certain embodiments are directed to a composition for altering the DNA sequence of a cell comprising a nucleic acid, wherein the nucleic acid encodes a gene-editing protein. Other embodiments are directed to a composition for altering the DNA sequence of a cell comprising a nucleic-acid mixture, wherein the nucleic-acid mixture comprises: a first nucleic acid that encodes a first gene-editing protein, and a second nucleic acid that encodes a second gene-editing protein. In one embodiment, the binding site of the first gene-editing protein and the binding site of the second gene-editing protein are present in the same target DNA molecule. In another embodiment, the binding site of the first gene-editing protein and the binding site of the second gene-editing protein are separated by less than about 50 bases, or less than about 40 bases, or less than about 30 bases or less than about 20 bases, or less than about 10 bases, or between about 10 bases and about 25 bases or about 15 bases.

In one embodiment, the nuclease domain of the first gene-editing protein and the nuclease domain of the second gene-editing protein are capable of forming a dimer. In another embodiment, the dimer is capable of generating a nick or double-strand break in a target DNA molecule. In one embodiment, the composition is a therapeutic composition. In another embodiment, the composition comprises a repair template. In a further embodiment, the repair template is a single-stranded DNA molecule or a double-stranded DNA molecule.

Other embodiments are directed to an article of manufacture for synthesizing a protein or a nucleic acid encoding a protein. In one embodiment, the article is a nucleic acid. In another embodiment, the protein comprises a DNA-binding domain. In a further embodiment, the nucleic acid comprises a nucleotide sequence encoding a DNA-binding domain. In one embodiment, the protein comprises a nuclease domain. In another embodiment, the nucleic acid comprises a nucleotide sequence encoding a nuclease domain. In one embodiment, the protein comprises a plurality of repeat sequences. In another embodiment, the nucleic acid encodes a plurality of repeat sequences. In a further embodiment, the nuclease domain is selected from: FokI, StsI, StsI-HA, StsI-HA2, StsI-UHA, StsI-UHA2, StsI-HF, and StsI-UHF or a natural or engineered variant or biologically active fragment thereof. In one embodiment, the nucleic acid comprises an RNA-polymerase promoter. In another embodiment, the RNA-polymerase promoter is a T7 promoter or a SP6 promoter. In a further embodiment, the nucleic acid comprises a viral promoter. In one embodiment, the nucleic acid comprises an untranslated region. In another embodiment, the nucleic acid is an in vitro-transcription template.

Certain embodiments are directed to a method for inducing a cell to express a protein. Other embodiments are directed to a method for altering the DNA sequence of a cell comprising transfecting the cell with a gene-editing protein or inducing the cell to express a gene-editing protein. Still other embodiments are directed to a method for reducing the expression of a protein of interest in a cell. In one embodiment, the cell is induced to express a gene-editing protein, wherein the gene-editing protein is capable of creating a nick or a double-strand break in a target DNA molecule. In another embodiment, the nick or double-strand break results in inactivation of a gene. Still other embodiments are directed to a method for generating an inactive, reduced-activity or dominant-negative form of a protein. In one embodiment, the protein is survivin. Still other embodiments are directed to a method for repairing one or more mutations in a cell. In one embodiment, the cell is contacted with a repair template. In another embodiment, the repair template is a DNA molecule. In a further embodiment, the repair template does not contain a binding site of the gene-editing protein. In a still further embodiment, the repair template encodes an amino-acid sequence that is encoded by a DNA sequence that comprises a binding site of the gene-editing protein.

Other embodiments are directed to a method for treating a patient comprising administering to the patient a therapeutically effective amount of a protein or a nucleic acid encoding a protein. In one embodiment, the treatment results in one or more of the patient's symptoms being ameliorated. Certain embodiments are directed to a method for treating a patient comprising: a. removing a cell from the patient, b. inducing the cell to express a gene-editing protein by transfecting the cell with a nucleic acid encoding a gene-editing protein, c. reprogramming the cell, and e. introducing the cell into the patient. In one embodiment, the cell is reprogrammed to a less differentiated state. In another embodiment, the cell is reprogrammed by transfecting the cell with one or more synthetic RNA molecules encoding one or more reprogramming proteins. In a further embodiment, the cell is differentiated. In a still further embodiment, the cell is differentiated into one of: a skin cell, a glucose-responsive insulin-producing cell, a hematopoietic cell, a cardiac cell, a retinal cell, a renal cell, a neural cell, a stromal cell, a fat cell, a bone cell, a muscle cell, an oocyte, and a sperm cell. Other embodiments are directed to a method for treating a patient comprising: a. removing a hematopoietic cell or a stem cell from the patient, b. inducing the cell to express a gene-editing protein by transfecting the cell with a nucleic acid encoding a gene-editing protein, and c. introducing the cell into the patient.

It has now been discovered that a cell-culture medium consisting essentially of or comprising: DMEM/F12, ascorbic acid, insulin, transferrin, sodium selenite, ethanolamine, basic fibroblast growth factor, and transforming growth factor-beta is sufficient to sustain pluripotent stem cells, including human pluripotent stem cells, in vitro. Certain embodiments are therefore directed to a cell-culture medium consisting essentially of or comprising: DMEM/F12, ascorbic acid, insulin, transferrin, sodium selenite, ethanolamine, basic fibroblast growth factor, and transforming growth factor-beta. In one embodiment, the ascorbic acid is present at about 50 µg/mL. In another embodiment, the insulin is present at about 10 µg/mL. In a further embodiment, the transferrin is present at about 5.5 µg/mL. In a still further embodiment, the sodium selenite is present at about 6.7 ng/mL. In a still further embodiment, the ethanolamine is present at about 2 µg/mL. In a still further embodiment, the basic fibroblast growth factor is present at about 20 ng/mL. In a still further embodiment, the transforming growth factor-beta is present at about 2 ng/mL. In one embodiment, the ascorbic acid is ascorbic acid-2-phosphate. In another embodiment, the transforming growth factor-beta is transforming growth factor-beta 1 or transforming growth factor-beta 3. In one embodiment, the cell-culture medium is used for the culture of pluripotent stem cells. In another embodiment, the pluripotent stem cells are human pluripotent stem cells. In a further embodiment, the cell-culture medium is used for the culture of cells during or after reprogramming. In one embodiment, the cell-culture medium contains no animal-derived components. In another embodiment, the cell-culture medium is manufactured according to a manufacturing standard. In a further embodiment, the manufacturing standard is GMP. In one embodiment, the cells are contacted with a cell-adhesion molecule. In another embodiment, the cell-adhesion molecule is selected from: fibronectin and vitronectin or a biologically active fragment thereof. In a further embodiment, the cells are contacted with fibronectin and vitronectin. In a still further embodiment, the cell-adhesion molecule is recombinant.

In certain situations, for example, when producing a therapeutic, it can be beneficial to replace animal-derived components with non-animal-derived components, in part to reduce the risk of contamination with viruses and/or other animal-borne pathogens. It has now been discovered that synthetic cholesterol, including semi-synthetic plant-derived cholesterol, can be substituted for animal-derived cholesterol in transfection medium without decreasing transfection efficiency or increasing transfection-associated toxicity. Certain embodiments are therefore directed to a transfection medium containing synthetic or semi-synthetic cholesterol. In one embodiment, the semi-synthetic cholesterol is plant-derived. In another embodiment, the transfection medium does not contain animal-derived cholesterol. In a further embodiment, the transfection medium is a reprogramming medium. Other embodiments are directed to a complexation medium. In one embodiment, the complexation medium has a pH greater than about 7, or greater than about 7.2, or greater than about 7.4, or greater than about 7.6, or greater than about 7.8, or greater than about 8.0, or greater than about 8.2, or greater than about 8.4, or greater than about 8.6, or greater than about 8.8, or greater than about 9.0. In another embodiment, the complexation medium comprises transferrin. In a further embodiment, the complexation medium comprises DMEM. In a still further embodiment, the complexation medium comprises DMEM/F12. Still other embodiments are directed to a method for forming nucleic-acid-transfection-reagent complexes. In one embodiment, the transfection reagent is incubated with a complexation medium. In another embodiment, the incubation occurs before a mixing step. In a further embodiment, the incubation step is between about 5 seconds and about 5 minutes or between about 10 seconds and about 2 minutes or between about 15 seconds and about 1 minute or between about 30 seconds and about 45 seconds. In one embodiment, the transfection reagent is selected from Table 1. In another embodiment, the transfection reagent is a lipid or lipidoid. In a further embodiment, the transfection reagent comprises a cation. In a still further embodiment, the cation is a multi-valent cation. In a still further embodiment, the transfection reagent is N1-[2-((1S)-1-[(3-aminopropyl)amino]-4-[di(3-amino-propyl)amino]butylcarboxamido)ethyl]-3,4-di[oleyloxy]-benzamide (a.k.a. MVL5) or a derivative thereof.

Certain embodiments are directed to a method for inducing a cell to express a protein by contacting the cell with a nucleic acid. In one embodiment, the cell is a mammalian cell. In another embodiment, the cell is a human cell or a rodent cell. Other embodiments are directed to a cell produced using one or more of the methods of the present invention. In one embodiment, the cell is present in a patient. In another embodiment, the cell is isolated from a patient. Other embodiments are directed to a screening library comprising a cell produced using one or more of the methods of the present invention. In one embodiment, the screening library is used for at least one of: toxicity screening, including: cardiotoxicity screening, neurotoxicity screening, and hepatotoxicity screening, efficacy screening, high-throughput screening, high-content screening, and other screening.

Other embodiments are directed to a kit containing a nucleic acid. In one embodiment, the kit contains a delivery reagent (a.k.a. "transfection reagent"). In another embodiment, the kit is a reprogramming kit. In a further embodiment, the kit is a gene-editing kit. Other embodiments are directed to a kit for producing nucleic acids. In one embodiment, the kit contains at least two of: pseudouridine-triphosphate, 5-methyluridine triphosphate, 5-methylcytidine triphosphate, 5-hydroxymethylcytidine triphosphate, N4-methylcytidine triphosphate, N4-acetylcytidine triphosphate, and 7-deazaguanosine triphosphate or one or more derivatives thereof. Other embodiments are directed to a therapeutic comprising a nucleic acid. In one embodiment, the therapeutic is a pharmaceutical composition. In another embodiment, the pharmaceutical composition is formulated. In a further embodiment, the formulation comprises an aqueous suspension of liposomes. Example liposome components are set forth in Table 1, and are given by way of example, and not by way of limitation. In one embodiment, the liposomes include one or more polyethylene glycol (PEG) chains. In another embodiment, the PEG is PEG2000.

In a further embodiment, the liposomes include 1,2-distearoyl-sn-glycero-3-phosphoethanolamine (DSPE) or a derivative thereof. In one embodiment, the therapeutic comprises one or more ligands. In another embodiment, the therapeutic comprises at least one of: androgen, CD30 (TNFRSF8), a cell-penetrating peptide, CXCR, estrogen, epidermal growth factor, EGFR, HER2, folate, insulin, insulin-like growth factor-I, interleukin-13, integrin, progesterone, stromal-derived-factor-1, thrombin, vitamin D, and transferrin or a biologically active fragment or variant thereof. Still other embodiments are directed to a therapeutic comprising a cell generated using one or more of the methods of the present invention. In one embodiment, the therapeutic is administered to a patient for the treatment of at least one of: type 1 diabetes, heart disease, including ischemic and dilated cardiomyopathy, macular degeneration, Parkinson's disease, cystic fibrosis, sickle-cell anemia, thalassemia, Fanconi anemia, severe combined immunodeficiency, hereditary sensory neuropathy, xeroderma pigmentosum, Huntington's disease, muscular dystrophy, amyotrophic lateral sclerosis, Alzheimer's disease, cancer, and infectious diseases including: hepatitis and HIV/AIDS.

TABLE 1

Exemplary Biocompatible Lipids 1 3β-[N-(N',N'-dimethylaminoethane)-carbamoyl]cholesterol (DC-Cholesterol)
2 1,2-dioleoyl-3-trimethylammonium-propane (DOTAP/18:1 TAP)
3 N-(4-carboxybenzyl)-N,N-dimethyl-2,3-bis(oleoyloxy)propan-1-aminium (DOBAQ)
4 1,2-dimyristoyl-3-trimethylammonium-propane (14:0 TAP)
5 1,2-dipalmitoyl-3-trimethylammonium-propane (16:0 TAP)
6 1,2-stearoyl-3-trimethylammonium-propane (18:0 TAP)
7 1,2-dioleoyl-3-dimethylammonium-propane (DODAP/18:1 DAP)
8 1,2-dimyristoyl-3-dimethylammonium-propane (14:0 DAP)
9 1,2-dipalmitoyl-3-dimethylammonium-propane (16:0 DAP)
10 1,2-distearoyl-3-dimethylammonium-propane (18:0 DAP)
11 dimethyldioctadecylammonium (18:0 DDAB)
12 1,2-dilauroyl-sn-glycero-3-ethylphosphocholine (12:0 EthylPC)
13 1,2-dimyristoyl-sn-glycero-3-ethylphosphocholine (14:0 EthylPC)
14 1,2-dimyristoleoyl-sn-glycero-3-ethylphosphocholine (14:1 EthylPC)
15 1,2-dipalmitoyl-sn-glycero-3-ethylphosphocholine (16:0 EthylPC)
16 1,2-distearoyl-sn-glycero-3-ethylphosphocholine (18:0 EthylPC)
17 1,2-dioleoyl-sn-glycero-3-ethylphosphocholine (18:1 EthylPC)
18 1-palmitoyl-2-oleoyl-sn-glycero-3-ethylphosphocholine (16:1-18:1 EthylPC)
19 1,2-di-O-octadecenyl-3-trimethylammonium propane (DOTMA)
20 N1-[2-((1S)-1-[(3-aminopropyl)amino]-4-[di(3-aminopropyl)amino]butylcarboxamido)ethyl]-3,4-di[oleyloxy]-benzamide (MVL5)
21 2,3-dioleyloxy-N-[2-spermine carboxamide]ethyl-N,N-dimethyl-1-propanammonium trifluoroacetate (DOSPA)
22 1,3-di-oleoyloxy-2-(6-carboxy-spermyl)-propylamid (DOSPER)
23 N-[1-(2,3-dimyristyloxy)propyl]-N,N-dimethyl-N-(2-hydroxyethyl)ammonium bromide (DMRIE)
24 dioctadecyl amidoglyceryl spermine (DOGS)
25 dioleoyl phosphatidyl ethanolamine (DOPE)

Certain embodiments are directed to a nucleic acid comprising a 5'-cap structure selected from Cap 0, Cap 1, Cap 2, and Cap 3 or a derivative thereof. In one embodiment, the nucleic acid comprises one or more UTRs. In another embodiment, the one or more UTRs increase the stability of the nucleic acid. In a further embodiment, the one or more UTRs comprise an alpha-globin or beta-globin 5'-UTR. In a still further embodiment, the one or more UTRs comprise an alpha-globin or beta-globin 3'-UTR. In a still further embodiment, the synthetic RNA molecule comprises an alpha-globin or beta-globin 5'-UTR and an alpha-globin or beta-globin 3'-UTR. In one embodiment, the 5'-UTR comprises a Kozak sequence that is substantially similar to the Kozak consensus sequence. In another embodiment, the nucleic acid comprises a 3'-poly(A) tail. In a further embodiment, the 3'-poly(A) tail is between about 20 nt and about 250 nt or between about 120 nt and about 150 nt long. In a further embodiment, the 3'-poly(A) tail is about 20 nt, or about 30 nt, or about 40 nt, or about 50 nt, or about 60 nt, or about 70 nt, or about 80 nt, or about 90 nt, or about 100 nt, or about 110 nt, or about 120 nt, or about 130 nt, or about 140 nt, or about 150 nt, or about 160 nt, or about 170 nt, or about 180 nt, or about 190 nt, or about 200 nt, or about 210 nt, or about 220 nt, or about 230 nt, or about 240 nt, or about 250 nt long.

Other embodiments are directed to a method for reprogramming a cell. In one embodiment, the cell is reprogrammed by contacting the cell with one or more nucleic acids. In one embodiment, the cell is contacted with a plurality of nucleic acids encoding at least one of: Oct4 protein, Sox2 protein, Klf4 protein, c-Myc protein, Lin28 protein or a biologically active fragment, variant or derivative thereof. In another embodiment, the cell is contacted with a plurality of nucleic acids encoding a plurality of proteins including: Oct4 protein, Sox2 protein, Klf4 protein, and c-Myc protein or one or more biologically active fragments, variants or derivatives thereof. Still other embodiments are directed to a method for gene editing a cell. In one embodiment, the cell is gene-edited by contacting the cell with one or more nucleic acids.

Animal models are routinely used to study the effects of biological processes. In certain situations, for example, when studying a human disease, an animal model containing a modified genome can be beneficial, in part because such an animal model may more closely mimic the human disease phenotype. Certain embodiments are therefore directed to a method for creating an organism containing one or more genetic modifications (a.k.a. "mutations", a.k.a. "gene edits"). In one embodiment, the one or more genetic modifications is generated by transfecting a cell with one or more nucleic acids encoding one or more gene-editing proteins. In another embodiment, the one or more nucleic acids include a synthetic RNA molecule. In one embodiment, the one or more gene-editing proteins include at least one of: a zinc finger nuclease, a TALEN, a clustered regularly interspaced short palindromic repeat (CRISPR)-associated protein, a nuclease, a meganuclease, and a nickase or a biologically active fragment or variant thereof. In one embodiment, the cell is a pluripotent cell. In another embodiment, the cell is an embryonic stem cell. In a further embodiment, the cell is an embryo. In a still further embodiment, the cell is a member of: an animal cell, a plant cell, a yeast cell, and a bacterial cell. In one embodiment, the cell is a rodent cell. In another embodiment, the cell is a human cell. In certain embodiments, the cell is transfected with one or more nucleic acids encoding one or more gene-editing proteins and one or more nucleic acids encoding one or more repair templates. In one embodiment, the cell is introduced into a blastocyst. In another embodiment, the cell is introduced into a pseudopregnant female. In a further embodiment, the presence or absence of the genetic modification in the offspring is determined. In a still further embodiment, the determining is by direct sequencing. In one embodiment, the organism is livestock, for example, a pig, a cow, etc. In another embodiment, the organism is a pet, for example, a dog, a cat, a fish, etc.

In certain situations, for example, when modifying the genome of a target cell by the addition of a nucleic-acid sequence, it can be advantageous to insert the nucleic-acid sequence into a safe-harbor location, in part to reduce the risks associated with random insertion. Certain embodiments are therefore directed to a method for inserting a nucleic-acid sequence into a safe-harbor location. In one embodiment, the cell is a human cell and the safe-harbor location is the AAVS1 locus. In another embodiment, the cell is a rodent cell and the safe-harbor location is the Rosa26 locus. In one embodiment, the cell is further contacted with one or more nucleic acids encoding one or more repair templates. Other embodiments are directed to a kit for altering the DNA sequence of a cell. In one embodiment, the cell is a human cell, and the target DNA molecule comprises a nucleotide sequence that encodes the AAVS1 locus. In another embodiment, the cell is a rodent cell, and the target DNA molecule comprises a nucleotide sequence that encodes the Rosa26 locus. Other embodiments are directed to a method for generating a reporter cell by contacting the cell with one or more nucleic acids encoding one or more gene-editing proteins and one or more nucleic acids encoding one or more repair templates. In one embodiment, the one or more repair templates comprise DNA. In another embodiment, the one or more repair templates encode one or more fluorescent proteins. In a further embodiment, the one or more repair templates encode at least part of the promoter region of a gene.

In certain situations, for example, when generating a library of gene-edited cells, it can be beneficial to increase the efficiency of gene editing, in part to reduce the cost of cell characterization. It has now been discovered that gene-editing efficiency can be increased by repeatedly contacting a cell with synthetic RNA encoding one or more gene-editing proteins. Certain embodiments are therefore directed to a method for gene editing a cell by repeatedly contacting the cell with one or more nucleic acids encoding one or more gene-editing proteins. In one embodiment, the cell is contacted at least twice during five consecutive days. In another embodiment, the cell is contacted twice at an interval of between about 24 hours and about 48 hours.

In cancer, the survival and proliferation of malignant cells can be due in part to the presence of specific genetic abnormalities that are not generally present in the patient. It has now been discovered that gene-editing proteins can be used to target survival and proliferation-associated pathways, and that when used in this manner, gene-editing proteins and nucleic acids encoding gene-editing proteins can constitute potent anti-cancer therapeutics. Certain embodiments are therefore directed to an anti-cancer therapeutic. In one embodiment, the therapeutic is a therapeutic composition that inhibits the survival and/or prevents, slows or otherwise limits the proliferation of a cell. In another embodiment, the cell is a cancer cell. In a further embodiment, the therapeutic comprises one or more gene-editing proteins or a nucleic acid that encodes one or more gene-editing proteins. In a still further embodiment, the one or more gene-editing proteins target one or more sequences that promote survival and/or proliferation of the cell. Such sequences include, but are not limited to: apoptosis-related genes, including genes of the inhibitor of apoptosis (IAP) family (See, e.g., Table 2 and Table 2 of U.S. Provisional Application No. 61/721,302, the contents of which are hereby incorporated by reference), such as BIRC5, sequences associated with telomere maintenance, such as the gene telomerase reverse transcriptase (TERT) and the telomerase RNA component (TERC), sequences affecting angiogenesis, such as the gene VEGF, and other cancer-associated genes, including: BRAF, BRCA1, BRCA2, CDKN2A, CTNNB1, EGFR, the MYC family, the RAS family, PIK3CA, PIK3R1, PKN3, TP53, PTEN, RET, SMAD4, KIT, MET, APC, RB1, the VEGF family, TNF, and genes of the ribonucleotide reductase family. Example gene-editing protein target sequences for BIRC5 are set forth in Table 3 and in Table 3 of U.S. Provisional Application No. 61/721,302, the contents of which are hereby incorporated by reference, and are given by way of example, and not by way of limitation. In one embodiment, at least one of the one or more sequences is present in both malignant and non-malignant cells. In another embodiment, at least one of the one or more sequences is enriched in malignant cells. In a further embodiment, at least one of the one or more sequences is enriched in non-malignant cells. In one embodiment, the therapeutic composition further comprises a nucleic acid encoding one or more repair templates. In another embodiment, the one or more gene-editing proteins induce the cells to express an inactive or dominant-negative form of a protein. In a further embodiment, the protein is a member of the IAP family. In a still further embodiment, the protein is survivin.

TABLE 2

Exemplary Inhibitor of Apoptosis (IAP) Genes

| Name | Length/aa | BIR Domains | CARD Domain | RING Domain |
|---|---|---|---|---|
| BIRC1 (neuronal apoptosis-inhibitory protein) | 1,403 | 3 | N | N |
| BIRC2 (c-IAP1 protein) | 604 | 3 | Y | Y |
| BIRC3 (c-IAP2 protein) | 618 | 3 | Y | Y |
| BIRC4 (X-linked IAP) | 497 | 3 | N | Y |
| BIRC5 (survivin protein) | 142 | 1 | N | N |
| BIRC6 (BRUCE/apollon protein) | 4845 | 1 | N | N |
| BIRC7 (livin protein) | 298 | 1 | N | Y |
| ILP2 (tissue-specific homolog of BIRC4) | 236 | 1 | N | Y |

TABLE 3

Exemplary Gene Editing-Protein Target Sequences for BIRC5

| Target | Left | SEQ ID NO. | Right | SEQ ID NO. |
|---|---|---|---|---|
| UTR | TAAGAGGGCGTGCGCTCCCG | 83 | TCAAATCTGGCGGTTAATGG | 84 |
| Start Codon | TTGGCAGAGGTGGCGGCGGC | 85 | TGCCAGGCAGGGGGCAACGT | 86 |
| Exon 1 | TTGCCCCCTGCCTGGCAGCC | 16 | TTCTTGAATGTAGAGATGCG | 17 |
| Exon 2 | TCCACTGCCCCACTGAGAAC | 87 | TCCTTGAAGCAGAAGAAACA | 88 |

TABLE 3-continued

Exemplary Gene Editing-Protein Target Sequences for BIRC5

| Target | Left | SEQ ID NO. | Right | SEQ ID NO. |
|---|---|---|---|---|
| Exon 4 | TAAAAAGCATTCGTCCGGTT | 89 | TTCTTCAAACTGCTTCTTGA | 90 |
| Exon 5 | TTGAGGAAACTGCGGAGAAA | 91 | TCCATGGCAGCCAGCTGCTC | 92 |

Other embodiments are directed to a method for treating cancer comprising administering to a patient a therapeutically effective amount of a gene-editing protein or a nucleic acid encoding one or more gene-editing proteins. In one embodiment, the treatment results in the growth of cancer cells in the patient being reduced or halted. In another embodiment, the treatment results in delayed progression or remission of the cancer. In one embodiment, the target DNA molecule comprises the BIRC5 gene. In another embodiment, the target DNA molecule comprises a sequence selected from: SEQ ID NO: 12, SEQ ID NO: 13, SEQ ID NO: 14, and SEQ ID NO: 15. In a further embodiment, a plurality of adjacent binding sites are at least about 50% or at least about 60% or at least about 70% or at least about 80% or at least about 90% or at least about 95% or at least about 98%, or at least about 99% homologous to one or more sequences listed in Table 3, Table 4, Table 3 of U.S. Provisional Application No. 61/721,302, the contents of which are hereby incorporated by reference, Table 1 of U.S. Provisional Application No. 61/785,404, the contents of which are hereby incorporated by reference or Table 1 of U.S. Provisional Application No. 61/842,874, the contents of which are hereby incorporated by reference. In certain situations, a gene-editing protein with a truncated N-terminal domain can be used to eliminate the first-base-T restriction on the binding-site sequence. In some embodiments, the cancer is glioma. In one embodiment, the patient has previously undergone surgery and/or radiation therapy and/or concurrently undergoes surgery and/or radiation therapy. In another embodiment, the administering is by one or more of: intrathecal injection, intracranial injection, intravenous injection, perfusion, subcutaneous injection, intraperitoneal injection, intraportal injection, and topical delivery.

TABLE 4

Exemplary BIRC5 Binding Sites

| Gene | # | Left | SEQ ID NO | Right | SEQ ID NO | Spacing |
|---|---|---|---|---|---|---|
| BIRC5 | 1 | TGGGTGCCCCGACGTTGCCC | 18 | TGCGGTGGTCCTTGAGAAAG | 19 | 14 |
| BIRC5 | 2 | TGGGTGCCCCGACGTTGCCC | 93 | TAGAGATGCGGTGGTCCTTG | 94 | 20 |
| BIRC5 | 3 | TGCCCCGACGTTGCCCCTG | 95 | TAGAGATGCGGTGGTCCTTG | 96 | 16 |
| BIRC5 | 4 | TGCCCCGACGTTGCCCCTG | 97 | TGTAGAGATGCGGTGGTCCT | 98 | 18 |
| BIRC5 | 5 | TCAAGGACCACCGCATCTCT | 20 | TGCAGGCGCAGCCCTCCAAG | 21 | 20 |
| BIRC5 | 6 | TCTCTACATTCAAGAACTGG | 99 | TCACCCGCTCCGGGGTGCAG | 100 | 20 |
| BIRC5 | 7 | TCTACATTCAAGAACTGGCC | 101 | TCACCCGCTCCGGGGTGCAG | 102 | 18 |
| BIRC5 | 8 | TCTACATTCAAGAACTGGCC | 103 | TCTCACCCGCTCCGGGGTGC | 104 | 20 |
| BIRC5 | 9 | TACATTCAAGAACTGGCCCT | 105 | TCACCCGCTCCGGGGTGCAG | 106 | 16 |
| BIRC5 | 10 | TACATTCAAGAACTGGCCCT | 107 | TCTCACCCGCTCCGGGGTGC | 108 | 18 |
| BIRC5 | 11 | TTCAAGAACTGGCCCTTCTT | 109 | TCTCACCCGCTCCGGGGTGC | 110 | 14 |
| BIRC5 | 1 | TCCCTTGCAGATGGCCGAGG | 111 | TGGCTCGTTCTCAGTGGGGC | 112 | 15 |
| BIRC5 | 2 | TCCCTTGCAGATGGCCGAGG | 113 | TCTGGCTCGTTCTCAGTGGG | 114 | 17 |

TABLE 4-continued

Exemplary BIRC5 Binding Sites

| Gene | # | Left | SEQ ID NO | Right | SEQ ID NO | Spacing |
|---|---|---|---|---|---|---|
| BIRC5 | 3 | TGGCCGAGGCTGGCTTCATC | 22 | TGGGCCAAGTCTGGCTCGTT | 23 | 15 |
| BIRC5 | 4 | TCCACTGCCCCACTGAGAAC | 115 | TCCTTGAAGCAGAAGAAACA | 116 | 18 |
| BIRC5 | 5 | TGCCCCACTGAGAACGAGCC | 117 | TCCAGCTCCTTGAAGCAGAA | 118 | 19 |
| BIRC5 | 6 | TGCCCCACTGAGAACGAGCC | 119 | TTCCAGCTCCTTGAAGCAGA | 120 | 20 |
| BIRC5 | 7 | TTGGCCCAGTGTTTCTTCTG | 24 | TCGTCATCTGGCTCCCAGCC | 25 | 16 |
| BIRC5 | 8 | TGGCCCAGTGTTTCTTCTGC | 121 | TCGTCATCTGGCTCCCAGCC | 122 | 15 |
| BIRC5 | 9 | TGGCCCAGTGTTTCTTCTGC | 123 | TGGGGTCGTCATCTGGCTCC | 124 | 20 |
| BIRC5 | 10 | TGTTTCTTCTGCTTCAAGGA | 125 | TACATGGGGTCGTCATCTGG | 126 | 16 |
| BIRC5 | 11 | TGTTTCTTCTGCTTCAAGGA | 127 | TTACATGGGGTCGTCATCTG | 128 | 17 |
| BIRC5 | 12 | TTTCTTCTGCTTCAAGGAGC | 129 | TACATGGGGTCGTCATCTGG | 130 | 14 |
| BIRC5 | 13 | TTTCTTCTGCTTCAAGGAGC | 131 | TTACATGGGGTCGTCATCTG | 132 | 15 |
| BIRC5 | 14 | TTCTTCTGCTTCAAGGAGCT | 133 | TTACATGGGGTCGTCATCTG | 134 | 14 |
| BIRC5 | 1 | TTTTCTAGAGAGGAACATAA | 135 | TGACAGAAAGGAAAGCGCAA | 136 | 15 |
| BIRC5 | 2 | TTTTCTAGAGAGGAACATAA | 137 | TTGACAGAAAGGAAAGCGCA | 138 | 16 |
| BIRC5 | 3 | TTTTCTAGAGAGGAACATAA | 139 | TCTTGACAGAAAGGAAAGCG | 140 | 18 |
| BIRC5 | 4 | TAGAGAGGAACATAAAAAGC | 141 | TGCTTCTTGACAGAAAGGAA | 142 | 17 |
| BIRC5 | 5 | TAAAAAGCATTCGTCCGGTT | 143 | TCTTCAAACTGCTTCTTGAC | 144 | 14 |
| BIRC5 | 6 | TAAAAAGCATTCGTCCGGTT | 145 | TTCTTCAAACTGCTTCTTGA | 146 | 15 |
| BIRC5 | 7 | TAAAAAGCATTCGTCCGGTT | 147 | TAATTCTTCAAACTGCTTCT | 148 | 18 |
| BIRC5 | 8 | TAAAAAGCATTCGTCCGGTT | 149 | TTAATTCTTCAAACTGCTTC | 150 | 19 |
| BIRC5 | 9 | TTCGTCCGGTTGCGCTTTCC | 151 | TCACCAAGGGTTAATTCTTC | 152 | 20 |
| BIRC5 | 10 | TCGTCCGGTTGCGCTTTCCT | 153 | TCACCAAGGGTTAATTCTTC | 154 | 19 |
| BIRC5 | 11 | TCGTCCGGTTGCGCTTTCCT | 155 | TTCACCAAGGGTTAATTCTT | 156 | 20 |
| BIRC5 | 12 | TCCGGTTGCGCTTTCCTTTC | 157 | TCACCAAGGGTTAATTCTTC | 158 | 16 |

TABLE 4-continued

Exemplary BIRC5 Binding Sites

| Gene | # | Left | SEQ ID NO | Right | SEQ ID NO | Spacing |
|---|---|---|---|---|---|---|
| BIRC5 | 13 | TCCGGTTGCGCTTTCCTTTC | 159 | TTCACCAAGGGTTAATTCTT | 160 | 17 |
| BIRC5 | 14 | TTGCGCTTTCCTTTCTGTCA | 161 | TCAAAAATTCACCAGGGTT | 162 | 19 |
| BIRC5 | 15 | TTGCGCTTTCCTTTCTGTCA | 163 | TTCAAAAATTCACCAGGGT | 164 | 20 |
| BIRC5 | 16 | TGCGCTTTCCTTTCTGTCAA | 26 | TCAAAAATTCACCAGGGTT | 27 | 18 |
| BIRC5 | 17 | TGCGCTTTCCTTTCTGTCAA | 165 | TTCAAAAATTCACCAGGGT | 166 | 19 |
| BIRC5 | 18 | TGCGCTTTCCTTTCTGTCAA | 167 | TTTCAAAAATTCACCAAGGG | 168 | 20 |
| BIRC5 | 19 | TTTCCTTTCTGTCAAGAAGC | 169 | TTCAAAAATTCACCAGGGT | 170 | 14 |
| BIRC5 | 20 | TTTCCTTTCTGTCAAGAAGC | 171 | TTTCAAAAATTCACCAAGGG | 172 | 15 |
| BIRC5 | 21 | TTTCCTTTCTGTCAAGAAGC | 173 | TCCAGTTTCAAAAATTCACC | 174 | 20 |
| BIRC5 | 22 | TTCCTTTCTGTCAAGAAGCA | 175 | TTTCAAAAATTCACCAAGGG | 176 | 14 |
| BIRC5 | 23 | TTCCTTTCTGTCAAGAAGCA | 177 | TCCAGTTTCAAAAATTCACC | 178 | 19 |
| BIRC5 | 24 | TCCTTTCTGTCAAGAAGCAG | 179 | TCCAGTTTCAAAAATTCACC | 180 | 18 |
| BIRC5 | 25 | TCCTTTCTGTCAAGAAGCAG | 181 | TGTCCAGTTTCAAAAATTCA | 182 | 20 |
| BIRC5 | 26 | TTTCTGTCAAGAAGCAGTTT | 183 | TCCAGTTTCAAAAATTCACC | 184 | 15 |
| BIRC5 | 27 | TTTCTGTCAAGAAGCAGTTT | 185 | TGTCCAGTTTCAAAAATTCA | 186 | 17 |
| BIRC5 | 28 | TTTCTGTCAAGAAGCAGTTT | 187 | TCTGTCCAGTTTCAAAAATT | 188 | 19 |
| BIRC5 | 29 | TTCTGTCAAGAAGCAGTTTG | 189 | TCCAGTTTCAAAAATTCACC | 190 | 14 |
| BIRC5 | 30 | TTCTGTCAAGAAGCAGTTTG | 191 | TGTCCAGTTTCAAAAATTCA | 192 | 16 |
| BIRC5 | 31 | TTCTGTCAAGAAGCAGTTTG | 193 | TCTGTCCAGTTTCAAAAATT | 194 | 18 |
| BIRC5 | 32 | TTCTGTCAAGAAGCAGTTTG | 195 | TCTCTGTCCAGTTTCAAAAA | 196 | 20 |
| BIRC5 | 33 | TCTGTCAAGAAGCAGTTTGA | 197 | TGTCCAGTTTCAAAAATTCA | 198 | 15 |
| BIRC5 | 34 | TCTGTCAAGAAGCAGTTTGA | 199 | TCTGTCCAGTTTCAAAAATT | 200 | 17 |
| BIRC5 | 35 | TCTGTCAAGAAGCAGTTTGA | 201 | TCTCTGTCCAGTTTCAAAAA | 202 | 19 |
| BIRC5 | 36 | TCTGTCAAGAAGCAGTTTGA | 203 | TTCTCTGTCCAGTTTCAAAA | 204 | 20 |

TABLE 4-continued

Exemplary BIRC5 Binding Sites

| Gene | # | Left | SEQ ID NO | Right | SEQ ID NO | Spacing |
|---|---|---|---|---|---|---|
| BIRC5 | 37 | TGTCAAGAAGCAGTTTGAAG | 205 | TCTGTCCAGTTTCAAAAATT | 206 | 15 |
| BIRC5 | 38 | TGTCAAGAAGCAGTTTGAAG | 207 | TCTCTGTCCAGTTTCAAAAA | 208 | 17 |
| BIRC5 | 39 | TGTCAAGAAGCAGTTTGAAG | 209 | TTCTCTGTCCAGTTTCAAAA | 210 | 18 |
| BIRC5 | 40 | TGTCAAGAAGCAGTTTGAAG | 211 | TTTCTCTGTCCAGTTTCAAA | 212 | 19 |
| BIRC5 | 41 | TCAAGAAGCAGTTTGAAGAA | 213 | TCTCTGTCCAGTTTCAAAAA | 214 | 15 |
| BIRC5 | 42 | TCAAGAAGCAGTTTGAAGAA | 215 | TTCTCTGTCCAGTTTCAAAA | 216 | 16 |
| BIRC5 | 43 | TCAAGAAGCAGTTTGAAGAA | 217 | TTTCTCTGTCCAGTTTCAAA | 218 | 17 |
| BIRC5 | 44 | TTTGAAGAATTAACCCTTGG | 219 | TCTTGGCTCTTTCTCTGTCC | 220 | 15 |
| BIRC5 | 45 | TTGAAGAATTAACCCTTGGT | 221 | TCTTGGCTCTTTCTCTGTCC | 222 | 14 |
| BIRC5 | 46 | TTGAAGAATTAACCCTTGGT | 223 | TTCTTGGCTCTTTCTCTGTC | 224 | 15 |
| BIRC5 | 47 | TGAAGAATTAACCCTTGGTG | 225 | TTCTTGGCTCTTTCTCTGTC | 226 | 14 |
| BIRC5 | 48 | TGAAGAATTAACCCTTGGTG | 227 | TGTTCTTGGCTCTTTCTCTG | 228 | 16 |
| BIRC5 | 49 | TTAACCCTTGGTGAATTTTT | 229 | TACAATTTTGTTCTTGGCTC | 230 | 17 |
| BIRC5 | 50 | TAACCCTTGGTGAATTTTTG | 231 | TACAATTTTGTTCTTGGCTC | 232 | 16 |
| BIRC5 | 51 | TAACCCTTGGTGAATTTTTG | 233 | TACATACAATTTTGTTCTTG | 234 | 20 |
| BIRC5 | 52 | TTGGTGAATTTTTGAAACTG | 235 | TACATACAATTTTGTTCTTG | 236 | 14 |
| BIRC5 | 1 | TTATTTCCAGGCAAAGGAAA | 237 | TCCGCAGTTTCCTCAAATTC | 238 | 17 |
| BIRC5 | 2 | TTATTTCCAGGCAAAGGAAA | 239 | TCTCCGCAGTTTCCTCAAAT | 240 | 19 |
| BIRC5 | 3 | TTATTTCCAGGCAAAGGAAA | 241 | TTCTCCGCAGTTTCCTCAAA | 242 | 20 |
| BIRC5 | 4 | TATTTCCAGGCAAAGGAAAC | 243 | TCCGCAGTTTCCTCAAATTC | 244 | 16 |
| BIRC5 | 5 | TATTTCCAGGCAAAGGAAAC | 245 | TCTCCGCAGTTTCCTCAAAT | 246 | 18 |
| BIRC5 | 6 | TATTTCCAGGCAAAGGAAAC | 247 | TTCTCCGCAGTTTCCTCAAA | 248 | 19 |
| BIRC5 | 7 | TATTTCCAGGCAAAGGAAAC | 249 | TTTCTCCGCAGTTTCCTCAA | 250 | 20 |
| BIRC5 | 8 | TCCAGGCAAAGGAAACCAAC | 251 | TCTCCGCAGTTTCCTCAAAT | 252 | 14 |

TABLE 4-continued

Exemplary BIRC5 Binding Sites

| Gene | # | Left | SEQ ID NO | Right | SEQ ID NO | Spacing |
|------|---|------|-----------|-------|-----------|---------|
| BIRC5 | 9 | TCCAGGCAAAGGAAACCAAC | 253 | TTCTCCGCAGTTTCCTCAAA | 254 | 15 |
| BIRC5 | 10 | TCCAGGCAAAGGAAACCAAC | 255 | TTTCTCCGCAGTTTCCTCAA | 256 | 16 |
| BIRC5 | 11 | TTTGAGGAAACTGCGGAGAA | 257 | TCCATGGCAGCCAGCTGCTC | 258 | 16 |
| BIRC5 | 12 | TTTGAGGAAACTGCGGAGAA | 259 | TCAATCCATGGCAGCCAGCT | 260 | 20 |
| BIRC5 | 13 | TTGAGGAAACTGCGGAGAAA | 261 | TCCATGGCAGCCAGCTGCTC | 262 | 15 |
| BIRC5 | 14 | TTGAGGAAACTGCGGAGAAA | 263 | TCAATCCATGGCAGCCAGCT | 264 | 19 |
| BIRC5 | 15 | TGAGGAAACTGCGGAGAAAG | 265 | TCCATGGCAGCCAGCTGCTC | 266 | 14 |
| BIRC5 | 16 | TGAGGAAACTGCGGAGAAAG | 267 | TCAATCCATGGCAGCCAGCT | 268 | 18 |

Certain embodiments are directed to a method for treating cancer comprising: a. removing a biopsy containing one or more cancerous cells from a patient, b. determining the sequence of a cancer-associated genetic marker in the one or more cancerous cells, and c. administering to the patient a therapeutically effective amount of a gene-editing protein or a nucleic acid encoding a gene-editing protein, wherein the sequence of the target DNA molecule is at least about 50% or about 60% or about 70% or about 80% or about 90% or about 95% or about 98%, or about 99% homologous to the sequence of the cancer-associated genetic marker. In one embodiment, the method further comprises comparing the sequence of one or more cancer-associated genetic markers in the one or more cancerous cells to the sequence of the same cancer-associated genetic markers in one or more non-cancerous cells, selecting a cancer-associated genetic marker having a sequence that is different in the one or more cancerous cells and the one or more non-cancerous cells, and wherein the sequence of the target DNA molecule or binding site is at least about 50% or about 60% or about 70% or about 80% or about 90% or about 95% or about 98% or about 99% homologous to the sequence of the selected cancer-associated genetic marker.

Many cancer cells express survivin, a member of the inhibitor of apoptosis (IAP) protein family that, in humans, is encoded by the BIRC5 gene. Using RNA interference to reduce expression of certain mRNA molecules, including survivin mRNA, can transiently inhibit the growth of certain cancer cells. However, previous methods of using RNA interference to reduce expression of survivin mRNA yield temporary effects, and result in only a short increase in mean time-to-death (TTD) in animal models. It has now been discovered that inducing a cell to express one or more gene-editing proteins that target the BIRC5 gene can result in disruption of the BIRC5 gene, can induce the cell to express and/or secrete a non-functional variant of survivin protein, can induce the cell to express and/or secrete a dominant-negative variant of survivin protein, can trigger activation of one or more apoptosis pathways in the cell and nearby cells, can slow or halt the growth of the cell and nearby cells, can result in the death of the cell and nearby cells, can inhibit the progression of cancer, and can result in remission in a cancer patient. Certain embodiments are therefore directed to a gene-editing protein that targets the BIRC5 gene. In one embodiment, the gene-editing protein binds to one or more regions in the BIRC5 gene. In another embodiment, the gene-editing protein binds to one or more regions of a sequence selected from: SEQ ID NO: 12, SEQ ID NO: 13, SEQ ID NO: 14, and SEQ ID NO: 15. In a further embodiment, the gene-editing protein binds to one or more sequences selected from: SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27. In a still further embodiment, the gene-editing protein binds to one or more nucleic-acid sequences that encode SEQ ID NO: 34 or a biologically active fragment, variant or analogue thereof. In a still further embodiment, the gene-editing protein binds to one or more sequences selected from Table 3, Table 4, Table 3 of U.S. Provisional Application No. 61/721,302, the contents of which are hereby incorporated by reference, Table 1 of U.S. Provisional Application No. 61/785,404, the contents of which are hereby incorporated by reference or Table 1 of U.S. Provisional Application No. 61/842,874, the contents of which are hereby incorporated by reference or to one or more sequences that is at least about 50% or at least about 60% or at least about 70% or at least about 80% or at least about 90% or at least about 95% or at least about 98%, or about 99% homologous to one or more sequences selected from Table 3, Table 4, Table 3 of U.S. Provisional Application No. 61/721,302, the contents of which are hereby incorporated by reference, Table 1 of U.S. Provisional Application No. 61/785,404, the contents of which are hereby incorporated by reference or Table 1 of U.S. Provisional Application No. 61/842,874, the contents of which are hereby incorporated by reference. In one embodiment, the gene-editing protein creates one or more nicks or double-strand breaks in the DNA of the cell. In another embodiment, the one or more nicks or double-strand breaks is created in the BIRC5 gene. In a further embodiment, the one or more nicks or double-strand breaks is created in one or more exons of the BIRC5 gene. In a still further embodiment, the one or more nicks or double-strand breaks is created in a sequence selected from: SEQ ID NO: 12, SEQ ID NO: 13, SEQ ID NO: 14, and SEQ ID NO: 15. In a still further embodiment, the one or more nicks or double-strand breaks is created within a sequence that encodes an inhibitor of apoptosis domain (aka. "IAP", "IAP domain", "IAP repeat", "baculovirus inhibitor of apoptosis protein repeat", "BIR", etc.). In a still further embodiment, the gene-editing protein binds to one or more sequences selected from Table 5, Table 2 of U.S. Provisional Application No. 61/785,404, the contents of which are hereby incorporated by reference or Table 2 of U.S. Provisional Application No. 61/842,874, the contents of which are hereby incorporated by reference or to one or more sequences that is at least about 50% or at least about 60% or at least about 70% or at least about 80% or at least about 90% or at least about 95% or at least about 98% homologous to one or more sequences selected from Table 5, Table 2 of U.S. Provisional Application No. 61/785,404, the contents of which are hereby incorporated by reference or Table 2 of U.S. Provisional Application No. 61/842,874, the contents of which are hereby incorporated by reference. In yet another embodiment, the gene editing protein binds to a sequence that encodes one or more genes selected from Table 2, Table 5, Table 6, Table 7, Table 4 of U.S. Provisional Application No. 61/721,302, the contents of which are hereby incorporated by reference, Table 2 of U.S. Provisional Application No. 61/785,404, the contents of which are hereby incorporated by reference or Table 2 of U.S. Provisional Application No. 61/842,874, the contents of which are hereby incorporated by reference.

TABLE 5

Exemplary Cancer-Associated Gene Binding Sites

| Gene | # | Left | SEQ ID NO | Right | SEQ ID NO | Spacing |
|---|---|---|---|---|---|---|
| CDK1 | 1 | TTTAGGATCTACCATACCCA | 269 | TCTCTATTTTGGTATAATCT | 270 | 15 |
| CDK1 | 2 | TTTAGGATCTACCATACCCA | 271 | TTCTCTATTTTGGTATAATC | 272 | 16 |
| CDK1 | 3 | TTTAGGATCTACCATACCCA | 273 | TTTCTCTATTTTGGTATAAT | 274 | 17 |
| CDK1 | 4 | TTAGGATCTACCATACCCAT | 275 | TCTCTATTTTGGTATAATCT | 276 | 14 |
| CDK1 | 5 | TTAGGATCTACCATACCCAT | 277 | TTCTCTATTTTGGTATAATC | 278 | 15 |
| CDK1 | 1 | TCACACAGCATATTATTTAC | 279 | TACCCTTATACACAACTCCA | 280 | 17 |
| CDK1 | 2 | TCACACAGCATATTATTTAC | 281 | TCTACCCTTATACACAACTC | 282 | 19 |
| CDK1 | 3 | TACTTTGTTTCAGGTACCTA | 283 | TGTAGTTTTGTGTCTACCCT | 284 | 14 |
| CDK1 | 4 | TACTTTGTTTCAGGTACCTA | 285 | TGACCTGTAGTTTTGTGTCT | 286 | 19 |
| CDK1 | 5 | TTTGTTTCAGGTACCTATGG | 287 | TGACCTGTAGTTTTGTGTCT | 288 | 16 |
| CDK2 | 1 | TGACCCGACTCGCTGGCGCT | 289 | TCCGATCTTTTCCACCTTTT | 290 | 15 |
| CDK2 | 2 | TGACCCGACTCGCTGGCGCT | 291 | TCTCCGATCTTTTCCACCTT | 292 | 17 |
| CDK2 | 3 | TCGCTGGCGCTTCATGGAGA | 293 | TACGTGCCCTCTCCGATCTT | 294 | 17 |
| CDK2 | 4 | TTCATGGAGAACTTCCAAAA | 295 | TACACAACTCCGTACGTGCC | 296 | 19 |
| CDK2 | 5 | TCATGGAGAACTTCCAAAAG | 297 | TACACAACTCCGTACGTGCC | 298 | 18 |
| CDK2 | 1 | TTTCCCAACCTCTCCAAGTG | 299 | TCTCGGATGGCAGTACTGGG | 300 | 14 |
| CDK2 | 2 | TTCCCAACCTCTCCAAGTGA | 301 | TCTCTCGGATGGCAGTACTG | 302 | 15 |

TABLE 5-continued

Exemplary Cancer-Associated Gene Binding Sites

| Gene | # | Left | SEQ ID NO | Right | SEQ ID NO | Spacing |
|---|---|---|---|---|---|---|
| CDK2 | 3 | TCCCAACCTCTCCAAGTGAG | 303 | TCTCTCGGATGGCAGTACTG | 304 | 14 |
| CDK2 | 4 | TCTCCAAGTGAGACTGAGGG | 305 | TAAGCAGAGAGATCTCTCGG | 306 | 18 |
| CDK2 | 5 | TCTCCAAGTGAGACTGAGGG | 307 | TTAAGCAGAGAGATCTCTCG | 308 | 19 |
| CDK3 | 1 | TGTTTCCCAGGCAGCTCTGT | 309 | TCTCCGATCTTCTCTACCTT | 310 | 19 |
| CDK3 | 2 | TTTCCCAGGCAGCTCTGTGG | 311 | TCTCCGATCTTCTCTACCTT | 312 | 17 |
| CDK3 | 3 | TTCCCAGGCAGCTCTGTGGC | 313 | TCTCCGATCTTCTCTACCTT | 314 | 16 |
| CDK3 | 4 | TCCCAGGCAGCTCTGTGGCC | 315 | TCTCCGATCTTCTCTACCTT | 316 | 15 |
| CDK3 | 5 | TGGATATGTTCCAGAAGGTA | 317 | TACACCACCCCATAGGTGCC | 318 | 15 |
| CDK3 | 1 | TGCCCACGGCTGTGCCCTTG | 319 | TGGCAGTGCTTGGGACCCCC | 320 | 19 |
| CDK3 | 2 | TGTGCCCTTGTTTCTTGCAG | 321 | TCCCTGATGGCAGTGCTTGG | 322 | 16 |
| CDK3 | 3 | TTTCTTGCAGGGAGATGGAG | 323 | TGAGCAGCGAGATCTCCCTG | 324 | 20 |
| CDK3 | 4 | TTCTTGCAGGGAGATGGAGG | 325 | TGAGCAGCGAGATCTCCCTG | 326 | 19 |
| CDK3 | 5 | TTCTTGCAGGGAGATGGAGG | 327 | TTGAGCAGCGAGATCTCCCT | 328 | 20 |
| CDK4 | 1 | TGTGATTGTAGGGTCTCCCT | 329 | TGGCTCATATCGAGAGGTAG | 330 | 14 |
| CDK4 | 2 | TGATTGTAGGGTCTCCCTTG | 331 | TCAGCCACTGGCTCATATCG | 332 | 20 |
| CDK4 | 3 | TTGTAGGGTCTCCCTTGATC | 333 | TCAGCCACTGGCTCATATCG | 334 | 17 |
| CDK4 | 4 | TGTAGGGTCTCCCTTGATCT | 335 | TCAGCCACTGGCTCATATCG | 336 | 16 |
| CDK4 | 5 | TAGGGTCTCCCTTGATCTGA | 337 | TCAGCCACTGGCTCATATCG | 338 | 14 |
| CDK4 | 1 | TTGAAAAGTGAGCATTTACT | 339 | TCGGGATGTGGCACAGACGT | 340 | 16 |
| CDK4 | 2 | TTGAAAAGTGAGCATTTACT | 341 | TTCGGGATGTGGCACAGACG | 342 | 17 |
| CDK4 | 3 | TGAAAAGTGAGCATTTACTC | 343 | TCGGGATGTGGCACAGACGT | 344 | 15 |
| CDK4 | 4 | TGAAAAGTGAGCATTTACTC | 345 | TTCGGGATGTGGCACAGACG | 346 | 16 |
| CDK4 | 5 | TGAAAAGTGAGCATTTACTC | 347 | TCAGTTCGGGATGTGGCACA | 348 | 20 |
| CDK5 | 1 | TACGAGAAACTGGAAAAGAT | 349 | TGCAGGAACATCTCGAGATT | 350 | 15 |

TABLE 5-continued

Exemplary Cancer-Associated Gene Binding Sites

| Gene | # | Left | SEQ ID NO | Right | SEQ ID NO | Spacing |
|---|---|---|---|---|---|---|
| CDK5 | 2 | TACGAGAAACTGGAAAAGAT | 351 | TTGCAGGAACATCTCGAGAT | 352 | 16 |
| CDK5 | 3 | TACGAGAAACTGGAAAAGAT | 353 | TCTTGCAGGAACATCTCGAG | 354 | 18 |
| CDK5 | 1 | TCCTTCCCCTAGGCACCTAC | 355 | TGAGTCTCCCGGTTTTTGGC | 356 | 15 |
| CDK5 | 2 | TCCTTCCCCTAGGCACCTAC | 357 | TCATGAGTCTCCCGGTTTTT | 358 | 18 |
| CDK5 | 3 | TCCTTCCCCTAGGCACCTAC | 359 | TCTCATGAGTCTCCCGGTTT | 360 | 20 |
| CDK5 | 4 | TTCCCCTAGGCACCTACGGA | 361 | TCATGAGTCTCCCGGTTTTT | 362 | 15 |
| CDK5 | 5 | TTCCCCTAGGCACCTACGGA | 363 | TCTCATGAGTCTCCCGGTTT | 364 | 17 |
| CDK6 | 1 | TGTGCCGCGCTGACCAGCAG | 365 | TAGGCGCCCTCCCCGATCTC | 366 | 15 |
| CDK6 | 2 | TGTGCCGCGCTGACCAGCAG | 367 | TCCCATAGGCGCCCTCCCCG | 368 | 20 |
| CDK6 | 3 | TGCCGCGCTGACCAGCAGTA | 369 | TCCCATAGGCGCCCTCCCCG | 370 | 18 |
| CDK6 | 4 | TGCCGCGCTGACCAGCAGTA | 371 | TTCCCATAGGCGCCCTCCCC | 372 | 19 |
| CDK6 | 5 | TGACCAGCAGTACGAATGCG | 373 | TGAACACCTTCCCATAGGCG | 374 | 19 |
| CDK6 | 1 | TCTAGGTTGTTTGATGTGTG | 375 | TAGTTTGGTTTCTCTGTCTG | 376 | 14 |
| CDK6 | 2 | TCTAGGTTGTTTGATGTGTG | 377 | TAAAGTTAGTTTGGTTTCTC | 378 | 20 |
| CDK6 | 3 | TAGGTTGTTTGATGTGTGCA | 379 | TAAAGTTAGTTTGGTTTCTC | 380 | 18 |
| CDK6 | 4 | TTGTTTGATGTGTGCACAGT | 381 | TAAAGTTAGTTTGGTTTCTC | 382 | 14 |
| CDK6 | 5 | TTGATGTGTGCACAGTGTCA | 383 | TCAAACACTAAAGTTAGTTT | 384 | 18 |
| EGFR | 1 | TCCGGGACGGCCGGGGCAGC | 385 | TCGCCGGGCAGAGCGCAGCC | 386 | 15 |
| EGFR | 1 | TCTTCCAGTTTGCCAAGGCA | 387 | TCAAAAGTGCCCAACTGCGT | 388 | 14 |
| EGFR | 2 | TCTTCCAGTTTGCCAAGGCA | 389 | TGATCTTCAAAAGTGCCCAA | 390 | 20 |
| EGFR | 3 | TTCCAGTTTGCCAAGGCACG | 391 | TGATCTTCAAAAGTGCCCAA | 392 | 18 |
| EGFR | 4 | TCCAGTTTGCCAAGGCACGA | 393 | TGATCTTCAAAAGTGCCCAA | 394 | 17 |
| EGFR | 5 | TCACGCAGTTGGGCACTTTT | 395 | TGAACATCCTCTGGAGGCTG | 396 | 14 |
| HIF1A | 1 | TGAAGACATCGCGGGGACCG | 397 | TGTCGTTCGCGCCGCCGGCG | 398 | 15 |

TABLE 5-continued

Exemplary Cancer-Associated Gene Binding Sites

| Gene | # | Left | SEQ ID NO | Right | SEQ ID NO | Spacing |
|---|---|---|---|---|---|---|
| HIF1A | 2 | TGAAGACATCGCGGGGACCG | 399 | TTGTCGTTCGCGCCGCCGGC | 400 | 16 |
| HIF1A | 3 | TGAAGACATCGCGGGGACCG | 401 | TCTTGTCGTTCGCGCGCCG | 402 | 18 |
| HIF1A | 4 | TGAAGACATCGCGGGGACCG | 403 | TTCTTGTCGTTCGCGCCGCC | 404 | 19 |
| HIF1A | 5 | TGAAGACATCGCGGGGACCG | 405 | TTTCTTGTCGTTCGCGCCGC | 406 | 20 |
| HIF1A | 1 | TCTCGTGTTTTCTTGTTGT | 407 | TCTTTTCGACGTTCAGAACT | 408 | 14 |
| HIF1A | 2 | TCTCGTGTTTTCTTGTTGT | 409 | TTCTTTTCGACGTTCAGAAC | 410 | 15 |
| HIF1A | 3 | TCTCGTGTTTTCTTGTTGT | 411 | TTTCTTTTCGACGTTCAGAA | 412 | 16 |
| HIF1A | 4 | TCTCGTGTTTTCTTGTTGT | 413 | TTTTCTTTTCGACGTTCAGA | 414 | 17 |
| HIF1A | 5 | TTCTTGTTGTTGTTAAGTAG | 415 | TCGAGACTTTTCTTTTCGAC | 416 | 14 |
| HSPA4 | 1 | TGGTGGGCATAGACCTGGGC | 417 | TGCCGCCGGCGCGGGCCACA | 418 | 20 |
| HSPA4 | 2 | TGGGCATAGACCTGGGCTTC | 419 | TGCCGCCGGCGCGGGCCACA | 420 | 17 |
| HSPA4 | 3 | TAGACCTGGGCTTCCAGAGC | 421 | TCGATGCCGCCGGCGCGGGC | 422 | 15 |
| HSPA4 | 4 | TAGACCTGGGCTTCCAGAGC | 423 | TCTCGATGCCGCCGGCGCGG | 424 | 17 |
| HSPA4 | 5 | TAGACCTGGGCTTCCAGAGC | 425 | TAGTCTCGATGCCGCCGGCG | 426 | 20 |
| HSPA4 | 1 | TCTTAAGTGCTTTTTTTGTC | 427 | TGAACGATTCTTAGGACCAA | 428 | 20 |
| HSPA4 | 2 | TTAAGTGCTTTTTTTGTCTT | 429 | TGAACGATTCTTAGGACCAA | 430 | 18 |
| HSPA4 | 3 | TTAAGTGCTTTTTTTGTCTT | 431 | TTGAACGATTCTTAGGACCA | 432 | 19 |
| HSPA4 | 4 | TAAGTGCTTTTTTTGTCTTC | 433 | TGAACGATTCTTAGGACCAA | 434 | 17 |
| HSPA4 | 5 | TAAGTGCTTTTTTTGTCTTC | 435 | TTGAACGATTCTTAGGACCA | 436 | 18 |
| HSP90AA1 | 1 | TGCCCCCGTGTTCGGGCGGG | 437 | TCCCGAAGGGAGGGCCCAGG | 438 | 15 |
| HSP90AA1 | 2 | TGCCCCCGTGTTCGGGCGGG | 439 | TGTCCCGAAGGGAGGGCCCA | 440 | 17 |
| HSP90AA1 | 3 | TCCTGGGCCCTCCCTTCGGG | 441 | TCGCGCGGGTATTCAGCACT | 442 | 20 |
| HSP90AA1 | 4 | TGGGCCCTCCCTTCGGGACA | 443 | TCGCGCGGGTATTCAGCACT | 444 | 17 |
| HSP90AA1 | 5 | TCCCTTCGGGACAGGGACTG | 445 | TCCAGACGGTCGCGCGGGTA | 446 | 19 |

TABLE 5-continued

Exemplary Cancer-Associated Gene Binding Sites

| Gene | # | Left | SEQ ID NO | Right | SEQ ID NO | Spacing |
|---|---|---|---|---|---|---|
| HSP90AA1 | 1 | TCCAGAAGATTGTGTTTATG | 447 | TCTTGGTACCAGTTAACAGG | 448 | 14 |
| HSP90AA1 | 2 | TGTGTTTATGTTCCCAGCAG | 449 | TTGGGCCTTTTCTTGGTACC | 450 | 14 |
| HSP90AA1 | 3 | TCCCAGCAGGGCACCTGTTA | 451 | TGCCAGAGAAACACTTGGGC | 452 | 17 |
| HSP90AA1 | 4 | TAACTGGTACCAAGAAAAGG | 453 | TCCAGACACCATCAGATGCC | 454 | 15 |
| HSP90AA1 | 5 | TAACTGGTACCAAGAAAAGG | 455 | TGGATCCAGACACCATCAGA | 456 | 19 |
| MYC | 1 | TCCAGCAGCCTCCCGCGACG | 457 | TAGTTCCTGTTGGTGAAGCT | 458 | 15 |
| MYC | 2 | TCCAGCAGCCTCCCGCGACG | 459 | TCATAGTTCCTGTTGGTGAA | 460 | 18 |
| MYC | 3 | TCCCGCGACGATGCCCCTCA | 461 | TCGAGGTCATAGTTCCTGTT | 462 | 14 |
| MYC | 4 | TCCCGCGACGATGCCCCTCA | 463 | TAGTCGAGGTCATAGTTCCT | 464 | 17 |
| MYC | 5 | TCCCGCGACGATGCCCCTCA | 465 | TCGTAGTCGAGGTCATAGTT | 466 | 20 |
| PKN3 | 1 | TGCAGCCTGGGCCGAGCCAG | 467 | TGGCCCGGCGGATCACCTCC | 468 | 20 |
| PKN3 | 2 | TGGGCCGAGCCAGTGGCCCC | 469 | TGGATGGCCCGGCGGATCAC | 470 | 17 |
| PKN3 | 3 | TGGGCCGAGCCAGTGGCCCC | 471 | TCTGGATGGCCCGGCGGATC | 472 | 19 |
| PKN3 | 4 | TGGGCCGAGCCAGTGGCCCC | 473 | TTCTGGATGGCCCGGCGGAT | 474 | 20 |
| PKN3 | 5 | TGGCCCCAGAGGATGAGAA | 475 | TCAGCTCTTTCTGGATGGCC | 476 | 15 |
| RRM2 | 1 | TGGGAAGGGTCGGAGGCATG | 477 | TGGCTTTGGTGCCCCGGCCC | 478 | 16 |
| RRM2 | 2 | TGGGAAGGGTCGGAGGCATG | 479 | TTGGCTTTGGTGCCCCGGCC | 480 | 17 |
| RRM2 | 3 | TCGGAGGCATGGCACAGCCA | 481 | TTCCCATTGGCTTTGGTGCC | 482 | 14 |
| RRM2 | 4 | TGGCACAGCCAATGGGAAGG | 483 | TCCCGGCCCTTCCCATTGGC | 484 | 14 |
| RRM2 | 5 | TGCACCCTGTCCCAGCCGTC | 485 | TGGAGGCGCAGCGAAGCAGA | 486 | 17 |
| APC | 1 | TATGTACGCCTCCCTGGGCT | 487 | TGGTACAGAAGCGGGCAAAG | 488 | 15 |
| APC | 2 | TGTACGCCTCCCTGGGCTCG | 489 | TGAGGGTGGTACAGAAGCGG | 490 | 19 |
| APC | 3 | TACGCCTCCCTGGGCTCGGG | 491 | TGAGGGTGGTACAGAAGCGG | 492 | 17 |
| APC | 4 | TCGGGTCCGGTCGCCCCTTT | 493 | TCCAGGACCCGAGAACTGAG | 494 | 18 |

TABLE 5-continued

Exemplary Cancer-Associated Gene Binding Sites

| Gene | # | Left | SEQ ID NO | Right | SEQ ID NO | Spacing |
|---|---|---|---|---|---|---|
| APC | 5 | TCCGGTCGCCCCTTTGCCCG | 495 | TGCTCCAGGACCCGAGAACT | 496 | 16 |
| APC | 1 | TTAAACAACTACAAGGAAGT | 497 | TCAATCTGTCCAGAAGAAGC | 498 | 18 |
| APC | 2 | TAAACAACTACAAGGAAGTA | 499 | TCAATCTGTCCAGAAGAAGC | 500 | 17 |
| APC | 3 | TACAAGGAAGTATTGAAGAT | 501 | TAATAAATCAATCTGTCCAG | 502 | 16 |
| APC | 4 | TATTGAAGATGAAGCTATGG | 503 | TAAGACGCTCTAATAAATCA | 504 | 16 |
| APC | 5 | TATTGAAGATGAAGCTATGG | 505 | TTAAGACGCTCTAATAAATC | 506 | 17 |
| BRCA1 | 1 | TGGATTTATCTGCTCTTCGC | 507 | TGCATAGCATTAATGACATT | 508 | 15 |
| BRCA1 | 2 | TGGATTTATCTGCTCTTCGC | 509 | TCTGCATAGCATTAATGACA | 510 | 17 |
| BRCA1 | 3 | TTATCTGCTCTTCGCGTTGA | 511 | TAAGATTTTCTGCATAGCAT | 512 | 20 |
| BRCA1 | 4 | TATCTGCTCTTCGCGTTGAA | 513 | TAAGATTTTCTGCATAGCAT | 514 | 19 |
| BRCA1 | 5 | TCTGCTCTTCGCGTTGAAGA | 515 | TAAGATTTTCTGCATAGCAT | 516 | 17 |
| BRCA1 | 1 | TGCTAGTCTGGAGTTGATCA | 517 | TGCAAAATATGTGGTCACAC | 518 | 19 |
| BRCA1 | 2 | TGCTAGTCTGGAGTTGATCA | 519 | TTGCAAAATATGTGGTCACA | 520 | 20 |
| BRCA1 | 3 | TAGTCTGGAGTTGATCAAGG | 521 | TGCAAAATATGTGGTCACAC | 522 | 16 |
| BRCA1 | 4 | TAGTCTGGAGTTGATCAAGG | 523 | TTGCAAAATATGTGGTCACA | 524 | 17 |
| BRCA1 | 5 | TAGTCTGGAGTTGATCAAGG | 525 | TACTTGCAAAATATGTGGTC | 526 | 20 |
| BRCA2 | 1 | TGCCTATTGGATCCAAAGAG | 527 | TGCAGCGTGTCTTAAAAATT | 528 | 17 |
| BRCA2 | 2 | TGCCTATTGGATCCAAAGAG | 529 | TTGCAGCGTGTCTTAAAAAT | 530 | 18 |
| BRCA2 | 3 | TGCCTATTGGATCCAAAGAG | 531 | TGTTGCAGCGTGTCTTAAAA | 532 | 20 |
| BRCA2 | 4 | TATTGGATCCAAAGAGAGGC | 533 | TTGCAGCGTGTCTTAAAAAT | 534 | 14 |
| BRCA2 | 5 | TATTGGATCCAAAGAGAGGC | 535 | TGTTGCAGCGTGTCTTAAAA | 536 | 16 |
| BRCA2 | 1 | TAGATTTAGGACCAATAAGT | 537 | TGGAGCTTCTGAAGAAAGTT | 538 | 16 |
| BRCA2 | 2 | TTAGGACCAATAAGTCTTAA | 539 | TAGGGTGGAGCTTCTGAAGA | 540 | 16 |
| BRCA2 | 3 | TTAGGACCAATAAGTCTTAA | 541 | TATAGGGTGGAGCTTCTGAA | 542 | 18 |

TABLE 5-continued

Exemplary Cancer-Associated Gene Binding Sites

| Gene | # | Left | SEQ ID NO | Right | SEQ ID NO | Spacing |
|---|---|---|---|---|---|---|
| BRCA2 | 4 | TTAGGACCAATAAGTCTTAA | 543 | TTATAGGGTGGAGCTTCTGA | 544 | 19 |
| BRCA2 | 5 | TAGGACCAATAAGTCTTAAT | 545 | TATAGGGTGGAGCTTCTGAA | 546 | 17 |
| TP53 | 1 | TCACTGCCATGGAGGAGCCG | 547 | TGACTCAGAGGGGGCTCGAC | 548 | 15 |
| TP53 | 2 | TCACTGCCATGGAGGAGCCG | 549 | TCCTGACTCAGAGGGGGCTC | 550 | 18 |
| TP53 | 3 | TCACTGCCATGGAGGAGCCG | 551 | TTCCTGACTCAGAGGGGGCT | 552 | 19 |
| TP53 | 4 | TCACTGCCATGGAGGAGCCG | 553 | TTTCCTGACTCAGAGGGGGC | 554 | 20 |
| TP53 | 5 | TGCCATGGAGGAGCCGCAGT | 555 | TCCTGACTCAGAGGGGGCTC | 556 | 14 |
| APP | 1 | TTCTTTCAGGTACCCACTGA | 557 | TGGCAATCTGGGGTTCAGCC | 558 | 18 |
| APP | 2 | TCTTTCAGGTACCCACTGAT | 559 | TGGCAATCTGGGGTTCAGCC | 560 | 17 |
| APP | 3 | TTTCAGGTACCCACTGATGG | 561 | TGGCAATCTGGGGTTCAGCC | 562 | 15 |
| APP | 4 | TTCAGGTACCCACTGATGGT | 563 | TGGCAATCTGGGGTTCAGCC | 564 | 14 |
| APP | 5 | TACCCACTGATGGTAATGCT | 565 | TGCCACAGAACATGGCAATC | 566 | 20 |
| IAPP | 1 | TGGGCATCCTGAAGCTGCAA | 567 | TGGTTCAATGCAACAGAGAG | 568 | 15 |
| IAPP | 2 | TGGGCATCCTGAAGCTGCAA | 569 | TCAGATGGTTCAATGCAACA | 570 | 20 |
| IAPP | 3 | TGCAAGTATTTCTCATTGTG | 571 | TGGGTGTAGCTTTCAGATGG | 572 | 17 |
| IAPP | 4 | TGCTCTCTGTTGCATTGAAC | 573 | TTACCAACCTTTCAATGGGT | 574 | 14 |
| IAPP | 1 | TGTTACCAGTCATCAGGTGG | 575 | TGCGTTGCACATGTGGCAGT | 576 | 17 |
| IAPP | 2 | TTACCAGTCATCAGGTGGAA | 577 | TGCGTTGCACATGTGGCAGT | 578 | 15 |
| IAPP | 3 | TACCAGTCATCAGGTGGAAA | 579 | TGCGTTGCACATGTGGCAGT | 580 | 14 |
| IAPP | 4 | TCATCAGGTGGAAAAGCGGA | 581 | TGCCAGGCGCTGCGTTGCAC | 582 | 18 |
| IAPP | 5 | TCATCAGGTGGAAAAGCGGA | 583 | TTGCCAGGCGCTGCGTTGCA | 584 | 19 |
| SNCA | 1 | TTTTGTAGGCTCCAAAACCA | 585 | TTACCTGTTGCCACACCATG | 586 | 14 |
| SNCA | 2 | TTTTGTAGGCTCCAAAACCA | 587 | TGGAGCTTACCTGTTGCCAC | 588 | 20 |
| SNCA | 3 | TTTGTAGGCTCCAAAACCAA | 589 | TGGAGCTTACCTGTTGCCAC | 590 | 19 |

TABLE 5-continued

Exemplary Cancer-Associated Gene Binding Sites

| Gene | # | Left | SEQ ID NO | Right | SEQ ID NO | Spacing |
|---|---|---|---|---|---|---|
| SNCA | 4 | TTGTAGGCTCCAAAACCAAG | 591 | TGGAGCTTACCTGTTGCCAC | 592 | 18 |
| SNCA | 5 | TGTAGGCTCCAAAACCAAGG | 593 | TGGAGCTTACCTGTTGCCAC | 594 | 17 |
| SOD1 | 1 | TAGCGAGTTATGGCGACGAA | 595 | TGCACTGGGCCGTCGCCCTT | 596 | 16 |
| SOD1 | 2 | TTATGGCGACGAAGGCCGTG | 597 | TGCCCTGCACTGGGCCGTCG | 598 | 14 |
| SOD1 | 3 | TTATGGCGACGAAGGCCGTG | 599 | TGATGCCCTGCACTGGGCCG | 600 | 17 |
| SOD1 | 4 | TTATGGCGACGAAGGCCGTG | 601 | TGATGATGCCCTGCACTGGG | 602 | 20 |
| SOD1 | 5 | TATGGCGACGAAGGCCGTGT | 603 | TGATGCCCTGCACTGGGCCG | 604 | 16 |
| SOD1 | 1 | TAATGGACCAGTGAAGGTGT | 605 | TGCAGGCCTTCAGTCAGTCC | 606 | 14 |
| SOD1 | 2 | TAATGGACCAGTGAAGGTGT | 607 | TCCATGCAGGCCTTCAGTCA | 608 | 18 |
| SOD1 | 3 | TGGACCAGTGAAGGTGTGGG | 609 | TCCATGCAGGCCTTCAGTCA | 610 | 15 |
| SOD1 | 4 | TGGACCAGTGAAGGTGTGGG | 611 | TGGAATCCATGCAGGCCTTC | 612 | 20 |
| SOD1 | 5 | TGTGGGGAAGCATTAAAGGA | 613 | TCATGAACATGGAATCCATG | 614 | 15 |

In some embodiments, the target DNA molecule comprises a gene that is overexpressed in cancer. Example genes that are overexpressed in cancer include, but are not limited to: ABL1, BIRC5, BLK, BTK, CDK family members, EGFR, ERBB2, FAS, FGR, FLT4, FRK, FYN, HCK, HIF1A, HRAS, HSP90AA1, HSP90AA1, HSPA4, KDR, KIF11, KIF11, KIF20A, KIF21A, KIF25, KIT, KRAS, LCK, LYN, MAPK1, MET, MYC, MYH1, MYO1G, NRAS, NTRK1, PDGFB, PDGFRA, PDGFRB, PKN3, PLK1, RAF1, RB1, RET, RRM1, RRM2, SRC, TNF, TPM2, TYRO3, VEGFA, VEGFB, VEGFC, YES1, and ZAP70. In some embodiments, the target DNA molecule comprises a gene selected from: ABL1, BIRC5, BLK, BTK, a CDK family member, EGFR, ERBB2, FAS, FGR, FLT4, FRK, FYN, HCK, HIF1A, HRAS, HSP90AA1, HSP90AA1, HSPA4, KDR, KIF11, KIF11, KIF20A, KIF21A, KIF25, KIT, KRAS, LCK, LYN, MAPK1, MET, MYC, MYH1, MYO1G, NRAS, NTRK1, PDGFB, PDGFRA, PDGFRB, PKN3, PLK1, RAF1, RB1, RET, RRM1, RRM2, SRC, TNF, TPM2, TYRO3, VEGFA, VEGFB, VEGFC, YES1, and ZAP70 or a fragment or variant thereof. In other embodiments, the target DNA molecule comprises a gene that is mutated in cancer. Example genes that are mutated in cancer include, but are not limited to: AIM1, APC, BRCA1, BRCA2, CDKN1B, CDKN2A, FAS, FZD family members, HNF1A, HOPX, KLF6, MEN1, MLH1, NTRK1, PTEN, RARRES1, RB1, SDHB, SDHD, SFRP1, ST family members, TNF, TP53, TP63, TP73, VBP1, VHL, WNT family members, BRAF, CTNNB1, PIK3CA, PIK3R1, SMAD4, and YPEL3. In some embodiments, the target DNA molecule comprises a gene selected from: AIM1, APC, BRCA1, BRCA2, CDKN1B, CDKN2A, FAS, a FZD family member, HNF1A, HOPX, KLF6, MEN1, MLH1, NTRK1, PTEN, RARRES1, RB1, SDHB, SDHD, SFRP1, a ST family member, TNF, TP53, TP63, TP73, VBP1, VHL, a WNT family member, BRAF, CTNNB1, PIK3CA, PIK3R1, SMAD4, and YPEL3 or a fragment or variant thereof. In one embodiment, the method further comprises administering to a patient a therapeutically effective amount of a repair template.

Mutations in certain genes can increase the likelihood of a cell becoming cancerous. In certain situations, however, it can be detrimental to inactivate a cancer-associated gene in non-cancerous cells, for example, if the non-mutated form of the cancer-associated gene is beneficial. It has now been discovered that gene-editing proteins can be used to specifically inactivate, partially or completely, mutated forms of genes. Examples of cancer-associated mutations include, but are not limited to: ALK (F1174, R1275), APC (R876, Q1378, R1450), BRAF (V600), CDKN2A (R58, R80, H83, D84, E88, D108G, W110, P114), CTNNB1 (D32, S33, G34, S37, T41, or S45), EGFR (G719, T790, L858), EZH2 (Y646), FGFR3 (S249, Y373), FLT3 (D835), GNAS (R201), HRAS (G12, G13, Q61), IDH1 (R132), JAK2 (V617), KIT (D816), KRAS (G12, G13), NRAS (G12, G13, Q61), PDGFRA (D842), PIK3CA (E542, E545, H1047), PTEN (R130), and TP53 (R175, H179, G245, R248, R249, R273, W282). Certain embodiments are therefore directed to a gene-editing protein that binds to a disease-associated mutation. In one embodiment, the gene-editing protein binds to DNA containing a specific mutation with greater affinity than DNA that does not contain the mutation. In another embodiment, the disease is cancer.

Neurodegenerative diseases, including Alzheimer's disease, Parkinson's disease, and dementia with Lewy bodies, are characterized by the progressive loss of function and/or death of cells of the central and/or peripheral nervous systems. Disease progression can be accompanied by the accumulation of protein-rich plaques that can comprise the protein α-synuclein (encoded, in humans, by the SNCA gene). As a result, researchers have sought to develop therapeutics that can break up these plaques, for example, by means of an antibody that binds to the plaque and tags it for destruction by the immune system. However, in many cases, breaking up plaques has little or no effect on patient symptoms or the progression of the disease. It has now been discovered that the failure of existing therapies that target neurodegenerative disease-associated plaques is due in part to the inability of the nervous system to repair the damage to cells that occurs during the early stages of plaque formation. It has been further discovered that inducing a cell to express one or more gene-editing proteins that target the SNCA gene can result in disruption of the SNCA gene, can induce the cell to express a plaque-resistant variant of α-synuclein protein, can slow or halt the growth of neurodegenerative disease-associated plaques, can protect the cell and nearby cells from the damaging effects of neurodegenerative disease-associated plaques, can slow and/or halt the progression of neurodegenerative diseases, including Alzheimer's disease, Parkinson's disease, and dementia with Lewy bodies, and can result in a reduction of symptoms and/or gain of function in patients with neurodegenerative diseases, including Alzheimer's disease, Parkinson's disease, and dementia with Lewy bodies. Other neurodegenerative diseases include, for example, vision loss, including blindness, hearing loss, including deafness, balance disorders, loss of taste and/or smell, and other sensory disorders. Certain embodiments are therefore directed to a gene-editing protein that targets the SNCA gene. In one embodiment, the gene-editing protein binds to one or more regions in the SNCA gene. In another embodiment, the gene-editing protein binds to one or more nucleic-acid sequences that encode SEQ ID NO: 51 or a biologically active fragment, variant or analogue thereof. Other embodiments are directed to a method for treating a neurodegenerative disease comprising administering to a patient a therapeutically effective amount of a gene-editing protein or a nucleic acid encoding a gene-editing protein, wherein the gene-editing protein is capable of binding to a nucleotide sequence that encodes a protein that forms disease-associated plaques, and resulting in a reduction of disease-associated plaques in the patient and/or delayed or halted progression of the disease. In one embodiment, the nucleotide sequence comprises the SNCA gene. In another embodiment, the nucleotide sequence encodes α-synuclein. In a further embodiment, the neurodegenerative disease is selected from: Parkinson's disease, Alzheimer's disease, and dementia.

Certain embodiments are directed to a method for identifying a disease-causing toxicant comprising transfecting a cell with a gene-editing protein or a nucleic acid encoding a gene-editing protein to alter the DNA sequence of the cell, wherein the altered DNA sequence confers susceptibility to a disease, contacting the cell with a suspected disease-causing toxicant, and assessing the degree to which the cell exhibits a phenotype associated with the disease. In one embodiment, the disease is a neurodegenerative disease, autoimmune disease, respiratory disease, reproductive disorder or cancer. Other embodiments are directed to a method for assessing the safety of a therapeutic substance comprising transfecting a cell with a gene-editing protein or a nucleic acid encoding a gene-editing protein to alter the DNA sequence of the cell, wherein the altered DNA sequence confers susceptibility to one or more toxic effects of the therapeutic substance, contacting the cell with the therapeutic substance, and measuring one or more toxic effects of the therapeutic substance on the cell. Still other embodiments are directed to a method for assessing the effectiveness of a therapeutic substance comprising transfecting a cell with a gene-editing protein or a nucleic acid encoding a gene-editing protein to alter the DNA sequence of the cell, wherein the altered DNA sequence causes the cell to exhibit one or more disease-associated phenotypes, contacting the cell with the therapeutic substance, and measuring the degree to which the one or more disease-associated phenotypes are reduced.

In some embodiments, the patient is diagnosed with a proteopathy. Example proteopathies and proteopathy-associated genes are given in Table 6, and are included by way of example, and not by way of limitation. In one embodiment, the proteopathy is selected from: AA (secondary) amyloidosis, Alexander disease, Alzheimer's disease, amyotrophic lateral sclerosis, aortic medial amyloidosis, ApoAI amyloidosis, ApoAII amyloidosis, ApoAIV amyloidosis, bibrinogen amyloidosis, cardiac atrial amyloidosis, cerebral autosomal dominant arteriopathy with subcortical infarcts and leukoencephalopathy, cerebral β-amyloid angiopathy, dialysis amyloidosis, familial amyloid cardiomyopathy, familial amyloid polyneuropathy, familial amyloidosis (Finnish type), familial British dementia, familial Danish dementia, frontotemporal lobar degeneration, hereditary cerebral amyloid angiopathy, hereditary lattice corneal dystrophy, Huntington's disease, inclusion body myositis/myopathy, lysozyme amyloidosis, medullary thyroid carcinoma, odontogenic (Pindborg) tumor amyloid, Parkinson's disease, pituitary prolactinoma, prion diseases, pulmonary alveolar proteinosis, retinal ganglion cell degeneration in glaucoma, retinitis pigmentosa with rhodopsin mutations, senile systemic amyloidosis, serpinopathies, synucleinopathies, tauopathies, type II diabetes, dementia pugilistica (chronic traumatic encephalopathy), frontotemporal dementia, frontotemporal lobar degeneration, gangliocytoma, ganglioglioma, Hallervorden-Spatz disease, lead encephalopathy, lipofuscinosis, Lytico-Bodig disease, meningioangiomatosis, progressive supranuclear palsy, subacute sclerosing panencephalitis, tangle-predominant dementia, and tuberous sclerosis. In another embodiment, the target DNA molecule comprises a gene selected from: APOA1, APOA2, APOA4, APP, B2M, CALCA, CST3, FGA, FGB, FGG, FUS, GFAP, GSN, HTT, IAPP, ITM2B, LYZ, MAPT, MFGE8, NOTCH3, NPPA, ODAM, PRL, PRNP, RHO, a SAA family member, a SERPIN family member, SFTPC, SNCA, a SOD family member, TARDBP, TGFBI, and TRR or a fragment or variant thereof. In a further embodiment, the target DNA molecule encodes a gene selected from Table 6 or a fragment thereof, and the patient is diagnosed with the corresponding disease listed in Table 6.

TABLE 6

Exemplary Proteopathies and Proteopathy-Associated Genes

| Gene/Family | Disease/Condition |
|---|---|
| APOA1 | ApoAI amyloidosis |
| APOA2 | ApoAII amyloidosis |
| APOA4 | ApoAIV amyloidosis |
| APP | Cerebral β-amyloid angiopathy |
| APP | Retinal ganglion cell degeneration in glaucoma |
| APP | Inclusion body myositis/myopathy |
| APP, MAPT | Alzheimer's disease |
| B2M | Dialysis amyloidosis |
| CALCA | Medullary thyroid carcinoma |
| CST3 | Hereditary cerebral amyloid angiopathy (Icelandic) |
| FGA, FGB, FGG | Fibrinogen amyloidosis |
| GFAP | Alexander disease |
| GSN | Familial amyloidosis, Finnish type |
| HTT | Huntington's disease |
| IAPP | Type II diabetes |
| ITM2B | Familial British dementia |
| ITM2B | Familial Danish dementia |
| LYZ | Lysozyme amyloidosis |
| MAPT | Tauopathies (multiple) |
| MFGE8 | Aortic medial amyloidosis |
| NOTCH3 | Cerebral autosomal dominant arteriopathy with subcortical infarcts and leukoencephalopathy (CADASIL) |
| NPPA | Cardiac atrial amyloidosis |
| ODAM | Odontogenic (Pindborg) tumor amyloid |
| PRL | Pituitary prolactinoma |
| PRNP | Prion diseases (multiple) |
| RHO | Retinitis pigmentosa with rhodopsin mutations |
| SAA family genes | AA (secondary) amyloidosis |
| SERPIN family genes | Serpinopathies (multiple) |
| SFTPC | Pulmonary alveolar proteinosis |
| SNCA | Parkinson's disease and other synucleinopathies (multiple) |
| SNCA | Other synucleinopathies |
| SOD family genes, TARDBP, FUS | Amyotrophic lateral sclerosis (ALS) |
| TARDBP, FUS | Frontotemporal lobar degeneration (FTLD) |
| TGFBI | Hereditary lattice corneal dystrophy |
| LMNA | Hutchinson-Gilford Progeria Syndrome |
| TRR | Senile systemic amyloidosis (SSA), familial amyloid polyneuropathy (FAP), familial amyloid cardiomyopathy (FAC) |

Example tauopathies include, but are not limited to Alzheimer's disease, Parkinson's disease, and Huntington's disease. Other example tauopathies include: dementia pugilistica (chronic traumatic encephalopathy), frontotemporal dementia, frontotemporal lobar degeneration, gangliocytoma, ganglioglioma, Hallervorden-Spatz disease, lead encephalopathy, lipofuscinosis, Lytico-Bodig disease, meningioangiomatosis, progressive supranuclear palsy, subacute sclerosing panencephalitis, tangle-predominant dementia, and tuberous sclerosis. In some embodiments, the patient is diagnosed with a tauopathy. In one embodiment, the tauopathy is selected from: Alzheimer's disease, Parkinson's disease, and Huntington's disease. In another embodiment, the tauopathy is selected from: dementia pugilistica (chronic traumatic encephalopathy), frontotemporal dementia, frontotemporal lobar degeneration, gangliocytoma, ganglioglioma, Hallervorden-Spatz disease, lead encephalopathy, lipofuscinosis, Lytico-Bodig disease, meningioangiomatosis, progressive supranuclear palsy, subacute sclerosing panencephalitis, tangle-predominant dementia, and tuberous sclerosis.

Autoimmune diseases, including but not limited to lupus, multiple sclerosis (MS), amyotrophic lateral sclerosis (ALS), and transplant rejection, are characterized by symptoms caused in part by one or more elements of the immune system attacking uninfected and non-cancerous isogenic cells and/or tissues. Certain embodiments are therefore directed to a method for treating an autoimmune disease. In one embodiment, the autoimmune disease is selected from: lupus, multiple sclerosis (MS), amyotrophic lateral sclerosis (ALS), and transplant rejection. In another embodiment, the target DNA molecule encodes a polypeptide sequence that can be recognized by the host immune system.

Infectious agents can contain nucleic acid sequences that are not present in the host organism. It has now been discovered that gene-editing proteins can be used to eliminate, reduce or otherwise alter, in whole or in part, infectious agents and/or the effects of infection, and that when used in this manner, gene-editing proteins and nucleic acids encoding gene-editing proteins, can constitute potent anti-infection therapeutics. Infectious agents that can be treated in such a manner include, but are not limited to: viruses, bacteria, fungi, yeast, and parasites. Certain embodiments are therefore directed to a method for inducing a cell to express a gene-editing protein that targets one or more infectious agent-associated sequences. In one embodiment, the cell is one of: a bacterial cell, a fungal cell, a yeast cell, and a parasite cell. In another embodiment, the cell is a mammalian cell. In a further embodiment, the cell is a human cell. Other embodiments are directed to a therapeutic composition comprising a nucleic acid that encodes one or more gene-editing proteins that targets one or more infectious agent-associated sequences. Certain embodiments are directed to a method for inducing a cell to express a gene-editing protein that targets one or more sequences associated with susceptibility or resistance to infection. Other embodiments are directed to a therapeutic composition comprising a nucleic acid that encodes one or more gene-editing proteins that targets one or more sequences associated with susceptibility or resistance to infection. In one embodiment, the cell is transfected with a nucleic acid encoding one or more gene-editing proteins and a nucleic acid encoding one or more repair templates. In another embodiment, the repair template contains a resistance gene or a biologically active fragment or variant thereof. In a further embodiment, the repair template contains an RNAi sequence. In a still further embodiment, the RNAi sequence is a shRNA. Other embodiments are directed to a method for treating an infectious disease comprising administering to a patient a therapeutically effective amount of a gene-editing protein or a nucleic acid encoding a gene-editing protein, wherein the gene-editing protein is capable of binding to one or more nucleotide sequences that are present in the infectious agent.

It has now been discovered that the ratio of non-homologous end joining events to homologous recombination events can be altered by altering the expression and/or function of one or more components of a DNA-repair pathway. Non-limiting examples of genes that encode components of a DNA-repair pathway include, but are not limited to: Artemis, BLM, CtIP, DNA-PK, DNA-PKcs, EXO1, FEN1, Ku70, Ku86, LIGIII, LIGIV, MRE11, NBS1, PARP1, RAD50, RAD54B, XLF, XRCC1, XRCC3, and XRCC4. Certain embodiments are therefore directed to a method for altering the expression and/or function of one or more components of a DNA-repair pathway. In certain embodiments, the expression and/or function is increased. In other embodiments, the expression and/or function is decreased. DNA-dependent protein kinase (DNA-PK) is a component of the non-homologous end-joining DNA-repair pathway. It has now been discovered that repair via homologous recombination can be increased by altering the expression of DNA-PK. In one embodiment, a cell is contacted with a DNA-PK inhibitor. Example DNA-PK inhibitors include, but are not limited to: Compound 401 (2-(4-Morpholinyl)-4H-pyrimido[2,1-a]isoquinolin-4-one), DMNB, IC87361, LY294002, NU7026, NU7441, OK-1035, PI 103 hydrochloride, vanillin, and wortmannin.

Genetic mutations can affect the length of a protein product, for example, by introducing a stop codon and/or disrupting an open reading frame. Certain diseases, including Duchenne muscular dystrophy, can be caused by the production of truncated and/or frameshifted proteins. It has now been discovered that gene-editing proteins can be used to treat diseases that are associated with the production of one or more truncated and/or frameshifted proteins. In one embodiment, the gene-editing protein creates a double strand break within about 1 kb or about 0.5 kb or about 0.1 kb of an exon containing a disease-contributing mutation. In another embodiment, the gene-editing protein is co-expressed with a DNA sequence comprising one or more wild-type sequences. In certain embodiments, the DNA is single-stranded. In other embodiments, the DNA is double-stranded. Diseases caused by the expression of truncated proteins can be treated by exon skipping. It has now been discovered that gene-editing proteins can be used to induce exon skipping. In one embodiment, the gene-editing protein creates a double-strand break within about 1 kb or about 0.5 kb or about 0.1 kb of the exon to be skipped. In another embodiment, the gene-editing protein creates a double-strand break within about 1 kb or about 0.5 kb or about 0.1 kb of an intron upstream of the exon to be skipped. In another embodiment, the gene-editing protein creates a double-strand break within about 1 kb or about 0.5 kb or about 0.1 kb of the splice-acceptor site of an intron upstream of the exon to be skipped.

Nucleic acids, including liposomal formulations containing nucleic acids, when delivered in vivo, can accumulate in the liver and/or spleen. It has now been discovered that nucleic acids encoding gene-editing proteins can modulate gene expression in the liver and spleen, and that nucleic acids used in this manner can constitute potent therapeutics for the treatment of liver and spleen diseases. Certain embodiments are therefore directed to a method for treating liver and/or spleen disease by delivering to a patient a nucleic acid encoding one or more gene-editing proteins. Other embodiments are directed to a therapeutic composition comprising a nucleic acid encoding one or more gene-editing proteins, for the treatment of liver and/or spleen disease. Diseases and conditions of the liver and/or spleen that can be treated include, but are not limited to: hepatitis, alcohol-induced liver disease, drug-induced liver disease, Epstein Barr virus infection, adenovirus infection, cytomegalovirus infection, toxoplasmosis, Rocky Mountain spotted fever, non-alcoholic fatty liver disease, hemochromatosis, Wilson's Disease, Gilbert's Disease, and cancer of the liver and/or spleen. Other examples of sequences (including genes, gene families, and loci) that can be targeted by gene-editing proteins using the methods of the present invention are set forth in Table 7, and are given by way of example, and not by way of limitation.

TABLE 7

Exemplary Gene Editing-Protein Targets

| Disease/Condition | Gene/Family/Locus |
| --- | --- |
| Age-related macular degeneration | VEGF family |

TABLE 7-continued

Exemplary Gene Editing-Protein Targets

| Disease/Condition | Gene/Family/Locus |
| --- | --- |
| Alzheimer's disease | APP, PSEN1, PSEN2, APOE, CR1, CLU, PICALM, BIN1, MS4A4, MS4A6E, CD2AP, CD33, EPHA1 |
| Amyotrophic lateral sclerosis | SOD1 |
| Cancer | BRCA1, EGFR, MYC family, TP53, PKN3, RAS family, BIRC5, PTEN, RET, KIT, MET, APC, RB1, BRCA2, VEGF family, TNF, HNPCC1, HNPCC2, HNPCC5 |
| Cystic fibrosis | CFTR |
| Diabetes | GCK, HNF1A, HNF4A, HNF1B |
| Duchenne muscular dystrophy | DMD |
| Fanconi anemia | BRCA2, FANCA, FANCB, FANCC, FANCD2, FANCE, FANCF, FANCG, FANCI, FANCJ, FANCL, FANCM, FANCN, FANCP, RAD51C |
| Hemochromatosis | HFE, HJV, HAMP, TFR2, SLC40A1 |
| Hemophilia | F8, F9, F11 |
| HIV/AIDS | CCR5, CXCR4 |
| Huntington's disease | HTT |
| Marfan's syndrome | FBN1 |
| Neurofibromatosis | NF1, NF2 |
| Parkinson's disease | SNCA, PRKN, LRRK2, PINK1, PARK7, ATP13A2 |
| Safe-harbor locus in humans | AAVS1 |
| Safe-harbor locus in mice and rats | Rosa26 |
| Sickle-cell anemia | HBB |
| Tay-Sachs disease | HEXA |
| Xeroderma pigmentosum | XPA, XPB, XPC, XPD, DDB2, ERCC4, ERCC5, ERCC6, RAD2, POLH |
| Psoriasis, Rheumatoid arthritis, Ankylosing spondylitis, Crohn's disease, Hidradenitis suppurativa, Refractory asthma | TNF |
| Psoriasis, Rheumatoid arthritis, Polycythemia vera, Essential thrombocythemia, Myeloid metaplasia with myelofibrosis | JAK family |

Certain embodiments are directed to a combination therapy comprising one or more of the therapeutic compositions of the present invention and one or more adjuvant therapies. Example adjuvant therapies are set forth in Table 8 and Table 5 of U.S. Provisional Application No. 61/721, 302, the contents of which are hereby incorporated by reference, and are given by way of example, and not by way of limitation.

TABLE 8

Exemplary Adjuvant Therapies

| Therapy Class | Disease/Condition | Example Therapy |
| --- | --- | --- |
| Acetylcholinesterase inhibitors | Myasthenia gravis, Glaucoma, Alzheimer's disease, Lewy body dementia, Postural tachycardia syndrome | Edrophonium |
| Angiotensin-converting-enzyme inhibitor | Hypertension, Congestive heart failure | Perindopril |
| Alkylating agents | Cancer | Cisplatin |
| Angiogenesis inhibitors | Cancer, Macular degeneration | Bevacizumab |
| Angiotensin II receptor antagonists | Hypertension, Diabetic nephropathy, Congestive heart failure | Valsartan |
| Antibiotics | Bacterial infection | Amoxicillin |
| Antidiabetic drugs | Diabetes | Metformin |
| Antimetabolites | Cancer, Infection | 5-fluorouracil (5FU) |
| Antisense oligonucleotides | Cancer, Diabetes, Amyotrophic lateral sclerosis (ALS), Hypercholesterolemia | Mipomersen |
| Cytotoxic antibiotics | Cancer | Doxorubicin |
| Deep-brain stimulation | Chronic pain, Parkinson's disease, Tremor, Dystonia | N/A |
| Dopamine agonists | Parkinson's disease, Type II diabetes, Pituitary tumors | Bromocriptine |
| Entry/Fusion inhibitors | HIV/AIDS | Maraviroc |
| Glucagon-like peptide-1 agonists | Diabetes | Exenatide |
| Glucocorticoids | Asthma, Adrenal insufficiency, Inflammatory diseases, Immune diseases, Bacterial meningitis | Dexamethasone |
| Immunosuppressive drugs | Organ transplantation, Inflammatory diseases, Immune diseases | Azathioprine |
| Insulin/Insulin analogs | Diabetes | NPH insulin |
| Integrase inhibitors | HIV/AIDS | Raltegravir |
| MAO-B inhibitors | Parkinson's disease, Depression, Dementia | Selegiline |
| Maturation inhibitors | HIV/AIDS | Bevirimat |
| Nucleoside analog reverse-transcriptase inhibitors | HIV/AIDS, Hepatitis B | Lamivudine |
| Nucleotide analog reverse-transcriptase inhibitors | HIV/AIDS, Hepatitis B | Tenofovir |
| Non-nucleoside reverse-transcriptase inhibitors | HIV/AIDS | Rilpivirine |
| Pegylated interferon | Hepatitis B/C, Multiple sclerosis | Interferon beta-1a |
| Plant alkaloids/terpenoids | Cancer | Paclitaxel |
| Protease inhibitors | HIV/AIDS, Hepatitis C, Other viral infections | Telaprevir |
| Radiotherapy | Cancer | Brachytherapy |
| Renin inhibitors | Hypertension | Aliskiren |
| Statins | Hypercholesterolemia | Atorvastatin |
| Topoisomerase inhibitors | Cancer | Topotecan |
| Vasopressin receptor antagonist | Hyponatremia, Kidney disease | Tolvaptan |

Pharmaceutical preparations may additionally comprise delivery reagents (a.k.a. "transfection reagents") and/or excipients. Pharmaceutically acceptable delivery reagents, excipients, and methods of preparation and use thereof, including methods for preparing and administering pharmaceutical preparations to patients (a.k.a. "subjects") are well known in the art, and are set forth in numerous publications, including, for example, in US Patent Appl. Pub. No. US 2008/0213377, the entirety of which is hereby incorporated by reference.

For example, the present compositions can be in the form pharmaceutically acceptable salts. Such salts include those listed in, for example, *J. Pharma. Sci.* 66, 2-19 (1977) and *The Handbook of Pharmaceutical Salts; Properties, Selection, and Use.* P. H. Stahl and C. G. Wermuth (eds.), Verlag, Zurich (Switzerland) 2002, which are hereby incorporated by reference in their entirety. Non-limiting examples of pharmaceutically acceptable salts include: sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, tartarate salts, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

The present pharmaceutical compositions can comprises excipients, including liquids such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

In various embodiments, the compositions described herein can administered in an effective dose of, for example, from about 1 mg/kg to about 100 mg/kg, about 2.5 mg/kg to about 50 mg/kg, or about 5 mg/kg to about 25 mg/kg. The precise determination of what would be considered an effective dose may be based on factors individual to each patient, including their size, age, and type of disease. Dosages can be readily ascertained by those of ordinary skill in the art from this disclosure and the knowledge in the art. For example, doses may be determined with reference *Physicians' Desk Reference*, 66th Edition, PDR Network; 2012 Edition (Dec. 27, 2011), the contents of which are incorporated by reference in its entirety.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cancer tissue. The agents disclosed herein may also be administered by catheter systems. Such compositions would normally be administered as pharmaceutically acceptable compositions as described herein.

Upon formulation, solutions may be administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic with, for example, sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure.

Exemplary subjects or patients refers to any vertebrate including, without limitation, humans and other primates (e.g., chimpanzees and other apes and monkey species), farm animals (e.g., cattle, sheep, pigs, goats, and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In some embodiments, the subject is a human.

This invention is further illustrated by the following non-limiting examples.

EXAMPLES

Example 1 RNA Synthesis

Figure 1A:
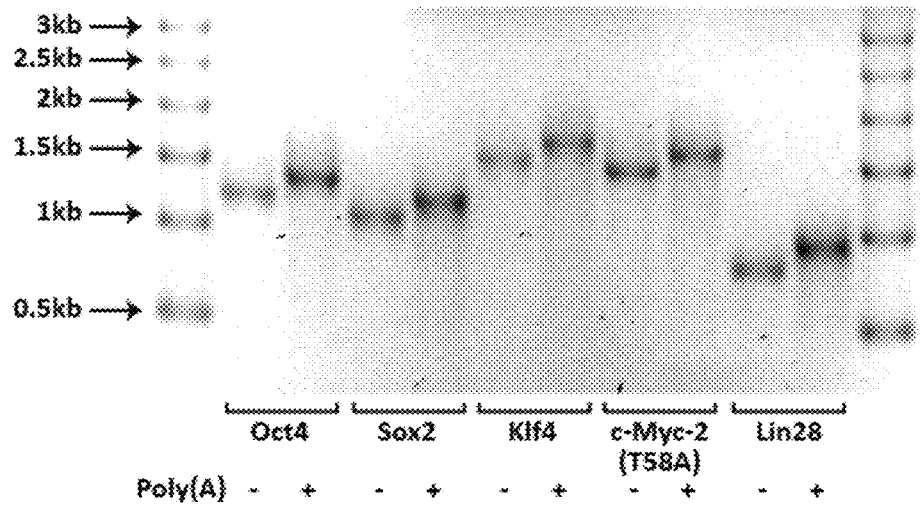
FIG. 1A depicts RNA encoding the indicated proteins and containing adenosine, 50% guanosine, 50% 7-deazaguanosine, 70% uridine, 30% 5-methyluridine, and 5-methylcytidine, resolved on a denaturing formaldehyde-agarose gel.
Figure 1B:
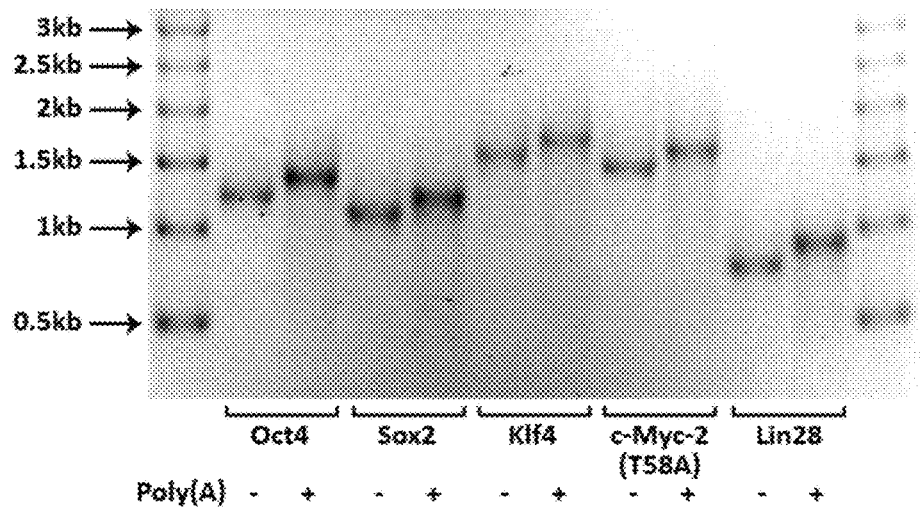
FIG. 1B depicts RNA encoding the indicated proteins and containing adenosine, 50% guanosine, 50% 7-deazaguanosine, 50% uridine, 50% 5-methyluridine, and 5-methylcytidine, resolved on a denaturing formaldehyde-agarose gel.

RNA encoding the human proteins Oct4, Sox2, Klf4, c-Myc-2 (T58A), and Lin28 or TALENs targeting the human genes XPA, CCR5, TERT, MYC, and BIRC5, and comprising various combinations of canonical and non-canonical nucleotides, was synthesized from DNA templates using the T7 High Yield RNA Synthesis Kit and the Vaccinia Capping System kit with mRNA Cap 2'-O-Methyltransferase (all from New England Biolabs, Inc.), according to the manufacturer's instructions and the present inventors' previously disclosed inventions (U.S. application Ser. No. 13/465,490 (now U.S. Pat. No. 8,497,124), U.S. Provisional Application No. 61/637,570, U.S. Provisional Application No. 61/664,494, International Application No. PCT/US12/67966, U.S. Provisional Application No. 61/785,404, U.S. application Ser. No. 13/931,251, and U.S. Provisional Application No. 61/842,874, the contents of all of which are hereby incorporated by reference in their entirety) (Table 9, FIG. 1A, FIG. 1B, and FIG. 15). The RNA was then diluted with nuclease-free water to between 100 ng/µL and 200 ng/µL. For certain experiments, an RNase inhibitor (Superase-In, Life Technologies Corporation) was added at a concentration of 1 µL/100 µg of RNA. RNA solutions were stored at 4° C. For reprogramming experiments, RNA encoding Oct4, Sox2, Klf4, c-Myc-2 (T58A), and Lin28 was mixed at a molar ratio of 3:1:1:1:1.

TABLE 9

RNA Synthesis

| Template | Nucleotides | Reaction Volume/µL | ivT Yield/µg |
|---|---|---|---|
| Oct4 | A, G, U, C | 10 | 64.9 |
| Oct4 | A, G, 0.25 4sU, C | 10 | 64.3 |
| Oct4 | A, G, 0.5 4sU, C | 10 | 62.8 |
| Oct4 | A, G, 0.75 4sU, C | 10 | 51.9 |
| Oct4 | A, G, 4sU, C | 10 | 0 |
| Oct4 | A, 0.5 7dG, 0.75 4sU, 0.25 piC | 20 | 70.1 |
| Sox2 | A, 0.5 7dG, 0.75 4sU, 0.25 piC | 10 | 29.6 |
| Klf4 | A, 0.5 7dG, 0.75 4sU, 0.25 piC | 10 | 29.5 |
| c-Myc-2 (T58A) | A, 0.5 7dG, 0.75 4sU, 0.25 piC | 10 | 25.9 |

TABLE 9-continued

RNA Synthesis

| Template | Nucleotides | Reaction Volume/μL | ivT Yield/μg |
|---|---|---|---|
| Lin28 | A, 0.5 7dG, 0.75 4sU, 0.25 piC | 10 | 36.7 |
| Oct4 | A, 0.5 7dG, 0.75 4sU, 0.5 piC | 20 | 51.7 |
| Sox2 | A, 0.5 7dG, 0.75 4sU, 0.5 piC | 10 | 23.0 |
| Klf4 | A, 0.5 7dG, 0.75 4sU, 0.5 piC | 10 | 22.3 |
| c-Myc-2 (T58A) | A, 0.5 7dG, 0.75 4sU, 0.5 piC | 10 | 21.4 |
| Lin28 | A, 0.5 7dG, 0.75 4sU, 0.5 piC | 10 | 23.3 |
| Oct4 | A, 0.5 7dG, 0.8 4sU, 0.2 5mU, 0.5 piC | 20 | 50.8 |
| Oct4 | A, 0.5 7dG, 0.7 4sU, 0.3 5mU, 0.5 piC | 20 | 58.3 |
| Oct4 | A, 0.5 7dG, 0.6 4sU, 0.4 5mU, 0.5 piC | 20 | 58.3 |
| Oct4 | A, 0.5 7dG, 0.5 4sU, 0.5 5mU, 0.5 piC | 20 | 68.2 |
| Oct4 | A, 0.5 7dG, 0.4 4sU, 0.6 5mU, 0.5 piC | 20 | 78.7 |
| Oct4 | A, G, psU, 5mC | 10 | 110.4 |
| Oct4 | A, G, psU, 0.5 piC | 10 | 85.0 |
| Oct4 | A, 0.5 7dG, psU, 0.5 piC | 10 | 58.3 |
| Oct4 | A, 0.5 7dG, psU, 5mC | 10 | 27.0 |
| Oct4 | A, 0.5 7dG, 0.5 5mU, 0.5 piC | 20 | 109.0 |
| Oct4 | A, 0.5 7dG, 0.6 5mU, 0.5 piC | 20 | 114.8 |
| Oct4 | A, 0.5 7dG, 0.7 5mU, 0.5 piC | 20 | 107.2 |
| Oct4 | A, 0.5 7dG, 0.8 5mU, 0.5 piC | 20 | 110.9 |
| Oct4 | A, 0.5 7dG, 0.9 5mU, 0.5 piC | 20 | 103.4 |
| Oct4 | A, 0.5 7dG, 5mU, 0.5 piC | 20 | 97.8 |
| Oct4 | A, 0.5 7dG, psU, 0.5 piC | 20 | 124.5 |
| Sox2 | A, 0.5 7dG, psU, 0.5 piC | 20 | 109.0 |
| Klf4 | A, 0.5 7dG, psU, 0.5 piC | 20 | 112.8 |
| c-Myc-2 (T58A) | A, 0.5 7dG, psU, 0.5 piC | 20 | 112.8 |
| Lin28 | A, 0.5 7dG, psU, 0.5 piC | 20 | 126.5 |
| Oct4 | A, G, psU, 5mC | 20 | 213.4 |
| Sox2 | A, G, psU, 5mC | 10 | 107.2 |
| Klf4 | A, G, psU, 5mC | 10 | 106.1 |
| c-Myc-2 (T58A) | A, G, psU, 5mC | 10 | 97.8 |
| Lin28 | A, G, psU, 5mC | 10 | 95.9 |
| Oct4 | A, 0.5 7dG, psU, 0.5 piC | 20 | 124.2 |
| Sox2 | A, 0.5 7dG, psU, 0.5 piC | 10 | 57.3 |
| Klf4 | A, 0.5 7dG, psU, 0.5 piC | 10 | 59.6 |
| c-Myc-2 (T58A) | A, 0.5 7dG, psU, 0.5 piC | 10 | 66.7 |
| Lin28 | A, 0.5 7dG, psU, 0.5 piC | 10 | 65.2 |
| Oct4 | A, 0.5 7dG, psU, 0.3 piC | 10 | 60.5 |
| Sox2 | A, 0.5 7dG, psU, 0.3 piC | 10 | 58.8 |
| Klf4 | A, 0.5 7dG, psU, 0.3 piC | 10 | 57.9 |
| c-Myc-2 (T58A) | A, 0.5 7dG, psU, 0.3 piC | 10 | 62.0 |
| Lin28 | A, 0.5 7dG, psU, 0.3 piC | 10 | 64.3 |
| Oct4 | A, 0.5 7dG, 0.5 5mU, 5mC | 10 | 64.7 |
| Sox2 | A, 0.5 7dG, 0.5 5mU, 5mC | 10 | 62.4 |
| Klf4 | A, 0.5 7dG, 0.5 5mU, 5mC | 10 | 75.6 |
| c-Myc-2 (T58A) | A, 0.5 7dG, 0.5 5mU, 5mC | 10 | 69.4 |
| Lin28 | A, 0.5 7dG, 0.5 5mU, 5mC | 10 | 60.7 |
| Oct4 | A, 0.5 7dG, 0.5 4sU, 0.5 5mU, 5mC | 10 | 48.3 |
| Sox2 | A, 0.5 7dG, 0.5 4sU, 0.5 5mU, 5mC | 10 | 54.0 |
| Klf4 | A, 0.5 7dG, 0.5 4sU, 0.5 5mU, 5mC | 10 | 58.7 |
| c-Myc-2 (T58A) | A, 0.5 7dG, 0.5 4sU, 0.5 5mU, 5mC | 10 | 54.7 |
| Lin28 | A, 0.5 7dG, 0.5 4sU, 0.5 5mU, 5mC | 10 | 54.1 |
| Oct4 | A, 0.5 7dG, 0.3 5mU, 5mC | 10 | 69.6 |
| Sox2 | A, 0.5 7dG, 0.3 5mU, 5mC | 10 | 69.6 |
| Klf4 | A, 0.5 7dG, 0.3 5mU, 5mC | 10 | 87.4 |
| c-Myc-2 (T58A) | A, 0.5 7dG, 0.3 5mU, 5mC | 10 | 68.1 |
| Lin28 | A, 0.5 7dG, 0.3 5mU, 5mC | 10 | 74.3 |
| Oct4 | A, 0.5 7dG, 0.4 5mU, 5mC | 10 | 71.3 |
| Sox2 | A, 0.5 7dG, 0.4 5mU, 5mC | 10 | 69.7 |
| Klf4 | A, 0.5 7dG, 0.4 5mU, 5mC | 10 | 74.8 |
| c-Myc-2 (T58A) | A, 0.5 7dG, 0.4 5mU, 5mC | 10 | 83.7 |
| Lin28 | A, 0.5 7dG, 0.4 5mU, 5mC | 10 | 69.9 |
| XPA-L1 | A, G, psU, 5mC | 20 | 120.0 |
| XPA-L2 | A, G, psU, 5mC | 20 | 114.0 |
| XPA-R1 | A, G, psU, 5mC | 20 | 159.6 |
| CCR5-L1 | A, G, psU, 5mC | 20 | 170.4 |
| CCR5-L2 | A, G, psU, 5mC | 20 | 142.8 |
| CCR5-R1 | A, G, psU, 5mC | 20 | 132.0 |
| CCR5-R2 | A, G, psU, 5mC | 20 | 154.8 |
| CCR5-L1 | A, G, psU, 5mC | 10 | 56.6 |
| CCR5-L2 | A, G, psU, 5mC | 10 | 58.5 |
| CCR5-R1 | A, G, psU, 5mC | 10 | 56.8 |
| CCR5-R2 | A, G, psU, 5mC | 10 | 58.7 |
| TERT-L | A, G, U, C | 10 | 49.4 |
| TERT-R | A, G, U, C | 10 | 37.6 |
| MYC-L | A, G, U, C | 10 | 39.6 |

TABLE 9-continued

RNA Synthesis

| Template | Nucleotides | Reaction Volume/μL | ivT Yield/μg |
|---|---|---|---|
| MYC-R | A, G, U, C | 10 | 33.7 |
| BIRC5-L | A, G, U, C | 10 | 63.0 |
| BIRC5-R | A, G, U, C | 10 | 44.5 |
| TERT-L | A, 0.5 7dG, 0.4 5mU, 5mC | 10 | 50.8 |
| TERT-R | A, 0.5 7dG, 0.4 5mU, 5mC | 10 | 58.3 |
| MYC-L | A, 0.5 7dG, 0.4 5mU, 5mC | 10 | 40.8 |
| MYC-R | A, 0.5 7dG, 0.4 5mU, 5mC | 10 | 41.4 |
| BIRC5-L | A, 0.5 7dG, 0.4 5mU, 5mC | 10 | 35.8 |
| BIRC5-R | A, 0.5 7dG, 0.4 5mU, 5mC | 10 | 41.5 |
| Oct4 (SEQ ID NO: 8) | A, 0.5 7dG, 0.4 5mU, 5mC | 300 | 2752.0 |
| Sox2 (SEQ ID NO: 9) | A, 0.5 7dG, 0.4 5mU, 5mC | 100 | 965.0 |
| Klf4 (SEQ ID NO: 10) | A, 0.5 7dG, 0.4 5mU, 5mC | 100 | 1093.8 |
| c-Myc-2 (T58A) | A, 0.5 7dG, 0.4 5mU, 5mC | 100 | 1265.6 |
| Lin28 | A, 0.5 7dG, 0.4 5mU, 5mC | 100 | 1197.8 |
| Oct4 | A, 0.5 7dG, 0.35 5mU, 5mC | 30 | 155.7 |
| Sox2 | A, 0.5 7dG, 0.35 5mU, 5mC | 15 | 79.8 |
| Klf4 | A, 0.5 7dG, 0.35 5mU, 5mC | 15 | 90.0 |
| c-Myc-2 (T58A) | A, 0.5 7dG, 0.35 5mU, 5mC | 15 | 83.2 |
| Lin28 | A, 0.5 7dG, 0.35 5mU, 5mC | 15 | 74.0 |
| APP UTR_L (Rat) | A, 0.5 7dG, 0.4 5mU, 5mC | 20 | 37.9 |
| APP UTR_R (Rat) | A, 0.5 7dG, 0.4 5mU, 5mC | 20 | 40.0 |
| APP Exon2L (Rat) | A, 0.5 7dG, 0.4 5mU, 5mC | 20 | 38.6 |
| APP Exon2R (Rat) | A, 0.5 7dG, 0.4 5mU, 5mC | 20 | 37.9 |
| APP 6L (Human) | A, 0.5 7dG, 0.4 5mU, 5mC | 20 | 43.1 |
| APP 6R (Human) | A, 0.5 7dG, 0.4 5mU, 5mC | 20 | 43.7 |
| APP 7L (Human) | A, 0.5 7dG, 0.4 5mU, 5mC | 20 | 42.1 |
| APP 7R (Human) | A, 0.5 7dG, 0.4 5mU, 5mC | 20 | 36.2 |
| APP 670L (Rat) | A, 0.5 7dG, 0.4 5mU, 5mC | 20 | 27.0 |
| APP 670R (Rat) | A, 0.5 7dG, 0.4 5mU, 5mC | 20 | 28.3 |
| APP 678L (Rat) | A, 0.5 7dG, 0.4 5mU, 5mC | 20 | 30.1 |
| APP 678R (Rat) | A, 0.5 7dG, 0.4 5mU, 5mC | 20 | 26.2 |
| APP 680L (Rat) | A, 0.5 7dG, 0.4 5mU, 5mC | 20 | 8.1 |
| APP 680R (Rat) | A, 0.5 7dG, 0.4 5mU, 5mC | 20 | 25.4 |
| APP 6L (Human) | A, 0.5 7dG, 0.4 5mU, 5mC | 40 | 48.6 |
| APP 6R (Human) | A, 0.5 7dG, 0.4 5mU, 5mC | 40 | 48.6 |
| APP 6L (Human) | A, G, U, C | 10 | 54.0 |
| APP 6R (Human) | A, G, U, C | 10 | 61.0 |
| APP 6L (Human) | A, 0.5 7dG, 0.4 5mU, 5mC | 10 | 35.4 |
| APP 6R (Human) | A, 0.5 7dG, 0.4 5mU, 5mC | 10 | 48.0 |

Example 2 Transfection of Cells with Synthetic RNA

For transfection in 6-well plates, 2 μg RNA and 6 μL transfection reagent (Lipofectamine RNAiMAX, Life Technologies Corporation) were first diluted separately in complexation medium (Opti-MEM, Life Technologies Corporation or DMEM/F12+10 μg/mL insulin+5.5 μg/mL transferrin+6.7 ng/mL sodium selenite+2 μg/mL ethanolamine) to a total volume of 60 μL each. Diluted RNA and transfection reagent were then mixed and incubated for 15 min at room temperature, according to the transfection reagent-manufacturer's instructions. Complexes were then added to cells in culture. Between 30 μL and 240 μL of complexes were added to each well of a 6-well plate, which already contained 2 mL of transfection medium per well. Plates were shaken gently to distribute the complexes throughout the well. Cells were incubated with complexes for 4 hours to overnight, before replacing the medium with fresh transfection medium (2 mL/well). Volumes were scaled for transfection in 24-well and 96-well plates. Alternatively, between 0.5 μg and 5 μg of RNA and between 2-3 μL of transfection reagent (Lipofectamine 2000, Life Technologies Corporation) per μg of RNA were first diluted separately in complexation medium (Opti-MEM, Life Technologies Corporation or DMEM/F12+10 μg/mL insulin+5.5 μg/mL transferrin+6.7 ng/mL sodium selenite+2 μg/mL ethanolamine) to a total volume of between 5 μL and 100 μL each. Diluted RNA and transfection reagent were then mixed and incubated for 10 min at room temperature. Complexes were then added to cells in culture. Between 10 μL and 200 μL of complexes were added to each well of a 6-well plate, which already contained 2 mL of transfection medium per well. In certain experiments, DMEM+10% FBS or DMEM+50% FBS was used in place of transfection medium. Plates were shaken gently to distribute the complexes throughout the well. Cells were incubated with complexes for 4 hours to overnight. In certain experiments, the medium was replaced with fresh transfection medium (2 mL/well) 4 h or 24 h after transfection.

Example 3 Toxicity of and Protein Translation from Synthetic RNA Containing Non-Canonical Nucleotides Primary human fibroblasts were transfected according to Example 2, using RNA synthesized according to Example 1. Cells were fixed and stained 20-24 h after transfection using an antibody against Oct4. The relative toxicity of the RNA was determined by assessing cell density at the time of fixation.

Example 4 Transfection Medium Formulation

A cell-culture medium was developed to support efficient transfection of cells with nucleic acids and efficient reprogramming ("transfection medium"):

DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+50 µg/mL L-ascorbic acid 2-phosphate sesquimagnesium salt hydrate+4 µg/mL cholesterol+1 µM hydrocortisone+25 µg/mL polyoxyethylenesorbitan monooleate+2 µg/mL D-alpha-tocopherol acetate+20 ng/mL bFGF+5 mg/mL treated human serum albumin.

A variant of this medium was developed to support robust, long-term culture of a variety of cell types, including pluripotent stem cells ("maintenance medium"):

DMEM/F12+2 mM L-alanyl-L-glutamine+10 µg/mL insulin+5.5 µg/mL transferrin+6.7 ng/mL sodium selenite+2 µg/mL ethanolamine+50 µg/mL L-ascorbic acid 2-phosphate sesquimagnesium salt hydrate+20 ng/mL bFGF+2 ng/mL TGF-β1.

Transfection medium, in which the treated human serum albumin was treated by addition of 32 mM sodium octanoate, followed by heating at 60° C. for 4 h, followed by treatment with ion-exchange resin (AG501-X8(D), Bio-Rad Laboratories, Inc.) for 6 h at room temperature, followed by treatment with dextran-coated activated charcoal (C6241, Sigma-Aldrich Co. LLC.) overnight at room temperature, followed by centrifugation, filtering, adjustment to a 10% solution with nuclease-free water, followed by addition to the other components of the medium, was used as the transfection medium in all Examples described herein, unless otherwise noted. For reprogramming experiments, cells were plated either on uncoated plates in DMEM+10%-20% serum or on fibronectin and vitronectin-coated plates in transfection medium, unless otherwise noted. The transfection medium was not conditioned, unless otherwise noted. It is recognized that the formulation of the transfection medium can be adjusted to meet the needs of the specific cell types being cultured. It is further recognized that treated human serum albumin can be replaced with other treated albumin, for example, treated bovine serum albumin, without negatively affecting the performance of the medium. It is further recognized that other glutamine sources can be used instead of or in addition to L-alanyl-L-glutamine, for example, L-glutamine, that other buffering systems can be used instead of or in addition to HEPES, for example, phosphate, bicarbonate, etc., that selenium can be provided in other forms instead of or in addition to sodium selenite, for example, selenous acid, that other antioxidants can be used instead of or in addition to L-ascorbic acid 2-phosphate sesquimagnesium salt hydrate and/or D-alpha-tocopherol acetate, for example, L-ascorbic acid, that other surfactants can be used instead of or in addition to polyoxyethylenesorbitan monooleate, for example, Pluronic F-68 and/or Pluronic F-127, that other basal media can be used instead of or in addition to DMEM/F12, for example, MEM, DMEM, etc., and that the components of the culture medium can be varied with time, for example, by using a medium without TGF-β from day 0 to day 5, and then using a medium containing 2 ng/mL TGF-β after day 5, without negatively affecting the performance of the medium. It is further recognized that other ingredients can be added, for example, fatty acids, lysophosphatidic acid, lysosphingomyelin, sphingosine-1-phosphate, other sphingolipids, ROCK inhibitors, including Y-27632 and thiazovivin, members of the TGF-β/NODAL family of proteins, IL-6, members of the Wnt family of proteins, etc., at appropriate concentrations, without negatively affecting the performance of the medium, and that ingredients that are known to promote or inhibit the growth of specific cell types and/or agonists and/or antagonists of proteins or other molecules that are known to promote or inhibit the growth of specific cell types can be added to the medium at appropriate concentrations when it is used with those cell types without negatively affecting the performance of the medium, for example, sphingosine-1-phosphate and pluripotent stem cells. The present invention relates equally to ingredients that are added as purified compounds, to ingredients that are added as parts of well-defined mixtures, to ingredients that are added as parts of complex or undefined mixtures, for example, animal or plant oils, and to ingredients that are added by biological processes, for example, conditioning. The concentrations of the components can be varied from the listed values within ranges that will be obvious to persons skilled in the art without negatively affecting the performance of the medium. An animal component-free version of the medium was produced by using recombinant versions of all protein ingredients, and non-animal-derived versions of all other components, including semi-synthetic plant-derived cholesterol (Avanti Polar Lipids, Inc.).

Example 5 Reprogramming Human Fibroblasts Using Synthetic RNA Containing Non-Canonical Nucleotides Primary human neonatal fibroblasts were plated in 6-well plates coated with recombinant human fibronectin and recombinant human vitronectin (each diluted in DMEM/F12 to a concentration of 1 µg/mL, 1 mL/well, and incubated at room temperature for 1 h) at a density of 10,000 cells/well in transfection medium. The following day, the cells were transfected as in Example 2, using RNA containing A, 0.5 7 dG, 0.5 5 mU, and 5 mC, and an RNA dose of 0.5 µg/well on day 1, 0.5 µg/well on day 2, 2 µg/well on day 3, 2 µg/well on day 4, and 4 µg/well on day 5. Small colonies of cells exhibiting morphology consistent with reprogramming became visible as early as day 5. The medium was replaced with maintenance medium on day 6. Cells were stained using an antibody against Oct4. Oct4-positive colonies of cells exhibiting a morphology consistent with reprogramming were visible throughout the well (FIG. 2).

Example 6 Feeder-Free, Passage-Free, Immunosuppressant-Free, Conditioning-Free Reprogramming of Primary Adult Human Fibroblasts Using Synthetic RNA Wells of a 6-well plate were coated with a mixture of recombinant human fibronectin and recombinant human vitronectin (1 µg/mL in DMEM/F12, 1 mL/well) for 1 h at room temperature.

Primary adult human fibroblasts were plated in the coated wells in transfection medium at a density of 10,000 cells/well. Cells were maintained at 37° C., 5% $CO_2$, and 5% $O_2$. Beginning the following day, cells were transfected according to Example 2 daily for 5 days with RNA synthesized according to Example 1. The total amount of RNA transfected on each of the 5 days was 0.5 µg, 0.5 µg, 2 µg, 2 µg, and 4 µg, respectively. Beginning with the fourth transfection, the medium was replaced twice a day. On the day following the final transfection, the medium was replaced with transfection medium, supplemented with 10 µM Y-27632. Compact colonies of cells with a reprogrammed morphology were visible in each transfected well by day 4 (FIG. 8).

Example 7 Efficient, Rapid Derivation and Reprogramming of Cells from Adult Human Skin Biopsy Tissue A full-thickness dermal punch biopsy was performed on a healthy, 31 year-old volunteer, according to an approved protocol. Briefly, an area of skin on the left, upper arm was anesthetized by topical application of 2.5% lidocaine. The field was disinfected with 70% isopropanol, and a full-thickness dermal biopsy was performed using a 1.5 mm-diameter punch. The tissue was rinsed in phosphate-buffered saline (PBS), was placed in a 1.5 mL tube containing 250 µL of TrypLE Select CTS (Life Technologies Corporation), and was incubated at 37° C. for 30 min. The tissue was then transferred to a 1.5 mL tube containing 250 µL of DMEM/F12-CTS (Life Technologies Corporation)+5 mg/mL collagenase, and was incubated at 37° C. for 2 h. The epidermis was removed using forceps, and the tissue was mechanically dissociated. Cells were rinsed twice in DMEM/F12-CTS. Phlebotomy was also performed on the same volunteer, and venous blood was collected in Vacutainer SST tubes (Becton, Dickinson and Company). Serum was isolated according to the manufacturer's instructions. Isogenic plating medium was prepared by mixing DMEM/F12-CTS+2 mM L-alanyl-L-glutamine (Sigma-Aldrich Co. LLC.)+20% human serum. Cells from the dermal tissue sample were plated in a fibronectin-coated well of a 6-well plate in isogenic plating medium. Many cells with a fibroblast morphology attached and began to spread by day 2 (FIG. 3A). Cells were expanded and frozen in Synth-a-Freeze (Life Technologies Corporation).

Cells were passaged into 6-well plates at a density of 5,000 cells/well. The following day, the medium was replaced with transfection medium, and the cells were transfected as in Example 2, using RNA containing A, 0.5 7 dG, 0.4 5 mU, and 5 mC, and an RNA dose of 0.5 µg/well on day 1, 0.5 µg/well on day 2, 2 µg/well on day 3, 2 µg/well on day 4, and 2 µg/well on day 5. Certain wells received additional 2 µg/well transfections on day 6 and day 7. In addition, certain wells received 2 ng/mL TGF-β1 from day 4 onward. The medium was replaced with maintenance medium on day 6. Colonies of cells exhibiting morphology consistent with reprogramming became visible between day 5 and day 10 (FIG. 3B). Colonies grew rapidly, and many exhibited a morphology similar to that of embryonic stem-cell colonies (FIG. 3C). Colonies were picked and plated in wells coated with recombinant human fibronectin and recombinant human vitronectin (each diluted in DMEM/F12 to a concentration of 1 µg/mL, 1 mL/well, incubated at room temperature for 1 h). Cells grew rapidly, and were passaged to establish lines.

Example 8 Synthesis of RiboSlice Targeting CCR5

RiboSlice pairs targeting the following sequences: L1: TCATTTTCCATACAGTCAGT (SEQ ID NO: 615), L2: TTTTCCATACAGTCAGTATC (SEQ ID NO: 616), R1: TGACTATCTTTAATGTCTGG (SEQ ID NO: 617), and R2: TATCTTTAATGTCTGGAAAT (SEQ ID NO: 618) were synthesized according to Example 1 (FIG. 4A and FIG. 4B). These pairs target 20-bp sites within the human CCR5 gene on the sense (L1 and L2) or antisense strand (R1 and R2). The following pairs were prepared: L1&R1, L1&R2, L2&R1, and L2&R2.

Example 9 Measurement of CCR5 Gene-Editing Efficiency Using a Mismatch-Detecting Nuclease Primary human fibroblasts were plated in 6-well plates coated with recombinant human fibronectin and recombinant human vitronectin (each diluted in DMEM/F12 to a concentration of 1 µg/mL, 1 mL/well, and incubated at room temperature for 1 h) at a density of 10,000 cells/well in transfection medium. The following day, the cells were transfected as in Example 2 with RNA synthesized according to Example 8. Two days after the transfection, genomic DNA was isolated and purified. A region within the CCR5 gene was amplified by PCR using the primers F: AGCTAGCAGCAAACCTTCCCTTCA (SEQ ID NO: 619) and R: AAGGACAATGTTGTAGGGAGCCCA (SEQ ID NO: 620). 150 ng of the amplified PCR product was hybridized with 150 ng of reference DNA in 10 mM Tris-Cl+50 mM KCl+1.5 mM MgCl$_2$. The hybridized DNA was treated with a mismatch-detecting endonuclease (SURVEYOR nuclease, Transgenomic, Inc.) and the resulting products were analyzed by agarose gel electrophoresis (FIG. 4C and FIG. 4D).

Example 10 High-Efficiency Gene Editing by Repeated Transfection with RiboSlice

Primary human fibroblasts were plated as in Example 9. The following day, the cells were transfected as in Example 2 with RNA synthesized according to Example 8. The following day cells in one of the wells were transfected a second time. Two days after the second transfection, the efficiency of gene editing was measured as in Example 9 (FIG. 4E).

Example 11 Gene-Editing of CCR5 Using RiboSlice and DNA-Free, Feeder-Free, Immunosuppressant-Free, Conditioning-Free Reprogramming of Human Fibroblasts Primary human fibroblasts were plated as in Example 9. The following day, the cells were transfected as in Example 2 with RNA synthesized according to Example 8. Approximately 48 h later, the cells were reprogrammed according to Example 5, using RNA synthesized according to Example 1. Large colonies of cells with a morphology characteristic of reprogramming became visible as in Example 5 (FIG. 4F). Colonies were picked to establish lines. Cell lines were subjected to direct sequencing to confirm successful gene editing (FIG. 4G).

Example 12 Personalized Cell-Replacement Therapy for HIV/AIDS Comprising Gene-Edited Reprogrammed Cells Patient skin cells are gene-edited and reprogrammed to hematopoietic cells according to the present inventors' previously disclosed inventions (U.S. application Ser. No. 13/465,490, U.S. Provisional Application No. 61/637,570, and U.S. Provisional Application No. 61/664,494) and/or Example 11. Cells are then enzymatically released from the culture vessel, and CD34+/CD90+/Lin− or CD34+/CD49f+/Lin− cells are isolated. Between about $1 \times 10^3$ and about $1 \times 10^5$ cells are infused into a main vein of the patient. Hematopoietic cells home to the bone marrow cavity and engraft.

Example 13 Production of APP-Inactivated Rat Embryonic Stem Cells

Rat embryonic stem cells are plated in 6-well plates at a density of 10,000 cells/well in rat stem cell medium. The following day, the cells are transfected as in Example 2 with 0.5 µg/well of RiboSlice synthesized according to Example 1 targeting the following sequences: L: TTCTGTGG- TAAACTCAACAT (SEQ ID NO: 621) and R: TCT-GACTCCCATTTTCCATT (SEQ ID NO: 622) (0.25 µg L and 0.25 µg R).

Example 14 Production of APP-Knockout Rats Using APP-Inactivated Rat Embryonic Stem Cells Rat embryonic stem cells are gene-editing according to Example 13 and microinjected into rat blastocysts. The microinjected blastocysts are then transferred to a pseudopregnant female rat.

Example 15 Production of APP-Inactivated Embryos for the Generation of Knockout Rats A RiboSlice pair targeting the following sequences: L: TTCTGTGGTAAACTCAACAT (SEQ ID NO: 623) and R: TCTGACTCCCATTTTCCATT (SEQ ID NO: 624) is synthesized according to Example 1. RiboSlice at a concentration of 5 µg/µL is injected into the pronucleus or cytoplasm of a 1-cell-stage rat embryo. The embryo is then transferred to a pseudopregnant female rat.

Example 16 Transfection of Cells with Synthetic RNA Containing Non-Canonical Nucleotides and DNA Encoding a Repair Template For transfection in 6-well plates, 1 µg RNA encoding gene-editing proteins targeting exon 16 of the human APP gene, 1 µg single-stranded repair template DNA containing a PstI restriction site that was not present in the target cells, and 6 µL transfection reagent (Lipofectamine RNAiMAX, Life Technologies Corporation) were first diluted separately in complexation medium (Opti-MEM, Life Technologies Corporation) to a total volume of 120 µL. Diluted RNA, repair template, and transfection reagent were then mixed and incubated for 15 min at room temperature, according to the transfection reagent-manufacturer's instructions. Complexes were added to cells in culture. Approximately 120 µL of complexes were added to each well of a 6-well plate, which already contained 2 mL of transfection medium per well. Plates were shaken gently to distribute the complexes throughout the well. Cells were incubated with complexes for 4 hours to overnight, before replacing the medium with fresh transfection medium (2 mL/well). The next day, the medium was changed to DMEM+10% FBS. Two days after transfection, genomic DNA was isolated and purified. A region within the APP gene was amplified by PCR, and the amplified product was digested with PstI and analyzed by gel electrophoresis (FIG. 16).

Example 17 Insertion of a Transgene into Rat Embryonic Stem Cells at a Safe Harbor Location Rat embryonic stem cells are plated in 6-well plates at a density of 10,000 cells/well in rat stem cell medium. The following day, the cells are transfected as in Example 13 with RiboSlice targeting the following sequences: L: TATCTTCCAGAAAGACTCCA (SEQ ID NO: 625) and R: TTCCCTTCCCCCTTCTTCCC (SEQ ID NO: 626), synthesized according to Example 1, and a repair template containing a transgene flanked by two regions each containing approximately 400 bases of homology to the region surrounding the rat Rosa26 locus.

Example 18 Humanized LRRK2 Rat

Rat embryonic stem cells are plated and transfected as in Example 13 with RiboSlice targeting the following sequences: L: TTGAAGGCAAAAATGTCCAC (SEQ ID NO: 627) and R: TCTCATGTAGGAGTCCAGGA (SEQ ID NO: 628), synthesized according to Example 1. Two days after transfection, the cells are transfected according Example 17, wherein the transgene contains the human LRRK2 gene, and, optionally, part or all of the human LRRK2 promoter region.

Example 19 Insertion of a Transgene into Human Fibroblasts at a Safe Harbor Location Primary human fibroblasts are plated as in Example 9. The following day, the cells are transfected as in Example 2 with RiboSlice targeting the following sequences: L: TTATCTGTCCCCTCCACCCC (SEQ ID NO: 629) and R: TTTTCTGTCACCAATCCTGT (SEQ ID NO: 630), synthesized according to Example 1, and a repair template containing a transgene flanked by two regions each containing approximately 400 bases of homology to the region surrounding the human AAVS1 locus.

Example 20 Inserting an RNAi Sequence into a Safe Harbor Location

Primary human fibroblasts are plated and transfected according to Example 19, wherein the transgene contains a sequence encoding an shRNA, preceded by the PolIII promoter.

Example 21 Gene Editing of Myc Using RiboSlice

Primary human fibroblasts were plated in 6-well plates at a density of 50,000 cells/well in DMEM+10% FBS. Two days later, the medium was changed to transfection medium. Four hours later, the cells were transfected as in Example 2 with 1 µg/well of RiboSlice targeting the following sequences: L: TCGGCCGCCGCCAAGCTCGT (SEQ ID NO: 631) and R: TGCGCGCAGCCTGGTAGGAG (SEQ ID NO: 632), synthesized according to Example 1. The following day gene-editing efficiency was measured as in Example 9 using the following primers: F: TAACT-CAAGACTGCCTCCCGCTTT (SEQ ID NO: 633) and R: AGCCCAAGGTTTCAGAGGTGATGA (SEQ ID NO: 634) (FIG. 5).

Example 22 Cancer Therapy Comprising RiboSlice Targeting Myc

HeLa cervical carcinoma cells were plated in 6-well plates at a density of 50,000 cells/well in folate-free DMEM+2 mM L-alanyl-L-glutamine+10% FBS. The following day, the medium was changed to transfection medium. The following day, the cells were transfected as in Example 21.

Example 23 Gene Editing of BIRC5 Using RiboSlice

Primary human fibroblasts were plated in 6-well plates at a density of 50,000 cells/well in DMEM+10% FBS. Two days later, the medium was changed to transfection medium. Four hours later, the cells were transfected as in Example 2 with 1 µg/well of RiboSlice targeting the following sequences: L: TTGCCCCCTGCCTGGCAGCC (SEQ ID NO: 16) and R: TTCTTGAATGTAGAGATGCG (SEQ ID NO: 17), synthesized according to Example 1. The following day gene-editing efficiency was measured as in Example 9 using the following primers: F: GCGCCATTAACCGC-CAGATTTGAA (SEQ ID NO: 635) and R: TGGGAGT-TCACAACAACAGGGTCT (SEQ ID NO: 636) (FIG. 6).

Example 24 Cancer Therapy Comprising RiboSlice Targeting BIRC5

HeLa cervical carcinoma cells were plated in 6-well plates at a density of 50,000 cells/well in folate-free DMEM+2 mM L-alanyl-L-glutamine+10% FBS. The following day, the medium was changed to transfection medium. The following day, the cells were transfected as in Example 23 (FIG. 7A and FIG. 7B).

Example 25 Culture of Cancer-Cell Lines

The cancer cell lines HeLa (cervical carcinoma), MDA-MB-231 (breast), HCT 116 (colon), U87 MG (glioma), and U-251 (glioma) were propagated in culture. Cells were cultured in DMEM+10% FBS or DMEM+50% FBS and maintained at 37° C., 5% $CO_2$, and either ambient 02 or 5% $O_2$. Cells grew rapidly under all conditions, and were routinely passaged every 2-5 days using a solution of trypsin in HBSS.

Example 26 RiboSlice Gene-Editing RNA Design Process and Algorithm

The annotated DNA sequence of the BIRC5 gene was retrieved from NCBI using the eFetch utility and a python script. The same python script was used to identify the DNA sequences encoding the protein within each of the four exons of the BIRC5 gene. The script then searched these sequences, and the 40 bases flanking each side, for sequence elements satisfying the following conditions: (i) one element exists on the primary strand, the other on the complementary strand, (ii) each element begins with a T, and (iii) the elements are separated by no fewer than 12 bases and no more than 20 bases. Each element was then assigned a score representing its likelihood of binding to other elements within the human genome using Qblast (NCBI). This score was computed as the sum of the inverse of the nine lowest E-values, excluding the match to the target sequence. Pair scores were computed by adding the scores for the individual elements.

Example 27 Synthesis of RNA Encoding Gene-Editing Proteins (RiboSlice)

RNA encoding gene-editing proteins was designed according to Example 26, and synthesized according to Example 1 (Table 10, FIG. 9). The RNA was diluted with nuclease-free water to between 200 ng/μL and 500 ng/μL, and was stored at 4° C.

TABLE 10

| RiboSlice Synthesis | | | |
|---|---|---|---|
| Template (SEQ ID of Binding Site) | Nucleotides | Reaction Volume/μL | ivT Yield/μg |
| BIRC5-1.1L (SEQ ID NO: 16) | A, 0.5 7dG, 0.4 5mU, 5mC | 20 | 124.1 |
| BIRC5-1.1R (SEQ ID NO: 17) | A, 0.5 7dG, 0.4 5mU, 5mC | 20 | 115.6 |
| BIRC5-1.2L (SEQ ID NO: 18) | A, 0.5 7dG, 0.4 5mU, 5mC | 20 | 120.3 |

TABLE 10-continued

| RiboSlice Synthesis | | | |
|---|---|---|---|
| Template (SEQ ID of Binding Site) | Nucleotides | Reaction Volume/μL | ivT Yield/μg |
| BIRC5-1.2R (SEQ ID NO: 19) | A, 0.5 7dG, 0.4 5mU, 5mC | 20 | 121.3 |
| BIRC5-1.3L (SEQ ID NO: 20) | A, 0.5 7dG, 0.4 5mU, 5mC | 20 | 120.3 |
| BIRC5-1.3R (SEQ ID NO: 21) | A, 0.5 7dG, 0.4 5mU, 5mC | 20 | 113.7 |
| BIRC5-2.1L (SEQ ID NO: 22) | A, 0.5 7dG, 0.4 5mU, 5mC | 20 | 105.3 |
| BIRC5-2.1R (SEQ ID NO: 23) | A, 0.5 7dG, 0.4 5mU, 5mC | 20 | 120.3 |
| BIRC5-2.2L (SEQ ID NO: 24) | A, 0.5 7dG, 0.4 5mU, 5mC | 20 | 101.5 |
| BIRC5-2.2R (SEQ ID NO: 25) | A, 0.5 7dG, 0.4 5mU, 5mC | 20 | 111.9 |
| BIRC5-3.1L (SEQ ID NO: 26) | A, 0.5 7dG, 0.4 5mU, 5mC | 20 | 107.2 |
| BIRC5-3.1R (SEQ ID NO: 27) | A, 0.5 7dG, 0.4 5mU, 5mC | 20 | 113.7 |
| BIRC5-2.1L (SEQ ID NO: 22) | A, 0.5 7dG, 0.35 5mU, 5mC | 300 | 577.9 |
| BIRC5-2.1R (SEQ ID NO: 23) | A, 0.5 7dG, 0.35 5mU, 5mC | 300 | 653.6 |

Example 28 Activity Analysis of RiboSlice Targeting BIRC5

Primary adult human fibroblasts were transfected according to Example 2 with 6 RiboSlice pairs targeting BIRC5, designed according to Example 26, and synthesized according to Example 27. Two days after transfection, genomic DNA was isolated and purified. To measure gene-editing efficiency, 150 ng of the amplified PCR product was hybridized with 150 ng of reference DNA in 10 mM Tris-Cl+50 mM KCl+1.5 mM $MgCl_2$. The hybridized DNA was treated with the SURVEYOR mismatch-specific endonuclease (Transgenomic, Inc.), and the resulting products were analyzed by agarose gel electrophoresis (FIG. 10A). All six of the tested RiboSlice pairs efficiently edited the BIRC5 gene, as demonstrated by the appearance of bands of the expected sizes (asterisks in FIG. 10A).

Example 29 Mitosis-Inhibition Analysis of RiboSlice Targeting BIRC5

Primary adult human fibroblasts were gene edited according to Example 28, and were then propagated in culture. After 11 days, genomic DNA was isolated and purified, and gene-editing efficiency was measured as in Example 28 (FIG. 10B). None of the tested RiboSlice pairs inhibited the proliferation of the fibroblasts, as shown by the appearance of bands of the expected sizes (asterisks in FIG. 10B) in genomic DNA isolated from the proliferating cells, demonstrating the low toxicity to normal fibroblasts of these RiboSlice pairs.

Example 30 Anti-Cancer-Activity Analysis of RiboSlice Targeting BIRC5

Primary adult human fibroblasts and HeLa cervical carcinoma cells, cultured according to Example 25 were transfected with RiboSlice pairs according to Example 28. Proliferation of the fibroblasts slowed briefly due to transfection reagent-associated toxicity, but recovered within 2 days of transfection. In contrast, proliferation of HeLa cells slowed markedly, and many enlarged cells with fragmented nuclei were observed in transfected wells. After 2-3 days, many cells exhibited morphology indicative of apoptosis, demonstrating the potent anti-cancer activity of RiboSlice targeting BIRC5.

Example 31 In Vivo RiboSlice Safety Study 40 female NCr nu/nu mice were injected subcutaneously with $5\times10^6$ MDA-MB-231 tumor cells in 50% Matrigel (BD Biosciences). Cell injection volume was 0.2 mL/mouse. The age of the mice at the start of the study was 8 to 12 weeks. A pair match was conducted, and animals were divided into 4 groups of 10 animals each when the tumors reached an average size of 100-150 mm$^3$, and treatment was begun. Body weight was measured every day for the first 5 days, and then biweekly to the end of the study. Treatment consisted of RiboSlice BIRC5-1.2 complexed with a vehicle (Lipofectamine 2000, Life Technologies Corporation). To prepare the dosing solution for each group, 308 µL of complexation buffer (Opti-MEM, Life Technologies Corporation) was pipetted into each of two sterile, RNase-free 1.5 mL tubes. 22 µL of RiboSlice BIRC5-1.2 (500 ng/µL) was added to one of the two tubes, and the contents of the tube were mixed by pipetting. 22 µL of vehicle was added to the second tube. The contents of the second tube were mixed, and then transferred to the first tube, and mixed with the contents of the first tube by pipetting to form complexes. Complexes were incubated at room temperature for 10 min. During the incubation, syringes were loaded. Animals were injected either intravenously or intratumorally with a total dose of 1 µg RNA/animal in 60 µL total volume/animal. A total of 5 treatments were given, with injections performed every other day. Doses were not adjusted for body weight. Animals were followed for 17 days. No significant reduction in mean body weight was observed (FIG. 11; RiboSlice BIRC5-1.2 is labeled "ZK1"), demonstrating the in vivo safety of RiboSlice gene-editing RNA.

Example 32 Anti-Cancer-Activity Analysis of RiboSlice Targeting BIRC5 in a Glioma Model The U-251 glioma cell line, cultured according to Example 25, was transfected with RiboSlice pairs according to Example 28. Glioma cells responded to treatment similarly to HeLa cells: proliferation slowed markedly, and many enlarged cells with fragmented nuclei were observed in transfected wells. After 2-3 days, many cells exhibited morphology indicative of apoptosis, demonstrating the potent anti-cancer activity of RiboSlice targeting BIRC5 in a glioma model.

Example 33 Screening of Reagents for Delivery of Nucleic Acids to Cells

Delivery reagents including polyethyleneimine (PEI), various commercial lipid-based transfection reagents, a peptide-based transfection reagent (N-TER, Sigma-Aldrich Co. LLC.), and several lipid-based and sterol-based delivery reagents were screened for transfection efficiency and toxicity in vitro. Delivery reagents were complexed with RiboSlice BIRC5-1.2, and complexes were delivered to HeLa cells, cultured according to Example 25. Toxicity was assessed by analyzing cell density 24 h after transfection. Transfection efficiency was assessed by analyzing morphological changes, as described in Example 30. The tested reagents exhibited a wide range of toxicities and transfection efficiencies. Reagents containing a higher proportion of ester bonds exhibited lower toxicities than reagents containing a lower proportion of ester bonds or no ester bonds.

Example 34 High-Concentration Liposomal RiboSlice

High-Concentration Liposomal RiboSlice was prepared by mixing 1 µg RNA at 500 ng/µL with 3 µL of complexation medium (Opti-MEM, Life Technologies Corporation), and 2.5 µL of transfection reagent (Lipofectamine 2000, Life Technologies Corporation) per µg of RNA with 2.5 µL of complexation medium. Diluted RNA and transfection reagent were then mixed and incubated for 10 min at room temperature to form High-Concentration Liposomal RiboSlice. Alternatively, a transfection reagent containing DOSPA or DOSPER is used.

Example 35 In Vivo RiboSlice Efficacy Study—Subcutaneous Glioma Model 40 female NCr nu/nu mice were injected subcutaneously with $1\times10^7$ U-251 tumor cells. Cell injection volume was 0.2 mL/mouse. The age of the mice at the start of the study was 8 to 12 weeks. A pair match was conducted, and animals were divided into 4 groups of 10 animals each when the tumors reached an average size of 35-50 mm$^3$, and treatment was begun. Body weight was measured every day for the first 5 days, and then biweekly to the end of the study. Caliper measurements were made biweekly, and tumor size was calculated. Treatment consisted of RiboSlice BIRC5-2.1 complexed with a vehicle (Lipofectamine 2000, Life Technologies Corporation). To prepare the dosing solution, 294 µL of complexation buffer (Opti-MEM, Life Technologies Corporation) was pipetted into a tube containing 196 µL of RiboSlice BIRC5-1.2 (500 ng/µL), and the contents of the tube were mixed by pipetting. 245 µL of complexation buffer was pipetted into a tube containing 245 µL of vehicle. The contents of the second tube were mixed, and then transferred to the first tube, and mixed with the contents of the first tube by pipetting to form complexes. Complexes were incubated at room temperature for 10 min. During the incubation, syringes were loaded. Animals were injected intratumorally with a total dose of either 2 µg or 5 µg RNA/animal in either 20 µL or 50 µL total volume/animal. A total of 5 treatments were given, with injections performed every other day. Doses were not adjusted for body weight. Animals were followed for 25 days.

Example 36 Synthesis of High-Activity/High-Fidelity RiboSlice In Vitro-Transcription Template An in vitro-transcription template encoding a T7 bacteriophage RNA-polymerase promoter, 5'-untranslated region, strong Kozak sequence, TALE N-terminal domain, 18 repeat sequences designed according to Example 26, TALE C-terminal domain, and nuclease domain comprising the StsI sequence (SEQ ID NO: 1), StsI-HA sequence (SEQ ID NO: 2), StsI-HA2 sequence (SEQ ID NO: 3), StsI-UHA sequence (SEQ ID NO: 4), StsI-UHA2 sequence (SEQ ID NO: 5), StsI-HF sequence (SEQ ID NO: 6) or StsI-HF2 sequence (SEQ ID NO: 7) is synthesized using standard cloning and molecular biology techniques, or alternatively, is synthesized by direct chemical synthesis, for example using a gene fragment assembly technique (e.g., gBlocks, Integrated DNA Technologies, Inc.).

Example 37 Synthesis of High-Activity/High-Fidelity RiboSlice Gene-Editing RNA High-Activity RiboSlice and High-Fidelity RiboSlice are synthesized according to Example 27, using in vitro-transcription templates synthesized according to Example 36.

Example 38 Generation of RiboSlice-Encoding Replication-Incompetent Virus for Treatment of Proteopathy A nucleotide sequence comprising RiboSlice targeting a DNA sequence that encodes a plaque-forming protein sequence is incorporated into a mammalian expression vector comprising a replication-incompetent viral genome, and transfected into a packaging cell line to produce replication-incompetent virus. The culture supernatant is collected, and filtered using a 0.45 µm filter to remove debris.

Example 39 Generation of RiboSlice-Encoding Replication-Competent Oncolytic Virus for Treatment of Cancer A nucleotide sequence comprising RiboSlice targeting the BIRC5 gene, is incorporated into a mammalian expression vector comprising a replication-competent viral genome, and transfected into a packaging cell line to produce replication-competent virus. The culture supernatant is collected and filtered, according to Example 38.

Example 40 In Vivo RiboSlice Efficacy Study Orthotopic Glioma Model, Intrathecal Route of Administration 40 female NCr nu/nu mice are injected intracranially with $1\times10^5$ U-251 tumor cells. Cell injection volume is 0.02 mL/mouse. The age of the mice at the start of the study is 8 to 12 weeks. After 10 days, animals are divided into 4 groups of 10 animals each, and treatment is begun. Body weight is measured every day for the first 5 days, and then biweekly to the end of the study. Treatment consists of RiboSlice BIRC5-2.1 complexed with a vehicle (Lipofectamine 2000, Life Technologies Corporation). To prepare the dosing solution, 294 µL of complexation buffer (Opti-MEM, Life Technologies Corporation) is pipetted into a tube containing 196 µL of RiboSlice BIRC5-1.2 (500 ng/µL), and the contents of the tube are mixed by pipetting. 245 µL of complexation buffer is pipetted into a tube containing 245 µL of vehicle. The contents of the second tube are mixed, and then transferred to the first tube, and mixed with the contents of the first tube by pipetting to form complexes. Complexes are incubated at room temperature for 10 min. During the incubation, syringes are loaded. Animals are injected intrathecally with a total dose of 1-2 µg RNA/animal in 10-20 µL total volume/animal. A total of 5 treatments are given, with injections performed every other day. Doses are not adjusted for body weight. Animals are followed for 60 days.

Example 41 Treatment of Glioma with RiboSlice—IV Perfusion

A patient with a diagnosis of glioma is administered 1 mg of High-Concentration Liposomal RiboSlice BIRC5-2.1, prepared according to Example 34 by IV infusion over the course of 1 h, 3 times a week for 4 weeks. For an initial tumor volume of greater than 500 $mm^3$, the tumor is debulked surgically and optionally by radiation therapy and/or chemotherapy before RiboSlice treatment is begun. The patient is optionally administered TNF-α and/or 5-FU using a standard dosing regimen as a combination therapy.

Example 42 Treatment of Glioma with RiboSlice—Replication-Competent Oncolytic Virus A patient is administered 1 mL of replicating virus particles (1000 CFU/mL), prepared according to Example 39, by intrathecal or intracranial injection.

Example 43 Treatment of Parkinson's Disease with RiboSlice Targeting SNCA

A patient with a diagnosis of Parkinson's disease is administered 50 µg of RiboSlice targeting the SNCA gene by intrathecal or intracranial injection.

Example 44 Treatment of Alzheimer's Disease with RiboSlice Targeting APP

A patient with a diagnosis of Alzheimer's disease is administered 50 µg of RiboSlice targeting the APP gene by intrathecal or intracranial injection.

Example 45 Treatment of Type II Diabetes with RiboSlice Targeting IAPP

A patient with a diagnosis of type II diabetes is administered 5 mg of RiboSlice targeting the IAPP gene by intravenous, intraperitoneal or intraportal injection.

Example 46 iRiboSlice Personalized Cancer Therapy

A biopsy is taken from a patient with a diagnosis of cancer. Genomic DNA is isolated and purified from the biopsy, and the sequence of the DNA (either the whole-genome sequence, exome sequence or the sequence of one or more cancer-associated genes) is determined. A RiboSlice pair targeting the patient's individual cancer sequence (iRiboSlice) is designed according to Example 26 and synthesized according to Example 27. The patient is administered the personalized iRiboSlice using a route of administration appropriate for the location and type of cancer.

Example 47 RiboSlice Mixtures for Genetically Diverse/Treatment-Resistant Cancer A patient with a diagnosis of genetically diverse and/or treatment-resistant cancer is administered a mixture of RiboSlice pairs targeting multiple cancer-associated genes and/or multiple sequences in one or more cancer-associated genes.

Example 48 Mito-RiboSlice for Mitochondrial Disease

A patient with a diagnosis of a mitochondrial disease is administered 2 mg of RiboSlice targeting the disease-associated sequence and containing a mitochondrial localization sequence by intramuscular injection.

Example 49 Treatment of Eye Disease with RiboSlice Eye Drops

A patient with a diagnosis of a corneal or conjunctival disease is administered RiboSlice formulated as a 0.5% isotonic solution.

Example 50 Treatment of Skin Disease with RiboSlice Topical Formulation

A patient with a diagnosis of a skin disease is administered RiboSlice formulated as a 1% topical cream/ointment containing one or more stabilizers that prevent degradation of the RNA.

Example 51 Treatment of Lung or Respiratory Disease with RiboSlice Aerosol Formulation A patient with a diagnosis of a lung or respiratory disease is administered RiboSlice formulated as a 0.5% aerosol spray.

Example 52 Treatment of Infectious Disease with RiboSlice Targeting a DNA Sequence Present in the Infectious Agent A patient with a diagnosis of an infectious disease is administered RiboSlice targeting a sequence present in the specific infectious agent with which the patient is infected using a route of administration appropriate to the location and type of infection, and a dose appropriate for the route of administration and severity of the infection.

Example 53 Gene-Edited Human Zygotes for In Vitro Fertilization

A human germ cell, zygote or early-stage blastocyst is transfected with RiboSlice targeting a gene that encodes a disease-associated mutation or mutation associated with an undesired trait. The genome is characterized, and the cell is prepared for in vitro fertilization.

Example 54 Cleavage-Domain Screen for Activity, Fidelity Enhancement of Gene-Editing Proteins A panel of RiboSlice pairs, each comprising a different cleavage domain, are designed according to Example 26 and synthesized according to Example 27. The activity of the RiboSlice pairs is determined as in Example 28.

Example 55 Gene-Edited Cells for Screening Parkinson's Disease-Causing Toxicants Primary human adult fibroblasts are gene edited according to Example 28 using RiboSlice targeting SNCA (Table 11) and repair templates to generate cells with the SNCA A30P, E46K, and A53T mutations. Cells are reprogrammed and differentiated to dopaminergic neurons. The neurons are used in a high-throughput α-synuclein-aggregation toxicant-screening assay to identify toxicants that can contribute to Parkinson's disease.

TABLE 11

| | | RiboSlice Pairs for Generation of SNCA A30P, E46K, and A53T. | | | | |
|---|---|---|---|---|---|---|
| Exon | Target Amino Acid | Left RiboSlice Binding Site | SEQ ID NO | Right RiboSlice Binding Site | SEQ ID NO | Spacing |
| 1 | A30 | TGAGAAAACCAAACAGGGTG | 637 | TAGAGAACACCCTCTTTTGT | 638 | 20 |
| 2 | E46 | TGTTTTTGTAGGCTCCAAAA | 639 | TACCTGTTGCCACACCATGC | 640 | 16 |
| 2 | A53 | TCCAAAACCAAGGAGGGAGT | 641 | TAAGCACAATGGAGCTTACC | 642 | 19 |

Example 56 Gene-Edited Cells for Screening Cancer-Causing Toxicants

Primary human adult fibroblasts are gene edited according to Example 28 using RiboSlice targeting TP53 (Table 12) and repair templates to generate cells with the TP53 P47S, R72P, and V217M mutations. Cells are reprogrammed and differentiated to hepatocytes. The hepatocytes are used in a high-throughput in vitro-transformation toxicant-screening assay to identify toxicants that can contribute to cancer.

TABLE 12

RiboSlice Pairs for Generation of TP53 P475, R72P, and V217M

| Exon | Target Amino Acid | Left Ribo Slice Binding Site | SEQ ID NO | Right Ribo Slice Binding Site | SEQ ID NO | Spacing |
|---|---|---|---|---|---|---|
| 4 | P47 | TCCCAAGCAATGGATGATTT | 643 | TGAACCATTGTTCAATATCG | 644 | 15 |
| 4 | R72 | TGAAGCTCCCAGAATGCCAG | 645 | TAGGAGCTGCTGGTGCAGGG | 646 | 19 |
| 6 | V217 | TGGATGACAGAAACACTTTT | 647 | TCAGGCGGCTCATAGGGCAC | 648 | 15 |

Example 57 Design and Synthesis of RNA Encoding Engineered Gene-Editing Proteins (RiboSlice)

RNA encoding gene-editing proteins designed according to Example 26 was synthesized according to Example 27 (Table 13). Each gene-editing protein comprised a DNA-binding domain comprising a transcription activator-like (TAL) effector repeat domain comprising 35-36 amino acid-long repeat sequences, as indicated in Table 13. Sequence ID numbers are given for the 36 amino acid-long repeat sequences. The label "18" in the template name indicates that the $18^{th}$ repeat sequence was 36 amino acids long. The label "EO" in the template name indicates that every other repeat sequence was 36 amino acids long. The amino acids following the label "18" or "EO" indicate the amino acids at the C-terminus of the 36 amino acid-long repeat sequence(s). The label "StsI" indicates that the nuclease domain contained the StsI cleavage domain. Templates without the "StsI" label contained the FokI cleavage domain.

TABLE 13

RiboSlice Encoding Engineered Gene-Editing Proteins.

| Template (SEQ ID of Repeat Sequence) | Nucleotides | Reaction Volume/μL | ivT Yield/μg |
|---|---|---|---|
| BIRC5-2.1L-18-AHGGG (SEQ ID NO: 54) | A, 0.5 7dG, 0.4 5mU, 5mC | 20 | 11.9 |
| BIRC5-2.1R-18-AHGGG (SEQ ID NO: 54) | A, 0.5 7dG, 0.4 5mU, 5mC | 20 | 11.9 |
| BIRC5-2.1L-18-AGHGG (SEQ ID NO: 55) | A, 0.5 7dG, 0.4 5mU, 5mC | 20 | 10.7 |
| BIRC5-2.1R-18-AGHGG (SEQ ID NO: 55) | A, 0.5 7dG, 0.4 5mU, 5mC | 20 | 10.9 |
| BIRC5-2.1L-18-AHGSG (SEQ ID NO: 56) | A, 0.5 7dG, 0.4 5mU, 5mC | 20 | 11.9 |
| BIRC5-2.1R-18-AHGSG (SEQ ID NO: 56) | A, 0.5 7dG, 0.4 5mU, 5mC | 20 | 12.7 |
| BIRC5-2.1L-18-AHGGG (SEQ ID NO: 54) | A, 0.5 7dG, 0.4 5mU, 5mC | 20 | 34.5 |
| BIRC5-2.1R-18-AHGGG (SEQ ID NO: 54) | A, 0.5 7dG, 0.4 5mU, 5mC | 20 | 34.8 |
| BIRC5-2.1L-18-AGHGG (SEQ ID NO: 55) | A, 0.5 7dG, 0.4 5mU, 5mC | 20 | 32.7 |
| BIRC5-2.1R-18-AGHGG (SEQ ID NO: 55) | A, 0.5 7dG, 0.4 5mU, 5mC | 20 | 37.4 |
| BIRC5-2.1L-18-AHGSG (SEQ ID NO: 56) | A, 0.5 7dG, 0.4 5mU, 5mC | 20 | 31.5 |
| BIRC5-2.1R-18-AHGSG (SEQ ID NO: 56) | A, 0.5 7dG, 0.4 5mU, 5mC | 20 | 34.1 |
| BIRC5-2.1L | A, 0.5 7dG, 0.4 5mU, 5mC | 20 | 34.9 |
| BIRC5-2.1R | A, 0.5 7dG, 0.4 5mU, 5mC | 20 | 25.9 |
| BIRC5-2.1L | A, 0.5 7dG, 0.4 5mU, 5mC | 20 | 41.5 |
| BIRC5-2.1R | A, 0.5 7dG, 0.4 5mU, 5mC | 20 | 38.8 |
| BIRC5-2.1L-StsI | A, 0.5 7dG, 0.4 5mU, 5mC | 20 | 22.2 |
| BIRC5-2.1R-StsI | A, 0.5 7dG, 0.4 5mU, 5mC | 20 | 18.4 |
| BIRC5-2.1L-EO-AGHGG (SEQ ID NO: 55) | A, 0.5 7dG, 0.4 5mU, 5mC | 20 | 21.6 |
| BIRC5-2.1L | A, 0.5 7dG, 0.4 5mU, 5mC | 20 | 17.3 |
| BIRC5-2.1L-StsI | A, G, U, C | 10 | 71.3 |
| BIRC5-2.1R-StsI | A, G, U, C | 10 | 75.1 |
| BIRC5-2.1L-EO-AGHGG (SEQ ID NO: 55) | A, G, U, C | 10 | 66.4 |
| BIRC5-2.1R-EO-AGHGG (SEQ ID NO: 55) | A, G, U, C | 10 | 52.4 |

Example 58 Activity Analysis of RiboSlice Targeting BIRC5

The activity of RiboSlice molecules synthesized according to Example 57 was analyzed according to Example 28 (FIG. 12A, FIG. 12B, and FIG. 14). High-efficiency gene editing was observed in cells expressing gene-editing proteins containing one or more 36 amino acid-long repeat sequences. Gene-editing efficiency was highest in cells expressing gene-editing proteins containing one or more repeat sequences containing the amino-acid sequence: GHGG (SEQ ID NO: 675).

Example 59 In Vivo RiboSlice AAV Safety and Efficacy Study Subcutaneous Glioma Model, Intratumoral Route of Delivery Animals were set up with tumors comprising U-251 human glioma cells according to Example 35. AAV serotype 2 encoding GFP, BIRC5-2.1L RiboSlice, and BIRC5-2.1R RiboSlice was prepared according to standard techniques (AAV-2 Helper Free Expression System, Cell Biolabs, Inc.). Viral stocks were stored at 4° C. (short term) or −80° C. (long term). Animals received intratumoral injections of either 160 µL GFP AAV on day 1 or 80 µL BIRC5-2.1L RiboSlice AAV+80 µL BIRC5-2.1R RiboSlice AAV on day 1 and day 15. Animals were followed for 25 days. No significant reduction in mean body weight was observed (FIG. 13A), demonstrating the in vivo safety of RiboSlice AAV. Tumor growth was inhibited in the RiboSlice AAV group (FIG. 13B), demonstrating the in vivo efficacy of RiboSlice AAV.

Example 60 Treatment of Cancer with RiboSlice AAV

A patient is administered 1 mL of RiboSlice AAV virus particles, prepared according to Example 59, by intrathecal or intracranial injection. Dosing is repeated as necessary. For a patient with an initial tumor volume of greater than 500 mm³, the tumor is debulked surgically and optionally by radiation therapy and/or chemotherapy before RiboSlice AAV treatment is begun. The patient is optionally administered TNF-α and/or 5-FU using a standard dosing regimen as a combination therapy.

Example 61 iRiboSlice AAV Personalized Cancer Therapy

A biopsy is taken from a patient with a diagnosis of cancer. Genomic DNA is isolated and purified from the biopsy, and the sequence of the DNA (either the whole-genome sequence, exome sequence or sequence of one or more cancer-associated genes) is determined. A RiboSlice pair targeting the patient's individual cancer sequence (iRiboSlice) is designed according to Example 26 and synthesized according to Example 59. The patient is administered the personalized iRiboSlice AAV using a route of administration appropriate for the location and type of cancer.

Example 62 Liposome Formulation and Nucleic-Acid Encapsulation

Liposomes are prepared using the following formulation: 3.2 mg/mL N-(carbonyl-ethoxypolyethylene glycol 2000)-1,2-distearoyl-sn-glycero-3-phosphoethanolamine (MPEG2000-DSPE), 9.6 mg/mL fully hydrogenated phosphatidylcholine, 3.2 mg/mL cholesterol, 2 mg/mL ammonium sulfate, and histidine as a buffer. pH is controlled using sodium hydroxide and isotonicity is maintained using sucrose. To form liposomes, lipids are mixed in an organic solvent, dried, hydrated with agitation, and sized by extrusion through a polycarbonate filter with a mean pore size of 800 nm. Nucleic acids are encapsulated by combining 10 µg of the liposome formulation per 1 µg of nucleic acid and incubating at room temperature for 5 minutes.

Example 63 Folate-Targeted Liposome Formulation

Liposomes are prepared according to Example 62, except that 0.27 mg/mL 1,2-distearoyl-sn-glycero-3-phosphoethanolamine-N-[folate(polyethylene glycol)-5000] (FA-MPEG5000-DSPE) is added to the lipid mixture

Example 64 Cancer Therapy Comprising Liposomal RiboSlice Targeting BIRC5

Liposomes encapsulating RiboSlice pairs synthesized according to Example 23 are prepared according to Example 62 or Example 63. The liposomes are administered by injection or intravenous infusion, and tumor response and interferon plasma levels are monitored daily.

Example 65 Cancer Therapy Comprising Liposomal RiboSlice Targeting a Cancer-Associated Gene Liposomes encapsulating RiboSlice targeting a cancer-associated gene, synthesized according to Example 1, are prepared according to Example 62 or Example 63. The liposomes are administered by injection or intravenous infusion, and tumor response and interferon plasma levels are monitored daily.

Example 66 Therapy Comprising Liposomal Protein-Encoding RNA

Liposomes encapsulating synthetic RNA encoding a therapeutic protein, synthesized according to Example 1, are prepared according to Example 62 or Example 63. The liposomes are administered by injection or intravenous infusion.

Example 67 Combination Cancer Therapy Comprising RiboSlice Targeting BIRC5 and TNF-α

Patients are administered isolated limb perfusion (ILP) with tumor necrosis factor alpha (TNF-α) and liposomes encapsulating RiboSlice targeting BIRC5 (see Example 64). Following warming of the limb, liposomes are injected into the arterial line of the extracorporeal ILP circuit over approximately 5 minutes, and perfusion proceeds for another 85 minutes. After 1-2 days, ILP is repeated with TNF-α injected into the arterial line of the extracorporeal ILP circuit over 3-5 minutes and perfusion continues for an additional 60 minutes. Tumor response and interferon plasma levels are monitored daily.

Example 68 Combination Cancer Therapy Comprising RiboSlice Targeting BIRC5 and Fluorouracil (5-FU)

On day 1 patients receive a 60-minute intravenous infusion of liposomes encapsulating RiboSlice targeting BIRC5

(see Example 64), followed by a 46-hour intravenous infusion of 5-FU on days 2 and 3. Tumor response and interferon plasma levels are monitored daily.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

What is claimed is:

1. A composition comprising a nucleic acid encoding a gene-editing protein, the gene-editing protein comprising: (a) a DNA-binding domain and (b) a nuclease domain, wherein:
  (a) the DNA-binding domain comprises a plurality of repeat sequences and at least one of the repeat sequences comprises the amino acid sequence: LTPvQVVAIAwxyzGHGG (SEQ ID NO: 75) and is between 36 and 39 amino acids long, wherein:
    "v" is Q, D or E,
    "w" is S or N,
    "x" is N,
    "y" is D, A, H, N, K, or G, and
    "z" is GGKQALETVQRLLPVLCQD (SEQ ID NO: 670) or GGKQALETVQRLLPVLCQA (SEQ ID NO: 671); and
  (b) the nuclease domain comprises a catalytic domain of a nuclease.

2. The composition of claim 1, wherein the nuclease domain is capable of forming a dimer with another nuclease domain.

3. The composition of claim 1, wherein the gene-editing protein is capable of generating a nick or double-strand break in a target DNA molecule.

4. The composition of claim 1, wherein the nucleic acid is a synthetic RNA molecule.

5. The composition of claim 4, wherein the synthetic RNA molecule comprises one or more non-canonical nucleotides.

6. The composition of claim 5, wherein the non-canonical nucleotide is 5-methylcytidine.

7. The composition of claim 1, wherein the nuclease domain comprises the catalytic domain of a protein comprising the amino acid sequence of SEQ ID NO: 53.

8. The composition of claim 1, wherein the nuclease is selected from the group consisting of FokI and StsI.

9. The composition of claim 1, wherein at least one of the repeat sequences contains a region capable of binding to a binding site in a target DNA molecule, the binding site containing a defined sequence of between 1 and 5 bases in length.

* * * * *

SEQUENCE LISTING

```
<160> NUMBER OF SEQ ID NOS: 679

<210> SEQ ID NO 1
<211> LENGTH: 195
<212> TYPE: PRT
<213> ORGANISM: Homo sapiens

<400> SEQUENCE: 1

Val Leu Glu Lys Ser Asp Ile Glu Lys Phe Lys Asn Gln Leu Arg Thr
1               5                   10                  15

Glu Leu Thr Asn Ile Asp His Ser Tyr Leu Lys Gly Ile Asp Ile Ala
            20                  25                  30

Ser Lys Lys Lys Thr Ser Asn Val Glu Asn Thr Glu Phe Glu Ala Ile
        35                  40                  45

Ser Thr Lys Ile Phe Thr Asp Glu Leu Gly Phe Ser Gly Lys His Leu
    50                  55                  60

Gly Gly Ser Asn Lys Pro Asp Gly Leu Leu Trp Asp Asp Cys Ala
65                  70                  75                  80

Ile Ile Leu Asp Ser Lys Ala Tyr Ser Glu Gly Phe Pro Leu Thr Ala
                85                  90                  95

Ser His Thr Asp Ala Met Gly Arg Tyr Leu Arg Gln Phe Thr Glu Arg
                100                 105                 110

Lys Glu Glu Ile Lys Pro Thr Trp Trp Asp Ile Ala Pro Glu His Leu
            115                 120                 125

Asp Asn Thr Tyr Phe Ala Tyr Val Ser Gly Ser Phe Ser Gly Asn Tyr
        130                 135                 140

Lys Glu Gln Leu Gln Lys Phe Arg Gln Asp Thr Asn His Leu Gly Gly
145                 150                 155                 160

Ala Leu Glu Phe Val Lys Leu Leu Leu Ala Asn Asn Tyr Lys Thr
                165                 170                 175

Gln Lys Met Ser Lys Lys Glu Val Lys Lys Ser Ile Leu Asp Tyr Asn
            180                 185                 190

Ile Ser Tyr
        195

<210> SEQ ID NO 2
<211> LENGTH: 195
<212> TYPE: PRT
<213> ORGANISM: Homo sapiens

<400> SEQUENCE: 2

Val Leu Glu Lys Ser Asp Ile Glu Lys Phe Lys Asn Gln Leu Arg Thr
1               5                   10                  15

Glu Leu Thr Asn Ile Asp His Ser Tyr Leu Lys Gly Ile Asp Ile Ala
            20                  25                  30

Ser Lys Lys Lys Thr Ser Asn Val Glu Asn Thr Glu Phe Glu Ala Ile
        35                  40                  45

Ser Thr Lys Ile Phe Thr Asp Glu Leu Gly Phe Ser Gly Glu His Leu
    50                  55                  60
```

Gly Gly Ser Asn Lys Pro Asp Gly Leu Leu Trp Asp Asp Cys Ala
65                  70                  75                  80

Ile Ile Leu Asp Ser Lys Ala Tyr Ser Glu Gly Phe Pro Leu Thr Ala
            85                  90                  95

Ser His Thr Asp Ala Met Gly Arg Tyr Leu Arg Gln Phe Thr Glu Arg
                100                 105                 110

Lys Glu Glu Ile Lys Pro Thr Trp Trp Asp Ile Ala Pro Glu His Leu
            115                 120                 125

Asp Asn Thr Tyr Phe Ala Tyr Val Ser Gly Ser Phe Ser Gly Asn Tyr
        130                 135                 140

Lys Glu Gln Leu Gln Lys Phe Arg Gln Asp Thr Asn His Leu Gly Gly
145                 150                 155                 160

Ala Leu Glu Phe Val Lys Leu Leu Leu Ala Asn Asn Tyr Lys Thr
                165                 170                 175

Gln Lys Met Ser Lys Lys Glu Val Lys Lys Ser Ile Leu Asp Tyr Asn
                180                 185                 190

Ile Ser Tyr
        195

<210> SEQ ID NO 3
<211> LENGTH: 195
<212> TYPE: PRT
<213> ORGANISM: Homo sapiens

<400> SEQUENCE: 3

Val Leu Glu Lys Ser Asp Ile Glu Lys Phe Lys Asn Gln Leu Arg Thr
1               5                   10                  15

Glu Leu Thr Asn Ile Asp His Ser Tyr Leu Lys Gly Ile Asp Ile Ala
                20                  25                  30

Ser Lys Pro Lys Thr Ser Asn Val Glu Asn Thr Glu Phe Glu Ala Ile
            35                  40                  45

Ser Thr Lys Ile Phe Thr Asp Glu Leu Gly Phe Ser Gly Lys His Leu
        50                  55                  60

Gly Gly Ser Asn Lys Pro Asp Gly Leu Leu Trp Asp Asp Cys Ala
65                  70                  75                  80

Ile Ile Leu Asp Ser Lys Ala Tyr Ser Glu Gly Phe Pro Leu Thr Ala
            85                  90                  95

Ser His Thr Asp Ala Met Gly Arg Tyr Leu Arg Gln Phe Thr Glu Arg
                100                 105                 110

Lys Glu Glu Ile Lys Pro Thr Trp Trp Asp Ile Ala Pro Glu His Leu
            115                 120                 125

Asp Asn Thr Tyr Phe Ala Tyr Val Ser Gly Ser Phe Ser Gly Asn Tyr
        130                 135                 140

Lys Glu Gln Leu Gln Lys Phe Arg Gln Asp Thr Asn His Leu Gly Gly
145                 150                 155                 160

Ala Leu Glu Phe Val Lys Leu Leu Leu Ala Asn Asn Tyr Lys Thr
                165                 170                 175

Gln Lys Met Ser Lys Lys Glu Val Lys Lys Ser Ile Leu Asp Tyr Asn
                180                 185                 190

Ile Ser Tyr
        195

<210> SEQ ID NO 4
<211> LENGTH: 195
<212> TYPE: PRT

<213> ORGANISM: Homo sapiens

<400> SEQUENCE: 4

Val Leu Glu Lys Ser Asp Ile Glu Lys Phe Lys Asn Gln Leu Arg Thr
1               5                   10                  15

Glu Leu Thr Asn Ile Asp His Ser Tyr Leu Lys Gly Ile Asp Ile Ala
            20                  25                  30

Ser Lys Pro Lys Thr Ser Asn Val Glu Asn Thr Glu Phe Glu Ala Ile
        35                  40                  45

Ser Thr Lys Ile Phe Thr Asp Glu Leu Gly Phe Ser Gly Glu His Leu
50                  55                  60

Gly Gly Ser Asn Lys Pro Asp Gly Leu Leu Trp Asp Asp Asp Cys Ala
65                  70                  75                  80

Ile Ile Leu Asp Ser Lys Ala Tyr Ser Glu Gly Phe Pro Leu Thr Ala
                85                  90                  95

Ser His Thr Asp Ala Met Gly Arg Tyr Leu Arg Gln Phe Thr Glu Arg
            100                 105                 110

Lys Glu Glu Ile Lys Pro Thr Trp Trp Asp Ile Ala Pro Glu His Leu
        115                 120                 125

Asp Asn Thr Tyr Phe Ala Tyr Val Ser Gly Ser Phe Ser Gly Asn Tyr
130                 135                 140

Lys Glu Gln Leu Gln Lys Phe Arg Gln Asp Thr Asn His Leu Gly Gly
145                 150                 155                 160

Ala Leu Glu Phe Val Lys Leu Leu Leu Ala Asn Asn Tyr Lys Thr
                165                 170                 175

Gln Lys Met Ser Lys Lys Glu Val Lys Lys Ser Ile Leu Asp Tyr Asn
            180                 185                 190

Ile Ser Tyr
        195

<210> SEQ ID NO 5
<211> LENGTH: 191
<212> TYPE: PRT
<213> ORGANISM: Homo sapiens

<400> SEQUENCE: 5

Val Leu Glu Lys Ser Asp Ile Glu Lys Phe Lys Asn Gln Leu Arg Thr
1               5                   10                  15

Glu Leu Thr Asn Ile Asp His Ser Tyr Leu Lys Gly Ile Asp Ile Ala
            20                  25                  30

Ser Lys Pro Val Glu Asn Thr Glu Phe Glu Ala Ile Ser Thr Lys Ile
        35                  40                  45

Phe Thr Asp Glu Leu Gly Phe Ser Gly Glu His Leu Gly Gly Ser Asn
    50                  55                  60

Lys Pro Asp Gly Leu Leu Trp Asp Asp Asp Cys Ala Ile Ile Leu Asp
65                  70                  75                  80

Ser Lys Ala Tyr Ser Glu Gly Phe Pro Leu Thr Ala Ser His Thr Asp
                85                  90                  95

Ala Met Gly Arg Tyr Leu Arg Gln Phe Thr Glu Arg Lys Glu Glu Ile
            100                 105                 110

Lys Pro Thr Trp Trp Asp Ile Ala Pro Glu His Leu Asp Asn Thr Tyr
        115                 120                 125

Phe Ala Tyr Val Ser Gly Ser Phe Ser Gly Asn Tyr Lys Glu Gln Leu
130                 135                 140

Gln Lys Phe Arg Gln Asp Thr Asn His Leu Gly Gly Ala Leu Glu Phe

```
                145                 150                 155                 160
Val Lys Leu Leu Leu Ala Asn Asn Tyr Lys Thr Gln Lys Met Ser
                    165                 170                 175
Lys Lys Glu Val Lys Ser Ile Leu Asp Tyr Asn Ile Ser Tyr
                180                 185                 190

<210> SEQ ID NO 6
<211> LENGTH: 195
<212> TYPE: PRT
<213> ORGANISM: Homo sapiens

<400> SEQUENCE: 6

Val Leu Glu Lys Ser Asp Ile Glu Lys Phe Lys Asn Gln Leu Arg Thr
1               5                   10                  15
Glu Leu Thr Asn Ile Asp His Ser Tyr Leu Lys Gly Ile Asp Ile Ala
                20                  25                  30
Ser Lys Lys Lys Thr Ser Asn Val Glu Asn Thr Glu Phe Glu Ala Ile
            35                  40                  45
Ser Thr Lys Ile Phe Thr Asp Glu Leu Gly Phe Ser Gly Lys His Leu
    50                  55                  60
Gly Gly Ser Asn Lys Pro Asp Gly Leu Leu Trp Asp Asp Cys Ala
65                  70                  75                  80
Ile Ile Leu Asp Ser Lys Ala Tyr Ser Glu Gly Phe Pro Leu Thr Ala
                85                  90                  95
Ser His Thr Asp Ala Met Gly Arg Tyr Leu Arg Gln Phe Thr Glu Arg
            100                 105                 110
Lys Glu Glu Ile Lys Pro Thr Trp Trp Asp Ile Ala Pro Glu His Leu
        115                 120                 125
Asp Asn Thr Tyr Phe Ala Tyr Val Ser Gly Ser Phe Ser Gly Asp Tyr
    130                 135                 140
Lys Glu Gln Leu Gln Lys Phe Arg Gln Asp Thr Asn His Leu Gly Gly
145                 150                 155                 160
Ala Leu Glu Phe Val Lys Leu Leu Leu Ala Asn Asn Tyr Lys Thr
                165                 170                 175
Gln Lys Met Ser Lys Lys Glu Val Lys Ser Ile Leu Asp Tyr Asn
            180                 185                 190
Ile Ser Tyr
        195

<210> SEQ ID NO 7
<211> LENGTH: 195
<212> TYPE: PRT
<213> ORGANISM: Homo sapiens

<400> SEQUENCE: 7

Val Leu Glu Lys Ser Asp Ile Glu Lys Phe Lys Asn Gln Leu Arg Thr
1               5                   10                  15
Glu Leu Thr Asn Ile Asp His Ser Tyr Leu Lys Gly Ile Asp Ile Ala
                20                  25                  30
Ser Lys Lys Lys Thr Ser Asn Val Glu Asn Thr Glu Phe Glu Ala Ile
            35                  40                  45
Ser Thr Lys Ile Phe Thr Asp Glu Leu Gly Phe Ser Gly Lys His Leu
    50                  55                  60
Gly Gly Ser Asn Lys Pro Asp Gly Leu Leu Trp Asp Asp Cys Ala
65                  70                  75                  80
Ile Ile Leu Asp Ser Lys Ala Tyr Ser Glu Gly Phe Pro Leu Thr Ala
```

```
                        85                  90                  95
Ser His Thr Asp Ala Met Gly Arg Tyr Leu Arg Gln Phe Thr Glu Arg
            100                 105                 110

Lys Glu Glu Ile Lys Pro Thr Trp Trp Asp Ile Ala Pro Glu His Leu
            115                 120                 125

Asp Asn Thr Tyr Phe Ala Tyr Val Ser Gly Ser Phe Ser Gly Asp Tyr
            130                 135                 140

Lys Glu Gln Leu Gln Lys Phe Arg Gln Asn Thr Asn His Leu Gly Gly
145                 150                 155                 160

Ala Leu Glu Phe Val Lys Leu Leu Leu Ala Asn Asn Tyr Lys Thr
            165                 170                 175

Gln Lys Met Ser Lys Lys Glu Val Lys Lys Ser Ile Leu Asp Tyr Asn
            180                 185                 190

Ile Ser Tyr
        195

<210> SEQ ID NO 8
<211> LENGTH: 360
<212> TYPE: PRT
<213> ORGANISM: Homo sapiens

<400> SEQUENCE: 8

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
            35                  40                  45

Pro Gly Val Gly Pro Gly Ser Glu Val Trp Gly Ile Pro Pro Cys Pro
        50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
            115                 120                 125

Leu Glu Gln Asn Pro Glu Glu Ser Gln Asp Ile Lys Ala Leu Gln Lys
130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
            165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
            195                 200                 205

Glu Glu Ala Asp Asn Asn Glu Asn Leu Gln Glu Ile Cys Lys Ala Glu
            210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
            245                 250                 255
```

```
Leu Gln Gln Ile Ser His Ile Ala Gln Leu Gly Leu Glu Lys Asp
              260                 265                 270

Val Val Arg Val Trp Phe Cys Asn Arg Arg Gln Lys Gly Lys Arg Ser
    275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360

<210> SEQ ID NO 9
<211> LENGTH: 317
<212> TYPE: PRT
<213> ORGANISM: Homo sapiens

<400> SEQUENCE: 9

Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
            35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
            115                 120                 125

Gly Gly Leu Leu Ala Pro Gly Gly Asn Ser Met Ala Ser Gly Val Gly
        130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
            195                 200                 205

Ser Met Thr Ser Ser Gln Thr Tyr Met Asn Gly Ser Pro Thr Tyr Ser
        210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Pro Val Val Thr
                245                 250                 255

Ser Ser Ser His Ser Arg Ala Pro Cys Gln Ala Gly Asp Leu Arg Asp
            260                 265                 270
```

```
Met Ile Ser Met Tyr Leu Pro Gly Ala Glu Val Pro Glu Pro Ala Ala
            275                 280                 285

Pro Ser Arg Leu His Met Ser Gln His Tyr Gln Ser Gly Pro Val Pro
            290                 295                 300

Gly Thr Ala Ile Asn Gly Thr Leu Pro Leu Ser His Met
305                 310                 315

<210> SEQ ID NO 10
<211> LENGTH: 479
<212> TYPE: PRT
<213> ORGANISM: Homo sapiens

<400> SEQUENCE: 10

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
```

```
                    325                 330                 335
Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
            355                 360                 365

Met Pro Pro Gly Ser Cys Met Pro Glu Glu Pro Lys Pro Lys Arg Gly
370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
            405                 410                 415

Leu Arg Thr His Thr Gly Glu Lys Pro Tyr His Cys Asp Trp Asp Gly
            420                 425                 430

Cys Gly Trp Lys Phe Ala Arg Ser Asp Glu Leu Thr Arg His Tyr Arg
            435                 440                 445

Lys His Thr Gly His Arg Pro Phe Gln Cys Gln Lys Cys Asp Arg Ala
            450                 455                 460

Phe Ser Arg Ser Asp His Leu Ala Leu His Met Lys Arg His Phe
465                 470                 475

<210> SEQ ID NO 11
<211> LENGTH: 454
<212> TYPE: PRT
<213> ORGANISM: Homo sapiens

<400> SEQUENCE: 11

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
            115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
            195                 200                 205

Val Phe Pro Tyr Pro Leu Asn Asp Ser Ser Ser Pro Lys Ser Cys Ala
    210                 215                 220
```

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
            245                 250                 255

Glu Glu Thr Pro Pro Thr Thr Ser Ser Asp Ser Glu Glu Gln Glu
        260                 265                 270

Asp Glu Glu Glu Ile Asp Val Val Ser Val Glu Lys Arg Gln Ala Pro
            275                 280                 285

Gly Lys Arg Ser Glu Ser Gly Ser Pro Ser Ala Gly Gly His Ser Lys
        290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450

<210> SEQ ID NO 12
<211> LENGTH: 191
<212> TYPE: DNA
<213> ORGANISM: Homo sapiens

<400> SEQUENCE: 12
ttgaatcgcg ggacccgttg gcagaggtgg cggcggcggc atgggtgccc cgacgttgcc     60
ccctgcctgg cagccctttc tcaaggacca ccgcatctct acattcaaga actggcccTT    120
cttggagggc tgcgcctgca ccccggagcg ggtgagactg cccggcctcc tggggtcccc    180
cacgcccgcc t                                                         191

<210> SEQ ID NO 13
<211> LENGTH: 190
<212> TYPE: DNA
<213> ORGANISM: Homo sapiens

<400> SEQUENCE: 13
ggctgccacg tccactcacg agctgtgctg tcccttgcag atggccgagg ctggcttcat     60
ccactgcccc actgagaacg agccagactt ggcccagtgt ttcttctgct tcaaggagct    120
ggaaggctgg gagccagatg acgaccccat gtaagtcttc tctggccagc ctcgatgggc    180
tttgttttga                                                           190

<210> SEQ ID NO 14

```
<211> LENGTH: 198
<212> TYPE: DNA
<213> ORGANISM: Homo sapiens

<400> SEQUENCE: 14
cccttcagct gcctttccgc tgttgttttg attttctag agaggaacat aaaaagcatt      60
cgtccggttg cgctttcctt tctgtcaaga agcagtttga agaattaacc cttggtgaat    120
ttttgaaact ggacagagaa agagccaaga acaaaattgt atgtattggg aataagaact    180
gctcaaaccc tgttcaat                                                  198

<210> SEQ ID NO 15
<211> LENGTH: 170
<212> TYPE: DNA
<213> ORGANISM: Homo sapiens

<400> SEQUENCE: 15
gctctggttt cagtgtcatg tgtctattct ttatttccag gcaaaggaaa ccaacaataa     60
gaagaaagaa tttgaggaaa ctgcggagaa agtgcgccgt gccatcgagc agctggctgc   120
catggattga ggcctctggc cggagctgcc tggtcccaga gtggctgcac                170

<210> SEQ ID NO 16
<211> LENGTH: 20
<212> TYPE: DNA
<213> ORGANISM: Homo sapiens

<400> SEQUENCE: 16 ttgcccctg cctggcagcc                                                  20

<210> SEQ ID NO 17
<211> LENGTH: 20
<212> TYPE: DNA
<213> ORGANISM: Homo sapiens

<400> SEQUENCE: 17
ttcttgaatg tagagatgcg                                                 20

<210> SEQ ID NO 18
<211> LENGTH: 20
<212> TYPE: DNA
<213> ORGANISM: Homo sapiens

<400> SEQUENCE: 18
tgggtgcccc gacgttgccc                                                 20

<210> SEQ ID NO 19
<211> LENGTH: 20
<212> TYPE: DNA
<213> ORGANISM: Homo sapiens

<400> SEQUENCE: 19
tgcggtggtc cttgagaaag                                                 20

<210> SEQ ID NO 20
<211> LENGTH: 20
<212> TYPE: DNA
<213> ORGANISM: Homo sapiens

<400> SEQUENCE: 20
tcaaggacca ccgcatctct                                                 20
```

```
<210> SEQ ID NO 21
<211> LENGTH: 20
<212> TYPE: DNA
<213> ORGANISM: Homo sapiens

<400> SEQUENCE: 21
tgcaggcgca gccctccaag                                               20

<210> SEQ ID NO 22
<211> LENGTH: 20
<212> TYPE: DNA
<213> ORGANISM: Homo sapiens

<400> SEQUENCE: 22
tggccgaggc tggcttcatc                                               20

<210> SEQ ID NO 23
<211> LENGTH: 20
<212> TYPE: DNA
<213> ORGANISM: Homo sapiens

<400> SEQUENCE: 23
tgggccaagt ctggctcgtt                                               20

<210> SEQ ID NO 24
<211> LENGTH: 20
<212> TYPE: DNA
<213> ORGANISM: Homo sapiens

<400> SEQUENCE: 24
ttggcccagt gtttcttctg                                               20

<210> SEQ ID NO 25
<211> LENGTH: 20
<212> TYPE: DNA
<213> ORGANISM: Homo sapiens

<400> SEQUENCE: 25
tcgtcatctg gctcccagcc                                               20

<210> SEQ ID NO 26
<211> LENGTH: 20
<212> TYPE: DNA
<213> ORGANISM: Homo sapiens

<400> SEQUENCE: 26
tgcgctttcc tttctgtcaa                                               20

<210> SEQ ID NO 27
<211> LENGTH: 20
<212> TYPE: DNA
<213> ORGANISM: Homo sapiens

<400> SEQUENCE: 27
tcaaaaattc accaagggtt                                               20

<210> SEQ ID NO 28
<211> LENGTH: 297
<212> TYPE: PRT
<213> ORGANISM: Homo sapiens

<400> SEQUENCE: 28

Met Glu Asp Tyr Thr Lys Ile Glu Lys Ile Gly Glu Gly Thr Tyr Gly
 1               5                  10                  15
```

```
Val Val Tyr Lys Gly Arg His Lys Thr Thr Gly Gln Val Val Ala Met
            20                  25                  30

Lys Lys Ile Arg Leu Glu Ser Glu Glu Gly Val Pro Ser Thr Ala
        35                  40                  45

Ile Arg Glu Ile Ser Leu Leu Lys Glu Leu Arg His Pro Asn Ile Val
 50                  55                  60

Ser Leu Gln Asp Val Leu Met Gln Asp Ser Arg Leu Tyr Leu Ile Phe
 65                  70                  75                  80

Glu Phe Leu Ser Met Asp Leu Lys Lys Tyr Leu Asp Ser Ile Pro Pro
                 85                  90                  95

Gly Gln Tyr Met Asp Ser Ser Leu Val Lys Ser Tyr Leu Tyr Gln Ile
            100                 105                 110

Leu Gln Gly Ile Val Phe Cys His Ser Arg Arg Val Leu His Arg Asp
        115                 120                 125

Leu Lys Pro Gln Asn Leu Leu Ile Asp Asp Lys Gly Thr Ile Lys Leu
130                 135                 140

Ala Asp Phe Gly Leu Ala Arg Ala Phe Gly Ile Pro Ile Arg Val Tyr
145                 150                 155                 160

Thr His Glu Val Val Thr Leu Trp Tyr Arg Ser Pro Glu Val Leu Leu
                165                 170                 175

Gly Ser Ala Arg Tyr Ser Thr Pro Val Asp Ile Trp Ser Ile Gly Thr
            180                 185                 190

Ile Phe Ala Glu Leu Ala Thr Lys Lys Pro Leu Phe His Gly Asp Ser
        195                 200                 205

Glu Ile Asp Gln Leu Phe Arg Ile Phe Arg Ala Leu Gly Thr Pro Asn
210                 215                 220

Asn Glu Val Trp Pro Glu Val Glu Ser Leu Gln Asp Tyr Lys Asn Thr
225                 230                 235                 240

Phe Pro Lys Trp Lys Pro Gly Ser Leu Ala Ser His Val Lys Asn Leu
                245                 250                 255

Asp Glu Asn Gly Leu Asp Leu Leu Ser Lys Met Leu Ile Tyr Asp Pro
            260                 265                 270

Ala Lys Arg Ile Ser Gly Lys Met Ala Leu Asn His Pro Tyr Phe Asn
        275                 280                 285

Asp Leu Asp Asn Gln Ile Lys Lys Met
    290                 295

<210> SEQ ID NO 29
<211> LENGTH: 298
<212> TYPE: PRT
<213> ORGANISM: Homo sapiens

<400> SEQUENCE: 29

Met Glu Asn Phe Gln Lys Val Glu Lys Ile Gly Glu Gly Thr Tyr Gly
1               5                   10                  15

Val Val Tyr Lys Ala Arg Asn Lys Leu Thr Gly Glu Val Val Ala Leu
            20                  25                  30

Lys Lys Ile Arg Leu Asp Thr Glu Thr Glu Gly Val Pro Ser Thr Ala
        35                  40                  45

Ile Arg Glu Ile Ser Leu Leu Lys Glu Leu Asn His Pro Asn Ile Val
 50                  55                  60

Lys Leu Leu Asp Val Ile His Thr Glu Asn Lys Leu Tyr Leu Val Phe
65                  70                  75                  80

Glu Phe Leu His Gln Asp Leu Lys Lys Phe Met Asp Ala Ser Ala Leu
```

```
                    85                  90                  95
Thr Gly Ile Pro Leu Pro Leu Ile Lys Ser Tyr Leu Phe Gln Leu Leu
                100                 105                 110

Gln Gly Leu Ala Phe Cys His Ser His Arg Val Leu His Arg Asp Leu
            115                 120                 125

Lys Pro Gln Asn Leu Leu Ile Asn Thr Glu Gly Ala Ile Lys Leu Ala
        130                 135                 140

Asp Phe Gly Leu Ala Arg Ala Phe Gly Val Pro Val Arg Thr Tyr Thr
145                 150                 155                 160

His Glu Val Val Thr Leu Trp Tyr Arg Ala Pro Glu Ile Leu Leu Gly
                165                 170                 175

Cys Lys Tyr Tyr Ser Thr Ala Val Asp Ile Trp Ser Leu Gly Cys Ile
                180                 185                 190

Phe Ala Glu Met Val Thr Arg Arg Ala Leu Phe Pro Gly Asp Ser Glu
                195                 200                 205

Ile Asp Gln Leu Phe Arg Ile Phe Arg Thr Leu Gly Thr Pro Asp Glu
            210                 215                 220

Val Val Trp Pro Gly Val Thr Ser Met Pro Asp Tyr Lys Pro Ser Phe
225                 230                 235                 240

Pro Lys Trp Ala Arg Gln Asp Phe Ser Lys Val Val Pro Pro Leu Asp
                245                 250                 255

Glu Asp Gly Arg Ser Leu Leu Ser Gln Met Leu His Tyr Asp Pro Asn
                260                 265                 270

Lys Arg Ile Ser Ala Lys Ala Ala Leu Ala His Pro Phe Phe Gln Asp
            275                 280                 285

Val Thr Lys Pro Val Pro His Leu Arg Leu
            290                 295

<210> SEQ ID NO 30
<211> LENGTH: 305
<212> TYPE: PRT
<213> ORGANISM: Homo sapiens

<400> SEQUENCE: 30

Met Asp Met Phe Gln Lys Val Glu Lys Ile Gly Glu Gly Thr Tyr Gly
1               5                   10                  15

Val Val Tyr Lys Ala Lys Asn Arg Glu Thr Gly Gln Leu Val Ala Leu
            20                  25                  30

Lys Lys Ile Arg Leu Asp Leu Glu Met Glu Gly Val Pro Ser Thr Ala
        35                  40                  45

Ile Arg Glu Ile Ser Leu Leu Lys Glu Leu Lys His Pro Asn Ile Val
    50                  55                  60

Arg Leu Leu Asp Val Val His Asn Glu Arg Lys Leu Tyr Leu Val Phe
65                  70                  75                  80

Glu Phe Leu Ser Gln Asp Leu Lys Lys Tyr Met Asp Ser Thr Pro Gly
                85                  90                  95

Ser Glu Leu Pro Leu His Leu Ile Lys Ser Tyr Leu Phe Gln Leu Leu
                100                 105                 110

Gln Gly Val Ser Phe Cys His Ser His Arg Val Ile His Arg Asp Leu
            115                 120                 125

Lys Pro Gln Asn Leu Leu Ile Asn Glu Leu Gly Ala Ile Lys Leu Ala
        130                 135                 140

Asp Phe Gly Leu Ala Arg Ala Phe Gly Val Pro Leu Arg Thr Tyr Thr
145                 150                 155                 160
```

-continued

```
His Glu Val Val Thr Leu Trp Tyr Arg Ala Pro Glu Ile Leu Leu Gly
            165                 170                 175

Ser Lys Phe Tyr Thr Thr Ala Val Asp Ile Trp Ser Ile Gly Cys Ile
        180                 185                 190

Phe Ala Glu Met Val Thr Arg Lys Ala Leu Phe Pro Gly Asp Ser Glu
        195                 200                 205

Ile Asp Gln Leu Phe Arg Ile Phe Arg Met Leu Gly Thr Pro Ser Glu
    210                 215                 220

Asp Thr Trp Pro Gly Val Thr Gln Leu Pro Asp Tyr Lys Gly Ser Phe
225                 230                 235                 240

Pro Lys Trp Thr Arg Lys Gly Leu Glu Glu Ile Val Pro Asn Leu Glu
                245                 250                 255

Pro Glu Gly Arg Asp Leu Leu Met Gln Leu Leu Gln Tyr Asp Pro Ser
            260                 265                 270

Gln Arg Ile Thr Ala Lys Thr Ala Leu Ala His Pro Tyr Phe Ser Ser
        275                 280                 285

Pro Glu Pro Ser Pro Ala Ala Arg Gln Tyr Val Leu Gln Arg Phe Arg
        290                 295                 300

His
305

<210> SEQ ID NO 31
<211> LENGTH: 303
<212> TYPE: PRT
<213> ORGANISM: Homo sapiens

<400> SEQUENCE: 31

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
                20                  25                  30

Ala Leu Lys Ser Val Arg Val Pro Asn Gly Gly Gly Gly Gly Gly Gly
            35                  40                  45

Leu Pro Ile Ser Thr Val Arg Glu Val Ala Leu Leu Arg Arg Leu Glu
    50                  55                  60

Ala Phe Glu His Pro Asn Val Val Arg Leu Met Asp Val Cys Ala Thr
65                  70                  75                  80

Ser Arg Thr Asp Arg Glu Ile Lys Val Thr Leu Val Phe Glu His Val
                85                  90                  95

Asp Gln Asp Leu Arg Thr Tyr Leu Asp Lys Ala Pro Pro Pro Gly Leu
            100                 105                 110

Pro Ala Glu Thr Ile Lys Asp Leu Met Arg Gln Phe Leu Arg Gly Leu
        115                 120                 125

Asp Phe Leu His Ala Asn Cys Ile Val His Arg Asp Leu Lys Pro Glu
    130                 135                 140

Asn Ile Leu Val Thr Ser Gly Gly Thr Val Lys Leu Ala Asp Phe Gly
145                 150                 155                 160

Leu Ala Arg Ile Tyr Ser Tyr Gln Met Ala Leu Thr Pro Val Val Val
                165                 170                 175

Thr Leu Trp Tyr Arg Ala Pro Glu Val Leu Leu Gln Ser Thr Tyr Ala
            180                 185                 190

Thr Pro Val Asp Met Trp Ser Val Gly Cys Ile Phe Ala Glu Met Phe
        195                 200                 205

Arg Arg Lys Pro Leu Phe Cys Gly Asn Ser Glu Ala Asp Gln Leu Gly
    210                 215                 220
```

```
Lys Ile Phe Asp Leu Ile Gly Leu Pro Pro Glu Asp Trp Pro Arg
225                 230                 235                 240

Asp Val Ser Leu Pro Arg Gly Ala Phe Pro Arg Gly Pro Arg Pro
                245                 250                 255

Val Gln Ser Val Val Pro Glu Met Glu Glu Ser Gly Ala Gln Leu Leu
            260                 265                 270

Leu Glu Met Leu Thr Phe Asn Pro His Lys Arg Ile Ser Ala Phe Arg
        275                 280                 285

Ala Leu Gln His Ser Tyr Leu His Lys Asp Glu Gly Asn Pro Glu
    290                 295                 300

<210> SEQ ID NO 32
<211> LENGTH: 292
<212> TYPE: PRT
<213> ORGANISM: Homo sapiens

<400> SEQUENCE: 32

Met Gln Lys Tyr Glu Lys Leu Glu Lys Ile Gly Glu Gly Thr Tyr Gly
1               5                   10                  15

Thr Val Phe Lys Ala Lys Asn Arg Glu Thr His Glu Ile Val Ala Leu
            20                  25                  30

Lys Arg Val Arg Leu Asp Asp Asp Glu Gly Val Pro Ser Ser Ala
        35                  40                  45

Leu Arg Glu Ile Cys Leu Leu Lys Glu Leu Lys His Lys Asn Ile Val
    50                  55                  60

Arg Leu His Asp Val Leu His Ser Asp Lys Lys Leu Thr Leu Val Phe
65                  70                  75                  80

Glu Phe Cys Asp Gln Asp Leu Lys Lys Tyr Phe Asp Ser Cys Asn Gly
                85                  90                  95

Asp Leu Asp Pro Glu Ile Val Lys Ser Phe Leu Phe Gln Leu Leu Lys
            100                 105                 110

Gly Leu Gly Phe Cys His Ser Arg Asn Val Leu His Arg Asp Leu Lys
        115                 120                 125

Pro Gln Asn Leu Leu Ile Asn Arg Asn Gly Glu Leu Lys Leu Ala Asp
    130                 135                 140

Phe Gly Leu Ala Arg Ala Phe Gly Ile Pro Val Arg Cys Tyr Ser Ala
145                 150                 155                 160

Glu Val Val Thr Leu Trp Tyr Arg Pro Pro Asp Val Leu Phe Gly Ala
                165                 170                 175

Lys Leu Tyr Ser Thr Ser Ile Asp Met Trp Ser Ala Gly Cys Ile Phe
            180                 185                 190

Ala Glu Leu Ala Asn Ala Gly Arg Pro Leu Phe Pro Gly Asn Asp Val
        195                 200                 205

Asp Asp Gln Leu Lys Arg Ile Phe Arg Leu Leu Gly Thr Pro Thr Glu
    210                 215                 220

Glu Gln Trp Pro Ser Met Thr Lys Leu Pro Asp Tyr Lys Pro Tyr Pro
225                 230                 235                 240

Met Tyr Pro Ala Thr Thr Ser Leu Val Asn Val Val Pro Lys Leu Asn
                245                 250                 255

Ala Thr Gly Arg Asp Leu Leu Gln Asn Leu Leu Lys Cys Asn Pro Val
            260                 265                 270

Gln Arg Ile Ser Ala Glu Glu Ala Leu Gln His Pro Tyr Phe Ser Asp
        275                 280                 285

Phe Cys Pro Pro
```

<210> SEQ ID NO 33
<211> LENGTH: 326
<212> TYPE: PRT
<213> ORGANISM: Homo sapiens

<400> SEQUENCE: 33

Met Glu Lys Asp Gly Leu Cys Arg Ala Asp Gln Gln Tyr Glu Cys Val
1               5                   10                  15

Ala Glu Ile Gly Glu Gly Ala Tyr Gly Lys Val Phe Lys Ala Arg Asp
            20                  25                  30

Leu Lys Asn Gly Gly Arg Phe Val Ala Leu Lys Arg Val Arg Val Gln
        35                  40                  45

Thr Gly Glu Glu Gly Met Pro Leu Ser Thr Ile Arg Glu Val Ala Val
    50                  55                  60

Leu Arg His Leu Glu Thr Phe Glu His Pro Asn Val Val Arg Leu Phe
65                  70                  75                  80

Asp Val Cys Thr Val Ser Arg Thr Asp Arg Glu Thr Lys Leu Thr Leu
                85                  90                  95

Val Phe Glu His Val Asp Gln Asp Leu Thr Thr Tyr Leu Asp Lys Val
            100                 105                 110

Pro Glu Pro Gly Val Pro Thr Glu Thr Ile Lys Asp Met Met Phe Gln
        115                 120                 125

Leu Leu Arg Gly Leu Asp Phe Leu His Ser His Arg Val Val His Arg
    130                 135                 140

Asp Leu Lys Pro Gln Asn Ile Leu Val Thr Ser Ser Gly Gln Ile Lys
145                 150                 155                 160

Leu Ala Asp Phe Gly Leu Ala Arg Ile Tyr Ser Phe Gln Met Ala Leu
                165                 170                 175

Thr Ser Val Val Val Thr Leu Trp Tyr Arg Ala Pro Glu Val Leu Leu
            180                 185                 190

Gln Ser Ser Tyr Ala Thr Pro Val Asp Leu Trp Ser Val Gly Cys Ile
        195                 200                 205

Phe Ala Glu Met Phe Arg Arg Lys Pro Leu Phe Arg Gly Ser Ser Asp
    210                 215                 220

Val Asp Gln Leu Gly Lys Ile Leu Asp Val Ile Gly Leu Pro Gly Glu
225                 230                 235                 240

Glu Asp Trp Pro Arg Asp Val Ala Leu Pro Arg Gln Ala Phe His Ser
                245                 250                 255

Lys Ser Ala Gln Pro Ile Glu Lys Phe Val Thr Asp Ile Asp Glu Leu
            260                 265                 270

Gly Lys Asp Leu Leu Leu Lys Cys Leu Thr Phe Asn Pro Ala Lys Arg
        275                 280                 285

Ile Ser Ala Tyr Ser Ala Leu Ser His Pro Tyr Phe Gln Asp Leu Glu
    290                 295                 300

Arg Cys Lys Glu Asn Leu Asp Ser His Leu Pro Pro Ser Gln Asn Thr
305                 310                 315                 320

Ser Glu Leu Asn Thr Ala
                325

<210> SEQ ID NO 34
<211> LENGTH: 142
<212> TYPE: PRT
<213> ORGANISM: Homo sapiens

```
<400> SEQUENCE: 34

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Glu Lys Val Arg Arg Ala Ile Glu Gln Leu Ala Ala Met Asp
    130                 135                 140

<210> SEQ ID NO 35
<211> LENGTH: 826
<212> TYPE: PRT
<213> ORGANISM: Homo sapiens

<400> SEQUENCE: 35

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220
```

```
Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
            245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
            355                 360                 365

Met Lys Met Thr Gln Leu Phe Thr Lys Val Glu Ser Glu Asp Thr Ser
370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
            435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
            485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
            595                 600                 605

Glu Pro Thr Ala Asn Ala Thr Thr Thr Thr Ala Thr Thr Asp Glu Leu
        610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
```

-continued

```
                645                 650                 655
Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
        675                 680                 685

Asn Val Leu Ser Val Ala Leu Ser Gln Arg Thr Thr Val Pro Glu Glu
690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
        755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 36
<211> LENGTH: 449
<212> TYPE: PRT
<213> ORGANISM: Homo sapiens

<400> SEQUENCE: 36

Met Gly Arg Val Gly Gly Met Ala Gln Pro Met Gly Arg Ala Gly Ala
1               5                   10                  15

Pro Lys Pro Met Gly Arg Ala Gly Ser Ala Arg Arg Gly Arg Phe Lys
            20                  25                  30

Gly Cys Trp Ser Glu Gly Ser Pro Val His Pro Val Pro Ala Val Leu
        35                  40                  45

Ser Trp Leu Leu Ala Leu Leu Arg Cys Ala Ser Thr Met Leu Ser Leu
    50                  55                  60

Arg Val Pro Leu Ala Pro Ile Thr Asp Pro Gln Gln Leu Gln Leu Ser
65                  70                  75                  80

Pro Leu Lys Gly Leu Ser Leu Val Asp Lys Glu Asn Thr Pro Pro Ala
                85                  90                  95

Leu Ser Gly Thr Arg Val Leu Ala Ser Lys Thr Ala Arg Arg Ile Phe
            100                 105                 110

Gln Glu Pro Thr Glu Pro Lys Thr Lys Ala Ala Ala Pro Gly Val Glu
        115                 120                 125

Asp Glu Pro Leu Leu Arg Glu Asn Pro Arg Arg Phe Val Ile Phe Pro
    130                 135                 140

Ile Glu Tyr His Asp Ile Trp Gln Met Tyr Lys Lys Ala Glu Ala Ser
145                 150                 155                 160

Phe Trp Thr Ala Glu Glu Val Asp Leu Ser Lys Asp Ile Gln His Trp
                165                 170                 175

Glu Ser Leu Lys Pro Glu Glu Arg Tyr Phe Ile Ser His Val Leu Ala
            180                 185                 190
```

```
Phe Phe Ala Ala Ser Asp Gly Ile Val Asn Glu Asn Leu Val Glu Arg
            195                 200                 205

Phe Ser Gln Glu Val Gln Ile Thr Glu Ala Arg Cys Phe Tyr Gly Phe
210                 215                 220

Gln Ile Ala Met Glu Asn Ile His Ser Glu Met Tyr Ser Leu Leu Ile
225                 230                 235                 240

Asp Thr Tyr Ile Lys Asp Pro Lys Glu Arg Glu Phe Leu Phe Asn Ala
            245                 250                 255

Ile Glu Thr Met Pro Cys Val Lys Lys Ala Asp Trp Ala Leu Arg
            260                 265                 270

Trp Ile Gly Asp Lys Glu Ala Thr Tyr Gly Glu Arg Val Val Ala Phe
            275                 280                 285

Ala Ala Val Glu Gly Ile Phe Phe Ser Gly Ser Phe Ala Ser Ile Phe
            290                 295                 300

Trp Leu Lys Lys Arg Gly Leu Met Pro Gly Leu Thr Phe Ser Asn Glu
305                 310                 315                 320

Leu Ile Ser Arg Asp Glu Gly Leu His Cys Asp Phe Ala Cys Leu Met
                325                 330                 335

Phe Lys His Leu Val His Lys Pro Ser Glu Glu Arg Val Arg Glu Ile
                340                 345                 350

Ile Ile Asn Ala Val Arg Ile Glu Gln Glu Phe Leu Thr Glu Ala Leu
            355                 360                 365

Pro Val Lys Leu Ile Gly Met Asn Cys Thr Leu Met Lys Gln Tyr Ile
            370                 375                 380

Glu Phe Val Ala Asp Arg Leu Met Leu Glu Leu Gly Phe Ser Lys Val
385                 390                 395                 400

Phe Arg Val Glu Asn Pro Phe Asp Phe Met Glu Asn Ile Ser Leu Glu
                405                 410                 415

Gly Lys Thr Asn Phe Phe Glu Lys Arg Val Gly Glu Tyr Gln Arg Met
                420                 425                 430

Gly Val Met Ser Ser Pro Thr Glu Asn Ser Phe Thr Leu Asp Ala Asp
                435                 440                 445

Phe

<210> SEQ ID NO 37
<211> LENGTH: 188
<212> TYPE: PRT
<213> ORGANISM: Homo sapiens

<400> SEQUENCE: 37

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110
```

```
Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 38
<211> LENGTH: 1210
<212> TYPE: PRT
<213> ORGANISM: Homo sapiens

<400> SEQUENCE: 38

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300
```

-continued

```
Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
            645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
            690                 695                 700

Arg Ile Leu Lys Glu Thr Glu Phe Lys Lys Ile Lys Val Leu Gly Ser
705                 710                 715                 720
```

```
Gly Ala Phe Gly Thr Val Tyr Lys Gly Leu Trp Ile Pro Glu Glu
            725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
            805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
            850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
            885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
            930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
            965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe
            1010                1015                1020

Phe Ser Ser Pro Ser Thr Ser Arg Thr Pro Leu Leu Ser Ser Leu
            1025                1030                1035

Ser Ala Thr Ser Asn Asn Ser Thr Val Ala Cys Ile Asp Arg Asn
            1040                1045                1050

Gly Leu Gln Ser Cys Pro Ile Lys Glu Asp Ser Phe Leu Gln Arg
            1055                1060                1065

Tyr Ser Ser Asp Pro Thr Gly Ala Leu Thr Glu Asp Ser Ile Asp
            1070                1075                1080

Asp Thr Phe Leu Pro Val Pro Glu Tyr Ile Asn Gln Ser Val Pro
            1085                1090                1095

Lys Arg Pro Ala Gly Ser Val Gln Asn Pro Val Tyr His Asn Gln
            1100                1105                1110

Pro Leu Asn Pro Ala Pro Ser Arg Asp Pro His Tyr Gln Asp Pro
            1115                1120                1125

His Ser Thr Ala Val Gly Asn Pro Glu Tyr Leu Asn Thr Val Gln
```

```
                  1130                1135                1140
Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205            1210

<210> SEQ ID NO 39
<211> LENGTH: 454
<212> TYPE: PRT
<213> ORGANISM: Homo sapiens

<400> SEQUENCE: 39

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285
```

```
Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
                340                 345                 350

Asn Asn Arg Lys Cys Thr Ser Pro Arg Ser Ser Asp Thr Glu Glu Asn
                355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
                420                 425                 430

Asp Leu Leu Arg Lys Arg Arg Glu Gln Leu Lys His Lys Leu Glu Gln
                435                 440                 445

Leu Arg Asn Ser Cys Ala
    450

<210> SEQ ID NO 40
<211> LENGTH: 889
<212> TYPE: PRT
<213> ORGANISM: Homo sapiens

<400> SEQUENCE: 40

Met Glu Glu Gly Ala Pro Arg Gln Pro Gly Pro Ser Gln Trp Pro Pro
1               5                   10                  15

Glu Asp Glu Lys Glu Val Ile Arg Arg Ala Ile Gln Lys Glu Leu Lys
                20                  25                  30

Ile Lys Glu Gly Val Glu Asn Leu Arg Arg Val Ala Thr Asp Arg Arg
                35                  40                  45

His Leu Gly His Val Gln Gln Leu Leu Arg Ser Ser Asn Arg Arg Leu
    50                  55                  60

Glu Gln Leu His Gly Glu Leu Arg Glu Leu His Ala Arg Ile Leu Leu
65                  70                  75                  80

Pro Gly Pro Gly Pro Gly Pro Ala Glu Pro Val Ala Ser Gly Pro Arg
                85                  90                  95

Pro Trp Ala Glu Gln Leu Arg Ala Arg His Leu Glu Ala Leu Arg Arg
                100                 105                 110

Gln Leu His Val Glu Leu Lys Val Lys Gln Gly Ala Glu Asn Met Thr
                115                 120                 125

His Thr Cys Ala Ser Gly Thr Pro Lys Glu Arg Lys Leu Leu Ala Ala
    130                 135                 140

Ala Gln Gln Met Leu Arg Asp Ser Gln Leu Lys Val Ala Leu Leu Arg
145                 150                 155                 160

Met Lys Ile Ser Ser Leu Glu Ala Ser Gly Ser Pro Glu Pro Gly Pro
                165                 170                 175

Glu Leu Leu Ala Glu Glu Leu Gln His Arg Leu His Val Glu Ala Ala
                180                 185                 190

Val Ala Glu Gly Ala Lys Asn Val Val Lys Leu Leu Ser Ser Arg Arg
    195                 200                 205
```

```
Thr Gln Asp Arg Lys Ala Leu Ala Glu Ala Gln Ala Gln Leu Gln Glu
    210                 215                 220

Ser Ser Gln Lys Leu Asp Leu Leu Arg Leu Ala Leu Glu Gln Leu Leu
225                 230                 235                 240

Glu Gln Leu Pro Pro Ala His Pro Leu Arg Ser Arg Val Thr Arg Glu
                245                 250                 255

Leu Arg Ala Ala Val Pro Gly Tyr Pro Gln Pro Ser Gly Thr Pro Val
                260                 265                 270

Lys Pro Thr Ala Leu Thr Gly Thr Leu Gln Val Arg Leu Leu Gly Cys
        275                 280                 285

Glu Gln Leu Leu Thr Ala Val Pro Gly Arg Ser Pro Ala Ala Ala Leu
    290                 295                 300

Ala Ser Ser Pro Ser Glu Gly Trp Leu Arg Thr Lys Ala Lys His Gln
305                 310                 315                 320

Arg Gly Arg Gly Glu Leu Ala Ser Glu Val Leu Ala Val Leu Lys Val
                325                 330                 335

Asp Asn Arg Val Val Gly Gln Thr Gly Trp Gly Gln Val Ala Glu Gln
                340                 345                 350

Ser Trp Asp Gln Thr Phe Val Ile Pro Leu Glu Arg Ala Arg Glu Leu
        355                 360                 365

Glu Ile Gly Val His Trp Arg Asp Trp Arg Gln Leu Cys Gly Val Ala
    370                 375                 380

Phe Leu Arg Leu Glu Asp Phe Leu Asp Asn Ala Cys His Gln Leu Ser
385                 390                 395                 400

Leu Ser Leu Val Pro Gln Gly Leu Leu Phe Ala Gln Val Thr Phe Cys
                405                 410                 415

Asp Pro Val Ile Glu Arg Arg Pro Arg Leu Gln Arg Gln Glu Arg Ile
                420                 425                 430

Phe Ser Lys Arg Arg Gly Gln Asp Phe Leu Arg Ala Ser Gln Met Asn
        435                 440                 445

Leu Gly Met Ala Ala Trp Gly Arg Leu Val Met Asn Leu Leu Pro Pro
    450                 455                 460

Cys Ser Ser Pro Ser Thr Ile Ser Pro Lys Gly Cys Pro Arg Thr
465                 470                 475                 480

Pro Thr Thr Leu Arg Glu Ala Ser Asp Pro Ala Thr Pro Ser Asn Phe
                485                 490                 495

Leu Pro Lys Lys Thr Pro Leu Gly Glu Glu Met Thr Pro Pro Lys
                500                 505                 510

Pro Pro Arg Leu Tyr Leu Pro Gln Glu Pro Thr Ser Glu Glu Thr Pro
        515                 520                 525

Arg Thr Lys Arg Pro His Met Glu Pro Arg Thr Arg Arg Gly Pro Ser
    530                 535                 540

Pro Pro Ala Ser Pro Thr Arg Lys Pro Pro Arg Leu Gln Asp Phe Arg
545                 550                 555                 560

Cys Leu Ala Val Leu Gly Arg Gly His Phe Gly Lys Val Leu Leu Val
                565                 570                 575

Gln Phe Lys Gly Thr Gly Lys Tyr Tyr Ala Ile Lys Ala Leu Lys Lys
                580                 585                 590

Gln Glu Val Leu Ser Arg Asp Glu Ile Glu Ser Leu Tyr Cys Glu Lys
        595                 600                 605

Arg Ile Leu Glu Ala Val Gly Cys Thr Gly His Pro Phe Leu Leu Ser
    610                 615                 620
```

Leu Leu Ala Cys Phe Gln Thr Ser Ser His Ala Cys Phe Val Thr Glu
625                 630                 635                 640

Phe Val Pro Gly Gly Asp Leu Met Met Gln Ile His Glu Asp Val Phe
            645                 650                 655

Pro Glu Pro Gln Ala Arg Phe Tyr Val Ala Cys Val Val Leu Gly Leu
        660                 665                 670

Gln Phe Leu His Glu Lys Lys Ile Ile Tyr Arg Asp Leu Lys Leu Asp
    675                 680                 685

Asn Leu Leu Asp Ala Gln Gly Phe Leu Lys Ile Ala Asp Phe Gly
690                 695                 700

Leu Cys Lys Glu Gly Ile Gly Phe Gly Asp Arg Thr Ser Thr Phe Cys
705                 710                 715                 720

Gly Thr Pro Glu Phe Leu Ala Pro Glu Val Leu Thr Gln Glu Ala Tyr
                725                 730                 735

Thr Arg Ala Val Asp Trp Trp Gly Leu Gly Val Leu Leu Tyr Glu Met
                740                 745                 750

Leu Val Gly Glu Cys Pro Phe Pro Gly Asp Thr Glu Glu Val Phe
            755                 760                 765

Asp Cys Ile Val Asn Met Asp Ala Pro Tyr Pro Gly Phe Leu Ser Val
770                 775                 780

Gln Gly Leu Glu Phe Ile Gln Lys Leu Leu Gln Lys Cys Pro Glu Lys
785                 790                 795                 800

Arg Leu Gly Ala Gly Glu Gln Asp Ala Glu Ile Lys Val Gln Pro
                805                 810                 815

Phe Phe Arg Thr Thr Asn Trp Gln Ala Leu Leu Ala Arg Thr Ile Gln
                820                 825                 830

Pro Pro Phe Val Pro Thr Leu Cys Gly Pro Ala Asp Leu Arg Tyr Phe
                835                 840                 845

Glu Gly Glu Phe Thr Gly Leu Pro Pro Ala Leu Thr Pro Pro Ala Pro
850                 855                 860

His Ser Leu Leu Thr Ala Arg Gln Gln Ala Ala Phe Arg Asp Phe Asp
865                 870                 875                 880

Phe Val Ser Glu Arg Phe Leu Glu Pro
                885

<210> SEQ ID NO 41
<211> LENGTH: 1056
<212> TYPE: PRT
<213> ORGANISM: Homo sapiens

<400> SEQUENCE: 41

Met Ala Ser Gln Pro Asn Ser Ser Ala Lys Lys Lys Glu Glu Lys Gly
1               5                   10                  15

Lys Asn Ile Gln Val Val Arg Cys Arg Pro Phe Asn Leu Ala Glu
            20                  25                  30

Arg Lys Ala Ser Ala His Ser Ile Val Glu Cys Asp Pro Val Arg Lys
        35                  40                  45

Glu Val Ser Val Arg Thr Gly Gly Leu Ala Asp Lys Ser Ser Arg Lys
    50                  55                  60

Thr Tyr Thr Phe Asp Met Val Phe Gly Ala Ser Thr Lys Gln Ile Asp
65                  70                  75                  80

Val Tyr Arg Ser Val Val Cys Pro Ile Leu Asp Glu Val Ile Met Gly
                85                  90                  95

Tyr Asn Cys Thr Ile Phe Ala Tyr Gly Gln Thr Gly Thr Gly Lys Thr
            100                 105                 110

```
Phe Thr Met Glu Gly Glu Arg Ser Pro Asn Glu Glu Tyr Thr Trp Glu
            115                 120                 125

Glu Asp Pro Leu Ala Gly Ile Ile Pro Arg Thr Leu His Gln Ile Phe
130                 135                 140

Glu Lys Leu Thr Asp Asn Gly Thr Glu Phe Ser Val Lys Val Ser Leu
145                 150                 155                 160

Leu Glu Ile Tyr Asn Glu Glu Leu Phe Asp Leu Leu Asn Pro Ser Ser
                165                 170                 175

Asp Val Ser Glu Arg Leu Gln Met Phe Asp Pro Arg Asn Lys Arg
                180                 185                 190

Gly Val Ile Ile Lys Gly Leu Glu Glu Ile Thr Val His Asn Lys Asp
                195                 200                 205

Glu Val Tyr Gln Ile Leu Glu Lys Gly Ala Ala Lys Arg Thr Thr Ala
                210                 215                 220

Ala Thr Leu Met Asn Ala Tyr Ser Ser Arg Ser His Ser Val Phe Ser
225                 230                 235                 240

Val Thr Ile His Met Lys Glu Thr Thr Ile Asp Gly Glu Glu Leu Val
                245                 250                 255

Lys Ile Gly Lys Leu Asn Leu Val Asp Leu Ala Gly Ser Glu Asn Ile
                260                 265                 270

Gly Arg Ser Gly Ala Val Asp Lys Arg Ala Arg Glu Ala Gly Asn Ile
                275                 280                 285

Asn Gln Ser Leu Leu Thr Leu Gly Arg Val Ile Thr Ala Leu Val Glu
                290                 295                 300

Arg Thr Pro His Val Pro Tyr Arg Glu Ser Lys Leu Thr Arg Ile Leu
305                 310                 315                 320

Gln Asp Ser Leu Gly Gly Arg Thr Arg Thr Ser Ile Ile Ala Thr Ile
                325                 330                 335

Ser Pro Ala Ser Leu Asn Leu Glu Glu Thr Leu Ser Thr Leu Glu Tyr
                340                 345                 350

Ala His Arg Ala Lys Asn Ile Leu Asn Lys Pro Glu Val Asn Gln Lys
                355                 360                 365

Leu Thr Lys Lys Ala Leu Ile Lys Glu Tyr Thr Glu Glu Ile Glu Arg
370                 375                 380

Leu Lys Arg Asp Leu Ala Ala Ala Arg Glu Lys Asn Gly Val Tyr Ile
385                 390                 395                 400

Ser Glu Glu Asn Phe Arg Val Met Ser Gly Lys Leu Thr Val Gln Glu
                405                 410                 415

Glu Gln Ile Val Glu Leu Ile Glu Lys Ile Gly Ala Val Glu Glu Glu
                420                 425                 430

Leu Asn Arg Val Thr Glu Leu Phe Met Asp Asn Lys Asn Glu Leu Asp
                435                 440                 445

Gln Cys Lys Ser Asp Leu Gln Asn Lys Thr Gln Glu Leu Glu Thr Thr
450                 455                 460

Gln Lys His Leu Gln Glu Thr Lys Leu Gln Leu Val Lys Glu Glu Tyr
465                 470                 475                 480

Ile Thr Ser Ala Leu Glu Ser Thr Glu Glu Lys Leu His Asp Ala Ala
                485                 490                 495

Ser Lys Leu Leu Asn Thr Val Glu Glu Thr Thr Lys Asp Val Ser Gly
                500                 505                 510

Leu His Ser Lys Leu Asp Arg Lys Lys Ala Val Asp Gln His Asn Ala
                515                 520                 525
```

-continued

```
Glu Ala Gln Asp Ile Phe Gly Lys Asn Leu Asn Ser Leu Phe Asn Asn
530                 535                 540
Met Glu Glu Leu Ile Lys Asp Gly Ser Ser Lys Gln Lys Ala Met Leu
545                 550                 555                 560
Glu Val His Lys Thr Leu Phe Gly Asn Leu Leu Ser Ser Ser Val Ser
                565                 570                 575
Ala Leu Asp Thr Ile Thr Thr Val Ala Leu Gly Ser Leu Thr Ser Ile
            580                 585                 590
Pro Glu Asn Val Ser Thr His Val Ser Gln Ile Phe Asn Met Ile Leu
        595                 600                 605
Lys Glu Gln Ser Leu Ala Ala Glu Ser Lys Thr Val Leu Gln Glu Leu
610                 615                 620
Ile Asn Val Leu Lys Thr Asp Leu Leu Ser Ser Leu Glu Met Ile Leu
625                 630                 635                 640
Ser Pro Thr Val Val Ser Ile Leu Lys Ile Asn Ser Gln Leu Lys His
                645                 650                 655
Ile Phe Lys Thr Ser Leu Thr Val Ala Asp Lys Ile Glu Asp Gln Lys
            660                 665                 670
Lys Glu Leu Asp Gly Phe Leu Ser Ile Leu Cys Asn Asn Leu His Glu
        675                 680                 685
Leu Gln Glu Asn Thr Ile Cys Ser Leu Val Glu Ser Gln Lys Gln Cys
690                 695                 700
Gly Asn Leu Thr Glu Asp Leu Lys Thr Ile Lys Gln Thr His Ser Gln
705                 710                 715                 720
Glu Leu Cys Lys Leu Met Asn Leu Trp Thr Glu Arg Phe Cys Ala Leu
                725                 730                 735
Glu Glu Lys Cys Glu Asn Ile Gln Lys Pro Leu Ser Ser Val Gln Glu
            740                 745                 750
Asn Ile Gln Gln Lys Ser Lys Asp Ile Val Asn Lys Met Thr Phe His
        755                 760                 765
Ser Gln Lys Phe Cys Ala Asp Ser Asp Gly Phe Ser Gln Glu Leu Arg
770                 775                 780
Asn Phe Asn Gln Glu Gly Thr Lys Leu Val Glu Glu Ser Val Lys His
785                 790                 795                 800
Ser Asp Lys Leu Asn Gly Asn Leu Glu Lys Ile Ser Gln Glu Thr Glu
                805                 810                 815
Gln Arg Cys Glu Ser Leu Asn Thr Arg Thr Val Tyr Phe Ser Glu Gln
            820                 825                 830
Trp Val Ser Ser Leu Asn Glu Arg Glu Gln Glu Leu His Asn Leu Leu
        835                 840                 845
Glu Val Val Ser Gln Cys Cys Glu Ala Ser Ser Ser Asp Ile Thr Glu
850                 855                 860
Lys Ser Asp Gly Arg Lys Ala Ala His Glu Lys Gln His Asn Ile Phe
865                 870                 875                 880
Leu Asp Gln Met Thr Ile Asp Glu Asp Lys Leu Ile Ala Gln Asn Leu
                885                 890                 895
Glu Leu Asn Glu Thr Ile Lys Ile Gly Leu Thr Lys Leu Asn Cys Phe
            900                 905                 910
Leu Glu Gln Asp Leu Lys Leu Asp Ile Pro Thr Gly Thr Thr Pro Gln
        915                 920                 925
Arg Lys Ser Tyr Leu Tyr Pro Ser Thr Leu Val Arg Thr Glu Pro Arg
930                 935                 940
Glu His Leu Leu Asp Gln Leu Lys Arg Lys Gln Pro Glu Leu Leu Met
```

```
                 945                 950                 955                 960
Met Leu Asn Cys Ser Glu Asn Asn Lys Glu Glu Thr Ile Pro Asp Val
                 965                 970                 975

Asp Val Glu Glu Ala Val Leu Gly Gln Tyr Thr Glu Pro Leu Ser
                 980                 985                 990

Gln Glu Pro Ser Val Asp Ala Gly  Val Asp Cys Ser Ser  Ile Gly Gly
                 995                1000                1005

Val Pro  Phe Phe Gln His Lys  Lys Ser His Gly Lys  Asp Lys Glu
        1010                 1015                1020

Asn Arg  Gly Ile Asn Thr Leu  Glu Arg Ser Lys Val  Glu Glu Thr
        1025                 1030                1035

Thr Glu  His Leu Val Thr Lys  Ser Arg Leu Pro Leu  Arg Ala Gln
        1040                 1045                1050

Ile Asn  Leu
        1055

<210> SEQ ID NO 42
<211> LENGTH: 2825
<212> TYPE: PRT
<213> ORGANISM: Homo sapiens

<400> SEQUENCE: 42

Met Tyr Ala Ser Leu Gly Ser Gly Pro Val Ala Pro Leu Pro Ala Ser
1               5                   10                  15

Val Pro Pro Ser Val Leu Gly Ser Trp Ser Thr Gly Gly Ser Arg Ser
                20                  25                  30

Cys Val Arg Gln Glu Thr Lys Ser Pro Gly Gly Ala Arg Thr Ser Gly
            35                  40                  45

His Trp Ala Ser Val Trp Gln Glu Val Leu Lys Gln Leu Gln Gly Ser
        50                  55                  60

Ile Glu Asp Glu Ala Met Ala Ser Ser Gly Gln Ile Asp Leu Leu Glu
65                  70                  75                  80

Arg Leu Lys Glu Leu Asn Leu Asp Ser Ser Asn Phe Pro Gly Val Lys
                85                  90                  95

Leu Arg Ser Lys Met Ser Leu Arg Ser Tyr Gly Ser Arg Glu Gly Ser
                100                 105                 110

Val Ser Ser Arg Ser Gly Glu Cys Ser Pro Val Pro Met Gly Ser Phe
            115                 120                 125

Pro Arg Arg Gly Phe Val Asn Gly Ser Arg Glu Ser Thr Gly Tyr Leu
        130                 135                 140

Glu Glu Leu Glu Lys Glu Arg Ser Leu Leu Leu Ala Asp Leu Asp Lys
145                 150                 155                 160

Glu Glu Lys Glu Lys Asp Trp Tyr Tyr Ala Gln Leu Gln Asn Leu Thr
                165                 170                 175

Lys Arg Ile Asp Ser Leu Pro Leu Thr Glu Asn Phe Ser Leu Gln Thr
                180                 185                 190

Asp Met Thr Arg Arg Gln Leu Glu Tyr Glu Ala Arg Gln Ile Arg Val
            195                 200                 205

Ala Met Glu Glu Gln Leu Gly Thr Cys Gln Asp Met Glu Lys Arg Ala
        210                 215                 220

Gln Arg Ser Ser Gln Asn Lys His Glu Thr Gly Ser His Asp Ala Glu
225                 230                 235                 240

Arg Gln Asn Glu Gly Gln Gly Val Gly Glu Ile Asn Met Ala Thr Ser
                245                 250                 255
```

```
Gly Asn Gly Gln Gly Ser Thr Thr Arg Met Asp His Glu Thr Ala Ser
            260                 265                 270

Val Leu Ser Ser Ser Ser Thr His Ser Ala Pro Arg Arg Leu Thr Ser
        275                 280                 285

His Leu Gly Thr Lys Val Glu Met Val Tyr Ser Leu Leu Ser Met Leu
    290                 295                 300

Gly Thr His Asp Lys Asp Asp Met Ser Arg Thr Leu Leu Ala Met Ser
305                 310                 315                 320

Ser Ser Gln Asp Ser Cys Ile Ser Met Arg Gln Ser Gly Cys Leu Pro
                325                 330                 335

Leu Leu Ile Gln Leu Leu His Gly Asn Asp Lys Asp Ser Val Leu Leu
            340                 345                 350

Gly Asn Ser Arg Gly Ser Lys Glu Ala Arg Ala Arg Ala Ser Ala Ala
        355                 360                 365

Leu His Asn Ile Ile His Ser Gln Pro Asp Asp Lys Arg Gly Arg Arg
    370                 375                 380

Glu Ile Arg Val Leu His Leu Leu Glu Gln Ile Arg Ala Tyr Cys Glu
385                 390                 395                 400

Thr Cys Trp Glu Trp Gln Glu Ala His Glu Pro Gly Met Asp Gln Asp
                405                 410                 415

Lys Asn Pro Met Pro Ala Pro Val Glu His Gln Ile Cys Pro Ala Val
            420                 425                 430

Cys Val Leu Met Lys Leu Ser Phe Asp Glu Glu His Arg His Ala Met
        435                 440                 445

Asn Glu Leu Gly Gly Leu Gln Ala Ile Ala Glu Leu Leu Gln Val Asp
    450                 455                 460

Cys Glu Met Tyr Gly Leu Thr Asn Asp His Tyr Ser Ile Thr Leu Arg
465                 470                 475                 480

Arg Tyr Ala Gly Met Ala Leu Thr Asn Leu Thr Phe Gly Asp Val Ala
                485                 490                 495

Asn Lys Ala Thr Leu Cys Ser Met Lys Gly Cys Met Arg Ala Leu Val
            500                 505                 510

Ala Gln Leu Lys Ser Glu Ser Glu Asp Leu Gln Gln Val Ile Ala Ser
        515                 520                 525

Val Leu Arg Asn Leu Ser Trp Arg Ala Asp Val Asn Ser Lys Lys Thr
    530                 535                 540

Leu Arg Glu Val Gly Ser Val Lys Ala Leu Met Glu Cys Ala Leu Glu
545                 550                 555                 560

Val Lys Lys Glu Ser Thr Leu Lys Ser Val Leu Ser Ala Leu Trp Asn
                565                 570                 575

Leu Ser Ala His Cys Thr Glu Asn Lys Ala Asp Ile Cys Ala Val Asp
            580                 585                 590

Gly Ala Leu Ala Phe Leu Val Gly Thr Leu Thr Tyr Arg Ser Gln Thr
        595                 600                 605

Asn Thr Leu Ala Ile Ile Glu Ser Gly Gly Ile Leu Arg Asn Val
    610                 615                 620

Ser Ser Leu Ile Ala Thr Asn Glu Asp His Arg Gln Ile Leu Arg Glu
625                 630                 635                 640

Asn Asn Cys Leu Gln Thr Leu Leu Gln His Leu Lys Ser His Ser Leu
                645                 650                 655

Thr Ile Val Ser Asn Ala Cys Gly Thr Leu Trp Asn Leu Ser Ala Arg
            660                 665                 670

Asn Pro Lys Asp Gln Glu Ala Leu Trp Asp Met Gly Ala Val Ser Met
```

-continued

```
              675                 680                 685
Leu Lys Asn Leu Ile His Ser Lys His Lys Met Ile Ala Met Gly Ser
    690                 695                 700
Ala Ala Ala Leu Arg Asn Leu Met Ala Asn Arg Pro Ala Lys Tyr Lys
705                 710                 715                 720
Asp Ala Asn Ile Met Ser Pro Gly Ser Ser Leu Pro Ser Leu His Val
                725                 730                 735
Arg Lys Gln Lys Ala Leu Glu Ala Glu Leu Asp Ala Gln His Leu Ser
                740                 745                 750
Glu Thr Phe Asp Asn Ile Asp Asn Leu Ser Pro Lys Ala Ser His Arg
                755                 760                 765
Ser Lys Gln Arg His Lys Gln Ser Leu Tyr Gly Asp Tyr Val Phe Asp
770                 775                 780
Thr Asn Arg His Asp Asp Asn Arg Ser Asp Asn Phe Asn Thr Gly Asn
785                 790                 795                 800
Met Thr Val Leu Ser Pro Tyr Leu Asn Thr Thr Val Leu Pro Ser Ser
                805                 810                 815
Ser Ser Ser Arg Gly Ser Leu Asp Ser Ser Arg Ser Glu Lys Asp Arg
                820                 825                 830
Ser Leu Glu Arg Glu Arg Gly Ile Gly Leu Gly Asn Tyr His Pro Ala
                835                 840                 845
Thr Glu Asn Pro Gly Thr Ser Ser Lys Arg Gly Leu Gln Ile Ser Thr
    850                 855                 860
Thr Ala Ala Gln Ile Ala Lys Val Met Glu Glu Val Ser Ala Ile His
865                 870                 875                 880
Thr Ser Gln Glu Asp Arg Ser Ser Gly Ser Thr Thr Glu Leu His Cys
                885                 890                 895
Val Thr Asp Glu Arg Asn Ala Leu Arg Arg Ser Ser Ala Ala His Thr
                900                 905                 910
His Ser Asn Thr Tyr Asn Phe Thr Lys Ser Glu Asn Ser Asn Arg Thr
            915                 920                 925
Cys Ser Met Pro Tyr Ala Lys Leu Glu Tyr Lys Arg Ser Ser Asn Asp
    930                 935                 940
Ser Leu Asn Ser Val Ser Ser Ser Asp Gly Tyr Gly Lys Arg Gly Gln
945                 950                 955                 960
Met Lys Pro Ser Ile Glu Ser Tyr Ser Glu Asp Asp Glu Ser Lys Phe
                965                 970                 975
Cys Ser Tyr Gly Gln Tyr Pro Ala Asp Leu Ala His Lys Ile His Ser
            980                 985                 990
Ala Asn His Met Asp Asp Asn Asp Gly Glu Leu Asp Thr Pro Ile Asn
        995                 1000                1005
Tyr Ser Leu Lys Tyr Ser Asp Glu Gln Leu Asn Ser Gly Arg Gln
    1010                1015                1020
Ser Pro Ser Gln Asn Glu Arg Trp Ala Arg Pro Lys His Ile Ile
    1025                1030                1035
Glu Asp Glu Ile Lys Gln Ser Glu Gln Arg Gln Ser Arg Asn Gln
    1040                1045                1050
Ser Thr Thr Tyr Pro Val Tyr Thr Glu Ser Thr Asp Asp Lys His
    1055                1060                1065
Leu Lys Phe Gln Pro His Phe Gly Gln Gln Glu Cys Val Ser Pro
    1070                1075                1080
Tyr Arg Ser Arg Gly Ala Asn Gly Ser Glu Thr Asn Arg Val Gly
    1085                1090                1095
```

-continued

Ser Asn His Gly Ile Asn Gln Asn Val Ser Gln Ser Leu Cys Gln
1100                1105                1110

Glu Asp Asp Tyr Glu Asp Asp Lys Pro Thr Asn Tyr Ser Glu Arg
1115                1120                1125

Tyr Ser Glu Glu Glu Gln His Glu Glu Glu Arg Pro Thr Asn
1130                1135                1140

Tyr Ser Ile Lys Tyr Asn Glu Glu Lys Arg His Val Asp Gln Pro
1145                1150                1155

Ile Asp Tyr Ser Leu Lys Tyr Ala Thr Asp Ile Pro Ser Ser Gln
1160                1165                1170

Lys Gln Ser Phe Ser Phe Ser Lys Ser Ser Ser Gly Gln Ser Ser
1175                1180                1185

Lys Thr Glu His Met Ser Ser Ser Ser Glu Asn Thr Ser Thr Pro
1190                1195                1200

Ser Ser Asn Ala Lys Arg Gln Asn Gln Leu His Pro Ser Ser Ala
1205                1210                1215

Gln Ser Arg Ser Gly Gln Pro Gln Lys Ala Ala Thr Cys Lys Val
1220                1225                1230

Ser Ser Ile Asn Gln Glu Thr Ile Gln Thr Tyr Cys Val Glu Asp
1235                1240                1245

Thr Pro Ile Cys Phe Ser Arg Cys Ser Ser Leu Ser Ser Leu Ser
1250                1255                1260

Ser Ala Glu Asp Glu Ile Gly Cys Asn Gln Thr Thr Gln Glu Ala
1265                1270                1275

Asp Ser Ala Asn Thr Leu Gln Ile Ala Glu Ile Lys Glu Lys Ile
1280                1285                1290

Gly Thr Arg Ser Ala Glu Asp Pro Val Ser Glu Val Pro Ala Val
1295                1300                1305

Ser Gln His Pro Arg Thr Lys Ser Ser Arg Leu Gln Gly Ser Ser
1310                1315                1320

Leu Ser Ser Glu Ser Ala Arg His Lys Ala Val Glu Phe Ser Ser
1325                1330                1335

Gly Ala Lys Ser Pro Ser Lys Ser Gly Ala Gln Thr Pro Lys Ser
1340                1345                1350

Pro Pro Glu His Tyr Val Gln Glu Thr Pro Leu Met Phe Ser Arg
1355                1360                1365

Cys Thr Ser Val Ser Ser Leu Asp Ser Phe Glu Ser Arg Ser Ile
1370                1375                1380

Ala Ser Ser Val Gln Ser Glu Pro Cys Ser Gly Met Val Ser Gly
1385                1390                1395

Ile Ile Ser Pro Ser Asp Leu Pro Asp Ser Pro Gly Gln Thr Met
1400                1405                1410

Pro Pro Ser Arg Ser Lys Thr Pro Pro Pro Pro Gln Thr Ala
1415                1420                1425

Gln Thr Lys Arg Glu Val Pro Lys Asn Lys Ala Pro Thr Ala Glu
1430                1435                1440

Lys Arg Glu Ser Gly Pro Lys Gln Ala Ala Val Asn Ala Ala Val
1445                1450                1455

Gln Arg Val Gln Val Leu Pro Asp Ala Asp Thr Leu Leu His Phe
1460                1465                1470

Ala Thr Glu Ser Thr Pro Asp Gly Phe Ser Cys Ser Ser Ser Leu
1475                1480                1485

```
Ser Ala Leu Ser Leu Asp Glu Pro Phe Ile Gln Lys Asp Val Glu
    1490            1495                1500
Leu Arg Ile Met Pro Pro Val Gln Glu Asn Asp Asn Gly Asn Glu
    1505            1510                1515
Thr Glu Ser Glu Gln Pro Lys Glu Ser Asn Glu Asn Gln Glu Lys
    1520            1525                1530
Glu Ala Glu Lys Thr Ile Asp Ser Glu Lys Asp Leu Leu Asp Asp
    1535            1540                1545
Ser Asp Asp Asp Asp Ile Glu Ile Leu Glu Glu Cys Ile Ile Ser
    1550            1555                1560
Ala Met Pro Thr Lys Ser Ser Arg Lys Ala Lys Lys Pro Ala Gln
    1565            1570                1575
Thr Ala Ser Lys Leu Pro Pro Pro Val Ala Arg Lys Pro Ser Gln
    1580            1585                1590
Leu Pro Val Tyr Lys Leu Leu Pro Ser Gln Asn Arg Leu Gln Pro
    1595            1600                1605
Gln Lys His Val Ser Phe Thr Pro Gly Asp Asp Met Pro Arg Val
    1610            1615                1620
Tyr Cys Val Glu Gly Thr Pro Ile Asn Phe Ser Thr Ala Thr Ser
    1625            1630                1635
Leu Ser Asp Leu Thr Ile Glu Ser Pro Pro Asn Glu Leu Ala Ala
    1640            1645                1650
Gly Glu Gly Val Arg Gly Gly Ala Gln Ser Gly Glu Phe Glu Lys
    1655            1660                1665
Arg Asp Thr Ile Pro Thr Glu Gly Arg Ser Thr Asp Glu Ala Gln
    1670            1675                1680
Gly Gly Lys Thr Ser Ser Val Thr Ile Pro Glu Leu Asp Asp Asn
    1685            1690                1695
Lys Ala Glu Glu Gly Asp Ile Leu Ala Glu Cys Ile Asn Ser Ala
    1700            1705                1710
Met Pro Lys Gly Lys Ser His Lys Pro Phe Arg Val Lys Lys Ile
    1715            1720                1725
Met Asp Gln Val Gln Gln Ala Ser Ala Ser Ser Ser Ala Pro Asn
    1730            1735                1740
Lys Asn Gln Leu Asp Gly Lys Lys Lys Lys Pro Thr Ser Pro Val
    1745            1750                1755
Lys Pro Ile Pro Gln Asn Thr Glu Tyr Arg Thr Arg Val Arg Lys
    1760            1765                1770
Asn Ala Asp Ser Lys Asn Asn Leu Asn Ala Glu Arg Val Phe Ser
    1775            1780                1785
Asp Asn Lys Asp Ser Lys Lys Gln Asn Leu Lys Asn Asn Ser Lys
    1790            1795                1800
Val Phe Asn Asp Lys Leu Pro Asn Asn Glu Asp Arg Val Arg Gly
    1805            1810                1815
Ser Phe Ala Phe Asp Ser Pro His His Tyr Thr Pro Ile Glu Gly
    1820            1825                1830
Thr Pro Tyr Cys Phe Ser Arg Asn Asp Ser Leu Ser Ser Leu Asp
    1835            1840                1845
Phe Asp Asp Asp Asp Val Asp Leu Ser Arg Glu Lys Ala Glu Leu
    1850            1855                1860
Arg Lys Ala Lys Glu Asn Lys Glu Ser Glu Ala Lys Val Thr Ser
    1865            1870                1875
His Thr Glu Leu Thr Ser Asn Gln Gln Ser Ala Asn Lys Thr Gln
```

-continued

```
            1880                1885                1890
Ala Ile Ala Lys Gln Pro Ile Asn Arg Gly Gln Pro Lys Pro Ile
            1895                1900                1905

Leu Gln Lys Gln Ser Thr Phe Pro Gln Ser Ser Lys Asp Ile Pro
            1910                1915                1920

Asp Arg Gly Ala Ala Thr Asp Glu Lys Leu Gln Asn Phe Ala Ile
            1925                1930                1935

Glu Asn Thr Pro Val Cys Phe Ser His Asn Ser Ser Leu Ser Ser
            1940                1945                1950

Leu Ser Asp Ile Asp Gln Glu Asn Asn Asn Lys Glu Asn Glu Pro
            1955                1960                1965

Ile Lys Glu Thr Glu Pro Pro Asp Ser Gln Gly Glu Pro Ser Lys
            1970                1975                1980

Pro Gln Ala Ser Gly Tyr Ala Pro Lys Ser Phe His Val Glu Asp
            1985                1990                1995

Thr Pro Val Cys Phe Ser Arg Asn Ser Ser Leu Ser Ser Leu Ser
            2000                2005                2010

Ile Asp Ser Glu Asp Asp Leu Leu Gln Glu Cys Ile Ser Ser Ala
            2015                2020                2025

Met Pro Lys Lys Lys Lys Pro Ser Arg Leu Lys Gly Asp Asn Glu
            2030                2035                2040

Lys His Ser Pro Arg Asn Met Gly Gly Ile Leu Gly Glu Asp Leu
            2045                2050                2055

Thr Leu Asp Leu Lys Asp Ile Gln Arg Pro Asp Ser Glu His Gly
            2060                2065                2070

Leu Ser Pro Asp Ser Glu Asn Phe Asp Trp Lys Ala Ile Gln Glu
            2075                2080                2085

Gly Ala Asn Ser Ile Val Ser Ser Leu His Gln Ala Ala Ala Ala
            2090                2095                2100

Ala Cys Leu Ser Arg Gln Ala Ser Ser Asp Ser Asp Ser Ile Leu
            2105                2110                2115

Ser Leu Lys Ser Gly Ile Ser Leu Gly Ser Pro Phe His Leu Thr
            2120                2125                2130

Pro Asp Gln Glu Glu Lys Pro Phe Thr Ser Asn Lys Gly Pro Arg
            2135                2140                2145

Ile Leu Lys Pro Gly Glu Lys Ser Thr Leu Glu Thr Lys Lys Ile
            2150                2155                2160

Glu Ser Glu Ser Lys Gly Ile Lys Gly Gly Lys Lys Val Tyr Lys
            2165                2170                2175

Ser Leu Ile Thr Gly Lys Val Arg Ser Asn Ser Glu Ile Ser Gly
            2180                2185                2190

Gln Met Lys Gln Pro Leu Gln Ala Asn Met Pro Ser Ile Ser Arg
            2195                2200                2205

Gly Arg Thr Met Ile His Ile Pro Gly Val Arg Asn Ser Ser Ser
            2210                2215                2220

Ser Thr Ser Pro Val Ser Lys Lys Gly Pro Pro Leu Lys Thr Pro
            2225                2230                2235

Ala Ser Lys Ser Pro Ser Glu Gly Gln Thr Ala Thr Thr Ser Pro
            2240                2245                2250

Arg Gly Ala Lys Pro Ser Val Lys Ser Glu Leu Ser Pro Val Ala
            2255                2260                2265

Arg Gln Thr Ser Gln Ile Gly Gly Ser Ser Lys Ala Pro Ser Arg
            2270                2275                2280
```

-continued

```
Ser Gly Ser Arg Asp Ser Thr Pro Ser Arg Pro Ala Gln Gln Pro
    2285                2290            2295

Leu Ser Arg Pro Ile Gln Ser Pro Gly Arg Asn Ser Ile Ser Pro
    2300                2305            2310

Gly Arg Asn Gly Ile Ser Pro Pro Asn Lys Leu Ser Gln Leu Pro
    2315                2320            2325

Arg Thr Ser Ser Pro Ser Thr Ala Ser Thr Lys Ser Ser Gly Ser
    2330                2335            2340

Gly Lys Met Ser Tyr Thr Ser Pro Gly Arg Gln Met Ser Gln Gln
    2345                2350            2355

Asn Leu Thr Lys Gln Thr Gly Leu Ser Lys Asn Ala Ser Ser Ile
    2360                2365            2370

Pro Arg Ser Glu Ser Ala Ser Lys Gly Leu Asn Gln Met Asn Asn
    2375                2380            2385

Gly Asn Gly Ala Asn Lys Lys Val Glu Leu Ser Arg Met Ser Ser
    2390                2395            2400

Thr Lys Ser Ser Gly Ser Glu Ser Asp Arg Ser Glu Arg Pro Val
    2405                2410            2415

Leu Val Arg Gln Ser Thr Phe Ile Lys Glu Ala Pro Ser Pro Thr
    2420                2425            2430

Leu Arg Arg Lys Leu Glu Glu Ser Ala Ser Phe Glu Ser Leu Ser
    2435                2440            2445

Pro Ser Ser Arg Pro Ala Ser Pro Thr Arg Ser Gln Ala Gln Thr
    2450                2455            2460

Pro Val Leu Ser Pro Ser Leu Pro Asp Met Ser Leu Ser Thr His
    2465                2470            2475

Ser Ser Val Gln Ala Gly Gly Trp Arg Lys Leu Pro Pro Asn Leu
    2480                2485            2490

Ser Pro Thr Ile Glu Tyr Asn Asp Gly Arg Pro Ala Lys Arg His
    2495                2500            2505

Asp Ile Ala Arg Ser His Ser Glu Ser Pro Ser Arg Leu Pro Ile
    2510                2515            2520

Asn Arg Ser Gly Thr Trp Lys Arg Glu His Ser Lys His Ser Ser
    2525                2530            2535

Ser Leu Pro Arg Val Ser Thr Trp Arg Arg Thr Gly Ser Ser Ser
    2540                2545            2550

Ser Ile Leu Ser Ala Ser Ser Glu Ser Ser Glu Lys Ala Lys Ser
    2555                2560            2565

Glu Asp Glu Lys His Val Asn Ser Ile Ser Gly Thr Lys Gln Ser
    2570                2575            2580

Lys Glu Asn Gln Val Ser Ala Lys Gly Thr Trp Arg Lys Ile Lys
    2585                2590            2595

Glu Asn Glu Phe Ser Pro Thr Asn Ser Thr Ser Gln Thr Val Ser
    2600                2605            2610

Ser Gly Ala Thr Asn Gly Ala Glu Ser Lys Thr Leu Ile Tyr Gln
    2615                2620            2625

Met Ala Pro Ala Val Ser Lys Thr Glu Asp Val Trp Val Arg Ile
    2630                2635            2640

Glu Asp Cys Pro Ile Asn Asn Pro Arg Ser Gly Arg Ser Pro Thr
    2645                2650            2655

Gly Asn Thr Pro Pro Val Ile Asp Ser Val Ser Glu Lys Ala Asn
    2660                2665            2670
```

```
Pro Asn Ile Lys Asp Ser Lys Asp Asn Gln Ala Lys Gln Asn Val
    2675              2680                2685

Gly Asn Gly Ser Val Pro Met Arg Thr Val Gly Leu Glu Asn Arg
    2690              2695                2700

Leu Asn Ser Phe Ile Gln Val Asp Ala Pro Asp Gln Lys Gly Thr
    2705              2710                2715

Glu Ile Lys Pro Gly Gln Asn Asn Pro Val Pro Val Ser Glu Thr
    2720              2725                2730

Asn Glu Ser Ser Ile Val Glu Arg Thr Pro Phe Ser Ser Ser Ser
    2735              2740                2745

Ser Ser Lys His Ser Ser Pro Ser Gly Thr Val Ala Ala Arg Val
    2750              2755                2760

Thr Pro Phe Asn Tyr Asn Pro Ser Pro Arg Lys Ser Ser Ala Asp
    2765              2770                2775

Ser Thr Ser Ala Arg Pro Ser Gln Ile Pro Thr Pro Val Asn Asn
    2780              2785                2790

Asn Thr Lys Lys Arg Asp Ser Lys Thr Asp Ser Thr Glu Ser Ser
    2795              2800                2805

Gly Thr Gln Ser Pro Lys Arg His Ser Gly Ser Tyr Leu Val Thr
    2810              2815                2820

Ser Val
    2825

<210> SEQ ID NO 43
<211> LENGTH: 1863
<212> TYPE: PRT
<213> ORGANISM: Homo sapiens

<400> SEQUENCE: 43

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
        50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205
```

-continued

```
Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
    370                 375                 380

Trp Phe Ser Arg Ser Asp Glu Leu Leu Gly Ser Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Glu Arg Val His
        435                 440                 445

Ser Lys Ser Val Glu Ser Asn Ile Glu Asp Lys Ile Phe Gly Lys Thr
    450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
    530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
    610                 615                 620
```

```
Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
            645                 650                 655

Gln Met Pro Val Arg His Ser Arg Asn Leu Gln Leu Met Glu Gly Lys
        660                 665                 670

Glu Pro Ala Thr Gly Ala Lys Lys Ser Asn Lys Pro Asn Glu Gln Thr
            675                 680                 685

Ser Lys Arg His Asp Ser Asp Thr Phe Pro Glu Leu Lys Leu Thr Asn
690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Ser Ser Ser
        755                 760                 765

Ile Ser Leu Val Pro Gly Thr Asp Tyr Gly Thr Gln Glu Ser Ile Ser
770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
        820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
            885                 890                 895

Pro Lys Val Thr Phe Glu Cys Glu Gln Lys Glu Glu Asn Gln Gly Lys
        900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
        930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
            965                 970                 975

Pro Tyr Arg Ile Pro Pro Leu Phe Pro Ile Lys Ser Phe Val Lys Thr
        980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val
        1010                1015                1020

Ser Thr Ile Ser Arg Asn Asn Ile Arg Glu Asn Val Phe Lys Glu
        1025                1030                1035

Ala Ser Ser Ser Asn Ile Asn Glu Val Gly Ser Ser Thr Asn Glu
```

```
                1040                1045                1050
Val Gly Ser Ser Ile Asn Glu Ile Gly Ser Ser Asp Glu Asn Ile
                1055                1060                1065

Gln Ala Glu Leu Gly Arg Asn Arg Gly Pro Lys Leu Asn Ala Met
                1070                1075                1080

Leu Arg Leu Gly Val Leu Gln Pro Glu Val Tyr Lys Gln Ser Leu
                1085                1090                1095

Pro Gly Ser Asn Cys Lys His Pro Glu Ile Lys Lys Gln Glu Tyr
                1100                1105                1110

Glu Glu Val Val Gln Thr Val Asn Thr Asp Phe Ser Pro Tyr Leu
                1115                1120                1125

Ile Ser Asp Asn Leu Glu Gln Pro Met Gly Ser Ser His Ala Ser
                1130                1135                1140

Gln Val Cys Ser Glu Thr Pro Asp Asp Leu Leu Asp Asp Gly Glu
                1145                1150                1155

Ile Lys Glu Asp Thr Ser Phe Ala Glu Asn Asp Ile Lys Glu Ser
                1160                1165                1170

Ser Ala Val Phe Ser Lys Ser Val Gln Lys Gly Glu Leu Ser Arg
                1175                1180                1185

Ser Pro Ser Pro Phe Thr His Thr His Leu Ala Gln Gly Tyr Arg
                1190                1195                1200

Arg Gly Ala Lys Lys Leu Glu Ser Ser Glu Glu Asn Leu Ser Ser
                1205                1210                1215

Glu Asp Glu Glu Leu Pro Cys Phe Gln His Leu Leu Phe Gly Lys
                1220                1225                1230

Val Asn Asn Ile Pro Ser Gln Ser Thr Arg His Ser Thr Val Ala
                1235                1240                1245

Thr Glu Cys Leu Ser Lys Asn Thr Glu Glu Asn Leu Leu Ser Leu
                1250                1255                1260

Lys Asn Ser Leu Asn Asp Cys Ser Asn Gln Val Ile Leu Ala Lys
                1265                1270                1275

Ala Ser Gln Glu His His Leu Ser Glu Glu Thr Lys Cys Ser Ala
                1280                1285                1290

Ser Leu Phe Ser Ser Gln Cys Ser Glu Leu Glu Asp Leu Thr Ala
                1295                1300                1305

Asn Thr Asn Thr Gln Asp Pro Phe Leu Ile Gly Ser Ser Lys Gln
                1310                1315                1320

Met Arg His Gln Ser Glu Ser Gln Gly Val Gly Leu Ser Asp Lys
                1325                1330                1335

Glu Leu Val Ser Asp Asp Glu Glu Arg Gly Thr Gly Leu Glu Glu
                1340                1345                1350

Asn Asn Gln Glu Glu Gln Ser Met Asp Ser Asn Leu Gly Glu Ala
                1355                1360                1365

Ala Ser Gly Cys Glu Ser Glu Thr Ser Val Ser Glu Asp Cys Ser
                1370                1375                1380

Gly Leu Ser Ser Gln Ser Asp Ile Leu Thr Thr Gln Gln Arg Asp
                1385                1390                1395

Thr Met Gln His Asn Leu Ile Lys Leu Gln Gln Glu Met Ala Glu
                1400                1405                1410

Leu Glu Ala Val Leu Glu Gln His Gly Ser Gln Pro Ser Asn Ser
                1415                1420                1425

Tyr Pro Ser Ile Ile Ser Asp Ser Ser Ala Leu Glu Asp Leu Arg
                1430                1435                1440
```

-continued

```
Asn Pro Glu Gln Ser Thr Ser Glu Lys Ala Val Leu Thr Ser Gln
    1445                1450                1455
Lys Ser Ser Glu Tyr Pro Ile Ser Gln Asn Pro Glu Gly Leu Ser
    1460                1465                1470
Ala Asp Lys Phe Glu Val Ser Ala Asp Ser Ser Thr Ser Lys Asn
    1475                1480                1485
Lys Glu Pro Gly Val Glu Arg Ser Ser Pro Ser Lys Cys Pro Ser
    1490                1495                1500
Leu Asp Asp Arg Trp Tyr Met His Ser Cys Ser Gly Ser Leu Gln
    1505                1510                1515
Asn Arg Asn Tyr Pro Ser Gln Glu Glu Leu Ile Lys Val Val Asp
    1520                1525                1530
Val Glu Glu Gln Gln Leu Glu Glu Ser Gly Pro His Asp Leu Thr
    1535                1540                1545
Glu Thr Ser Tyr Leu Pro Arg Gln Asp Leu Glu Gly Thr Pro Tyr
    1550                1555                1560
Leu Glu Ser Gly Ile Ser Leu Phe Ser Asp Asp Pro Glu Ser Asp
    1565                1570                1575
Pro Ser Glu Asp Arg Ala Pro Glu Ser Ala Arg Val Gly Asn Ile
    1580                1585                1590
Pro Ser Ser Thr Ser Ala Leu Lys Val Pro Gln Leu Lys Val Ala
    1595                1600                1605
Glu Ser Ala Gln Ser Pro Ala Ala Ala His Thr Thr Asp Thr Ala
    1610                1615                1620
Gly Tyr Asn Ala Met Glu Glu Ser Val Ser Arg Glu Lys Pro Glu
    1625                1630                1635
Leu Thr Ala Ser Thr Glu Arg Val Asn Lys Arg Met Ser Met Val
    1640                1645                1650
Val Ser Gly Leu Thr Pro Glu Glu Phe Met Leu Val Tyr Lys Phe
    1655                1660                1665
Ala Arg Lys His His Ile Thr Leu Thr Asn Leu Ile Thr Glu Glu
    1670                1675                1680
Thr Thr His Val Val Met Lys Thr Asp Ala Glu Phe Val Cys Glu
    1685                1690                1695
Arg Thr Leu Lys Tyr Phe Leu Gly Ile Ala Gly Gly Lys Trp Val
    1700                1705                1710
Val Ser Tyr Phe Trp Val Thr Gln Ser Ile Lys Glu Arg Lys Met
    1715                1720                1725
Leu Asn Glu His Asp Phe Glu Val Arg Gly Asp Val Val Asn Gly
    1730                1735                1740
Arg Asn His Gln Gly Pro Lys Arg Ala Arg Glu Ser Gln Asp Arg
    1745                1750                1755
Lys Ile Phe Arg Gly Leu Glu Ile Cys Cys Tyr Gly Pro Phe Thr
    1760                1765                1770
Asn Met Pro Thr Asp Gln Leu Glu Trp Met Val Gln Leu Cys Gly
    1775                1780                1785
Ala Ser Val Val Lys Glu Leu Ser Ser Phe Thr Leu Gly Thr Gly
    1790                1795                1800
Val His Pro Ile Val Val Val Gln Pro Asp Ala Trp Thr Glu Asp
    1805                1810                1815
Asn Gly Phe His Ala Ile Gly Gln Met Cys Glu Ala Pro Val Val
    1820                1825                1830
```

```
Thr Arg Glu Trp Val Leu Asp Ser Val Ala Leu Tyr Gln Cys Gln
1835                1840                1845

Glu Leu Asp Thr Tyr Leu Ile Pro Gln Ile Pro His Ser His Tyr
1850                1855                1860

<210> SEQ ID NO 44
<211> LENGTH: 3418
<212> TYPE: PRT
<213> ORGANISM: Homo sapiens

<400> SEQUENCE: 44

Met Pro Ile Gly Ser Lys Glu Arg Pro Thr Phe Phe Glu Ile Phe Lys
1               5                   10                  15

Thr Arg Cys Asn Lys Ala Asp Leu Gly Pro Ile Ser Leu Asn Trp Phe
                20                  25                  30

Glu Glu Leu Ser Ser Glu Ala Pro Pro Tyr Asn Ser Glu Pro Ala Glu
            35                  40                  45

Glu Ser Glu His Lys Asn Asn Asn Tyr Glu Pro Asn Leu Phe Lys Thr
        50                  55                  60

Pro Gln Arg Lys Pro Ser Tyr Asn Gln Leu Ala Ser Thr Pro Ile Ile
65                  70                  75                  80

Phe Lys Glu Gln Gly Leu Thr Leu Pro Leu Tyr Gln Ser Pro Val Lys
                85                  90                  95

Glu Leu Asp Lys Phe Lys Leu Asp Leu Gly Arg Asn Val Pro Asn Ser
            100                 105                 110

Arg His Lys Ser Leu Arg Thr Val Lys Thr Lys Met Asp Gln Ala Asp
        115                 120                 125

Asp Val Ser Cys Pro Leu Leu Asn Ser Cys Leu Ser Glu Ser Pro Val
130                 135                 140

Val Leu Gln Cys Thr His Val Thr Pro Gln Arg Asp Lys Ser Val Val
145                 150                 155                 160

Cys Gly Ser Leu Phe His Thr Pro Lys Phe Val Lys Gly Arg Gln Thr
                165                 170                 175

Pro Lys His Ile Ser Glu Ser Leu Gly Ala Glu Val Asp Pro Asp Met
            180                 185                 190

Ser Trp Ser Ser Ser Leu Ala Thr Pro Pro Thr Leu Ser Ser Thr Val
        195                 200                 205

Leu Ile Val Arg Asn Glu Glu Ala Ser Glu Thr Val Phe Pro His Asp
210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                245                 250                 255

Asn Gln Arg Glu Ala Ala Ser His Gly Phe Gly Lys Thr Ser Gly Asn
            260                 265                 270

Ser Phe Lys Val Asn Ser Cys Lys Asp His Ile Gly Lys Ser Met Pro
        275                 280                 285

Asn Val Leu Glu Asp Glu Val Tyr Glu Thr Val Val Asp Thr Ser Glu
290                 295                 300

Glu Asp Ser Phe Ser Leu Cys Phe Ser Lys Cys Arg Thr Lys Asn Leu
305                 310                 315                 320

Gln Lys Val Arg Thr Ser Lys Thr Arg Lys Lys Ile Phe His Glu Ala
                325                 330                 335

Asn Ala Asp Glu Cys Glu Lys Ser Lys Asn Gln Val Lys Glu Lys Tyr
            340                 345                 350
```

```
Ser Phe Val Ser Glu Val Glu Pro Asn Asp Thr Asp Pro Leu Asp Ser
            355                 360                 365

Asn Val Ala Asn Gln Lys Pro Phe Glu Ser Gly Ser Asp Lys Ile Ser
370                 375                 380

Lys Glu Val Val Pro Ser Leu Ala Cys Glu Trp Ser Gln Leu Thr Leu
385                 390                 395                 400

Ser Gly Leu Asn Gly Ala Gln Met Glu Lys Ile Pro Leu Leu His Ile
            405                 410                 415

Ser Ser Cys Asp Gln Asn Ile Ser Glu Lys Asp Leu Leu Asp Thr Glu
            420                 425                 430

Asn Lys Arg Lys Lys Asp Phe Leu Thr Ser Glu Asn Ser Leu Pro Arg
            435                 440                 445

Ile Ser Ser Leu Pro Lys Ser Glu Lys Pro Leu Asn Glu Glu Thr Val
            450                 455                 460

Val Asn Lys Arg Asp Glu Glu Gln His Leu Glu Ser His Thr Asp Cys
465                 470                 475                 480

Ile Leu Ala Val Lys Gln Ala Ile Ser Gly Thr Ser Pro Val Ala Ser
            485                 490                 495

Ser Phe Gln Gly Ile Lys Lys Ser Ile Phe Arg Ile Arg Glu Ser Pro
            500                 505                 510

Lys Glu Thr Phe Asn Ala Ser Phe Ser Gly His Met Thr Asp Pro Asn
            515                 520                 525

Phe Lys Lys Glu Thr Glu Ala Ser Glu Ser Gly Leu Glu Ile His Thr
530                 535                 540

Val Cys Ser Gln Lys Glu Asp Ser Leu Cys Pro Asn Leu Ile Asp Asn
545                 550                 555                 560

Gly Ser Trp Pro Ala Thr Thr Thr Gln Asn Ser Val Ala Leu Lys Asn
            565                 570                 575

Ala Gly Leu Ile Ser Thr Leu Lys Lys Lys Thr Asn Lys Phe Ile Tyr
            580                 585                 590

Ala Ile His Asp Glu Thr Ser Tyr Lys Gly Lys Lys Ile Pro Lys Asp
            595                 600                 605

Gln Lys Ser Glu Leu Ile Asn Cys Ser Ala Gln Phe Glu Ala Asn Ala
            610                 615                 620

Phe Glu Ala Pro Leu Thr Phe Ala Asn Ala Asp Ser Gly Leu Leu His
625                 630                 635                 640

Ser Ser Val Lys Arg Ser Cys Ser Gln Asn Asp Ser Glu Glu Pro Thr
            645                 650                 655

Leu Ser Leu Thr Ser Ser Phe Gly Thr Ile Leu Arg Lys Cys Ser Arg
            660                 665                 670

Asn Glu Thr Cys Ser Asn Asn Thr Val Ile Ser Gln Asp Leu Asp Tyr
            675                 680                 685

Lys Glu Ala Lys Cys Asn Lys Glu Lys Leu Gln Leu Phe Ile Thr Pro
690                 695                 700

Glu Ala Asp Ser Leu Ser Cys Leu Gln Glu Gly Gln Cys Glu Asn Asp
705                 710                 715                 720

Pro Lys Ser Lys Lys Val Ser Asp Ile Lys Glu Glu Val Leu Ala Ala
            725                 730                 735

Ala Cys His Pro Val Gln His Ser Lys Val Glu Tyr Ser Asp Thr Asp
            740                 745                 750

Phe Gln Ser Gln Lys Ser Leu Leu Tyr Asp His Glu Asn Ala Ser Thr
            755                 760                 765
```

```
Leu Ile Leu Thr Pro Thr Ser Lys Asp Val Leu Ser Asn Leu Val Met
770                 775                 780

Ile Ser Arg Gly Lys Glu Ser Tyr Lys Met Ser Asp Lys Leu Lys Gly
785                 790                 795                 800

Asn Asn Tyr Glu Ser Asp Val Glu Leu Thr Lys Asn Ile Pro Met Glu
            805                 810                 815

Lys Asn Gln Asp Val Cys Ala Leu Asn Glu Asn Tyr Lys Asn Val Glu
        820                 825                 830

Leu Leu Pro Pro Glu Lys Tyr Met Arg Val Ala Ser Pro Ser Arg Lys
            835                 840                 845

Val Gln Phe Asn Gln Asn Thr Asn Leu Arg Val Ile Gln Lys Asn Gln
850                 855                 860

Glu Glu Thr Thr Ser Ile Ser Lys Ile Thr Val Asn Pro Asp Ser Glu
865                 870                 875                 880

Glu Leu Phe Ser Asp Asn Glu Asn Asn Phe Val Phe Gln Val Ala Asn
                885                 890                 895

Glu Arg Asn Asn Leu Ala Leu Gly Asn Thr Lys Glu Leu His Glu Thr
            900                 905                 910

Asp Leu Thr Cys Val Asn Glu Pro Ile Phe Lys Asn Ser Thr Met Val
        915                 920                 925

Leu Tyr Gly Asp Thr Gly Asp Lys Gln Ala Thr Gln Val Ser Ile Lys
930                 935                 940

Lys Asp Leu Val Tyr Val Leu Ala Glu Glu Asn Lys Asn Ser Val Lys
945                 950                 955                 960

Gln His Ile Lys Met Thr Leu Gly Gln Asp Leu Lys Ser Asp Ile Ser
                965                 970                 975

Leu Asn Ile Asp Lys Ile Pro Glu Lys Asn Asn Asp Tyr Met Asn Lys
            980                 985                 990

Trp Ala Gly Leu Leu Gly Pro Ile Ser Asn His Ser Phe Gly Gly Ser
            995                 1000                1005

Phe Arg Thr Ala Ser Asn Lys Glu Ile Lys Leu Ser Glu His Asn
    1010                1015                1020

Ile Lys Lys Ser Lys Met Phe Phe Lys Asp Ile Glu Glu Gln Tyr
    1025                1030                1035

Pro Thr Ser Leu Ala Cys Val Glu Ile Val Asn Thr Leu Ala Leu
    1040                1045                1050

Asp Asn Gln Lys Lys Leu Ser Lys Pro Gln Ser Ile Asn Thr Val
    1055                1060                1065

Ser Ala His Leu Gln Ser Ser Val Val Val Ser Asp Cys Lys Asn
    1070                1075                1080

Ser His Ile Thr Pro Gln Met Leu Phe Ser Lys Gln Asp Phe Asn
    1085                1090                1095

Ser Asn His Asn Leu Thr Pro Ser Gln Lys Ala Glu Ile Thr Glu
    1100                1105                1110

Leu Ser Thr Ile Leu Glu Glu Ser Gly Ser Gln Phe Glu Phe Thr
    1115                1120                1125

Gln Phe Arg Lys Pro Ser Tyr Ile Leu Gln Lys Ser Thr Phe Glu
    1130                1135                1140

Val Pro Glu Asn Gln Met Thr Ile Leu Lys Thr Thr Ser Glu Glu
    1145                1150                1155

Cys Arg Asp Ala Asp Leu His Val Ile Met Asn Ala Pro Ser Ile
    1160                1165                1170

Gly Gln Val Asp Ser Ser Lys Gln Phe Glu Gly Thr Val Glu Ile
```

-continued

```
            1175                1180                1185

Lys Arg Lys Phe Ala Gly Leu Leu Lys Asn Asp Cys Asn Lys Ser
        1190                1195                1200

Ala Ser Gly Tyr Leu Thr Asp Glu Asn Glu Val Gly Phe Arg Gly
        1205                1210                1215

Phe Tyr Ser Ala His Gly Thr Lys Leu Asn Val Ser Thr Glu Ala
        1220                1225                1230

Leu Gln Lys Ala Val Lys Leu Phe Ser Asp Ile Glu Asn Ile Ser
        1235                1240                1245

Glu Glu Thr Ser Ala Glu Val His Pro Ile Ser Leu Ser Ser Ser
        1250                1255                1260

Lys Cys His Asp Ser Val Val Ser Met Phe Lys Ile Glu Asn His
        1265                1270                1275

Asn Asp Lys Thr Val Ser Glu Lys Asn Asn Lys Cys Gln Leu Ile
        1280                1285                1290

Leu Gln Asn Asn Ile Glu Met Thr Thr Gly Thr Phe Val Glu Glu
        1295                1300                1305

Ile Thr Glu Asn Tyr Lys Arg Asn Thr Glu Asn Glu Asp Asn Lys
        1310                1315                1320

Tyr Thr Ala Ala Ser Arg Asn Ser His Asn Leu Glu Phe Asp Gly
        1325                1330                1335

Ser Asp Ser Ser Lys Asn Asp Thr Val Cys Ile His Lys Asp Glu
        1340                1345                1350

Thr Asp Leu Leu Phe Thr Asp Gln His Asn Ile Cys Leu Lys Leu
        1355                1360                1365

Ser Gly Gln Phe Met Lys Glu Gly Asn Thr Gln Ile Lys Glu Asp
        1370                1375                1380

Leu Ser Asp Leu Thr Phe Leu Glu Val Ala Lys Ala Gln Glu Ala
        1385                1390                1395

Cys His Gly Asn Thr Ser Asn Lys Glu Gln Leu Thr Ala Thr Lys
        1400                1405                1410

Thr Glu Gln Asn Ile Lys Asp Phe Glu Thr Ser Asp Thr Phe Phe
        1415                1420                1425

Gln Thr Ala Ser Gly Lys Asn Ile Ser Val Ala Lys Glu Ser Phe
        1430                1435                1440

Asn Lys Ile Val Asn Phe Phe Asp Gln Lys Pro Glu Glu Leu His
        1445                1450                1455

Asn Phe Ser Leu Asn Ser Glu Leu His Ser Asp Ile Arg Lys Asn
        1460                1465                1470

Lys Met Asp Ile Leu Ser Tyr Glu Glu Thr Asp Ile Val Lys His
        1475                1480                1485

Lys Ile Leu Lys Glu Ser Val Pro Val Gly Thr Gly Asn Gln Leu
        1490                1495                1500

Val Thr Phe Gln Gly Gln Pro Glu Arg Asp Glu Lys Ile Lys Glu
        1505                1510                1515

Pro Thr Leu Leu Gly Phe His Thr Ala Ser Gly Lys Lys Val Lys
        1520                1525                1530

Ile Ala Lys Glu Ser Leu Asp Lys Val Lys Asn Leu Phe Asp Glu
        1535                1540                1545

Lys Glu Gln Gly Thr Ser Glu Ile Thr Ser Phe Ser His Gln Trp
        1550                1555                1560

Ala Lys Thr Leu Lys Tyr Arg Glu Ala Cys Lys Asp Leu Glu Leu
        1565                1570                1575
```

```
Ala Cys Glu Thr Ile Glu Ile Thr Ala Ala Pro Lys Cys Lys Glu
1580                1585                1590

Met Gln Asn Ser Leu Asn Asn Asp Lys Asn Leu Val Ser Ile Glu
1595                1600                1605

Thr Val Val Pro Pro Lys Leu Leu Ser Asp Asn Leu Cys Arg Gln
1610                1615                1620

Thr Glu Asn Leu Lys Thr Ser Lys Ser Ile Phe Leu Lys Val Lys
1625                1630                1635

Val His Glu Asn Val Glu Lys Glu Thr Ala Lys Ser Pro Ala Thr
1640                1645                1650

Cys Tyr Thr Asn Gln Ser Pro Tyr Ser Val Ile Glu Asn Ser Ala
1655                1660                1665

Leu Ala Phe Tyr Thr Ser Cys Ser Arg Lys Thr Ser Val Ser Gln
1670                1675                1680

Thr Ser Leu Leu Glu Ala Lys Lys Trp Leu Arg Glu Gly Ile Phe
1685                1690                1695

Asp Gly Gln Pro Glu Arg Ile Asn Thr Ala Asp Tyr Val Gly Asn
1700                1705                1710

Tyr Leu Tyr Glu Asn Asn Ser Asn Ser Thr Ile Ala Glu Asn Asp
1715                1720                1725

Lys Asn His Leu Ser Glu Lys Gln Asp Thr Tyr Leu Ser Asn Ser
1730                1735                1740

Ser Met Ser Asn Ser Tyr Ser Tyr His Ser Asp Glu Val Tyr Asn
1745                1750                1755

Asp Ser Gly Tyr Leu Ser Lys Asn Lys Leu Asp Ser Gly Ile Glu
1760                1765                1770

Pro Val Leu Lys Asn Val Glu Asp Gln Lys Asn Thr Ser Phe Ser
1775                1780                1785

Lys Val Ile Ser Asn Val Lys Asp Ala Asn Ala Tyr Pro Gln Thr
1790                1795                1800

Val Asn Glu Asp Ile Cys Val Glu Glu Leu Val Thr Ser Ser Ser
1805                1810                1815

Pro Cys Lys Asn Lys Asn Ala Ala Ile Lys Leu Ser Ile Ser Asn
1820                1825                1830

Ser Asn Asn Phe Glu Val Gly Pro Pro Ala Phe Arg Ile Ala Ser
1835                1840                1845

Gly Lys Ile Val Cys Val Ser His Glu Thr Ile Lys Lys Val Lys
1850                1855                1860

Asp Ile Phe Thr Asp Ser Phe Ser Lys Val Ile Lys Glu Asn Asn
1865                1870                1875

Glu Asn Lys Ser Lys Ile Cys Gln Thr Lys Ile Met Ala Gly Cys
1880                1885                1890

Tyr Glu Ala Leu Asp Asp Ser Glu Asp Ile Leu His Asn Ser Leu
1895                1900                1905

Asp Asn Asp Glu Cys Ser Thr His Ser His Lys Val Phe Ala Asp
1910                1915                1920

Ile Gln Ser Glu Glu Ile Leu Gln His Asn Gln Asn Met Ser Gly
1925                1930                1935

Leu Glu Lys Val Ser Lys Ile Ser Pro Cys Asp Val Ser Leu Glu
1940                1945                1950

Thr Ser Asp Ile Cys Lys Cys Ser Ile Gly Lys Leu His Lys Ser
1955                1960                1965
```

```
Val Ser Ser Ala Asn Thr Cys Gly Ile Phe Ser Thr Ala Ser Gly
1970                1975                1980

Lys Ser Val Gln Val Ser Asp Ala Ser Leu Gln Asn Ala Arg Gln
1985                1990                1995

Val Phe Ser Glu Ile Glu Asp Ser Thr Lys Gln Val Phe Ser Lys
2000                2005                2010

Val Leu Phe Lys Ser Asn Glu His Ser Asp Gln Leu Thr Arg Glu
2015                2020                2025

Glu Asn Thr Ala Ile Arg Thr Pro Glu His Leu Ile Ser Gln Lys
2030                2035                2040

Gly Phe Ser Tyr Asn Val Val Asn Ser Ser Ala Phe Ser Gly Phe
2045                2050                2055

Ser Thr Ala Ser Gly Lys Gln Val Ser Ile Leu Glu Ser Ser Leu
2060                2065                2070

His Lys Val Lys Gly Val Leu Glu Glu Phe Asp Leu Ile Arg Thr
2075                2080                2085

Glu His Ser Leu His Tyr Ser Pro Thr Ser Arg Gln Asn Val Ser
2090                2095                2100

Lys Ile Leu Pro Arg Val Asp Lys Arg Asn Pro Glu His Cys Val
2105                2110                2115

Asn Ser Glu Met Glu Lys Thr Cys Ser Lys Glu Phe Lys Leu Ser
2120                2125                2130

Asn Asn Leu Asn Val Glu Gly Gly Ser Ser Glu Asn Asn His Ser
2135                2140                2145

Ile Lys Val Ser Pro Tyr Leu Ser Gln Phe Gln Gln Asp Lys Gln
2150                2155                2160

Gln Leu Val Leu Gly Thr Lys Val Ser Leu Val Glu Asn Ile His
2165                2170                2175

Val Leu Gly Lys Glu Gln Ala Ser Pro Lys Asn Val Lys Met Glu
2180                2185                2190

Ile Gly Lys Thr Glu Thr Phe Ser Asp Val Pro Val Lys Thr Asn
2195                2200                2205

Ile Glu Val Cys Ser Thr Tyr Ser Lys Asp Ser Glu Asn Tyr Phe
2210                2215                2220

Glu Thr Glu Ala Val Glu Ile Ala Lys Ala Phe Met Glu Asp Asp
2225                2230                2235

Glu Leu Thr Asp Ser Lys Leu Pro Ser His Ala Thr His Ser Leu
2240                2245                2250

Phe Thr Cys Pro Glu Asn Glu Glu Met Val Leu Ser Asn Ser Arg
2255                2260                2265

Ile Gly Lys Arg Arg Gly Glu Pro Leu Ile Leu Val Gly Glu Pro
2270                2275                2280

Ser Ile Lys Arg Asn Leu Leu Asn Glu Phe Asp Arg Ile Ile Glu
2285                2290                2295

Asn Gln Glu Lys Ser Leu Lys Ala Ser Lys Ser Thr Pro Asp Gly
2300                2305                2310

Thr Ile Lys Asp Arg Arg Leu Phe Met His His Val Ser Leu Glu
2315                2320                2325

Pro Ile Thr Cys Val Pro Phe Arg Thr Thr Lys Glu Arg Gln Glu
2330                2335                2340

Ile Gln Asn Pro Asn Phe Thr Ala Pro Gly Gln Glu Phe Leu Ser
2345                2350                2355

Lys Ser His Leu Tyr Glu His Leu Thr Leu Glu Lys Ser Ser Ser
```

```
            2360                2365                2370

Asn Leu Ala Val Ser Gly His Pro Phe Tyr Gln Val Ser Ala Thr
    2375                2380                2385

Arg Asn Glu Lys Met Arg His Leu Ile Thr Thr Gly Arg Pro Thr
    2390                2395                2400

Lys Val Phe Val Pro Pro Phe Lys Thr Lys Ser His Phe His Arg
    2405                2410                2415

Val Glu Gln Cys Val Arg Asn Ile Asn Leu Glu Glu Asn Arg Gln
    2420                2425                2430

Lys Gln Asn Ile Asp Gly His Gly Ser Asp Ser Lys Asn Lys
    2435                2440                2445

Ile Asn Asp Asn Glu Ile His Gln Phe Asn Lys Asn Asn Ser Asn
    2450                2455                2460

Gln Ala Ala Ala Val Thr Phe Thr Lys Cys Glu Glu Pro Leu
    2465                2470                2475

Asp Leu Ile Thr Ser Leu Gln Asn Ala Arg Asp Ile Gln Asp Met
    2480                2485                2490

Arg Ile Lys Lys Lys Gln Arg Gln Arg Val Phe Pro Gln Pro Gly
    2495                2500                2505

Ser Leu Tyr Leu Ala Lys Thr Ser Thr Leu Pro Arg Ile Ser Leu
    2510                2515                2520

Lys Ala Ala Val Gly Gly Gln Val Pro Ser Ala Cys Ser His Lys
    2525                2530                2535

Gln Leu Tyr Thr Tyr Gly Val Ser Lys His Cys Ile Lys Ile Asn
    2540                2545                2550

Ser Lys Asn Ala Glu Ser Phe Gln Phe His Thr Glu Asp Tyr Phe
    2555                2560                2565

Gly Lys Glu Ser Leu Trp Thr Gly Lys Gly Ile Gln Leu Ala Asp
    2570                2575                2580

Gly Gly Trp Leu Ile Pro Ser Asn Asp Gly Lys Ala Gly Lys Glu
    2585                2590                2595

Glu Phe Tyr Arg Ala Leu Cys Asp Thr Pro Gly Val Asp Pro Lys
    2600                2605                2610

Leu Ile Ser Arg Ile Trp Val Tyr Asn His Tyr Arg Trp Ile Ile
    2615                2620                2625

Trp Lys Leu Ala Ala Met Glu Cys Ala Phe Pro Lys Glu Phe Ala
    2630                2635                2640

Asn Arg Cys Leu Ser Pro Glu Arg Val Leu Leu Gln Leu Lys Tyr
    2645                2650                2655

Arg Tyr Asp Thr Glu Ile Asp Arg Ser Arg Arg Ser Ala Ile Lys
    2660                2665                2670

Lys Ile Met Glu Arg Asp Asp Thr Ala Ala Lys Thr Leu Val Leu
    2675                2680                2685

Cys Val Ser Asp Ile Ile Ser Leu Ser Ala Asn Ile Ser Glu Thr
    2690                2695                2700

Ser Ser Asn Lys Thr Ser Ser Ala Asp Thr Gln Lys Val Ala Ile
    2705                2710                2715

Ile Glu Leu Thr Asp Gly Trp Tyr Ala Val Lys Ala Gln Leu Asp
    2720                2725                2730

Pro Pro Leu Leu Ala Val Leu Lys Asn Gly Arg Leu Thr Val Gly
    2735                2740                2745

Gln Lys Ile Ile Leu His Gly Ala Glu Leu Val Gly Ser Pro Asp
    2750                2755                2760
```

```
Ala Cys Thr Pro Leu Glu Ala Pro Glu Ser Leu Met  Leu Lys Ile
2765                2770                2775

Ser Ala Asn Ser Thr Arg Pro Ala Arg Trp Tyr Thr  Lys Leu Gly
2780                2785                2790

Phe Phe Pro Asp Pro Arg Pro Phe Pro Leu Pro Leu  Ser Ser Leu
2795                2800                2805

Phe Ser Asp Gly Gly Asn Val Gly Cys Val Asp Val  Ile Ile Gln
2810                2815                2820

Arg Ala Tyr Pro Ile Gln Trp Met Glu Lys Thr Ser  Ser Gly Leu
2825                2830                2835

Tyr Ile Phe Arg Asn Glu Arg Glu Glu Glu Lys Glu  Ala Ala Lys
2840                2845                2850

Tyr Val Glu Ala Gln Gln Lys Arg Leu Glu Ala Leu  Phe Thr Lys
2855                2860                2865

Ile Gln Glu Glu Phe Glu Glu His Glu Glu Asn Thr  Thr Lys Pro
2870                2875                2880

Tyr Leu Pro Ser Arg Ala Leu Thr Arg Gln Gln Val  Arg Ala Leu
2885                2890                2895

Gln Asp Gly Ala Glu Leu Tyr Glu Ala Val Lys Asn  Ala Ala Asp
2900                2905                2910

Pro Ala Tyr Leu Glu Gly Tyr Phe Ser Glu Glu Gln  Leu Arg Ala
2915                2920                2925

Leu Asn Asn His Arg Gln Met Leu Asn Asp Lys Lys  Gln Ala Gln
2930                2935                2940

Ile Gln Leu Glu Ile Arg Lys Ala Met Glu Ser Ala  Glu Gln Lys
2945                2950                2955

Glu Gln Gly Leu Ser Arg Asp Val Thr Thr Val Trp  Lys Leu Arg
2960                2965                2970

Ile Val Ser Tyr Ser Lys Lys Glu Lys Asp Ser Val  Ile Leu Ser
2975                2980                2985

Ile Trp Arg Pro Ser Ser Asp Leu Tyr Ser Leu Leu  Thr Glu Gly
2990                2995                3000

Lys Arg Tyr Arg Ile Tyr His Leu Ala Thr Ser Lys  Ser Lys Ser
3005                3010                3015

Lys Ser Glu Arg Ala Asn Ile Gln Leu Ala Ala Thr  Lys Lys Thr
3020                3025                3030

Gln Tyr Gln Gln Leu Pro Val Ser Asp Glu Ile Leu  Phe Gln Ile
3035                3040                3045

Tyr Gln Pro Arg Glu Pro Leu His Phe Ser Lys Phe  Leu Asp Pro
3050                3055                3060

Asp Phe Gln Pro Ser Cys Ser Glu Val Asp Leu Ile  Gly Phe Val
3065                3070                3075

Val Ser Val Val Lys Lys Thr Gly Leu Ala Pro Phe  Val Tyr Leu
3080                3085                3090

Ser Asp Glu Cys Tyr Asn Leu Leu Ala Ile Lys Phe  Trp Ile Asp
3095                3100                3105

Leu Asn Glu Asp Ile Ile Lys Pro His Met Leu Ile  Ala Ala Ser
3110                3115                3120

Asn Leu Gln Trp Arg Pro Glu Ser Lys Ser Gly Leu  Leu Thr Leu
3125                3130                3135

Phe Ala Gly Asp Phe Ser Val Phe Ser Ala Ser Pro  Lys Glu Gly
3140                3145                3150
```

-continued

```
His Phe Gln Glu Thr Phe Asn Lys Met Lys Asn Thr Val Glu Asn
    3155                3160                3165

Ile Asp Ile Leu Cys Asn Glu Ala Glu Asn Lys Leu Met His Ile
3170                3175                3180

Leu His Ala Asn Asp Pro Lys Trp Ser Thr Pro Thr Lys Asp Cys
    3185                3190                3195

Thr Ser Gly Pro Tyr Thr Ala Gln Ile Ile Pro Gly Thr Gly Asn
    3200                3205                3210

Lys Leu Leu Met Ser Ser Pro Asn Cys Glu Ile Tyr Tyr Gln Ser
    3215                3220                3225

Pro Leu Ser Leu Cys Met Ala Lys Arg Lys Ser Val Ser Thr Pro
    3230                3235                3240

Val Ser Ala Gln Met Thr Ser Lys Ser Cys Lys Gly Glu Lys Glu
    3245                3250                3255

Ile Asp Asp Gln Lys Asn Cys Lys Lys Arg Arg Ala Leu Asp Phe
    3260                3265                3270

Leu Ser Arg Leu Pro Leu Pro Pro Pro Val Ser Pro Ile Cys Thr
    3275                3280                3285

Phe Val Ser Pro Ala Ala Gln Lys Ala Phe Gln Pro Pro Arg Ser
    3290                3295                3300

Cys Gly Thr Lys Tyr Glu Thr Pro Ile Lys Lys Lys Glu Leu Asn
    3305                3310                3315

Ser Pro Gln Met Thr Pro Phe Lys Lys Phe Asn Glu Ile Ser Leu
    3320                3325                3330

Leu Glu Ser Asn Ser Ile Ala Asp Glu Glu Leu Ala Leu Ile Asn
    3335                3340                3345

Thr Gln Ala Leu Leu Ser Gly Ser Thr Gly Glu Lys Gln Phe Ile
    3350                3355                3360

Ser Val Ser Glu Ser Thr Arg Thr Ala Pro Thr Ser Ser Glu Asp
    3365                3370                3375

Tyr Leu Arg Leu Lys Arg Arg Cys Thr Thr Ser Leu Ile Lys Glu
    3380                3385                3390

Gln Glu Ser Ser Gln Ala Ser Thr Glu Glu Cys Glu Lys Asn Lys
    3395                3400                3405

Gln Asp Thr Ile Thr Thr Lys Lys Tyr Ile
    3410                3415
```

<210> SEQ ID NO 45
<211> LENGTH: 393
<212> TYPE: PRT
<213> ORGANISM: Homo sapiens

<400> SEQUENCE: 45

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
            85                  90                  95
```

```
Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Cys
                165                 170                 175

Pro His His Glu Arg Cys Ser Asp Ser Asp Gly Leu Ala Pro Pro Gln
                180                 185                 190

His Leu Ile Arg Val Glu Gly Asn Leu Arg Val Glu Tyr Leu Asp Asp
                195                 200                 205

Arg Asn Thr Phe Arg His Ser Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
                260                 265                 270

Arg Val Cys Ala Cys Pro Gly Arg Asp Arg Arg Thr Glu Glu Glu Asn
                275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
                355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 46
<211> LENGTH: 770
<212> TYPE: PRT
<213> ORGANISM: Homo sapiens

<400> SEQUENCE: 46

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
```

```
           65                  70                  75                  80
    Gln Ile Thr Asn Val Val Glu Ala Asn Gln Pro Val Thr Ile Gln Asn
                        85                  90                  95
    Trp Cys Lys Arg Gly Arg Lys Gln Cys Lys Thr His Pro His Phe Val
                        100                 105                 110
    Ile Pro Tyr Arg Cys Leu Val Gly Glu Phe Val Ser Asp Ala Leu Leu
                        115                 120                 125
    Val Pro Asp Lys Cys Lys Phe Leu His Gln Glu Arg Met Asp Val Cys
                130                 135                 140
    Glu Thr His Leu His Trp His Thr Val Ala Lys Glu Thr Cys Ser Glu
    145                 150                 155                 160
    Lys Ser Thr Asn Leu His Asp Tyr Gly Met Leu Leu Pro Cys Gly Ile
                        165                 170                 175
    Asp Lys Phe Arg Gly Val Glu Phe Val Cys Cys Pro Leu Ala Glu Glu
                        180                 185                 190
    Ser Asp Asn Val Asp Ser Ala Asp Ala Glu Glu Asp Asp Ser Asp Val
                        195                 200                 205
    Trp Trp Gly Gly Ala Asp Thr Asp Tyr Ala Asp Gly Ser Glu Asp Lys
                210                 215                 220
    Val Val Glu Val Ala Glu Glu Glu Val Ala Glu Val Glu Glu Glu Glu
    225                 230                 235                 240
    Glu Ala Asp Asp Asp Glu Asp Asp Glu Asp Gly Asp Glu Val Glu Glu
                        245                 250                 255
    Glu Ala Glu Glu Pro Tyr Glu Glu Ala Thr Glu Arg Thr Thr Ser Ile
                        260                 265                 270
    Ala Thr Thr Thr Thr Thr Thr Thr Glu Ser Val Glu Glu Val Val Arg
                275                 280                 285
    Glu Val Cys Ser Glu Gln Ala Glu Thr Gly Pro Cys Arg Ala Met Ile
                        290                 295                 300
    Ser Arg Trp Tyr Phe Asp Val Thr Glu Gly Lys Cys Ala Pro Phe Phe
    305                 310                 315                 320
    Tyr Gly Gly Cys Gly Gly Asn Arg Asn Asn Phe Asp Thr Glu Glu Tyr
                        325                 330                 335
    Cys Met Ala Val Cys Gly Ser Ala Met Ser Gln Ser Leu Leu Lys Thr
                        340                 345                 350
    Thr Gln Glu Pro Leu Ala Arg Asp Pro Val Lys Leu Pro Thr Thr Ala
                        355                 360                 365
    Ala Ser Thr Pro Asp Ala Val Asp Lys Tyr Leu Glu Thr Pro Gly Asp
                370                 375                 380
    Glu Asn Glu His Ala His Phe Gln Lys Ala Lys Glu Arg Leu Glu Ala
    385                 390                 395                 400
    Lys His Arg Glu Arg Met Ser Gln Val Met Arg Glu Trp Glu Glu Ala
                        405                 410                 415
    Glu Arg Gln Ala Lys Asn Leu Pro Lys Ala Asp Lys Lys Ala Val Ile
                        420                 425                 430
    Gln His Phe Gln Glu Lys Val Glu Ser Leu Glu Gln Glu Ala Ala Asn
                        435                 440                 445
    Glu Arg Gln Gln Leu Val Glu Thr His Met Ala Arg Val Glu Ala Met
                450                 455                 460
    Leu Asn Asp Arg Arg Arg Leu Ala Leu Glu Asn Tyr Ile Thr Ala Leu
    465                 470                 475                 480
    Gln Ala Val Pro Pro Arg Pro Arg His Val Phe Asn Met Leu Lys Lys
                        485                 490                 495
```

-continued

```
Tyr Val Arg Ala Glu Gln Lys Asp Arg Gln His Thr Leu Lys His Phe
            500                 505                 510
Glu His Val Arg Met Val Asp Pro Lys Lys Ala Ala Gln Ile Arg Ser
        515                 520                 525
Gln Val Met Thr His Leu Arg Val Ile Tyr Glu Arg Met Asn Gln Ser
    530                 535                 540
Leu Ser Leu Leu Tyr Asn Val Pro Ala Val Ala Glu Glu Ile Gln Asp
545                 550                 555                 560
Glu Val Asp Glu Leu Leu Gln Lys Glu Gln Asn Tyr Ser Asp Asp Val
                565                 570                 575
Leu Ala Asn Met Ile Ser Glu Pro Arg Ile Ser Tyr Gly Asn Asp Ala
            580                 585                 590
Leu Met Pro Ser Leu Thr Glu Thr Lys Thr Thr Val Glu Leu Leu Pro
        595                 600                 605
Val Asn Gly Glu Phe Ser Leu Asp Asp Leu Gln Pro Trp His Ser Phe
    610                 615                 620
Gly Ala Asp Ser Val Pro Ala Asn Thr Glu Asn Glu Val Glu Pro Val
625                 630                 635                 640
Asp Ala Arg Pro Ala Ala Asp Arg Gly Leu Thr Thr Arg Pro Gly Ser
                645                 650                 655
Gly Leu Thr Asn Ile Lys Thr Glu Glu Ile Ser Glu Val Lys Met Asp
            660                 665                 670
Ala Glu Phe Arg His Asp Ser Gly Tyr Glu Val His His Gln Lys Leu
        675                 680                 685
Val Phe Phe Ala Glu Asp Val Gly Ser Asn Lys Gly Ala Ile Ile Gly
    690                 695                 700
Leu Met Val Gly Gly Val Val Ile Ala Thr Val Ile Val Ile Thr Leu
705                 710                 715                 720
Val Met Leu Lys Lys Lys Gln Tyr Thr Ser Ile His His Gly Val Val
                725                 730                 735
Glu Val Asp Ala Ala Val Thr Pro Glu Glu Arg His Leu Ser Lys Met
            740                 745                 750
Gln Gln Asn Gly Tyr Glu Asn Pro Thr Tyr Lys Phe Phe Glu Gln Met
        755                 760                 765
Gln Asn
    770

<210> SEQ ID NO 47
<211> LENGTH: 3144
<212> TYPE: PRT
<213> ORGANISM: Homo sapiens

<400> SEQUENCE: 47

Met Ala Thr Leu Glu Lys Leu Met Lys Ala Phe Glu Ser Leu Lys Ser
1               5                   10                  15
Phe Gln Gln Gln Gln Gln Gln Gln Gln Gln Gln Gln Gln Gln Gln Gln
            20                  25                  30
Gln Gln Gln Gln Gln Gln Gln Pro Pro Pro Pro Pro Pro Pro Pro Pro
        35                  40                  45
Pro Pro Pro Gln Leu Pro Gln Pro Pro Pro Gln Ala Gln Pro Leu Leu
    50                  55                  60
Pro Gln Pro Gln Pro Pro Pro Pro Pro Pro Pro Pro Gly Pro
65                  70                  75                  80
Ala Val Ala Glu Glu Pro Leu His Arg Pro Lys Lys Glu Leu Ser Ala
```

```
                        85                  90                  95
Thr Lys Lys Asp Arg Val Asn His Cys Leu Thr Ile Cys Glu Asn Ile
                100                 105                 110

Val Ala Gln Ser Val Arg Asn Ser Pro Glu Phe Gln Lys Leu Leu Gly
            115                 120                 125

Ile Ala Met Glu Leu Phe Leu Leu Cys Ser Asp Asp Ala Glu Ser Asp
        130                 135                 140

Val Arg Met Val Ala Asp Glu Cys Leu Asn Lys Val Ile Lys Ala Leu
145                 150                 155                 160

Met Asp Ser Asn Leu Pro Arg Leu Gln Leu Glu Leu Tyr Lys Glu Ile
                165                 170                 175

Lys Lys Asn Gly Ala Pro Arg Ser Leu Arg Ala Ala Leu Trp Arg Phe
            180                 185                 190

Ala Glu Leu Ala His Leu Val Arg Pro Gln Lys Cys Arg Pro Tyr Leu
        195                 200                 205

Val Asn Leu Leu Pro Cys Leu Thr Arg Thr Ser Lys Arg Pro Glu Glu
    210                 215                 220

Ser Val Gln Glu Thr Leu Ala Ala Ala Val Pro Lys Ile Met Ala Ser
225                 230                 235                 240

Phe Gly Asn Phe Ala Asn Asp Asn Glu Ile Lys Val Leu Leu Lys Ala
                245                 250                 255

Phe Ile Ala Asn Leu Lys Ser Ser Pro Thr Ile Arg Arg Thr Ala
            260                 265                 270

Ala Gly Ser Ala Val Ser Ile Cys Gln His Ser Arg Arg Thr Gln Tyr
        275                 280                 285

Phe Tyr Ser Trp Leu Leu Asn Val Leu Leu Gly Leu Leu Val Pro Val
    290                 295                 300

Glu Asp Glu His Ser Thr Leu Leu Ile Leu Gly Val Leu Leu Thr Leu
305                 310                 315                 320

Arg Tyr Leu Val Pro Leu Leu Gln Gln Val Lys Asp Thr Ser Leu
                325                 330                 335

Lys Gly Ser Phe Gly Val Thr Arg Lys Glu Met Glu Val Ser Pro Ser
            340                 345                 350

Ala Glu Gln Leu Val Gln Val Tyr Glu Leu Thr Leu His His Thr Gln
        355                 360                 365

His Gln Asp His Asn Val Val Thr Gly Ala Leu Glu Leu Leu Gln Gln
    370                 375                 380

Leu Phe Arg Thr Pro Pro Glu Leu Leu Gln Thr Leu Thr Ala Val
385                 390                 395                 400

Gly Gly Ile Gly Gln Leu Thr Ala Ala Lys Glu Glu Ser Gly Gly Arg
                405                 410                 415

Ser Arg Ser Gly Ser Ile Val Glu Leu Ile Ala Gly Gly Ser Ser
            420                 425                 430

Cys Ser Pro Val Leu Ser Arg Lys Gln Lys Gly Lys Val Leu Leu Gly
        435                 440                 445

Glu Glu Glu Ala Leu Glu Asp Asp Ser Glu Ser Arg Ser Asp Val Ser
    450                 455                 460

Ser Ser Ala Leu Thr Ala Ser Val Lys Asp Glu Ile Ser Gly Glu Leu
465                 470                 475                 480

Ala Ala Ser Ser Gly Val Ser Thr Pro Gly Ser Ala Gly His Asp Ile
                485                 490                 495

Ile Thr Glu Gln Pro Arg Ser Gln His Thr Leu Gln Ala Asp Ser Val
            500                 505                 510
```

```
Asp Leu Ala Ser Cys Asp Leu Thr Ser Ser Ala Thr Asp Gly Asp Glu
            515                 520                 525

Glu Asp Ile Leu Ser His Ser Ser Gln Val Ser Ala Val Pro Ser
530                 535                 540

Asp Pro Ala Met Asp Leu Asn Asp Gly Thr Gln Ala Ser Ser Pro Ile
545                 550                 555                 560

Ser Asp Ser Ser Gln Thr Thr Thr Glu Gly Pro Asp Ser Ala Val Thr
                565                 570                 575

Pro Ser Asp Ser Ser Glu Ile Val Leu Asp Gly Thr Asp Asn Gln Tyr
            580                 585                 590

Leu Gly Leu Gln Ile Gly Gln Pro Gln Asp Glu Asp Glu Glu Ala Thr
            595                 600                 605

Gly Ile Leu Pro Asp Glu Ala Ser Glu Ala Phe Arg Asn Ser Ser Met
            610                 615                 620

Ala Leu Gln Gln Ala His Leu Leu Lys Asn Met Ser His Cys Arg Gln
625                 630                 635                 640

Pro Ser Asp Ser Ser Val Asp Lys Phe Val Leu Arg Asp Glu Ala Thr
                645                 650                 655

Glu Pro Gly Asp Gln Glu Asn Lys Pro Cys Arg Ile Lys Gly Asp Ile
            660                 665                 670

Gly Gln Ser Thr Asp Asp Ser Ala Pro Leu Val His Cys Val Arg
            675                 680                 685

Leu Leu Ser Ala Ser Phe Leu Leu Thr Gly Gly Lys Asn Val Leu Val
            690                 695                 700

Pro Asp Arg Asp Val Arg Val Ser Val Lys Ala Leu Ala Leu Ser Cys
705                 710                 715                 720

Val Gly Ala Ala Val Ala Leu His Pro Glu Ser Phe Phe Ser Lys Leu
                725                 730                 735

Tyr Lys Val Pro Leu Asp Thr Thr Glu Tyr Pro Glu Glu Gln Tyr Val
            740                 745                 750

Ser Asp Ile Leu Asn Tyr Ile Asp His Gly Asp Pro Gln Val Arg Gly
            755                 760                 765

Ala Thr Ala Ile Leu Cys Gly Thr Leu Ile Cys Ser Ile Leu Ser Arg
            770                 775                 780

Ser Arg Phe His Val Gly Asp Trp Met Gly Thr Ile Arg Thr Leu Thr
785                 790                 795                 800

Gly Asn Thr Phe Ser Leu Ala Asp Cys Ile Pro Leu Leu Arg Lys Thr
            805                 810                 815

Leu Lys Asp Glu Ser Ser Val Thr Cys Lys Leu Ala Cys Thr Ala Val
            820                 825                 830

Arg Asn Cys Val Met Ser Leu Cys Ser Ser Tyr Ser Glu Leu Gly
            835                 840                 845

Leu Gln Leu Ile Ile Asp Val Leu Thr Leu Arg Asn Ser Ser Tyr Trp
850                 855                 860

Leu Val Arg Thr Glu Leu Leu Glu Thr Leu Ala Glu Ile Asp Phe Arg
865                 870                 875                 880

Leu Val Ser Phe Leu Glu Ala Lys Ala Glu Asn Leu His Arg Gly Ala
                885                 890                 895

His His Tyr Thr Gly Leu Leu Lys Leu Gln Glu Arg Val Leu Asn Asn
            900                 905                 910

Val Val Ile His Leu Leu Gly Asp Glu Asp Pro Arg Val Arg His Val
            915                 920                 925
```

```
Ala Ala Ala Ser Leu Ile Arg Leu Val Pro Lys Leu Phe Tyr Lys Cys
930                 935                 940

Asp Gln Gly Gln Ala Asp Pro Val Val Ala Val Ala Arg Asp Gln Ser
945                 950                 955                 960

Ser Val Tyr Leu Lys Leu Leu Met His Glu Thr Gln Pro Pro Ser His
                965                 970                 975

Phe Ser Val Ser Thr Ile Thr Arg Ile Tyr Arg Gly Tyr Asn Leu Leu
                980                 985                 990

Pro Ser Ile Thr Asp Val Thr Met Glu Asn Asn Leu Ser Arg Val Ile
            995                 1000                1005

Ala Ala Val Ser His Glu Leu Ile Thr Ser Thr Arg Ala Leu
1010                1015                1020

Thr Phe Gly Cys Cys Glu Ala Leu Cys Leu Leu Ser Thr Ala Phe
1025                1030                1035

Pro Val Cys Ile Trp Ser Leu Gly Trp His Cys Gly Val Pro Pro
1040                1045                1050

Leu Ser Ala Ser Asp Glu Ser Arg Lys Ser Cys Thr Val Gly Met
1055                1060                1065

Ala Thr Met Ile Leu Thr Leu Leu Ser Ser Ala Trp Phe Pro Leu
1070                1075                1080

Asp Leu Ser Ala His Gln Asp Ala Leu Ile Leu Ala Gly Asn Leu
1085                1090                1095

Leu Ala Ala Ser Ala Pro Lys Ser Leu Arg Ser Ser Trp Ala Ser
1100                1105                1110

Glu Glu Glu Ala Asn Pro Ala Ala Thr Lys Gln Glu Glu Val Trp
1115                1120                1125

Pro Ala Leu Gly Asp Arg Ala Leu Val Pro Met Val Glu Gln Leu
1130                1135                1140

Phe Ser His Leu Leu Lys Val Ile Asn Ile Cys Ala His Val Leu
1145                1150                1155

Asp Asp Val Ala Pro Gly Pro Ala Ile Lys Ala Ala Leu Pro Ser
1160                1165                1170

Leu Thr Asn Pro Pro Ser Leu Ser Pro Ile Arg Arg Lys Gly Lys
1175                1180                1185

Glu Lys Glu Pro Gly Glu Gln Ala Ser Val Pro Leu Ser Pro Lys
1190                1195                1200

Lys Gly Ser Glu Ala Ser Ala Ala Ser Arg Gln Ser Asp Thr Ser
1205                1210                1215

Gly Pro Val Thr Thr Ser Lys Ser Ser Ser Leu Gly Ser Phe Tyr
1220                1225                1230

His Leu Pro Ser Tyr Leu Lys Leu His Asp Val Leu Lys Ala Thr
1235                1240                1245

His Ala Asn Tyr Lys Val Thr Leu Asp Leu Gln Asn Ser Thr Glu
1250                1255                1260

Lys Phe Gly Gly Phe Leu Arg Ser Ala Leu Asp Val Leu Ser Gln
1265                1270                1275

Ile Leu Glu Leu Ala Thr Leu Gln Asp Ile Gly Lys Cys Val Glu
1280                1285                1290

Glu Ile Leu Gly Tyr Leu Lys Ser Cys Phe Ser Arg Glu Pro Met
1295                1300                1305

Met Ala Thr Val Cys Val Gln Gln Leu Leu Lys Thr Leu Phe Gly
1310                1315                1320

Thr Asn Leu Ala Ser Gln Phe Asp Gly Leu Ser Ser Asn Pro Ser
```

```
                 1325                1330                1335

Lys Ser Gln Gly Arg Ala Gln Arg Leu Gly Ser Ser Ser Val Arg
    1340                1345                1350

Pro Gly Leu Tyr His Tyr Cys Phe Met Ala Pro Tyr Thr His Phe
    1355                1360                1365

Thr Gln Ala Leu Ala Asp Ala Ser Leu Arg Asn Met Val Gln Ala
    1370                1375                1380

Glu Gln Glu Asn Asp Thr Ser Gly Trp Phe Asp Val Leu Gln Lys
    1385                1390                1395

Val Ser Thr Gln Leu Lys Thr Asn Leu Thr Ser Val Thr Lys Asn
    1400                1405                1410

Arg Ala Asp Lys Asn Ala Ile His Asn His Ile Arg Leu Phe Glu
    1415                1420                1425

Pro Leu Val Ile Lys Ala Leu Lys Gln Tyr Thr Thr Thr Thr Cys
    1430                1435                1440

Val Gln Leu Gln Lys Gln Val Leu Asp Leu Leu Ala Gln Leu Val
    1445                1450                1455

Gln Leu Arg Val Asn Tyr Cys Leu Leu Asp Ser Asp Gln Val Phe
    1460                1465                1470

Ile Gly Phe Val Leu Lys Gln Phe Glu Tyr Ile Glu Val Gly Gln
    1475                1480                1485

Phe Arg Glu Ser Glu Ala Ile Ile Pro Asn Ile Phe Phe Phe Leu
    1490                1495                1500

Val Leu Leu Ser Tyr Glu Arg Tyr His Ser Lys Gln Ile Ile Gly
    1505                1510                1515

Ile Pro Lys Ile Ile Gln Leu Cys Asp Gly Ile Met Ala Ser Gly
    1520                1525                1530

Arg Lys Ala Val Thr His Ala Ile Pro Ala Leu Gln Pro Ile Val
    1535                1540                1545

His Asp Leu Phe Val Leu Arg Gly Thr Asn Lys Ala Asp Ala Gly
    1550                1555                1560

Lys Glu Leu Glu Thr Gln Lys Glu Val Val Val Ser Met Leu Leu
    1565                1570                1575

Arg Leu Ile Gln Tyr His Gln Val Leu Glu Met Phe Ile Leu Val
    1580                1585                1590

Leu Gln Gln Cys His Lys Glu Asn Glu Asp Lys Trp Lys Arg Leu
    1595                1600                1605

Ser Arg Gln Ile Ala Asp Ile Ile Leu Pro Met Leu Ala Lys Gln
    1610                1615                1620

Gln Met His Ile Asp Ser His Glu Ala Leu Gly Val Leu Asn Thr
    1625                1630                1635

Leu Phe Glu Ile Leu Ala Pro Ser Ser Leu Arg Pro Val Asp Met
    1640                1645                1650

Leu Leu Arg Ser Met Phe Val Thr Pro Asn Thr Met Ala Ser Val
    1655                1660                1665

Ser Thr Val Gln Leu Trp Ile Ser Gly Ile Leu Ala Ile Leu Arg
    1670                1675                1680

Val Leu Ile Ser Gln Ser Thr Glu Asp Ile Val Leu Ser Arg Ile
    1685                1690                1695

Gln Glu Leu Ser Phe Ser Pro Tyr Leu Ile Ser Cys Thr Val Ile
    1700                1705                1710

Asn Arg Leu Arg Asp Gly Asp Ser Thr Ser Thr Leu Glu Glu His
    1715                1720                1725
```

```
Ser Glu Gly Lys Gln Ile Lys Asn Leu Pro Glu Glu Thr Phe Ser
    1730            1735                1740

Arg Phe Leu Leu Gln Leu Val Gly Ile Leu Leu Glu Asp Ile Val
    1745            1750                1755

Thr Lys Gln Leu Lys Val Glu Met Ser Glu Gln Gln His Thr Phe
    1760            1765                1770

Tyr Cys Gln Glu Leu Gly Thr Leu Leu Met Cys Leu Ile His Ile
    1775            1780                1785

Phe Lys Ser Gly Met Phe Arg Arg Ile Thr Ala Ala Ala Thr Arg
    1790            1795                1800

Leu Phe Arg Ser Asp Gly Cys Gly Gly Ser Phe Tyr Thr Leu Asp
    1805            1810                1815

Ser Leu Asn Leu Arg Ala Arg Ser Met Ile Thr Thr His Pro Ala
    1820            1825                1830

Leu Val Leu Leu Trp Cys Gln Ile Leu Leu Val Asn His Thr
    1835            1840                1845

Asp Tyr Arg Trp Trp Ala Glu Val Gln Gln Thr Pro Lys Arg His
    1850            1855                1860

Ser Leu Ser Ser Thr Lys Leu Leu Ser Pro Gln Met Ser Gly Glu
    1865            1870                1875

Glu Glu Asp Ser Asp Leu Ala Ala Lys Leu Gly Met Cys Asn Arg
    1880            1885                1890

Glu Ile Val Arg Arg Gly Ala Leu Ile Leu Phe Cys Asp Tyr Val
    1895            1900                1905

Cys Gln Asn Leu His Asp Ser Glu His Leu Thr Trp Leu Ile Val
    1910            1915                1920

Asn His Ile Gln Asp Leu Ile Ser Leu Ser His Glu Pro Pro Val
    1925            1930                1935

Gln Asp Phe Ile Ser Ala Val His Arg Asn Ser Ala Ala Ser Gly
    1940            1945                1950

Leu Phe Ile Gln Ala Ile Gln Ser Arg Cys Glu Asn Leu Ser Thr
    1955            1960                1965

Pro Thr Met Leu Lys Lys Thr Leu Gln Cys Leu Glu Gly Ile His
    1970            1975                1980

Leu Ser Gln Ser Gly Ala Val Leu Thr Leu Tyr Val Asp Arg Leu
    1985            1990                1995

Leu Cys Thr Pro Phe Arg Val Leu Ala Arg Met Val Asp Ile Leu
    2000            2005                2010

Ala Cys Arg Arg Val Glu Met Leu Leu Ala Ala Asn Leu Gln Ser
    2015            2020                2025

Ser Met Ala Gln Leu Pro Met Glu Glu Leu Asn Arg Ile Gln Glu
    2030            2035                2040

Tyr Leu Gln Ser Ser Gly Leu Ala Gln Arg His Gln Arg Leu Tyr
    2045            2050                2055

Ser Leu Leu Asp Arg Phe Arg Leu Ser Thr Met Gln Asp Ser Leu
    2060            2065                2070

Ser Pro Ser Pro Pro Val Ser Ser His Pro Leu Asp Gly Asp Gly
    2075            2080                2085

His Val Ser Leu Glu Thr Val Ser Pro Asp Lys Asp Trp Tyr Val
    2090            2095                2100

His Leu Val Lys Ser Gln Cys Trp Thr Arg Ser Asp Ser Ala Leu
    2105            2110                2115
```

```
Leu Glu Gly Ala Glu Leu Val Asn Arg Ile Pro Ala Glu Asp Met
2120                2125                2130

Asn Ala Phe Met Met Asn Ser Glu Phe Asn Leu Ser Leu Leu Ala
2135                2140                2145

Pro Cys Leu Ser Leu Gly Met Ser Glu Ile Ser Gly Gly Gln Lys
2150                2155                2160

Ser Ala Leu Phe Glu Ala Ala Arg Glu Val Thr Leu Ala Arg Val
2165                2170                2175

Ser Gly Thr Val Gln Gln Leu Pro Ala Val His His Val Phe Gln
2180                2185                2190

Pro Glu Leu Pro Ala Glu Pro Ala Ala Tyr Trp Ser Lys Leu Asn
2195                2200                2205

Asp Leu Phe Gly Asp Ala Ala Leu Tyr Gln Ser Leu Pro Thr Leu
2210                2215                2220

Ala Arg Ala Leu Ala Gln Tyr Leu Val Val Ser Lys Leu Pro
2225                2230                2235

Ser His Leu His Leu Pro Pro Glu Lys Glu Lys Asp Ile Val Lys
2240                2245                2250

Phe Val Val Ala Thr Leu Glu Ala Leu Ser Trp His Leu Ile His
2255                2260                2265

Glu Gln Ile Pro Leu Ser Leu Asp Leu Gln Ala Gly Leu Asp Cys
2270                2275                2280

Cys Cys Leu Ala Leu Gln Leu Pro Gly Leu Trp Ser Val Val Ser
2285                2290                2295

Ser Thr Glu Phe Val Thr His Ala Cys Ser Leu Ile Tyr Cys Val
2300                2305                2310

His Phe Ile Leu Glu Ala Val Ala Val Gln Pro Gly Glu Gln Leu
2315                2320                2325

Leu Ser Pro Glu Arg Arg Thr Asn Thr Pro Lys Ala Ile Ser Glu
2330                2335                2340

Glu Glu Glu Glu Val Asp Pro Asn Thr Gln Asn Pro Lys Tyr Ile
2345                2350                2355

Thr Ala Ala Cys Glu Met Val Ala Glu Met Val Glu Ser Leu Gln
2360                2365                2370

Ser Val Leu Ala Leu Gly His Lys Arg Asn Ser Gly Val Pro Ala
2375                2380                2385

Phe Leu Thr Pro Leu Leu Arg Asn Ile Ile Ser Leu Ala Arg
2390                2395                2400

Leu Pro Leu Val Asn Ser Tyr Thr Arg Val Pro Pro Leu Val Trp
2405                2410                2415

Lys Leu Gly Trp Ser Pro Lys Pro Gly Gly Asp Phe Gly Thr Ala
2420                2425                2430

Phe Pro Glu Ile Pro Val Glu Phe Leu Gln Glu Lys Glu Val Phe
2435                2440                2445

Lys Glu Phe Ile Tyr Arg Ile Asn Thr Leu Gly Trp Thr Ser Arg
2450                2455                2460

Thr Gln Phe Glu Glu Thr Trp Ala Thr Leu Leu Gly Val Leu Val
2465                2470                2475

Thr Gln Pro Leu Val Met Glu Gln Glu Glu Ser Pro Pro Glu Glu
2480                2485                2490

Asp Thr Glu Arg Thr Gln Ile Asn Val Leu Ala Val Gln Ala Ile
2495                2500                2505

Thr Ser Leu Val Leu Ser Ala Met Thr Val Pro Val Ala Gly Asn
```

-continued

```
            2510                2515                2520

Pro Ala Val Ser Cys Leu Glu Gln Gln Pro Arg Asn Lys Pro Leu
    2525                2530                2535

Lys Ala Leu Asp Thr Arg Phe Gly Arg Lys Leu Ser Ile Ile Arg
    2540                2545                2550

Gly Ile Val Glu Gln Glu Ile Gln Ala Met Val Ser Lys Arg Glu
    2555                2560                2565

Asn Ile Ala Thr His His Leu Tyr Gln Ala Trp Asp Pro Val Pro
    2570                2575                2580

Ser Leu Ser Pro Ala Thr Thr Gly Ala Leu Ile Ser His Glu Lys
    2585                2590                2595

Leu Leu Leu Gln Ile Asn Pro Glu Arg Glu Leu Gly Ser Met Ser
    2600                2605                2610

Tyr Lys Leu Gly Gln Val Ser Ile His Ser Val Trp Leu Gly Asn
    2615                2620                2625

Ser Ile Thr Pro Leu Arg Glu Glu Glu Trp Asp Glu Glu Glu Glu
    2630                2635                2640

Glu Glu Ala Asp Ala Pro Ala Pro Ser Ser Pro Pro Thr Ser Pro
    2645                2650                2655

Val Asn Ser Arg Lys His Arg Ala Gly Val Asp Ile His Ser Cys
    2660                2665                2670

Ser Gln Phe Leu Leu Glu Leu Tyr Ser Arg Trp Ile Leu Pro Ser
    2675                2680                2685

Ser Ser Ala Arg Arg Thr Pro Ala Ile Leu Ile Ser Glu Val Val
    2690                2695                2700

Arg Ser Leu Leu Val Val Ser Asp Leu Phe Thr Glu Arg Asn Gln
    2705                2710                2715

Phe Glu Leu Met Tyr Val Thr Leu Thr Glu Leu Arg Arg Val His
    2720                2725                2730

Pro Ser Glu Asp Glu Ile Leu Ala Gln Tyr Leu Val Pro Ala Thr
    2735                2740                2745

Cys Lys Ala Ala Ala Val Leu Gly Met Asp Lys Ala Val Ala Glu
    2750                2755                2760

Pro Val Ser Arg Leu Leu Glu Ser Thr Leu Arg Ser Ser His Leu
    2765                2770                2775

Pro Ser Arg Val Gly Ala Leu His Gly Val Leu Tyr Val Leu Glu
    2780                2785                2790

Cys Asp Leu Leu Asp Asp Thr Ala Lys Gln Leu Ile Pro Val Ile
    2795                2800                2805

Ser Asp Tyr Leu Leu Ser Asn Leu Lys Gly Ile Ala His Cys Val
    2810                2815                2820

Asn Ile His Ser Gln Gln His Val Leu Val Met Cys Ala Thr Ala
    2825                2830                2835

Phe Tyr Leu Ile Glu Asn Tyr Pro Leu Asp Val Gly Pro Glu Phe
    2840                2845                2850

Ser Ala Ser Ile Ile Gln Met Cys Gly Val Met Leu Ser Gly Ser
    2855                2860                2865

Glu Glu Ser Thr Pro Ser Ile Ile Tyr His Cys Ala Leu Arg Gly
    2870                2875                2880

Leu Glu Arg Leu Leu Leu Ser Glu Gln Leu Ser Arg Leu Asp Ala
    2885                2890                2895

Glu Ser Leu Val Lys Leu Ser Val Asp Arg Val Asn Val His Ser
    2900                2905                2910
```

-continued

Pro His Arg Ala Met Ala Ala Leu Gly Leu Met Leu Thr Cys Met
    2915                2920                2925

Tyr Thr Gly Lys Glu Lys Val Ser Pro Gly Arg Thr Ser Asp Pro
    2930                2935                2940

Asn Pro Ala Ala Pro Asp Ser Glu Ser Val Ile Val Ala Met Glu
    2945                2950                2955

Arg Val Ser Val Leu Phe Asp Arg Ile Arg Lys Gly Phe Pro Cys
    2960                2965                2970

Glu Ala Arg Val Val Ala Arg Ile Leu Pro Gln Phe Leu Asp Asp
    2975                2980                2985

Phe Phe Pro Pro Gln Asp Ile Met Asn Lys Val Ile Gly Glu Phe
    2990                2995                3000

Leu Ser Asn Gln Gln Pro Tyr Pro Gln Phe Met Ala Thr Val Val
    3005                3010                3015

Tyr Lys Val Phe Gln Thr Leu His Ser Thr Gly Gln Ser Ser Met
    3020                3025                3030

Val Arg Asp Trp Val Met Leu Ser Leu Ser Asn Phe Thr Gln Arg
    3035                3040                3045

Ala Pro Val Ala Met Ala Thr Trp Ser Leu Ser Cys Phe Phe Val
    3050                3055                3060

Ser Ala Ser Thr Ser Pro Trp Val Ala Ala Ile Leu Pro His Val
    3065                3070                3075

Ile Ser Arg Met Gly Lys Leu Glu Gln Val Asp Val Asn Leu Phe
    3080                3085                3090

Cys Leu Val Ala Thr Asp Phe Tyr Arg His Gln Ile Glu Glu Glu
    3095                3100                3105

Leu Asp Arg Arg Ala Phe Gln Ser Val Leu Glu Val Val Ala Ala
    3110                3115                3120

Pro Gly Ser Pro Tyr His Arg Leu Leu Thr Cys Leu Arg Asn Val
    3125                3130                3135

His Lys Val Thr Thr Cys
    3140

<210> SEQ ID NO 48
<211> LENGTH: 89
<212> TYPE: PRT
<213> ORGANISM: Homo sapiens

<400> SEQUENCE: 48

Met Gly Ile Leu Lys Leu Gln Val Phe Leu Ile Val Leu Ser Val Ala
1               5                   10                  15

Leu Asn His Leu Lys Ala Thr Pro Ile Glu Ser His Gln Val Glu Lys
                20                  25                  30

Arg Lys Cys Asn Thr Ala Thr Cys Ala Thr Gln Arg Leu Ala Asn Phe
            35                  40                  45

Leu Val His Ser Ser Asn Asn Phe Gly Ala Ile Leu Ser Ser Thr Asn
        50                  55                  60

Val Gly Ser Asn Thr Tyr Gly Lys Arg Asn Ala Val Glu Val Leu Lys
65                  70                  75                  80

Arg Glu Pro Leu Asn Tyr Leu Pro Leu
                85

<210> SEQ ID NO 49
<211> LENGTH: 776
<212> TYPE: PRT

-continued

<213> ORGANISM: Homo sapiens

<400> SEQUENCE: 49

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400
```

Ala Lys Thr Leu Lys Asn Arg Pro Cys Leu Ser Lys His Pro Thr
            405                 410                 415

Pro Gly Ser Ser Asp Pro Leu Ile Gln Pro Ser Ser Pro Ala Val Cys
        420                 425                 430

Pro Glu Pro Pro Ser Ser Pro Lys Tyr Val Ser Ser Val Thr Ser Arg
    435                 440                 445

Thr Gly Ser Ser Gly Ala Lys Glu Met Lys Leu Lys Gly Ala Asp Gly
450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Ala Thr Lys Gln Val Gln Arg Arg Pro Pro
            500                 505                 510

Pro Ala Gly Pro Arg Ser Glu Arg Gly Glu Pro Pro Lys Ser Gly Asp
        515                 520                 525

Arg Ser Gly Tyr Ser Ser Pro Gly Ser Pro Gly Thr Pro Gly Ser Arg
    530                 535                 540

Ser Arg Thr Pro Ser Leu Pro Thr Pro Pro Thr Arg Glu Pro Lys Lys
545                 550                 555                 560

Val Ala Val Val Arg Thr Pro Pro Lys Ser Pro Ser Ala Lys Ser
                565                 570                 575

Arg Leu Gln Thr Ala Pro Val Pro Met Pro Asp Leu Lys Asn Val Lys
                580                 585                 590

Ser Lys Ile Gly Ser Thr Glu Asn Leu Lys His Gln Pro Gly Gly Gly
            595                 600                 605

Lys Val Gln Ile Ile Asn Lys Lys Leu Asp Leu Ser Asn Val Gln Ser
        610                 615                 620

Lys Cys Gly Ser Lys Asp Asn Ile Lys His Val Pro Gly Gly Gly Ser
625                 630                 635                 640

Val Gln Ile Val Tyr Lys Pro Val Asp Leu Ser Lys Val Thr Ser Lys
                645                 650                 655

Cys Gly Ser Leu Gly Asn Ile His His Lys Pro Gly Gly Gly Gln Val
                660                 665                 670

Glu Val Lys Ser Glu Lys Leu Asp Phe Lys Asp Arg Val Gln Ser Lys
            675                 680                 685

Ile Gly Ser Leu Asp Asn Ile Thr His Val Pro Gly Gly Gly Asn Lys
        690                 695                 700

Lys Ile Glu Thr His Lys Leu Thr Phe Arg Glu Asn Ala Lys Ala Lys
705                 710                 715                 720

Thr Asp His Gly Ala Glu Ile Val Tyr Lys Ser Pro Val Val Ser Gly
                725                 730                 735

Asp Thr Ser Pro Arg His Leu Ser Asn Val Ser Ser Thr Gly Ser Ile
            740                 745                 750

Asp Met Val Asp Ser Pro Gln Leu Ala Thr Leu Ala Asp Glu Val Ser
        755                 760                 765

Ala Ser Leu Ala Lys Gln Gly Leu
770                 775

<210> SEQ ID NO 50
<211> LENGTH: 253
<212> TYPE: PRT
<213> ORGANISM: Homo sapiens

<400> SEQUENCE: 50

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
50                  55                  60

Trp Gly Gln Pro His Gly Gly Trp Gly Gln Pro His Gly Gly Gly
65              70                  75                  80

Trp Gly Gln Pro His Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Gln Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 51
<211> LENGTH: 140
<212> TYPE: PRT
<213> ORGANISM: Homo sapiens

<400> SEQUENCE: 51

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro

```
              115                 120                 125
Ser Glu Glu Gly Tyr Gln Asp Tyr Glu Pro Glu Ala
        130                 135                 140

<210> SEQ ID NO 52
<211> LENGTH: 140
<212> TYPE: PRT
<213> ORGANISM: Homo sapiens

<400> SEQUENCE: 52

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 53
<211> LENGTH: 196
<212> TYPE: PRT
<213> ORGANISM: Homo sapiens

<400> SEQUENCE: 53

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
```

```
                   165                 170                 175

Ala Gly Thr Leu Thr Leu Glu Glu Val Arg Arg Lys Phe Asn Asn Gly
            180                 185                 190

Glu Ile Asn Phe
        195
```

<210> SEQ ID NO 54
<211> LENGTH: 36
<212> TYPE: PRT
<213> ORGANISM: Homo sapiens
<220> FEATURE:
<221> NAME/KEY: MOD_RES
<222> LOCATION: (12)..(13)
<223> OTHER INFORMATION: Any naturally occurring amino acid

<400> SEQUENCE: 54

```
Leu Thr Pro Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly Gly Gly
        35
```

<210> SEQ ID NO 55
<211> LENGTH: 36
<212> TYPE: PRT
<213> ORGANISM: Homo sapiens
<220> FEATURE:
<221> NAME/KEY: MOD_RES
<222> LOCATION: (12)..(13)
<223> OTHER INFORMATION: Any naturally occurring amino acid

<400> SEQUENCE: 55

```
Leu Thr Pro Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

Gly His Gly Gly
        35
```

<210> SEQ ID NO 56
<211> LENGTH: 36
<212> TYPE: PRT
<213> ORGANISM: Homo sapiens
<220> FEATURE:
<221> NAME/KEY: MOD_RES
<222> LOCATION: (12)..(13)
<223> OTHER INFORMATION: Any naturally occurring amino acid

<400> SEQUENCE: 56

```
Leu Thr Pro Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly Ser Gly
        35
```

<210> SEQ ID NO 57
<211> LENGTH: 1089
<212> TYPE: PRT
<213> ORGANISM: Homo sapiens
<220> FEATURE:
<221> NAME/KEY: MOD_RES
<222> LOCATION: (188)..(189)

```
<223> OTHER INFORMATION: Any naturally occurring amino acid
<220> FEATURE:
<221> NAME/KEY: MOD_RES
<222> LOCATION: (224)..(225)
<223> OTHER INFORMATION: Any naturally occurring amino acid
<220> FEATURE:
<221> NAME/KEY: MOD_RES
<222> LOCATION: (258)..(259)
<223> OTHER INFORMATION: Any naturally occurring amino acid
<220> FEATURE:
<221> NAME/KEY: MOD_RES
<222> LOCATION: (294)..(295)
<223> OTHER INFORMATION: Any naturally occurring amino acid
<220> FEATURE:
<221> NAME/KEY: MOD_RES
<222> LOCATION: (328)..(329)
<223> OTHER INFORMATION: Any naturally occurring amino acid
<220> FEATURE:
<221> NAME/KEY: MOD_RES
<222> LOCATION: (364)..(365)
<223> OTHER INFORMATION: Any naturally occurring amino acid
<220> FEATURE:
<221> NAME/KEY: MOD_RES
<222> LOCATION: (398)..(399)
<223> OTHER INFORMATION: Any naturally occurring amino acid
<220> FEATURE:
<221> NAME/KEY: MOD_RES
<222> LOCATION: (434)..(435)
<223> OTHER INFORMATION: Any naturally occurring amino acid
<220> FEATURE:
<221> NAME/KEY: MOD_RES
<222> LOCATION: (468)..(469)
<223> OTHER INFORMATION: Any naturally occurring amino acid
<220> FEATURE:
<221> NAME/KEY: MOD_RES
<222> LOCATION: (504)..(505)
<223> OTHER INFORMATION: Any naturally occurring amino acid
<220> FEATURE:
<221> NAME/KEY: MOD_RES
<222> LOCATION: (538)..(539)
<223> OTHER INFORMATION: Any naturally occurring amino acid
<220> FEATURE:
<221> NAME/KEY: MOD_RES
<222> LOCATION: (574)..(575)
<223> OTHER INFORMATION: Any naturally occurring amino acid
<220> FEATURE:
<221> NAME/KEY: MOD_RES
<222> LOCATION: (608)..(609)
<223> OTHER INFORMATION: Any naturally occurring amino acid
<220> FEATURE:
<221> NAME/KEY: MOD_RES
<222> LOCATION: (644)..(645)
<223> OTHER INFORMATION: Any naturally occurring amino acid
<220> FEATURE:
<221> NAME/KEY: MOD_RES
<222> LOCATION: (678)..(679)
<223> OTHER INFORMATION: Any naturally occurring amino acid
<220> FEATURE:
<221> NAME/KEY: MOD_RES
<222> LOCATION: (714)..(715)
<223> OTHER INFORMATION: Any naturally occurring amino acid
<220> FEATURE:
<221> NAME/KEY: MOD_RES
<222> LOCATION: (748)..(749)
<223> OTHER INFORMATION: Any naturally occurring amino acid
<220> FEATURE:
<221> NAME/KEY: MOD_RES
<222> LOCATION: (784)..(785)
<223> OTHER INFORMATION: Any naturally occurring amino acid
<220> FEATURE:
<221> NAME/KEY: MOD_RES
<222> LOCATION: (818)..(819)
<223> OTHER INFORMATION: Any naturally occurring amino acid

<400> SEQUENCE: 57

Met Asp Tyr Lys Asp His Asp Gly Asp Tyr Lys Asp His Asp Ile Asp
1               5                   10                  15
```

```
Tyr Lys Asp Asp Asp Lys Met Ala Pro Lys Lys Lys Arg Lys Val
         20                  25                  30

Gly Ile His Gly Val Pro Ala Ala Val Asp Leu Arg Thr Leu Gly Tyr
         35                  40                  45

Ser Gln Gln Gln Gln Glu Lys Ile Lys Pro Lys Val Arg Ser Thr Val
     50                  55                  60

Ala Gln His His Glu Ala Leu Val Gly His Gly Phe Thr His Ala His
 65                  70                  75                  80

Ile Val Ala Leu Ser Gln His Pro Ala Ala Leu Gly Thr Val Ala Val
             85                  90                  95

Lys Tyr Gln Asp Met Ile Ala Ala Leu Pro Glu Ala Thr His Glu Ala
             100                 105                 110

Ile Val Gly Val Gly Lys Gln Trp Ser Gly Ala Arg Ala Leu Glu Ala
         115                 120                 125

Leu Leu Thr Val Ala Gly Glu Leu Arg Gly Pro Pro Leu Gln Leu Asp
     130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                 165                 170                 175

Leu Thr Pro Glu Gln Val Val Ala Ile Ala Ser Xaa Xaa Gly Gly Lys
             180                 185                 190

Gln Ala Leu Glu Thr Val Gln Arg Leu Leu Pro Val Leu Cys Gln Ala
         195                 200                 205

Gly His Gly Gly Leu Thr Pro Glu Gln Val Val Ala Ile Ala Ser Xaa
     210                 215                 220

Xaa Gly Gly Lys Gln Ala Leu Glu Thr Val Gln Arg Leu Leu Pro Val
225                 230                 235                 240

Leu Cys Gln Ala His Gly Leu Thr Pro Glu Gln Val Val Ala Ile Ala
                 245                 250                 255

Ser Xaa Xaa Gly Gly Lys Gln Ala Leu Glu Thr Val Gln Arg Leu Leu
             260                 265                 270

Pro Val Leu Cys Gln Ala Gly His Gly Gly Leu Thr Pro Glu Gln Val
         275                 280                 285

Val Ala Ile Ala Ser Xaa Xaa Gly Gly Lys Gln Ala Leu Glu Thr Val
     290                 295                 300

Gln Arg Leu Leu Pro Val Leu Cys Gln Ala His Gly Leu Thr Pro Glu
305                 310                 315                 320

Gln Val Val Ala Ile Ala Ser Xaa Xaa Gly Gly Lys Gln Ala Leu Glu
                 325                 330                 335

Thr Val Gln Arg Leu Leu Pro Val Leu Cys Gln Ala Gly His Gly Gly
             340                 345                 350

Leu Thr Pro Glu Gln Val Val Ala Ile Ala Ser Xaa Xaa Gly Gly Lys
         355                 360                 365

Gln Ala Leu Glu Thr Val Gln Arg Leu Leu Pro Val Leu Cys Gln Ala
     370                 375                 380

His Gly Leu Thr Pro Glu Gln Val Val Ala Ile Ala Ser Xaa Xaa Gly
385                 390                 395                 400

Gly Lys Gln Ala Leu Glu Thr Val Gln Arg Leu Leu Pro Val Leu Cys
                 405                 410                 415

Gln Ala Gly His Gly Gly Leu Thr Pro Glu Gln Val Val Ala Ile Ala
             420                 425                 430

Ser Xaa Xaa Gly Gly Lys Gln Ala Leu Glu Thr Val Gln Arg Leu Leu
```

-continued

```
                435                 440                 445
Pro Val Leu Cys Gln Ala His Gly Leu Thr Pro Glu Gln Val Val Ala
450                 455                 460
Ile Ala Ser Xaa Xaa Gly Gly Lys Gln Ala Leu Glu Thr Val Gln Arg
465                 470                 475                 480
Leu Leu Pro Val Leu Cys Gln Ala Gly His Gly Gly Leu Thr Pro Glu
                485                 490                 495
Gln Val Val Ala Ile Ala Ser Xaa Xaa Gly Gly Lys Gln Ala Leu Glu
                500                 505                 510
Thr Val Gln Arg Leu Leu Pro Val Leu Cys Gln Ala His Gly Leu Thr
                515                 520                 525
Pro Glu Gln Val Val Ala Ile Ala Ser Xaa Xaa Gly Gly Lys Gln Ala
530                 535                 540
Leu Glu Thr Val Gln Arg Leu Leu Pro Val Leu Cys Gln Ala Gly His
545                 550                 555                 560
Gly Gly Leu Thr Pro Glu Gln Val Val Ala Ile Ala Ser Xaa Xaa Gly
                565                 570                 575
Gly Lys Gln Ala Leu Glu Thr Val Gln Arg Leu Leu Pro Val Leu Cys
                580                 585                 590
Gln Ala His Gly Leu Thr Pro Glu Gln Val Val Ala Ile Ala Ser Xaa
                595                 600                 605
Xaa Gly Gly Lys Gln Ala Leu Glu Thr Val Gln Arg Leu Leu Pro Val
610                 615                 620
Leu Cys Gln Ala Gly His Gly Gly Leu Thr Pro Glu Gln Val Val Ala
625                 630                 635                 640
Ile Ala Ser Xaa Xaa Gly Gly Lys Gln Ala Leu Glu Thr Val Gln Arg
                645                 650                 655
Leu Leu Pro Val Leu Cys Gln Ala His Gly Leu Thr Pro Glu Gln Val
                660                 665                 670
Val Ala Ile Ala Ser Xaa Xaa Gly Gly Lys Gln Ala Leu Glu Thr Val
                675                 680                 685
Gln Arg Leu Leu Pro Val Leu Cys Gln Ala Gly His Gly Gly Leu Thr
690                 695                 700
Pro Glu Gln Val Val Ala Ile Ala Ser Xaa Xaa Gly Gly Lys Gln Ala
705                 710                 715                 720
Leu Glu Thr Val Gln Arg Leu Leu Pro Val Leu Cys Gln Ala His Gly
                725                 730                 735
Leu Thr Pro Glu Gln Val Val Ala Ile Ala Ser Xaa Xaa Gly Gly Lys
                740                 745                 750
Gln Ala Leu Glu Thr Val Gln Arg Leu Leu Pro Val Leu Cys Gln Ala
                755                 760                 765
Gly His Gly Gly Leu Thr Pro Glu Gln Val Val Ala Ile Ala Ser Xaa
                770                 775                 780
Xaa Gly Gly Lys Gln Ala Leu Glu Thr Val Gln Arg Leu Leu Pro Val
785                 790                 795                 800
Leu Cys Gln Ala His Gly Leu Thr Pro Glu Gln Val Val Ala Ile Ala
                805                 810                 815
Ser Xaa Xaa Gly Gly Arg Pro Ala Leu Glu Ser Ile Val Ala Gln Leu
                820                 825                 830
Ser Arg Pro Asp Pro Ala Leu Ala Ala Leu Thr Asn Asp His Leu Val
                835                 840                 845
Ala Leu Ala Cys Leu Gly Gly Arg Pro Ala Leu Asp Ala Val Lys Lys
850                 855                 860
```

Gly Leu Pro His Ala Pro Ala Leu Ile Lys Arg Thr Asn Arg Arg Ile
865                 870                 875                 880

Pro Glu Arg Thr Ser His Arg Val Ala Gly Ser Gln Leu Val Lys Ser
            885                 890                 895

Glu Leu Glu Glu Lys Lys Ser Glu Leu Arg His Lys Leu Lys Tyr Val
        900                 905                 910

Pro His Glu Tyr Ile Glu Leu Ile Glu Ile Ala Arg Asn Ser Thr Gln
    915                 920                 925

Asp Arg Ile Leu Glu Met Lys Val Met Glu Phe Phe Met Lys Val Tyr
930                 935                 940

Gly Tyr Arg Gly Lys His Leu Gly Gly Ser Arg Lys Pro Asp Gly Ala
945                 950                 955                 960

Ile Tyr Thr Val Gly Ser Pro Ile Asp Tyr Gly Val Ile Val Asp Thr
                965                 970                 975

Lys Ala Tyr Ser Gly Gly Tyr Asn Leu Pro Ile Gly Gln Ala Asp Glu
            980                 985                 990

Met Gln Arg Tyr Val Glu Glu Asn Gln Thr Arg Asn Lys His Ile Asn
        995                 1000                1005

Pro Asn Glu Trp Trp Lys Val Tyr Pro Ser Ser Val Thr Glu Phe
    1010                1015                1020

Lys Phe Leu Phe Val Ser Gly His Phe Lys Gly Asn Tyr Lys Ala
    1025                1030                1035

Gln Leu Thr Arg Leu Asn His Ile Thr Asn Cys Asn Gly Ala Val
    1040                1045                1050

Leu Ser Val Glu Glu Leu Leu Ile Gly Gly Glu Met Ile Lys Ala
    1055                1060                1065

Gly Thr Leu Thr Leu Glu Glu Val Arg Arg Lys Phe Asn Asn Gly
    1070                1075                1080

Glu Ile Asn Phe Arg Ser
    1085

<210> SEQ ID NO 58
<211> LENGTH: 1107
<212> TYPE: PRT
<213> ORGANISM: Homo sapiens
<220> FEATURE:
<221> NAME/KEY: MOD_RES
<222> LOCATION: (188)..(189)
<223> OTHER INFORMATION: Any naturally occurring amino acid
<220> FEATURE:
<221> NAME/KEY: MOD_RES
<222> LOCATION: (224)..(225)
<223> OTHER INFORMATION: Any naturally occurring amino acid
<220> FEATURE:
<221> NAME/KEY: MOD_RES
<222> LOCATION: (260)..(261)
<223> OTHER INFORMATION: Any naturally occurring amino acid
<220> FEATURE:
<221> NAME/KEY: MOD_RES
<222> LOCATION: (296)..(297)
<223> OTHER INFORMATION: Any naturally occurring amino acid
<220> FEATURE:
<221> NAME/KEY: MOD_RES
<222> LOCATION: (332)..(333)
<223> OTHER INFORMATION: Any naturally occurring amino acid
<220> FEATURE:
<221> NAME/KEY: MOD_RES
<222> LOCATION: (368)..(369)
<223> OTHER INFORMATION: Any naturally occurring amino acid
<220> FEATURE:
<221> NAME/KEY: MOD_RES
<222> LOCATION: (404)..(405)
<223> OTHER INFORMATION: Any naturally occurring amino acid

```
<220> FEATURE:
<221> NAME/KEY: MOD_RES
<222> LOCATION: (440)..(441)
<223> OTHER INFORMATION: Any naturally occurring amino acid
<220> FEATURE:
<221> NAME/KEY: MOD_RES
<222> LOCATION: (476)..(477)
<223> OTHER INFORMATION: Any naturally occurring amino acid
<220> FEATURE:
<221> NAME/KEY: MOD_RES
<222> LOCATION: (512)..(513)
<223> OTHER INFORMATION: Any naturally occurring amino acid
<220> FEATURE:
<221> NAME/KEY: MOD_RES
<222> LOCATION: (548)..(549)
<223> OTHER INFORMATION: Any naturally occurring amino acid
<220> FEATURE:
<221> NAME/KEY: MOD_RES
<222> LOCATION: (584)..(585)
<223> OTHER INFORMATION: Any naturally occurring amino acid
<220> FEATURE:
<221> NAME/KEY: MOD_RES
<222> LOCATION: (620)..(621)
<223> OTHER INFORMATION: Any naturally occurring amino acid
<220> FEATURE:
<221> NAME/KEY: MOD_RES
<222> LOCATION: (656)..(657)
<223> OTHER INFORMATION: Any naturally occurring amino acid
<220> FEATURE:
<221> NAME/KEY: MOD_RES
<222> LOCATION: (692)..(693)
<223> OTHER INFORMATION: Any naturally occurring amino acid
<220> FEATURE:
<221> NAME/KEY: MOD_RES
<222> LOCATION: (728)..(729)
<223> OTHER INFORMATION: Any naturally occurring amino acid
<220> FEATURE:
<221> NAME/KEY: MOD_RES
<222> LOCATION: (764)..(765)
<223> OTHER INFORMATION: Any naturally occurring amino acid
<220> FEATURE:
<221> NAME/KEY: MOD_RES
<222> LOCATION: (800)..(801)
<223> OTHER INFORMATION: Any naturally occurring amino acid
<220> FEATURE:
<221> NAME/KEY: MOD_RES
<222> LOCATION: (836)..(837)
<223> OTHER INFORMATION: Any naturally occurring amino acid

<400> SEQUENCE: 58

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
```

```
            145                 150                 155                 160
        Glu Ala Val His Ala Trp Arg Asn Ala Leu Thr Gly Ala Pro Leu Asn
                        165                 170                 175
        Leu Thr Pro Glu Gln Val Val Ala Ile Ala Ser Xaa Xaa Gly Gly Lys
                        180                 185                 190
        Gln Ala Leu Glu Thr Val Gln Arg Leu Leu Pro Val Leu Cys Gln Ala
                        195                 200                 205
        Gly His Gly Gly Leu Thr Pro Glu Gln Val Val Ala Ile Ala Ser Xaa
                        210                 215                 220
        Xaa Gly Gly Lys Gln Ala Leu Glu Thr Val Gln Arg Leu Leu Pro Val
        225                 230                 235                 240
        Leu Cys Gln Ala Gly His Gly Gly Leu Thr Pro Glu Gln Val Val Ala
                        245                 250                 255
        Ile Ala Ser Xaa Xaa Gly Gly Lys Gln Ala Leu Glu Thr Val Gln Arg
                        260                 265                 270
        Leu Leu Pro Val Leu Cys Gln Ala Gly His Gly Gly Leu Thr Pro Glu
                        275                 280                 285
        Gln Val Val Ala Ile Ala Ser Xaa Xaa Gly Gly Lys Gln Ala Leu Glu
                        290                 295                 300
        Thr Val Gln Arg Leu Leu Pro Val Leu Cys Gln Ala Gly His Gly Gly
        305                 310                 315                 320
        Leu Thr Pro Glu Gln Val Val Ala Ile Ala Ser Xaa Xaa Gly Gly Lys
                        325                 330                 335
        Gln Ala Leu Glu Thr Val Gln Arg Leu Leu Pro Val Leu Cys Gln Ala
                        340                 345                 350
        Gly His Gly Gly Leu Thr Pro Glu Gln Val Val Ala Ile Ala Ser Xaa
                        355                 360                 365
        Xaa Gly Gly Lys Gln Ala Leu Glu Thr Val Gln Arg Leu Leu Pro Val
                        370                 375                 380
        Leu Cys Gln Ala Gly His Gly Gly Leu Thr Pro Glu Gln Val Val Ala
        385                 390                 395                 400
        Ile Ala Ser Xaa Xaa Gly Gly Lys Gln Ala Leu Glu Thr Val Gln Arg
                        405                 410                 415
        Leu Leu Pro Val Leu Cys Gln Ala Gly His Gly Gly Leu Thr Pro Glu
                        420                 425                 430
        Gln Val Val Ala Ile Ala Ser Xaa Xaa Gly Gly Lys Gln Ala Leu Glu
                        435                 440                 445
        Thr Val Gln Arg Leu Leu Pro Val Leu Cys Gln Ala Gly His Gly Gly
        450                 455                 460
        Leu Thr Pro Glu Gln Val Val Ala Ile Ala Ser Xaa Xaa Gly Gly Lys
        465                 470                 475                 480
        Gln Ala Leu Glu Thr Val Gln Arg Leu Leu Pro Val Leu Cys Gln Ala
                        485                 490                 495
        Gly His Gly Gly Leu Thr Pro Glu Gln Val Val Ala Ile Ala Ser Xaa
                        500                 505                 510
        Xaa Gly Gly Lys Gln Ala Leu Glu Thr Val Gln Arg Leu Leu Pro Val
                        515                 520                 525
        Leu Cys Gln Ala Gly His Gly Gly Leu Thr Pro Glu Gln Val Val Ala
                        530                 535                 540
        Ile Ala Ser Xaa Xaa Gly Gly Lys Gln Ala Leu Glu Thr Val Gln Arg
        545                 550                 555                 560
        Leu Leu Pro Val Leu Cys Gln Ala Gly His Gly Gly Leu Thr Pro Glu
                        565                 570                 575
```

```
Gln Val Val Ala Ile Ala Ser Xaa Xaa Gly Gly Lys Gln Ala Leu Glu
            580                 585                 590

Thr Val Gln Arg Leu Leu Pro Val Leu Cys Gln Ala Gly His Gly Gly
        595                 600                 605

Leu Thr Pro Glu Gln Val Val Ala Ile Ala Ser Xaa Xaa Gly Gly Lys
    610                 615                 620

Gln Ala Leu Glu Thr Val Gln Arg Leu Leu Pro Val Leu Cys Gln Ala
625                 630                 635                 640

Gly His Gly Gly Leu Thr Pro Glu Gln Val Val Ala Ile Ala Ser Xaa
                645                 650                 655

Xaa Gly Gly Lys Gln Ala Leu Glu Thr Val Gln Arg Leu Leu Pro Val
            660                 665                 670

Leu Cys Gln Ala Gly His Gly Gly Leu Thr Pro Glu Gln Val Val Ala
        675                 680                 685

Ile Ala Ser Xaa Xaa Gly Gly Lys Gln Ala Leu Glu Thr Val Gln Arg
    690                 695                 700

Leu Leu Pro Val Leu Cys Gln Ala Gly His Gly Gly Leu Thr Pro Glu
705                 710                 715                 720

Gln Val Val Ala Ile Ala Ser Xaa Xaa Gly Gly Lys Gln Ala Leu Glu
                725                 730                 735

Thr Val Gln Arg Leu Leu Pro Val Leu Cys Gln Ala Gly His Gly Gly
            740                 745                 750

Leu Thr Pro Glu Gln Val Val Ala Ile Ala Ser Xaa Xaa Gly Gly Lys
        755                 760                 765

Gln Ala Leu Glu Thr Val Gln Arg Leu Leu Pro Val Leu Cys Gln Ala
    770                 775                 780

Gly His Gly Gly Leu Thr Pro Glu Gln Val Val Ala Ile Ala Ser Xaa
785                 790                 795                 800

Xaa Gly Gly Lys Gln Ala Leu Glu Thr Val Gln Arg Leu Leu Pro Val
                805                 810                 815

Leu Cys Gln Ala Gly His Gly Gly Leu Thr Pro Glu Gln Val Val Ala
            820                 825                 830

Ile Ala Ser Xaa Xaa Gly Gly Arg Pro Ala Leu Glu Ser Ile Val Ala
        835                 840                 845

Gln Leu Ser Arg Pro Asp Pro Ala Leu Ala Ala Leu Thr Asn Asp His
    850                 855                 860

Leu Val Ala Leu Ala Cys Leu Gly Gly Arg Pro Ala Leu Asp Ala Val
865                 870                 875                 880

Lys Lys Gly Leu Pro His Ala Pro Ala Leu Ile Lys Arg Thr Asn Arg
                885                 890                 895

Arg Ile Pro Glu Arg Thr Ser His Arg Val Ala Gly Ser Gln Leu Val
            900                 905                 910

Lys Ser Glu Leu Glu Glu Lys Lys Ser Glu Leu Arg His Lys Leu Lys
        915                 920                 925

Tyr Val Pro His Glu Tyr Ile Glu Leu Ile Glu Ile Ala Arg Asn Ser
    930                 935                 940

Thr Gln Asp Arg Ile Leu Glu Met Lys Val Met Glu Phe Phe Met Lys
945                 950                 955                 960

Val Tyr Gly Tyr Arg Gly Lys His Leu Gly Gly Ser Arg Lys Pro Asp
                965                 970                 975

Gly Ala Ile Tyr Thr Val Gly Ser Pro Ile Asp Tyr Gly Val Ile Val
            980                 985                 990
```

```
Asp Thr Lys Ala Tyr Ser Gly Gly Tyr Asn Leu Pro Ile Gly Gln Ala
            995                1000                 1005

Asp Glu Met Gln Arg Tyr Val Glu Glu Asn Gln Thr Arg Asn Lys
    1010                1015                1020

His Ile Asn Pro Asn Glu Trp Trp Lys Val Tyr Pro Ser Ser Val
    1025                1030                1035

Thr Glu Phe Lys Phe Leu Phe Val Ser Gly His Phe Lys Gly Asn
    1040                1045                1050

Tyr Lys Ala Gln Leu Thr Arg Leu Asn His Ile Thr Asn Cys Asn
    1055                1060                1065

Gly Ala Val Leu Ser Val Glu Leu Leu Ile Gly Gly Glu Met
    1070                1075                1080

Ile Lys Ala Gly Thr Leu Thr Leu Glu Glu Val Arg Arg Lys Phe
    1085                1090                1095

Asn Asn Gly Glu Ile Asn Phe Arg Ser
    1100                1105

<210> SEQ ID NO 59
<211> LENGTH: 1086
<212> TYPE: PRT
<213> ORGANISM: Homo sapiens
<220> FEATURE:
<221> NAME/KEY: MOD_RES
<222> LOCATION: (188)..(189)
<223> OTHER INFORMATION: Any naturally occurring amino acid
<220> FEATURE:
<221> NAME/KEY: MOD_RES
<222> LOCATION: (224)..(225)
<223> OTHER INFORMATION: Any naturally occurring amino acid
<220> FEATURE:
<221> NAME/KEY: MOD_RES
<222> LOCATION: (258)..(259)
<223> OTHER INFORMATION: Any naturally occurring amino acid
<220> FEATURE:
<221> NAME/KEY: MOD_RES
<222> LOCATION: (294)..(295)
<223> OTHER INFORMATION: Any naturally occurring amino acid
<220> FEATURE:
<221> NAME/KEY: MOD_RES
<222> LOCATION: (328)..(329)
<223> OTHER INFORMATION: Any naturally occurring amino acid
<220> FEATURE:
<221> NAME/KEY: MOD_RES
<222> LOCATION: (364)..(365)
<223> OTHER INFORMATION: Any naturally occurring amino acid
<220> FEATURE:
<221> NAME/KEY: MOD_RES
<222> LOCATION: (398)..(399)
<223> OTHER INFORMATION: Any naturally occurring amino acid
<220> FEATURE:
<221> NAME/KEY: MOD_RES
<222> LOCATION: (434)..(435)
<223> OTHER INFORMATION: Any naturally occurring amino acid
<220> FEATURE:
<221> NAME/KEY: MOD_RES
<222> LOCATION: (468)..(469)
<223> OTHER INFORMATION: Any naturally occurring amino acid
<220> FEATURE:
<221> NAME/KEY: MOD_RES
<222> LOCATION: (504)..(505)
<223> OTHER INFORMATION: Any naturally occurring amino acid
<220> FEATURE:
<221> NAME/KEY: MOD_RES
<222> LOCATION: (538)..(539)
<223> OTHER INFORMATION: Any naturally occurring amino acid
<220> FEATURE:
<221> NAME/KEY: MOD_RES
<222> LOCATION: (574)..(575)
<223> OTHER INFORMATION: Any naturally occurring amino acid
<220> FEATURE:
<221> NAME/KEY: MOD_RES
```

```
<222> LOCATION: (608)..(609)
<223> OTHER INFORMATION: Any naturally occurring amino acid
<220> FEATURE:
<221> NAME/KEY: MOD_RES
<222> LOCATION: (644)..(645)
<223> OTHER INFORMATION: Any naturally occurring amino acid
<220> FEATURE:
<221> NAME/KEY: MOD_RES
<222> LOCATION: (678)..(679)
<223> OTHER INFORMATION: Any naturally occurring amino acid
<220> FEATURE:
<221> NAME/KEY: MOD_RES
<222> LOCATION: (714)..(715)
<223> OTHER INFORMATION: Any naturally occurring amino acid
<220> FEATURE:
<221> NAME/KEY: MOD_RES
<222> LOCATION: (748)..(749)
<223> OTHER INFORMATION: Any naturally occurring amino acid
<220> FEATURE:
<221> NAME/KEY: MOD_RES
<222> LOCATION: (784)..(785)
<223> OTHER INFORMATION: Any naturally occurring amino acid
<220> FEATURE:
<221> NAME/KEY: MOD_RES
<222> LOCATION: (818)..(819)
<223> OTHER INFORMATION: Any naturally occurring amino acid

<400> SEQUENCE: 59

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Val Asp Leu Arg Thr Leu Gly Tyr
            35                  40                  45

Ser Gln Gln Gln Gln Glu Lys Ile Lys Pro Lys Val Arg Ser Thr Val
50                  55                  60

Ala Gln His His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
            115                 120                 125

Leu Leu Thr Val Ala Gly Glu Leu Arg Gly Pro Pro Leu Gln Leu Asp
130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Xaa Xaa Gly Gly Lys
            180                 185                 190

Gln Ala Leu Glu Thr Val Gln Arg Leu Leu Pro Val Leu Cys Gln Ala
            195                 200                 205

Gly His Gly Gly Leu Thr Pro Glu Gln Val Val Ala Ile Ala Ser Xaa
        210                 215                 220

Xaa Gly Gly Lys Gln Ala Leu Glu Thr Val Gln Arg Leu Leu Pro Val
225                 230                 235                 240

Leu Cys Gln Ala His Gly Leu Thr Pro Glu Gln Val Val Ala Ile Ala
                245                 250                 255

Ser Xaa Xaa Gly Gly Lys Gln Ala Leu Glu Thr Val Gln Arg Leu Leu
            260                 265                 270
```

```
Pro Val Leu Cys Gln Ala Gly His Gly Gly Leu Thr Pro Glu Gln Val
        275                 280                 285

Val Ala Ile Ala Ser Xaa Xaa Gly Gly Lys Gln Ala Leu Glu Thr Val
        290                 295                 300

Gln Arg Leu Leu Pro Val Leu Cys Gln Ala His Gly Leu Thr Pro Glu
305                 310                 315                 320

Gln Val Val Ala Ile Ala Ser Xaa Xaa Gly Gly Lys Gln Ala Leu Glu
                325                 330                 335

Thr Val Gln Arg Leu Leu Pro Val Leu Cys Gln Ala Gly His Gly Gly
            340                 345                 350

Leu Thr Pro Glu Gln Val Val Ala Ile Ala Ser Xaa Xaa Gly Gly Lys
        355                 360                 365

Gln Ala Leu Glu Thr Val Gln Arg Leu Leu Pro Val Leu Cys Gln Ala
    370                 375                 380

His Gly Leu Thr Pro Glu Gln Val Val Ala Ile Ala Ser Xaa Xaa Gly
385                 390                 395                 400

Gly Lys Gln Ala Leu Glu Thr Val Gln Arg Leu Leu Pro Val Leu Cys
                405                 410                 415

Gln Ala Gly His Gly Gly Leu Thr Pro Glu Gln Val Val Ala Ile Ala
            420                 425                 430

Ser Xaa Xaa Gly Gly Lys Gln Ala Leu Glu Thr Val Gln Arg Leu Leu
        435                 440                 445

Pro Val Leu Cys Gln Ala His Gly Leu Thr Pro Glu Gln Val Val Ala
    450                 455                 460

Ile Ala Ser Xaa Xaa Gly Gly Lys Gln Ala Leu Glu Thr Val Gln Arg
465                 470                 475                 480

Leu Leu Pro Val Leu Cys Gln Ala Gly His Gly Gly Leu Thr Pro Glu
                485                 490                 495

Gln Val Val Ala Ile Ala Ser Xaa Xaa Gly Gly Lys Gln Ala Leu Glu
            500                 505                 510

Thr Val Gln Arg Leu Leu Pro Val Leu Cys Gln Ala His Gly Leu Thr
        515                 520                 525

Pro Glu Gln Val Val Ala Ile Ala Ser Xaa Xaa Gly Gly Lys Gln Ala
    530                 535                 540

Leu Glu Thr Val Gln Arg Leu Leu Pro Val Leu Cys Gln Ala Gly His
545                 550                 555                 560

Gly Gly Leu Thr Pro Glu Gln Val Val Ala Ile Ala Ser Xaa Xaa Gly
                565                 570                 575

Gly Lys Gln Ala Leu Glu Thr Val Gln Arg Leu Leu Pro Val Leu Cys
            580                 585                 590

Gln Ala His Gly Leu Thr Pro Glu Gln Val Val Ala Ile Ala Ser Xaa
        595                 600                 605

Xaa Gly Gly Lys Gln Ala Leu Glu Thr Val Gln Arg Leu Leu Pro Val
    610                 615                 620

Leu Cys Gln Ala Gly His Gly Gly Leu Thr Pro Glu Gln Val Val Ala
625                 630                 635                 640

Ile Ala Ser Xaa Xaa Gly Gly Lys Gln Ala Leu Glu Thr Val Gln Arg
                645                 650                 655

Leu Leu Pro Val Leu Cys Gln Ala His Gly Leu Thr Pro Glu Gln Val
            660                 665                 670

Val Ala Ile Ala Ser Xaa Xaa Gly Gly Lys Gln Ala Leu Glu Thr Val
        675                 680                 685
```

```
Gln Arg Leu Leu Pro Val Leu Cys Gln Ala Gly His Gly Gly Leu Thr
    690                 695                 700
Pro Glu Gln Val Val Ala Ile Ala Ser Xaa Xaa Gly Gly Lys Gln Ala
705                 710                 715                 720
Leu Glu Thr Val Gln Arg Leu Leu Pro Val Leu Cys Gln Ala His Gly
                725                 730                 735
Leu Thr Pro Glu Gln Val Val Ala Ile Ala Ser Xaa Xaa Gly Gly Lys
            740                 745                 750
Gln Ala Leu Glu Thr Val Gln Arg Leu Leu Pro Val Leu Cys Gln Ala
        755                 760                 765
Gly His Gly Gly Leu Thr Pro Glu Gln Val Val Ala Ile Ala Ser Xaa
    770                 775                 780
Xaa Gly Gly Lys Gln Ala Leu Glu Thr Val Gln Arg Leu Leu Pro Val
785                 790                 795                 800
Leu Cys Gln Ala His Gly Leu Thr Pro Glu Gln Val Val Ala Ile Ala
                805                 810                 815
Ser Xaa Xaa Gly Gly Arg Pro Ala Leu Glu Ser Ile Val Ala Gln Leu
            820                 825                 830
Ser Arg Pro Asp Pro Ala Leu Ala Ala Leu Thr Asn Asp His Leu Val
        835                 840                 845
Ala Leu Ala Cys Leu Gly Gly Arg Pro Ala Leu Asp Ala Val Lys Lys
    850                 855                 860
Gly Leu Pro His Ala Pro Ala Leu Ile Lys Arg Thr Asn Arg Arg Ile
865                 870                 875                 880
Pro Glu Arg Thr Ser His Arg Val Ala Gly Ser Val Leu Glu Lys Ser
                885                 890                 895
Asp Ile Glu Lys Phe Lys Asn Gln Leu Arg Thr Glu Leu Thr Asn Ile
            900                 905                 910
Asp His Ser Tyr Leu Lys Gly Ile Asp Ile Ala Ser Lys Lys Lys Thr
        915                 920                 925
Ser Asn Val Glu Asn Thr Glu Phe Glu Ala Ile Ser Thr Lys Ile Phe
    930                 935                 940
Thr Asp Glu Leu Gly Phe Ser Gly Lys His Leu Gly Gly Ser Asn Lys
945                 950                 955                 960
Pro Asp Gly Leu Leu Trp Asp Asp Cys Ala Ile Ile Leu Asp Ser
                965                 970                 975
Lys Ala Tyr Ser Glu Gly Phe Pro Leu Thr Ala Ser His Thr Asp Ala
            980                 985                 990
Met Gly Arg Tyr Leu Arg Gln Phe Thr Glu Arg Lys Glu Glu Ile Lys
        995                 1000                1005
Pro Thr Trp Trp Asp Ile Ala Pro Glu His Leu Asp Asn Thr Tyr
    1010                1015                1020
Phe Ala Tyr Val Ser Gly Ser Phe Ser Gly Asn Tyr Lys Glu Gln
    1025                1030                1035
Leu Gln Lys Phe Arg Gln Asp Thr Asn His Leu Gly Gly Ala Leu
    1040                1045                1050
Glu Phe Val Lys Leu Leu Leu Ala Asn Asn Tyr Lys Thr Gln
    1055                1060                1065
Lys Met Ser Lys Lys Glu Val Lys Lys Ser Ile Leu Asp Tyr Asn
    1070                1075                1080

Ile Ser Tyr
    1085
```

```
<210> SEQ ID NO 60
<211> LENGTH: 1104
<212> TYPE: PRT
<213> ORGANISM: Homo sapiens
<220> FEATURE:
<221> NAME/KEY: MOD_RES
<222> LOCATION: (188)..(189)
<223> OTHER INFORMATION: Any naturally occurring amino acid
<220> FEATURE:
<221> NAME/KEY: MOD_RES
<222> LOCATION: (224)..(225)
<223> OTHER INFORMATION: Any naturally occurring amino acid
<220> FEATURE:
<221> NAME/KEY: MOD_RES
<222> LOCATION: (260)..(261)
<223> OTHER INFORMATION: Any naturally occurring amino acid
<220> FEATURE:
<221> NAME/KEY: MOD_RES
<222> LOCATION: (296)..(297)
<223> OTHER INFORMATION: Any naturally occurring amino acid
<220> FEATURE:
<221> NAME/KEY: MOD_RES
<222> LOCATION: (332)..(333)
<223> OTHER INFORMATION: Any naturally occurring amino acid
<220> FEATURE:
<221> NAME/KEY: MOD_RES
<222> LOCATION: (368)..(369)
<223> OTHER INFORMATION: Any naturally occurring amino acid
<220> FEATURE:
<221> NAME/KEY: MOD_RES
<222> LOCATION: (404)..(405)
<223> OTHER INFORMATION: Any naturally occurring amino acid
<220> FEATURE:
<221> NAME/KEY: MOD_RES
<222> LOCATION: (440)..(441)
<223> OTHER INFORMATION: Any naturally occurring amino acid
<220> FEATURE:
<221> NAME/KEY: MOD_RES
<222> LOCATION: (476)..(477)
<223> OTHER INFORMATION: Any naturally occurring amino acid
<220> FEATURE:
<221> NAME/KEY: MOD_RES
<222> LOCATION: (512)..(513)
<223> OTHER INFORMATION: Any naturally occurring amino acid
<220> FEATURE:
<221> NAME/KEY: MOD_RES
<222> LOCATION: (548)..(549)
<223> OTHER INFORMATION: Any naturally occurring amino acid
<220> FEATURE:
<221> NAME/KEY: MOD_RES
<222> LOCATION: (584)..(585)
<223> OTHER INFORMATION: Any naturally occurring amino acid
<220> FEATURE:
<221> NAME/KEY: MOD_RES
<222> LOCATION: (620)..(621)
<223> OTHER INFORMATION: Any naturally occurring amino acid
<220> FEATURE:
<221> NAME/KEY: MOD_RES
<222> LOCATION: (656)..(657)
<223> OTHER INFORMATION: Any naturally occurring amino acid
<220> FEATURE:
<221> NAME/KEY: MOD_RES
<222> LOCATION: (692)..(693)
<223> OTHER INFORMATION: Any naturally occurring amino acid
<220> FEATURE:
<221> NAME/KEY: MOD_RES
<222> LOCATION: (728)..(729)
<223> OTHER INFORMATION: Any naturally occurring amino acid
<220> FEATURE:
<221> NAME/KEY: MOD_RES
<222> LOCATION: (764)..(765)
<223> OTHER INFORMATION: Any naturally occurring amino acid
<220> FEATURE:
<221> NAME/KEY: MOD_RES
<222> LOCATION: (800)..(801)
<223> OTHER INFORMATION: Any naturally occurring amino acid
<220> FEATURE:
<221> NAME/KEY: MOD_RES
<222> LOCATION: (836)..(837)
```

<223> OTHER INFORMATION: Any naturally occurring amino acid

<400> SEQUENCE: 60

```
Met Asp Tyr Lys Asp His Asp Gly Asp Tyr Lys Asp His Asp Ile Asp
1               5                   10                  15
Tyr Lys Asp Asp Asp Asp Lys Met Ala Pro Lys Lys Lys Arg Lys Val
            20                  25                  30
Gly Ile His Gly Val Pro Ala Ala Val Asp Leu Arg Thr Leu Gly Tyr
        35                  40                  45
Ser Gln Gln Gln Gln Glu Lys Ile Lys Pro Lys Val Arg Ser Thr Val
    50                  55                  60
Ala Gln His His Glu Ala Leu Val Gly His Gly Phe Thr His Ala His
65                  70                  75                  80
Ile Val Ala Leu Ser Gln His Pro Ala Ala Leu Gly Thr Val Ala Val
                85                  90                  95
Lys Tyr Gln Asp Met Ile Ala Ala Leu Pro Glu Ala Thr His Glu Ala
            100                 105                 110
Ile Val Gly Val Gly Lys Gln Trp Ser Gly Ala Arg Ala Leu Glu Ala
        115                 120                 125
Leu Leu Thr Val Ala Gly Glu Leu Arg Gly Pro Pro Leu Gln Leu Asp
130                 135                 140
Thr Gly Gln Leu Leu Lys Ile Ala Lys Arg Gly Gly Val Thr Ala Val
145                 150                 155                 160
Glu Ala Val His Ala Trp Arg Asn Ala Leu Thr Gly Ala Pro Leu Asn
                165                 170                 175
Leu Thr Pro Glu Gln Val Val Ala Ile Ala Ser Xaa Xaa Gly Gly Lys
            180                 185                 190
Gln Ala Leu Glu Thr Val Gln Arg Leu Leu Pro Val Leu Cys Gln Ala
        195                 200                 205
Gly His Gly Gly Leu Thr Pro Glu Gln Val Val Ala Ile Ala Ser Xaa
    210                 215                 220
Xaa Gly Gly Lys Gln Ala Leu Glu Thr Val Gln Arg Leu Leu Pro Val
225                 230                 235                 240
Leu Cys Gln Ala Gly His Gly Gly Leu Thr Pro Glu Gln Val Val Ala
                245                 250                 255
Ile Ala Ser Xaa Xaa Gly Gly Lys Gln Ala Leu Glu Thr Val Gln Arg
            260                 265                 270
Leu Leu Pro Val Leu Cys Gln Ala Gly His Gly Gly Leu Thr Pro Glu
        275                 280                 285
Gln Val Val Ala Ile Ala Ser Xaa Xaa Gly Gly Lys Gln Ala Leu Glu
    290                 295                 300
Thr Val Gln Arg Leu Leu Pro Val Leu Cys Gln Ala Gly His Gly Gly
305                 310                 315                 320
Leu Thr Pro Glu Gln Val Val Ala Ile Ala Ser Xaa Xaa Gly Gly Lys
                325                 330                 335
Gln Ala Leu Glu Thr Val Gln Arg Leu Leu Pro Val Leu Cys Gln Ala
            340                 345                 350
Gly His Gly Gly Leu Thr Pro Glu Gln Val Val Ala Ile Ala Ser Xaa
        355                 360                 365
Xaa Gly Gly Lys Gln Ala Leu Glu Thr Val Gln Arg Leu Leu Pro Val
    370                 375                 380
Leu Cys Gln Ala Gly His Gly Gly Leu Thr Pro Glu Gln Val Val Ala
385                 390                 395                 400
```

Ile Ala Ser Xaa Xaa Gly Gly Lys Gln Ala Leu Glu Thr Val Gln Arg
            405                 410                 415

Leu Leu Pro Val Leu Cys Gln Ala Gly His Gly Gly Leu Thr Pro Glu
        420                 425                 430

Gln Val Val Ala Ile Ala Ser Xaa Xaa Gly Gly Lys Gln Ala Leu Glu
    435                 440                 445

Thr Val Gln Arg Leu Leu Pro Val Leu Cys Gln Ala Gly His Gly Gly
450                 455                 460

Leu Thr Pro Glu Gln Val Val Ala Ile Ala Ser Xaa Xaa Gly Gly Lys
465                 470                 475                 480

Gln Ala Leu Glu Thr Val Gln Arg Leu Leu Pro Val Leu Cys Gln Ala
                485                 490                 495

Gly His Gly Gly Leu Thr Pro Glu Gln Val Val Ala Ile Ala Ser Xaa
            500                 505                 510

Xaa Gly Gly Lys Gln Ala Leu Glu Thr Val Gln Arg Leu Leu Pro Val
        515                 520                 525

Leu Cys Gln Ala Gly His Gly Gly Leu Thr Pro Glu Gln Val Val Ala
    530                 535                 540

Ile Ala Ser Xaa Xaa Gly Gly Lys Gln Ala Leu Glu Thr Val Gln Arg
545                 550                 555                 560

Leu Leu Pro Val Leu Cys Gln Ala Gly His Gly Gly Leu Thr Pro Glu
                565                 570                 575

Gln Val Val Ala Ile Ala Ser Xaa Xaa Gly Gly Lys Gln Ala Leu Glu
            580                 585                 590

Thr Val Gln Arg Leu Leu Pro Val Leu Cys Gln Ala Gly His Gly Gly
        595                 600                 605

Leu Thr Pro Glu Gln Val Val Ala Ile Ala Ser Xaa Xaa Gly Gly Lys
    610                 615                 620

Gln Ala Leu Glu Thr Val Gln Arg Leu Leu Pro Val Leu Cys Gln Ala
625                 630                 635                 640

Gly His Gly Gly Leu Thr Pro Glu Gln Val Val Ala Ile Ala Ser Xaa
                645                 650                 655

Xaa Gly Gly Lys Gln Ala Leu Glu Thr Val Gln Arg Leu Leu Pro Val
            660                 665                 670

Leu Cys Gln Ala Gly His Gly Gly Leu Thr Pro Glu Gln Val Val Ala
        675                 680                 685

Ile Ala Ser Xaa Xaa Gly Gly Lys Gln Ala Leu Glu Thr Val Gln Arg
    690                 695                 700

Leu Leu Pro Val Leu Cys Gln Ala Gly His Gly Gly Leu Thr Pro Glu
705                 710                 715                 720

Gln Val Val Ala Ile Ala Ser Xaa Xaa Gly Gly Lys Gln Ala Leu Glu
                725                 730                 735

Thr Val Gln Arg Leu Leu Pro Val Leu Cys Gln Ala Gly His Gly Gly
            740                 745                 750

Leu Thr Pro Glu Gln Val Val Ala Ile Ala Ser Xaa Xaa Gly Gly Lys
        755                 760                 765

Gln Ala Leu Glu Thr Val Gln Arg Leu Leu Pro Val Leu Cys Gln Ala
    770                 775                 780

Gly His Gly Gly Leu Thr Pro Glu Gln Val Val Ala Ile Ala Ser Xaa
785                 790                 795                 800

Xaa Gly Gly Lys Gln Ala Leu Glu Thr Val Gln Arg Leu Leu Pro Val
                805                 810                 815

Leu Cys Gln Ala Gly His Gly Gly Leu Thr Pro Glu Gln Val Val Ala 820                 825                 830

Ile Ala Ser Xaa Xaa Gly Gly Arg Pro Ala Leu Glu Ser Ile Val Ala
            835                 840                 845

Gln Leu Ser Arg Pro Asp Pro Ala Leu Ala Ala Leu Thr Asn Asp His
850                 855                 860

Leu Val Ala Leu Ala Cys Leu Gly Gly Arg Pro Ala Leu Asp Ala Val
865                 870                 875                 880

Lys Lys Gly Leu Pro His Ala Pro Ala Leu Ile Lys Arg Thr Asn Arg
                885                 890                 895

Arg Ile Pro Glu Arg Thr Ser His Arg Val Ala Gly Ser Val Leu Glu
            900                 905                 910

Lys Ser Asp Ile Glu Lys Phe Lys Asn Gln Leu Arg Thr Glu Leu Thr
        915                 920                 925

Asn Ile Asp His Ser Tyr Leu Lys Gly Ile Asp Ile Ala Ser Lys Lys
    930                 935                 940

Lys Thr Ser Asn Val Glu Asn Thr Glu Phe Glu Ala Ile Ser Thr Lys
945                 950                 955                 960

Ile Phe Thr Asp Glu Leu Gly Phe Ser Gly Lys His Leu Gly Gly Ser
                965                 970                 975

Asn Lys Pro Asp Gly Leu Leu Trp Asp Asp Cys Ala Ile Ile Leu
            980                 985                 990

Asp Ser Lys Ala Tyr Ser Glu Gly Phe Pro Leu Thr Ala Ser His Thr
        995                 1000                1005

Asp Ala Met Gly Arg Tyr Leu Arg Gln Phe Thr Glu Arg Lys Glu
    1010                1015                1020

Glu Ile Lys Pro Thr Trp Trp Asp Ile Ala Pro Glu His Leu Asp
    1025                1030                1035

Asn Thr Tyr Phe Ala Tyr Val Ser Gly Ser Phe Ser Gly Asn Tyr
    1040                1045                1050

Lys Glu Gln Leu Gln Lys Phe Arg Gln Asp Thr Asn His Leu Gly
    1055                1060                1065

Gly Ala Leu Glu Phe Val Lys Leu Leu Leu Leu Ala Asn Asn Tyr
    1070                1075                1080

Lys Thr Gln Lys Met Ser Lys Lys Glu Val Lys Lys Ser Ile Leu
    1085                1090                1095

Asp Tyr Asn Ile Ser Tyr
    1100

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Lys Lys Lys Arg Lys Val
1               5

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 62

Leu Gly Arg Val Ile Pro Arg Lys Ile Ala Ser Arg Ala Ser Leu Met
1               5                   10                  15

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu or Gln

<400> SEQUENCE: 63

Leu Thr Pro Xaa Gln Val Val Ala Ile Ala Ser
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu or Gln

<400> SEQUENCE: 64

Leu Thr Pro Xaa Gln Val Val Ala Ile Ala Ser
1               5                   10

<210> SEQ ID NO 65
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (12)..(12)
<223> OTHER INFORMATION: Asn, His or Ile
<220> FEATURE:
<221> NAME/KEY: MOD_RES
<222> LOCATION: (13)..(13)
<223> OTHER INFORMATION: Any amino acid or not present
<220> FEATURE:
<221> NAME/KEY: MOD_RES
<222> LOCATION: (14)..(34)
<223> OTHER INFORMATION: This region may encompass GGRPALE, GGKQALE,
      GGKQALETVQRLLPVLCQDHG, GGKQALETVQRLLPVLCQAHG,
      GKQALETVQRLLPVLCQDHG, or GKQALETVQRLLPVLCQAHG,
      wherein some positions may be absent
<220> FEATURE:
<223> OTHER INFORMATION: See specification as filed for detailed
      description of substitutions and preferred embodiments

<400> SEQUENCE: 65

Leu Thr Pro Xaa Gln Val Val Ala Ile Ala Xaa Xaa Xaa Xaa Xaa Xaa
```

```
                1               5                  10                 15
Xaa Xaa Xaa Xaa Xaa Xaa Xaa Xaa Xaa Xaa Xaa Xaa Xaa Xaa Xaa
                        20                 25                 30
Xaa Xaa His Gly
        35

<210> SEQ ID NO 66
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (12)..(12)
<223> OTHER INFORMATION: Asn, His or Ile
<220> FEATURE:
<221> NAME/KEY: MOD_RES
<222> LOCATION: (13)..(13)
<223> OTHER INFORMATION: Asp, Ala, Ile, Asn, His, Lys, Ser or Gly
<220> FEATURE:
<221> NAME/KEY: MOD_RES
<222> LOCATION: (14)..(34)
<223> OTHER INFORMATION: This region may encompass GGRPALE, GGKQALE,
      GGKQALETVQRLLPVLCQDHG, GGKQALETVQRLLPVLCQAHG,
      GKQALETVQRLLPVLCQDHG, or GKQALETVQRLLPVLCQAHG,
      wherein some positions may be absent
<220> FEATURE:
<223> OTHER INFORMATION: See specification as filed for detailed
      description of substitutions and preferred embodiments

<400> SEQUENCE: 66

Leu Thr Pro Xaa Gln Val Val Ala Ile Ala Xaa Xaa Xaa Xaa Xaa
1               5                  10                 15

Xaa Xaa Xaa Xaa Xaa Xaa Xaa Xaa Xaa Xaa Xaa Xaa Xaa Xaa Xaa
                    20                  25                 30

Xaa Xaa His Gly
        35

<210> SEQ ID NO 67
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (12)..(12)
<223> OTHER INFORMATION: Any amino acid except Asn, His or Ile
<220> FEATURE:
<221> NAME/KEY: MOD_RES
<222> LOCATION: (13)..(13)
<223> OTHER INFORMATION: Any amino acid or not present
<220> FEATURE:
```

```
<221> NAME/KEY: MOD_RES
<222> LOCATION: (14)..(34)
<223> OTHER INFORMATION: This region may encompass GGRPALE, GGKQALE,
      GGKQALETVQRLLPVLCQDHG, GGKQALETVQRLLPVLCQAHG,
      GKQALETVQRLLPVLCQDHG, or GKQALETVQRLLPVLCQAHG,
      wherein some positions may be absent
<220> FEATURE:
<223> OTHER INFORMATION: See specification as filed for detailed
      description of substitutions and preferred embodiments

<400> SEQUENCE: 67

Leu Thr Pro Xaa Gln Val Val Ala Ile Ala Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa His Gly
        35

<210> SEQ ID NO 68
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (13)..(13)
<223> OTHER INFORMATION: Any amino acid except Gly
<220> FEATURE:
<221> NAME/KEY: MOD_RES
<222> LOCATION: (14)..(34)
<223> OTHER INFORMATION: This region may encompass GGRPALE, GGKQALE,
      GGKQALETVQRLLPVLCQDHG, GGKQALETVQRLLPVLCQAHG,
      GKQALETVQRLLPVLCQDHG, or GKQALETVQRLLPVLCQAHG,
      wherein some positions may be absent
<220> FEATURE:
<223> OTHER INFORMATION: See specification as filed for detailed
      description of substitutions and preferred embodiments

<400> SEQUENCE: 68

Leu Thr Pro Xaa Gln Val Val Ala Ile Ala Xaa Ile Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa His Gly
        35

<210> SEQ ID NO 69
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Asp or Glu
<220> FEATURE:
<221> NAME/KEY: MOD_RES
<222> LOCATION: (11)..(11)
<223> OTHER INFORMATION: Ser or Asn
```

```
<220> FEATURE:
<221> NAME/KEY: MOD_RES
<222> LOCATION: (14)..(34)
<223> OTHER INFORMATION: This region may encompass GGRPALE, GGKQALE,
      GGKQALETVQRLLPVLCQDHG, GGKQALETVQRLLPVLCQAHG,
      GKQALETVQRLLPVLCQDHG, or GKQALETVQRLLPVLCQAHG,
      wherein some positions may be absent
<220> FEATURE:
<223> OTHER INFORMATION: See specification as filed for detailed
      description of substitutions and preferred embodiments

<400> SEQUENCE: 69

Leu Thr Pro Xaa Gln Val Val Ala Ile Ala Xaa Ile Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa His Gly
        35

<210> SEQ ID NO 70
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (12)..(12)
<223> OTHER INFORMATION: Ser, Thr or Gln
<220> FEATURE:
<221> NAME/KEY: MOD_RES
<222> LOCATION: (13)..(13)
<223> OTHER INFORMATION: Any amino acid or not present
<220> FEATURE:
<221> NAME/KEY: MOD_RES
<222> LOCATION: (14)..(34)
<223> OTHER INFORMATION: This region may encompass GGRPALE, GGKQALE,
      GGKQALETVQRLLPVLCQDHG, GGKQALETVQRLLPVLCQAHG,
      GKQALETVQRLLPVLCQDHG, or GKQALETVQRLLPVLCQAHG,
      wherein some positions may be absent
<220> FEATURE:
<223> OTHER INFORMATION: See specification as filed for detailed
      description of substitutions and preferred embodiments

<400> SEQUENCE: 70

Leu Thr Pro Xaa Gln Val Val Ala Ile Ala Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa His Gly
        35

<210> SEQ ID NO 71
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
```

```
<223> OTHER INFORMATION: Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (12)..(12)
<223> OTHER INFORMATION: Ser, Thr or Gln
<220> FEATURE:
<221> NAME/KEY: MOD_RES
<222> LOCATION: (13)..(13)
<223> OTHER INFORMATION: Asp, Ala, Ile, Asn, His, Lys, Ser or Gly
<220> FEATURE:
<221> NAME/KEY: MOD_RES
<222> LOCATION: (14)..(34)
<223> OTHER INFORMATION: This region may encompass GGRPALE, GGKQALE,
      GGKQALETVQRLLPVLCQDHG, GGKQALETVQRLLPVLCQAHG,
      GKQALETVQRLLPVLCQDHG, or GKQALETVQRLLPVLCQAHG,
      wherein some positions may be absent
<220> FEATURE:
<223> OTHER INFORMATION: See specification as filed for detailed
      description of substitutions and preferred embodiments

<400> SEQUENCE: 71

Leu Thr Pro Xaa Gln Val Val Ala Ile Ala Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa His Gly
        35

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (12)..(12)
<223> OTHER INFORMATION: Ser, Thr or Gln
<220> FEATURE:
<223> OTHER INFORMATION: See specification as filed for detailed
      description of substitutions and preferred embodiments

<400> SEQUENCE: 72

Leu Thr Pro Xaa Gln Val Val Ala Ile Ala Xaa Xaa
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asp or Glu
<220> FEATURE:
<221> NAME/KEY: MOD_RES
<222> LOCATION: (11)..(11)
```

```
<223> OTHER INFORMATION: Ser or Asn
<220> FEATURE:
<221> NAME/KEY: MOD_RES
<222> LOCATION: (12)..(12)
<223> OTHER INFORMATION: Ser, Thr or Gln
<220> FEATURE:
<221> NAME/KEY: MOD_RES
<222> LOCATION: (13)..(13)
<223> OTHER INFORMATION: Asp, Ala, Ile, Asn, His, Lys, Ser or Gly
<220> FEATURE:
<223> OTHER INFORMATION: See specification as filed for detailed
      description of substitutions and preferred embodiments

<400> SEQUENCE: 73

Leu Thr Pro Xaa Gln Val Val Ala Ile Ala Xaa Xaa Xaa
1               5                   10

<210> SEQ ID NO 74
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Gln, Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (12)..(12)
<223> OTHER INFORMATION: Asn, His or Ile
<220> FEATURE:
<221> NAME/KEY: MOD_RES
<222> LOCATION: (13)..(13)
<223> OTHER INFORMATION: Any amino acid or not present
<220> FEATURE:
<221> NAME/KEY: MOD_RES
<222> LOCATION: (14)..(32)
<223> OTHER INFORMATION: This region may encompass GGRPALE, GGKQALE,
      GGKQALETVQRLLPVLCQD, GGKQALETVQRLLPVLCQA,
      GKQALETVQRLLPVLCQD, or GKQALETVQRLLPVLCQA,
      wherein some positions may be absent
<220> FEATURE:
<223> OTHER INFORMATION: See specification as filed for detailed
      description of substitutions and preferred embodiments

<400> SEQUENCE: 74

Leu Thr Pro Xaa Gln Val Val Ala Ile Ala Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Gly His Gly Gly
        35

<210> SEQ ID NO 75
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Gln, Asp or Glu
<220> FEATURE:
<221> NAME/KEY: MOD_RES
<222> LOCATION: (11)..(11)
```

```
<223> OTHER INFORMATION: Ser or Asn
<220> FEATURE:
<221> NAME/KEY: MOD_RES
<222> LOCATION: (12)..(12)
<223> OTHER INFORMATION: Asn, His or Ile
<220> FEATURE:
<221> NAME/KEY: MOD_RES
<222> LOCATION: (13)..(13)
<223> OTHER INFORMATION: Asp, Ala, Ile, Asn, His, Lys, Ser or Gly
<220> FEATURE:
<221> NAME/KEY: MOD_RES
<222> LOCATION: (14)..(32)
<223> OTHER INFORMATION: This region may encompass GGRPALE, GGKQALE,
      GGKQALETVQRLLPVLCQD, GGKQALETVQRLLPVLCQA,
      GKQALETVQRLLPVLCQD, or GKQALETVQRLLPVLCQA,
      wherein some positions may be absent
<220> FEATURE:
<223> OTHER INFORMATION: See specification as filed for detailed
      description of substitutions and preferred embodiments

<400> SEQUENCE: 75

Leu Thr Pro Xaa Gln Val Val Ala Ile Ala Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Gly His Gly Gly
        35

<210> SEQ ID NO 76
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Gln, Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (12)..(12)
<223> OTHER INFORMATION: Any amino acid except Asn, His or Ile
<220> FEATURE:
<221> NAME/KEY: MOD_RES
<222> LOCATION: (13)..(13)
<223> OTHER INFORMATION: Any amino acid or not present
<220> FEATURE:
<221> NAME/KEY: MOD_RES
<222> LOCATION: (14)..(32)
<223> OTHER INFORMATION: This region may encompass GGRPALE, GGKQALE,
      GGKQALETVQRLLPVLCQD, GGKQALETVQRLLPVLCQA,
      GKQALETVQRLLPVLCQD, or GKQALETVQRLLPVLCQA,
      wherein some positions may be absent
<220> FEATURE:
<223> OTHER INFORMATION: See specification as filed for detailed
      description of substitutions and preferred embodiments

<400> SEQUENCE: 76

Leu Thr Pro Xaa Gln Val Val Ala Ile Ala Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Gly His Gly Gly
        35

<210> SEQ ID NO 77
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Gln, Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (13)..(13)
<223> OTHER INFORMATION: Any amino acid except Gly
<220> FEATURE:
<221> NAME/KEY: MOD_RES
<222> LOCATION: (14)..(32)
<223> OTHER INFORMATION: This region may encompass GGRPALE, GGKQALE,
      GGKQALETVQRLLPVLCQD, GGKQALETVQRLLPVLCQA,
      GKQALETVQRLLPVLCQD, or GKQALETVQRLLPVLCQA,
      wherein some positions may be absent
<220> FEATURE:
<223> OTHER INFORMATION: See specification as filed for detailed
      description of substitutions and preferred embodiments

<400> SEQUENCE: 77

Leu Thr Pro Xaa Gln Val Val Ala Ile Ala Xaa Ile Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Gly His Gly Gly
        35

<210> SEQ ID NO 78
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Gln, Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (14)..(32)
<223> OTHER INFORMATION: This region may encompass GGRPALE, GGKQALE,
      GGKQALETVQRLLPVLCQD, GGKQALETVQRLLPVLCQA,
      GKQALETVQRLLPVLCQD, or GKQALETVQRLLPVLCQA,
      wherein some positions may be absent
<220> FEATURE:
<223> OTHER INFORMATION: See specification as filed for detailed
      description of substitutions and preferred embodiments

<400> SEQUENCE: 78

Leu Thr Pro Xaa Gln Val Val Ala Ile Ala Xaa Ile Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Gly His Gly Gly
        35
```

```
<210> SEQ ID NO 79
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Gln, Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (12)..(12)
<223> OTHER INFORMATION: Ser, Thr or Gln
<220> FEATURE:
<221> NAME/KEY: MOD_RES
<222> LOCATION: (13)..(13)
<223> OTHER INFORMATION: Any amino acid or not present
<220> FEATURE:
<221> NAME/KEY: MOD_RES
<222> LOCATION: (14)..(32)
<223> OTHER INFORMATION: This region may encompass GGRPALE, GGKQALE,
      GGKQALETVQRLLPVLCQD, GGKQALETVQRLLPVLCQA,
      GKQALETVQRLLPVLCQD, or GKQALETVQRLLPVLCQA,
      wherein some positions may be absent
<220> FEATURE:
<223> OTHER INFORMATION: See specification as filed for detailed
      description of substitutions and preferred embodiments

<400> SEQUENCE: 79

Leu Thr Pro Xaa Gln Val Val Ala Ile Ala Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Gly His Gly Gly
        35

<210> SEQ ID NO 80
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Gln, Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (12)..(12)
<223> OTHER INFORMATION: Ser, Thr or Gln
<220> FEATURE:
<221> NAME/KEY: MOD_RES
<222> LOCATION: (13)..(13)
<223> OTHER INFORMATION: Asp, Ala, Ile, Asn, His, Lys, Ser or Gly
<220> FEATURE:
<221> NAME/KEY: MOD_RES
<222> LOCATION: (14)..(32)
<223> OTHER INFORMATION: This region may encompass GGRPALE, GGKQALE,
      GGKQALETVQRLLPVLCQD, GGKQALETVQRLLPVLCQA,
      GKQALETVQRLLPVLCQD, or GKQALETVQRLLPVLCQA,
      wherein some positions may be absent
<220> FEATURE:
<223> OTHER INFORMATION: See specification as filed for detailed
      description of substitutions and preferred embodiments
```

```
<400> SEQUENCE: 80

Leu Thr Pro Xaa Gln Val Val Ala Ile Ala Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Gly His Gly Gly
        35

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Gln, Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (12)..(12)
<223> OTHER INFORMATION: Ser, Thr or Gln
<220> FEATURE:
<223> OTHER INFORMATION: See specification as filed for detailed
      description of substitutions and preferred embodiments

<400> SEQUENCE: 81

Leu Thr Pro Xaa Gln Val Val Ala Ile Ala Xaa Xaa
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Gln, Asp or Glu
<220> FEATURE:
<221> NAME/KEY: MOD_RES
<222> LOCATION: (11)..(11)
<223> OTHER INFORMATION: Ser or Asn
<220> FEATURE:
<221> NAME/KEY: MOD_RES
<222> LOCATION: (12)..(12)
<223> OTHER INFORMATION: Ser, Thr or Gln
<220> FEATURE:
<221> NAME/KEY: MOD_RES
<222> LOCATION: (13)..(13)
<223> OTHER INFORMATION: Asp, Ala, Ile, Asn, His, Lys, Ser or Gly
<220> FEATURE:
<223> OTHER INFORMATION: See specification as filed for detailed
      description of substitutions and preferred embodiments

<400> SEQUENCE: 82

Leu Thr Pro Xaa Gln Val Val Ala Ile Ala Xaa Xaa Xaa
1               5                   10

<210> SEQ ID NO 83
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 83
taagagggcg tgcgctcccg                                              20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tcaaatctgg cggttaatgg                                              20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ttggcagagg tggcggcggc                                              20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tgccaggcag ggggcaacgt                                              20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
tccactgccc cactgagaac                                              20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tccttgaagc agaagaaaca                                              20

<210> SEQ ID NO 89
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 89
taaaaagcat tcgtccggtt                                                    20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ttcttcaaac tgcttcttga                                                    20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ttgaggaaac tgcggagaaa                                                    20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tccatggcag ccagctgctc                                                    20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tgggtgcccc gacgttgccc                                                    20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tagagatgcg gtggtccttg                                                    20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 95
tgccccgacg ttgccccctg                                              20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tagagatgcg gtggtccttg                                              20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tgccccgacg ttgccccctg                                              20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tgtagagatg cggtggtcct                                              20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tctctacatt caagaactgg                                              20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tcacccgctc cggggtgcag                                              20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 101
tctacattca agaactggcc                                               20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tcacccgctc cggggtgcag                                               20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tctacattca agaactggcc                                               20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tctcacccgc tccggggtgc                                               20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tacattcaag aactggccct                                               20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tcacccgctc cggggtgcag                                               20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 107
tacattcaag aactggccct                                        20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tctcacccgc tccggggtgc                                        20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ttcaagaact ggcccttctt                                        20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
tctcacccgc tccggggtgc                                        20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tcccttgcag atggccgagg                                        20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tggctcgttc tcagtggggc                                        20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tcccttgcag atggccgagg                                           20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tctggctcgt tctcagtggg                                           20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tccactgccc cactgagaac                                           20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tccttgaagc agaagaaaca                                           20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tgccccactg agaacgagcc                                           20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
tccagctcct tgaagcagaa                                           20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119

```
tgccccactg agaacgagcc                                               20
```

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120

```
ttccagctcc ttgaagcaga                                               20
```

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121

```
tggcccagtg tttcttctgc                                               20
```

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122

```
tcgtcatctg gctcccagcc                                               20
```

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123

```
tggcccagtg tttcttctgc                                               20
```

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124

```
tggggtcgtc atctggctcc                                               20
```

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125

```
tgtttcttct gcttcaagga                                               20
```

```
<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
tacatggggt cgtcatctgg                                              20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tgtttcttct gcttcaagga                                              20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ttacatgggg tcgtcatctg                                              20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tttcttctgc ttcaaggagc                                              20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tacatggggt cgtcatctgg                                              20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tttcttctgc ttcaaggagc                                              20
```

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ttacatgggg tcgtcatctg                                                    20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ttcttctgct tcaaggagct                                                    20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
ttacatgggg tcgtcatctg                                                    20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ttttctagag aggaacataa                                                    20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
tgacagaaag gaaagcgcaa                                                    20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ttttctagag aggaacataa                                                    20

```
<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ttgacagaaa ggaaagcgca                                                20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ttttctagag aggaacataa                                                20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
tcttgacaga aaggaaagcg                                                20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
tagagaggaa cataaaaagc                                                20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tgcttcttga cagaaaggaa                                                20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
taaaaagcat tcgtccggtt                                                20

<210> SEQ ID NO 144
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
tcttcaaact gcttcttgac                                                    20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
taaaaagcat tcgtccggtt                                                    20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ttcttcaaac tgcttcttga                                                    20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
taaaaagcat tcgtccggtt                                                    20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
taattcttca aactgcttct                                                    20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
taaaaagcat tcgtccggtt                                                    20

<210> SEQ ID NO 150
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ttaattcttc aaactgcttc                                                   20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ttcgtccggt tgcgctttcc                                                   20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
tcaccaaggg ttaattcttc                                                   20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tcgtccggtt gcgctttcct                                                   20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
tcaccaaggg ttaattcttc                                                   20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tcgtccggtt gcgctttcct                                                   20

<210> SEQ ID NO 156
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 156
ttcaccaagg gttaattctt                                               20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tccggttgcg ctttccttc                                                20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tcaccaaggg ttaattcttc                                               20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tccggttgcg ctttccttc                                                20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ttcaccaagg gttaattctt                                               20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ttgcgctttc ctttctgtca                                               20

<210> SEQ ID NO 162
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 162
tcaaaaattc accaagggtt                                                    20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ttgcgctttc ctttctgtca                                                    20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ttcaaaaatt caccaagggt                                                    20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tgcgctttcc tttctgtcaa                                                    20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ttcaaaaatt caccaagggt                                                    20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tgcgctttcc tttctgtcaa                                                    20

<210> SEQ ID NO 168
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 168
tttcaaaaat tcaccaaggg                                              20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tttcctttct gtcaagaagc                                              20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ttcaaaaatt caccaagggt                                              20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
tttcctttct gtcaagaagc                                              20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
tttcaaaaat tcaccaaggg                                              20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
tttcctttct gtcaagaagc                                              20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 174
tccagtttca aaaattcacc                                              20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ttcctttctg tcaagaagca                                              20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tttcaaaaat tcaccaaggg                                              20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
ttcctttctg tcaagaagca                                              20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
tccagtttca aaaattcacc                                              20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
tcctttctgt caagaagcag                                              20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 180
tccagtttca aaaattcacc                                               20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tcctttctgt caagaagcag                                               20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tgtccagttt caaaaattca                                               20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tttctgtcaa gaagcagttt                                               20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tccagtttca aaaattcacc                                               20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tttctgtcaa gaagcagttt                                               20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 186
tgtccagttt caaaaattca                                           20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tttctgtcaa gaagcagttt                                           20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
tctgtccagt ttcaaaaatt                                           20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ttctgtcaag aagcagtttg                                           20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tccagtttca aaaattcacc                                           20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ttctgtcaag aagcagtttg                                           20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
tgtccagttt caaaaattca                                          20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ttctgtcaag aagcagtttg                                          20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
tctgtccagt ttcaaaaatt                                          20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ttctgtcaag aagcagtttg                                          20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
tctctgtcca gtttcaaaaa                                          20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tctgtcaaga agcagtttga                                          20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
tgtccagttt caaaaattca                                               20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tctgtcaaga agcagtttga                                               20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tctgtccagt ttcaaaaatt                                               20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
tctgtcaaga agcagtttga                                               20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
tctctgtcca gtttcaaaaa                                               20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tctgtcaaga agcagtttga                                               20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
ttctctgtcc agtttcaaaa                                               20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
tgtcaagaag cagtttgaag                                           20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
tctgtccagt ttcaaaaatt                                           20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tgtcaagaag cagtttgaag                                           20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
tctctgtcca gtttcaaaaa                                           20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
tgtcaagaag cagtttgaag                                           20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ttctctgtcc agtttcaaaa                                           20

```
<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
tgtcaagaag cagtttgaag                                          20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tttctctgtc cagtttcaaa                                          20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
tcaagaagca gtttgaagaa                                          20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
tctctgtcca gtttcaaaaa                                          20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
tcaagaagca gtttgaagaa                                          20

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
ttctctgtcc agtttcaaaa                                          20
```

```
<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
tcaagaagca gtttgaagaa                                                   20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
tttctctgtc cagtttcaaa                                                   20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
tttgaagaat taacccttgg                                                   20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
tcttggctct ttctctgtcc                                                   20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
ttgaagaatt aacccttggt                                                   20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
tcttggctct ttctctgtcc                                                   20

<210> SEQ ID NO 223
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
ttgaagaatt aaccttggt                                                    20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
ttcttggctc tttctctgtc                                                   20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
tgaagaatta acccttggtg                                                   20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
ttcttggctc tttctctgtc                                                   20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
tgaagaatta acccttggtg                                                   20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
tgttcttggc tctttctctg                                                   20

<210> SEQ ID NO 229
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ttaacccttg gtgaattttt                                              20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
tacaattttg ttcttggctc                                              20

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
taaccctcgg tgaatttttg                                              20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
tacaattttg ttcttggctc                                              20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
taaccctcgg tgaatttttg                                              20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
tacatacaat tttgttcttg                                              20

<210> SEQ ID NO 235
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 235
ttggtgaatt tttgaaactg                                              20

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
tacatacaat tttgttcttg                                              20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
ttatttccag gcaaaggaaa                                              20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
tccgcagttt cctcaaattc                                              20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ttatttccag gcaaaggaaa                                              20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
tctccgcagt ttcctcaaat                                              20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ttatttccag gcaaaggaaa                                              20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ttctccgcag tttcctcaaa                                              20

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
tatttccagg caaaggaaac                                              20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
tccgcagttt cctcaaattc                                              20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
tatttccagg caaaggaaac                                              20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
tctccgcagt ttcctcaaat                                              20

<210> SEQ ID NO 247
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 247
tatttccagg caaaggaaac                                                    20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
ttctccgcag tttcctcaaa                                                    20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
tatttccagg caaaggaaac                                                    20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tttctccgca gtttcctcaa                                                    20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
tccaggcaaa ggaaaccaac                                                    20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
tctccgcagt ttcctcaaat                                                    20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 253
tccaggcaaa ggaaaccaac                                               20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ttctccgcag tttcctcaaa                                               20

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
tccaggcaaa ggaaaccaac                                               20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
tttctccgca gtttcctcaa                                               20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tttgaggaaa ctgcggagaa                                               20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
tccatggcag ccagctgctc                                               20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
tttgaggaaa ctgcggagaa                                            20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
tcaatccatg gcagccagct                                            20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
ttgaggaaac tgcggagaaa                                            20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
tccatggcag ccagctgctc                                            20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ttgaggaaac tgcggagaaa                                            20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
tcaatccatg gcagccagct                                            20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
tgaggaaact gcggagaaag                          20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
tccatggcag ccagctgctc                          20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
tgaggaaact gcggagaaag                          20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
tcaatccatg gcagccagct                          20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
tttaggatct accataccca                          20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
tctctatttt ggtataatct                          20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
tttaggatct accatacccca       20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ttctctattt tggtataatc       20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
tttaggatct accatacccca       20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
tttctctatt ttggtataat       20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ttaggatcta ccatacccat       20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
tctctatttt ggtataatct       20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ttaggatcta ccatacccat                                           20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ttctctattt tggtataatc                                           20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
tcacacagca tattatttac                                           20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280 taccottata cacaactcca                                           20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
tcacacagca tattatttac                                           20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282 tctacccta tacacaactc                                            20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
tactttgttt caggtaccta                                           20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
tgtagttttg tgtctaccct                                          20

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
tactttgttt caggtaccta                                          20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
tgacctgtag ttttgtgtct                                          20

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
tttgtttcag gtacctatgg                                          20

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
tgacctgtag ttttgtgtct                                          20

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
tgacccgact cgctggcgct                                          20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
tccgatcttt tccacctttt                                              20

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
tgacccgact cgctggcgct                                              20

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
tctccgatct tttccacctt                                              20

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
tcgctggcgc ttcatggaga                                              20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
tacgtgccct ctccgatctt                                              20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
ttcatggaga acttccaaaa                                              20

```
<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
tacacaactc cgtacgtgcc                                              20

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
tcatggagaa cttccaaaag                                              20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
tacacaactc cgtacgtgcc                                              20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
tttcccaacc tctccaagtg                                              20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
tctcggatgg cagtactggg                                              20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
ttcccaacct ctccaagtga                                              20

<210> SEQ ID NO 302
```

```
<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
tctctcggat ggcagtactg                                               20

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
tcccaacctc tccaagtgag                                               20

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
tctctcggat ggcagtactg                                               20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
tctccaagtg agactgaggg                                               20

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
taagcagaga gatctctcgg                                               20

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
tctccaagtg agactgaggg                                               20

<210> SEQ ID NO 308
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
ttaagcagag agatctctcg                                              20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
tgtttcccag gcagctctgt                                              20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
tctccgatct tctctacctt                                              20

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
tttcccaggc agctctgtgg                                              20

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
tctccgatct tctctacctt                                              20

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
ttcccaggca gctctgtggc                                              20

<210> SEQ ID NO 314
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 314
tctccgatct tctctacctt                                               20

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
tcccaggcag ctctgtggcc                                               20

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
tctccgatct tctctacctt                                               20

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
tggatatgtt ccagaaggta                                               20

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
tacaccaccc cataggtgcc                                               20

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
tgcccacggc tgtgcccttg                                               20

<210> SEQ ID NO 320
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 320
tggcagtgct tgggaccccc                                                      20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
tgtgcccttg tttcttgcag                                                      20

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
tccctgatgg cagtgcttgg                                                      20

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
tttcttgcag ggagatggag                                                      20

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
tgagcagcga gatctccctg                                                      20

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
ttcttgcagg gagatggagg                                                      20

<210> SEQ ID NO 326
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 326
tgagcagcga gatctccctg                                                    20

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ttcttgcagg gagatggagg                                                    20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
ttgagcagcg agatctccct                                                    20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
tgtgattgta gggtctccct                                                    20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
tggctcatat cgagaggtag                                                    20

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
tgattgtagg gtctcccttg                                                    20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 332
tcagccactg gctcatatcg          20

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
ttgtagggtc tcccttgatc          20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
tcagccactg gctcatatcg          20

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
tgtagggtct cccttgatct          20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
tcagccactg gctcatatcg          20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
tagggtctcc cttgatctga          20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
tcagccactg gctcatatcg                                           20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
ttgaaaagtg agcatttact                                           20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
tcgggatgtg gcacagacgt                                           20

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
ttgaaaagtg agcatttact                                           20

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
ttcgggatgt ggcacagacg                                           20

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
tgaaaagtga gcatttactc                                           20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
tcgggatgtg gcacagacgt                                               20

<210> SEQ ID NO 345
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
tgaaaagtga gcatttactc                                               20

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
ttcgggatgt ggcacagacg                                               20

<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
tgaaaagtga gcatttactc                                               20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
tcagttcggg atgtggcaca                                               20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
tacgagaaac tggaaaagat                                               20

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
tgcaggaaca tctcgagatt				20

<210> SEQ ID NO 351
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
tacgagaaac tggaaaagat				20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
ttgcaggaac atctcgagat				20

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
tacgagaaac tggaaaagat				20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
tcttgcagga acatctcgag				20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
tccttcccct aggcacctac				20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
tgagtctccc ggttttttggc					20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
tccttcccct aggcacctac					20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
tcatgagtct cccggttttt					20

<210> SEQ ID NO 359
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
tccttcccct aggcacctac					20

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
tctcatgagt ctcccggttt					20

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
ttcccctagg cacctacgga					20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
tcatgagtct cccggttttt					20

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
ttcccctagg cacctacgga                                                 20

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
tctcatgagt ctcccggttt                                                 20

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
tgtgccgcgc tgaccagcag                                                 20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
taggcgccct ccccgatctc                                                 20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
tgtgccgcgc tgaccagcag                                                 20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
tcccataggc gccctccccg                                                 20

```
<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
tgccgcgctg accagcagta                                                  20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
tcccataggc gccctccccg                                                  20

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
tgccgcgctg accagcagta                                                  20

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
ttcccatagg cgccctcccc                                                  20

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
tgaccagcag tacgaatgcg                                                  20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
tgaacacctt cccataggcg                                                  20
```

```
<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
tctaggttgt ttgatgtgtg                                              20

<210> SEQ ID NO 376
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
tagtttggtt tctctgtctg                                              20

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
tctaggttgt ttgatgtgtg                                              20

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
taaagttagt ttggtttctc                                              20

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
taggttgttt gatgtgtgca                                              20

<210> SEQ ID NO 380
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
taaagttagt ttggtttctc                                              20

<210> SEQ ID NO 381
```

<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
ttgtttgatg tgtgcacagt                                              20

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
taaagttagt ttggtttctc                                              20

<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
ttgatgtgtg cacagtgtca                                              20

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
tcaaacacta aagttagttt                                              20

<210> SEQ ID NO 385
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
tccgggacgg ccggggcagc                                              20

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
tcgccgggca gagcgcagcc                                              20

<210> SEQ ID NO 387
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
tcttccagtt tgccaaggca                                              20

<210> SEQ ID NO 388
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
tcaaaagtgc ccaactgcgt                                              20

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
tcttccagtt tgccaaggca                                              20

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
tgatcttcaa aagtgcccaa                                              20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
ttccagtttg ccaaggcacg                                              20

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
tgatcttcaa aagtgcccaa                                              20

<210> SEQ ID NO 393
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 393
tccagtttgc caaggcacga                                                  20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
tgatcttcaa aagtgcccaa                                                  20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
tcacgcagtt gggcactttt                                                  20

<210> SEQ ID NO 396
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
tgaacatcct ctggaggctg                                                  20

<210> SEQ ID NO 397
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
tgaagacatc gcggggaccg                                                  20

<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
tgtcgttcgc gccgccggcg                                                  20

<210> SEQ ID NO 399
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 399
tgaagacatc gcggggaccg                                                 20

<210> SEQ ID NO 400
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
ttgtcgttcg cgccgccggc                                                 20

<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
tgaagacatc gcggggaccg                                                 20

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
tcttgtcgtt cgcgccgccg                                                 20

<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
tgaagacatc gcggggaccg                                                 20

<210> SEQ ID NO 404
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
ttcttgtcgt tcgcgccgcc                                                 20

<210> SEQ ID NO 405
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 405
tgaagacatc gcggggaccg                                                20

<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
tttcttgtcg ttcgcgccgc                                                20

<210> SEQ ID NO 407
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
tctcgtgttt ttcttgttgt                                                20

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
tcttttcgac gttcagaact                                                20

<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
tctcgtgttt ttcttgttgt                                                20

<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
ttcttttcga cgttcagaac                                                20

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 411
tctcgtgttt ttcttgttgt                                               20

<210> SEQ ID NO 412
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
tttcttttcg acgttcagaa                                               20

<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
tctcgtgttt ttcttgttgt                                               20

<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
ttttcttttc gacgttcaga                                               20

<210> SEQ ID NO 415
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
ttcttgttgt tgttaagtag                                               20

<210> SEQ ID NO 416
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
tcgagacttt tcttttcgac                                               20

<210> SEQ ID NO 417
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 417
tggtgggcat agacctgggc                                                  20

<210> SEQ ID NO 418
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
tgccgccggc gcgggccaca                                                  20

<210> SEQ ID NO 419
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
tgggcataga cctgggcttc                                                  20

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
tgccgccggc gcgggccaca                                                  20

<210> SEQ ID NO 421
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
tagacctggg cttccagagc                                                  20

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
tcgatgccgc cggcgcgggc                                                  20

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 423
tagacctggg cttccagagc                                              20

<210> SEQ ID NO 424
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
tctcgatgcc gccggcgcgg                                              20

<210> SEQ ID NO 425
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
tagacctggg cttccagagc                                              20

<210> SEQ ID NO 426
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
tagtctcgat gccgccggcg                                              20

<210> SEQ ID NO 427
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
tcttaagtgc tttttttgtc                                              20

<210> SEQ ID NO 428
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
tgaacgattc ttaggaccaa                                              20

<210> SEQ ID NO 429
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
ttaagtgctt tttttgtctt 20

<210> SEQ ID NO 430
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
tgaacgattc ttaggaccaa 20

<210> SEQ ID NO 431
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
ttaagtgctt tttttgtctt 20

<210> SEQ ID NO 432
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
ttgaacgatt cttaggacca 20

<210> SEQ ID NO 433
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
taagtgcttt ttttgtcttc 20

<210> SEQ ID NO 434
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
tgaacgattc ttaggaccaa 20

<210> SEQ ID NO 435
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435

```
taagtgctttt ttttgtcttc                                              20
```

<210> SEQ ID NO 436
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436

```
ttgaacgatt cttaggacca                                               20
```

<210> SEQ ID NO 437
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437

```
tgcccccgtg ttcgggcggg                                               20
```

<210> SEQ ID NO 438
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438

```
tcccgaaggg agggcccagg                                               20
```

<210> SEQ ID NO 439
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439

```
tgcccccgtg ttcgggcggg                                               20
```

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440

```
tgtcccgaag ggagggccca                                               20
```

<210> SEQ ID NO 441
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441

```
tcctgggccc tcccttcggg                                               20
```

<210> SEQ ID NO 442
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
tcgcgcgggt attcagcact                                              20

<210> SEQ ID NO 443
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
tgggccctcc cttcgggaca                                              20

<210> SEQ ID NO 444
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
tcgcgcgggt attcagcact                                              20

<210> SEQ ID NO 445
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
tcccttcggg acagggactg                                              20

<210> SEQ ID NO 446
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
tccagacggt cgcgcgggta                                              20

<210> SEQ ID NO 447
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
tccagaagat tgtgtttatg                                              20

<210> SEQ ID NO 448
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 448
tcttggtacc agttaacagg                                        20

<210> SEQ ID NO 449
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 449
tgtgtttatg ttcccagcag                                        20

<210> SEQ ID NO 450
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 450 ttgggcctttt tcttggtacc                                       20

<210> SEQ ID NO 451
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 451
tcccagcagg gcacctgtta                                        20

<210> SEQ ID NO 452
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 452
tgccagagaa acacttgggc                                        20

<210> SEQ ID NO 453
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 453
taactggtac caagaaaagg                                        20

```
<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
tccagacacc atcagatgcc                                               20

<210> SEQ ID NO 455
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
taactggtac caagaaaagg                                               20

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
tggatccaga caccatcaga                                               20

<210> SEQ ID NO 457
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
tccagcagcc tcccgcgacg                                               20

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
tagttcctgt tggtgaagct                                               20

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
tccagcagcc tcccgcgacg                                               20

<210> SEQ ID NO 460
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
tcatagttcc tgttggtgaa                                                 20

<210> SEQ ID NO 461
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
tcccgcgacg atgcccctca                                                 20

<210> SEQ ID NO 462
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
tcgaggtcat agttcctgtt                                                 20

<210> SEQ ID NO 463
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
tcccgcgacg atgcccctca                                                 20

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
tagtcgaggt catagttcct                                                 20

<210> SEQ ID NO 465
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
tcccgcgacg atgcccctca                                                 20

<210> SEQ ID NO 466
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
tcgtagtcga ggtcatagtt                                              20

<210> SEQ ID NO 467
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
tgcagcctgg gccgagccag                                              20

<210> SEQ ID NO 468
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
tggcccggcg gatcacctcc                                              20

<210> SEQ ID NO 469
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
tgggccgagc cagtggcccc                                              20

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
tggatggccc ggcggatcac                                              20

<210> SEQ ID NO 471
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
tgggccgagc cagtggcccc                                              20

<210> SEQ ID NO 472
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 472
tctggatggc ccggcggatc                                              20

<210> SEQ ID NO 473
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
tgggccgagc cagtggcccc                                              20

<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
ttctggatgg cccggcggat                                              20

<210> SEQ ID NO 475
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
tggcccccag aggatgagaa                                              20

<210> SEQ ID NO 476
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
tcagctcttt ctggatggcc                                              20

<210> SEQ ID NO 477
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
tgggaagggt cggaggcatg                                              20

<210> SEQ ID NO 478
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 478
tggctttggt gccccggccc                                                   20

<210> SEQ ID NO 479
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
tgggaagggt cggaggcatg                                                   20

<210> SEQ ID NO 480
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
ttggctttgg tgccccggcc                                                   20

<210> SEQ ID NO 481
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
tcggaggcat ggcacagcca                                                   20

<210> SEQ ID NO 482
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
ttcccattgg ctttggtgcc                                                   20

<210> SEQ ID NO 483
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
tggcacagcc aatgggaagg                                                   20

<210> SEQ ID NO 484
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 484
tcccggccct tcccattggc                                               20

<210> SEQ ID NO 485
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
tgcaccctgt cccagccgtc                                               20

<210> SEQ ID NO 486
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
tggaggcgca gcgaagcaga                                               20

<210> SEQ ID NO 487
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
tatgtacgcc tccctgggct                                               20

<210> SEQ ID NO 488
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
tggtacagaa gcgggcaaag                                               20

<210> SEQ ID NO 489
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
tgtacgcctc cctgggctcg                                               20

<210> SEQ ID NO 490
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 490
tgagggtggt acagaagcgg                                              20

<210> SEQ ID NO 491
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
tacgcctccc tgggctcggg                                              20

<210> SEQ ID NO 492
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
tgagggtggt acagaagcgg                                              20

<210> SEQ ID NO 493
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
tcgggtccgg tcgccccttt                                              20

<210> SEQ ID NO 494
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
tccaggaccc gagaactgag                                              20

<210> SEQ ID NO 495
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
tccggtcgcc cctttgcccg                                              20

<210> SEQ ID NO 496
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 496
tgctccagga cccgagaact                                               20

<210> SEQ ID NO 497
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
ttaaacaact acaaggaagt                                               20

<210> SEQ ID NO 498
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
tcaatctgtc cagaagaagc                                               20

<210> SEQ ID NO 499
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
taaacaacta caaggaagta                                               20

<210> SEQ ID NO 500
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
tcaatctgtc cagaagaagc                                               20

<210> SEQ ID NO 501
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
tacaaggaag tattgaagat                                               20

<210> SEQ ID NO 502
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 502
taataaatca atctgtccag    20

<210> SEQ ID NO 503
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
tattgaagat gaagctatgg    20

<210> SEQ ID NO 504
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
taagacgctc taataaatca    20

<210> SEQ ID NO 505
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
tattgaagat gaagctatgg    20

<210> SEQ ID NO 506
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
ttaagacgct ctaataaatc    20

<210> SEQ ID NO 507
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
tggatttatc tgctcttcgc    20

<210> SEQ ID NO 508
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
tgcatagcat taatgacatt					20

<210> SEQ ID NO 509
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
tggatttatc tgctcttcgc					20

<210> SEQ ID NO 510
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
tctgcatagc attaatgaca					20

<210> SEQ ID NO 511
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
ttatctgctc ttcgcgttga					20

<210> SEQ ID NO 512
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
taagattttc tgcatagcat					20

<210> SEQ ID NO 513
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
tatctgctct tcgcgttgaa					20

<210> SEQ ID NO 514
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
taagattttc tgcatagcat 20

<210> SEQ ID NO 515
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
tctgctcttc gcgttgaaga 20

<210> SEQ ID NO 516
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
taagattttc tgcatagcat 20

<210> SEQ ID NO 517
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
tgctagtctg gagttgatca 20

<210> SEQ ID NO 518
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
tgcaaaatat gtggtcacac 20

<210> SEQ ID NO 519
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
tgctagtctg gagttgatca 20

<210> SEQ ID NO 520
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
ttgcaaaata tgtggtcaca 20

<210> SEQ ID NO 521
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
tagtctggag ttgatcaagg                                              20

<210> SEQ ID NO 522
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
tgcaaaatat gtggtcacac                                              20

<210> SEQ ID NO 523
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
tagtctggag ttgatcaagg                                              20

<210> SEQ ID NO 524
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
ttgcaaaata tgtggtcaca                                              20

<210> SEQ ID NO 525
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
tagtctggag ttgatcaagg                                              20

<210> SEQ ID NO 526
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
tacttgcaaa atatgtggtc                                              20

<210> SEQ ID NO 527
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
tgcctattgg atccaaagag                                            20

<210> SEQ ID NO 528
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
tgcagcgtgt cttaaaaatt                                            20

<210> SEQ ID NO 529
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
tgcctattgg atccaaagag                                            20

<210> SEQ ID NO 530
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
ttgcagcgtg tcttaaaaat                                            20

<210> SEQ ID NO 531
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
tgcctattgg atccaaagag                                            20

<210> SEQ ID NO 532
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
tgttgcagcg tgtcttaaaa                                            20

```
<210> SEQ ID NO 533
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
tattggatcc aaagagaggc                                                   20

<210> SEQ ID NO 534
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
ttgcagcgtg tcttaaaaat                                                   20

<210> SEQ ID NO 535
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
tattggatcc aaagagaggc                                                   20

<210> SEQ ID NO 536
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
tgttgcagcg tgtcttaaaa                                                   20

<210> SEQ ID NO 537
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
tagatttagg accaataagt                                                   20

<210> SEQ ID NO 538
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
tggagcttct gaagaaagtt                                                   20

<210> SEQ ID NO 539
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
ttaggaccaa taagtcttaa                                                   20

<210> SEQ ID NO 540
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
tagggtggag cttctgaaga                                                   20

<210> SEQ ID NO 541
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
ttaggaccaa taagtcttaa                                                   20

<210> SEQ ID NO 542
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
tatagggtgg agcttctgaa                                                   20

<210> SEQ ID NO 543
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
ttaggaccaa taagtcttaa                                                   20

<210> SEQ ID NO 544
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
ttatagggtg gagcttctga                                                   20

<210> SEQ ID NO 545
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
taggaccaat aagtcttaat                                                    20

<210> SEQ ID NO 546
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
tatagggtgg agcttctgaa                                                    20

<210> SEQ ID NO 547
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
tcactgccat ggaggagccg                                                    20

<210> SEQ ID NO 548
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
tgactcagag ggggctcgac                                                    20

<210> SEQ ID NO 549
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
tcactgccat ggaggagccg                                                    20

<210> SEQ ID NO 550
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
tcctgactca gagggggctc                                                    20

<210> SEQ ID NO 551
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 551
tcactgccat ggaggagccg                                                    20

<210> SEQ ID NO 552
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
ttcctgactc agaggggggct                                                   20

<210> SEQ ID NO 553
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
tcactgccat ggaggagccg                                                    20

<210> SEQ ID NO 554
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
tttcctgact cagaggggggc                                                   20

<210> SEQ ID NO 555
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
tgccatggag gagccgcagt                                                    20

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
tcctgactca gaggggggctc                                                   20

<210> SEQ ID NO 557
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 557
ttctttcagg tacccactga          20

<210> SEQ ID NO 558
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 558
tggcaatctg gggttcagcc          20

<210> SEQ ID NO 559
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 559
tctttcaggt acccactgat          20

<210> SEQ ID NO 560
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 560
tggcaatctg gggttcagcc          20

<210> SEQ ID NO 561
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 561
tttcaggtac ccactgatgg          20

<210> SEQ ID NO 562
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 562
tggcaatctg gggttcagcc          20

<210> SEQ ID NO 563
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 563
ttcaggtacc cactgatggt                                                20

<210> SEQ ID NO 564
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
tggcaatctg gggttcagcc                                                20

<210> SEQ ID NO 565
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
tacccactga tggtaatgct                                                20

<210> SEQ ID NO 566
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
tgccacagaa catggcaatc                                                20

<210> SEQ ID NO 567
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
tgggcatcct gaagctgcaa                                                20

<210> SEQ ID NO 568
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
tggttcaatg caacagagag                                                20

<210> SEQ ID NO 569
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 569
tgggcatcct gaagctgcaa                                               20

<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
tcagatggtt caatgcaaca                                               20

<210> SEQ ID NO 571
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
tgcaagtatt tctcattgtg                                               20

<210> SEQ ID NO 572
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
tgggtgtagc tttcagatgg                                               20

<210> SEQ ID NO 573
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
tgctctctgt tgcattgaac                                               20

<210> SEQ ID NO 574
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
ttaccaacct ttcaatgggt                                               20

<210> SEQ ID NO 575
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 575
tgttaccagt catcaggtgg                                                   20

<210> SEQ ID NO 576
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
tgcgttgcac atgtggcagt                                                   20

<210> SEQ ID NO 577
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
ttaccagtca tcaggtggaa                                                   20

<210> SEQ ID NO 578
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
tgcgttgcac atgtggcagt                                                   20

<210> SEQ ID NO 579
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
taccagtcat caggtggaaa                                                   20

<210> SEQ ID NO 580
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
tgcgttgcac atgtggcagt                                                   20

<210> SEQ ID NO 581
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 581
tcatcaggtg gaaaagcgga                                                   20

<210> SEQ ID NO 582
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
tgccaggcgc tgcgttgcac                                                   20

<210> SEQ ID NO 583
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
tcatcaggtg gaaaagcgga                                                   20

<210> SEQ ID NO 584
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584
ttgccaggcg ctgcgttgca                                                   20

<210> SEQ ID NO 585
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585
ttttgtaggc tccaaaacca                                                   20

<210> SEQ ID NO 586
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586
ttacctgttg ccacaccatg                                                   20

<210> SEQ ID NO 587
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
```
ttttgtaggc tccaaaacca                                           20

<210> SEQ ID NO 588
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
tggagcttac ctgttgccac                                           20

<210> SEQ ID NO 589
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
tttgtaggct ccaaaaccaa                                           20

<210> SEQ ID NO 590
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 590
tggagcttac ctgttgccac                                           20

<210> SEQ ID NO 591
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
ttgtaggctc caaaaccaag                                           20

<210> SEQ ID NO 592
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
tggagcttac ctgttgccac                                           20

<210> SEQ ID NO 593
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
tgtaggctcc aaaaccaagg                                              20

<210> SEQ ID NO 594
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
tggagcttac ctgttgccac                                              20

<210> SEQ ID NO 595
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
tagcgagtta tggcgacgaa                                              20

<210> SEQ ID NO 596
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
tgcactgggc cgtcgccctt                                              20

<210> SEQ ID NO 597
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
ttatggcgac gaaggccgtg                                              20

<210> SEQ ID NO 598
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
tgccctgcac tgggccgtcg                                              20

<210> SEQ ID NO 599
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
ttatggcgac gaaggccgtg                                              20

<210> SEQ ID NO 600
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 600
tgatgccctg cactgggccg                                              20

<210> SEQ ID NO 601
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 601
ttatggcgac gaaggccgtg                                              20

<210> SEQ ID NO 602
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 602
tgatgatgcc ctgcactggg                                              20

<210> SEQ ID NO 603
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 603
tatggcgacg aaggccgtgt                                              20

<210> SEQ ID NO 604
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 604
tgatgccctg cactgggccg                                              20

<210> SEQ ID NO 605
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 605
taatggacca gtgaaggtgt                                              20

```
<210> SEQ ID NO 606
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
tgcaggcctt cagtcagtcc                                                      20

<210> SEQ ID NO 607
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
taatggacca gtgaaggtgt                                                      20

<210> SEQ ID NO 608
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
tccatgcagg ccttcagtca                                                      20

<210> SEQ ID NO 609
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
tggaccagtg aaggtgtggg                                                      20

<210> SEQ ID NO 610
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
tccatgcagg ccttcagtca                                                      20

<210> SEQ ID NO 611
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
tggaccagtg aaggtgtggg                                                      20
```

```
<210> SEQ ID NO 612
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
tggaatccat gcaggccttc                                              20

<210> SEQ ID NO 613
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
tgtggggaag cattaaagga                                              20

<210> SEQ ID NO 614
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
tcatgaacat ggaatccatg                                              20

<210> SEQ ID NO 615
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
tcattttcca tacagtcagt                                              20

<210> SEQ ID NO 616
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
ttttccatac agtcagtatc                                              20

<210> SEQ ID NO 617
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
tgactatctt taatgtctgg                                              20

<210> SEQ ID NO 618
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
tatctttaat gtctggaaat                                              20

<210> SEQ ID NO 619
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 619
agctagcagc aaaccttccc ttca                                         24

<210> SEQ ID NO 620
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 620
aaggacaatg ttgtagggag ccca                                         24

<210> SEQ ID NO 621
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 621
ttctgtggta aactcaacat                                              20

<210> SEQ ID NO 622
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622
tctgactccc attttccatt                                              20

<210> SEQ ID NO 623
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 623
ttctgtggta aactcaacat                                              20

<210> SEQ ID NO 624
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 624
tctgactccc attttccatt                                              20

<210> SEQ ID NO 625
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625
tatcttccag aaagactcca                                              20

<210> SEQ ID NO 626
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
ttcccttccc ccttcttccc                                              20

<210> SEQ ID NO 627
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
ttgaaggcaa aaatgtccac                                              20

<210> SEQ ID NO 628
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
tctcatgtag gagtccagga                                              20

<210> SEQ ID NO 629
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
ttatctgtcc cctccacccc                                              20

<210> SEQ ID NO 630
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 630
ttttctgtca ccaatcctgt                                              20

<210> SEQ ID NO 631
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
tcggccgccg ccaagctcgt                                              20

<210> SEQ ID NO 632
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
tgcgcgcagc ctggtaggag                                              20

<210> SEQ ID NO 633
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 633
taactcaaga ctgcctcccg cttt                                         24

<210> SEQ ID NO 634
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 634
agcccaaggt ttcagaggtg atga                                         24

<210> SEQ ID NO 635
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 635
gcgccattaa ccgccagatt tgaa                                         24

<210> SEQ ID NO 636
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 636
tgggagttca caacaacagg gtct                                          24

<210> SEQ ID NO 637
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 637
tgagaaaacc aaacagggtg                                               20

<210> SEQ ID NO 638
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
tagagaacac cctcttttgt                                               20

<210> SEQ ID NO 639
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639 tgttttgta ggctccaaaa                                                20

<210> SEQ ID NO 640
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
tacctgttgc cacaccatgc                                               20

<210> SEQ ID NO 641
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
tccaaaacca aggagggagt                                               20

<210> SEQ ID NO 642
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 642
taagcacaat ggagcttacc                                                   20

<210> SEQ ID NO 643
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
tcccaagcaa tggatgattt                                                   20

<210> SEQ ID NO 644
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
tgaaccattg ttcaatatcg                                                   20

<210> SEQ ID NO 645
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
tgaagctccc agaatgccag                                                   20

<210> SEQ ID NO 646
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
taggagctgc tggtgcaggg                                                   20

<210> SEQ ID NO 647
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
tggatgacag aaaactttt                                                    20

<210> SEQ ID NO 648
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 648
tcaggcggct catagggcac                                                   20

<210> SEQ ID NO 649
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
ctgcagctct cattttccat acagtcagta tcaattctgg aagaatttcc agacattaaa       60
gatagtcatc ttggggc                                                      77

<210> SEQ ID NO 650
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
gccccaagat gactatcttt aatgtctgga aattcttcca gaattgatac tgactgtatg       60
gaaaatgaga gctgcag                                                      77

<210> SEQ ID NO 651
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
ctgcagctct cattttccat acagtcagta tcaattctgg aagaatttcc agacattaaa       60
gatagtcatc ttggggc                                                      77

<210> SEQ ID NO 652
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
gccccaagat gactatcttt aatgtctgga aattcttcca gaattgatac tgactgtatg       60
gaaaatgaga gctgcag                                                      77

<210> SEQ ID NO 653
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 653
ctgcagctct cattttccat acattaaaga tagtcatctt ggggc                       45

<210> SEQ ID NO 654
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 654
gccccaagat gactatcttt aatgtatgga aaatgagagc tgcag            45

<210> SEQ ID NO 655
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655
ctgcagctct cattttccat acagtcagta tcaattctgg aagaatttcc agacattaaa    60
gatagtcatc ttggggc                                                  77

<210> SEQ ID NO 656
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 656
ctgcagctct cattttccat acagtcagta tcattctgga agaatttcca gacattaaag    60
atagtcatct tggggc                                                   76

<210> SEQ ID NO 657
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
gccccaagat gactatcttt aatgtctgga aattcttcca gaatgatact gactgtatgg    60
aaaatgagag ctgcag                                                   76

<210> SEQ ID NO 658
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 658
ctgcagctct cattttccat acagtcagta tcaaaatttc cagacattaa agatagtcat    60
cttggggc                                                            68

<210> SEQ ID NO 659
<211> LENGTH: 68
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 659
gccccaagat gactatcttt aatgtctgga aattttgata ctgactgtat ggaaaatgag    60
agctgcag                                                             68

<210> SEQ ID NO 660
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 660
ctgcagctct cattttccat acagtcagta tcaattcaat ttccagacat taaagatagt    60
catcttgggg c                                                         71

<210> SEQ ID NO 661
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 661
gccccaagat gactatcttt aatgtctgga aattgaattg atactgactg tatggaaaat    60
gagagctgca g                                                         71

<210> SEQ ID NO 662
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662
ctgcagctct cattttccat acagtcagta tcaaaagaat ttccagacat taaagatagt    60
catcttgggg c                                                         71

<210> SEQ ID NO 663
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663
gccccaagat gactatcttt aatgtctgga aattcttttg atactgactg tatggaaaat    60
gagagctgca g                                                         71

<210> SEQ ID NO 664
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664
```

Gly Gly Arg Pro Ala Leu Glu
1               5

<210> SEQ ID NO 665
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

Gly Gly Lys Gln Ala Leu Glu
1               5

<210> SEQ ID NO 666
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

Gly Gly Lys Gln Ala Leu Glu Thr Val Gln Arg Leu Leu Pro Val Leu
1               5                   10                  15

Cys Gln Asp His Gly
            20

<210> SEQ ID NO 667
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

Gly Gly Lys Gln Ala Leu Glu Thr Val Gln Arg Leu Leu Pro Val Leu
1               5                   10                  15

Cys Gln Ala His Gly
            20

<210> SEQ ID NO 668
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 668

Gly Lys Gln Ala Leu Glu Thr Val Gln Arg Leu Leu Pro Val Leu Cys
1               5                   10                  15

Gln Asp His Gly
            20

<210> SEQ ID NO 669
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669

```
Gly Lys Gln Ala Leu Glu Thr Val Gln Arg Leu Leu Pro Val Leu Cys
1               5                   10                  15

Gln Ala His Gly
            20

<210> SEQ ID NO 670
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

Gly Gly Lys Gln Ala Leu Glu Thr Val Gln Arg Leu Leu Pro Val Leu
1               5                   10                  15

Cys Gln Asp

<210> SEQ ID NO 671
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Gly Gly Lys Gln Ala Leu Glu Thr Val Gln Arg Leu Leu Pro Val Leu
1               5                   10                  15

Cys Gln Ala

<210> SEQ ID NO 672
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Gly Lys Gln Ala Leu Glu Thr Val Gln Arg Leu Leu Pro Val Leu Cys
1               5                   10                  15

Gln Asp

<210> SEQ ID NO 673
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Gly Lys Gln Ala Leu Glu Thr Val Gln Arg Leu Leu Pro Val Leu Cys
1               5                   10                  15

Gln Ala

<210> SEQ ID NO 674
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(3)
<223> OTHER INFORMATION: Any naturally occurring amino acid

<400> SEQUENCE: 674

Gly Xaa Xaa Gly
1

<210> SEQ ID NO 675
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Gly His Gly Gly
1

<210> SEQ ID NO 676
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 676
gccccaagat gactatcttt aatgtctgga aattcttcca gaattgatac tgactgtatg    60
gaaaatgaga gctgcag                                                   77

<210> SEQ ID NO 677
<211> LENGTH: 5
<212> TYPE: PRT
<213> ORGANISM: Homo sapiens

<400> SEQUENCE: 677

Ala His Gly Gly Gly
1               5

<210> SEQ ID NO 678
<211> LENGTH: 5
<212> TYPE: PRT
<213> ORGANISM: Homo sapiens

<400> SEQUENCE: 678

Ala Gly His Gly Gly
1               5

<210> SEQ ID NO 679
<211> LENGTH: 5
<212> TYPE: PRT
<213> ORGANISM: Homo sapiens

<400> SEQUENCE: 679

Ala His Gly Ser Gly
1               5
```